US006969763B1

(12) United States Patent
Ecker et al.

(10) Patent No.: US 6,969,763 B1
(45) Date of Patent: Nov. 29, 2005

(54) MOLECULAR INTERACTION SITES OF INTERLEUKIN-2 RNA AND METHODS OF MODULATING THE SAME

(75) Inventors: David J. Ecker, Encinitas, CA (US); Richard Griffey, Vista, CA (US); Stanley T. Crooke, Carlsbad, CA (US); Ranga Sampath, San Diego, CA (US); Eric Swayze, Carlsbad, CA (US); Venkatraman Mohan, Carlsbad, CA (US); Steven Hofstadler, Oceanside, CA (US); John McNeil, La Jolla, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/310,844

(22) Filed: May 12, 1999

(51) Int. Cl.[7] .................................... C07H 21/04
(52) U.S. Cl. .................................... 536/24.3; 536/24.31
(58) Field of Search .................................... 536/23.1, 23.5, 536/24.1, 24.3, 24.31, 24.33; 435/6

(56) References Cited

U.S. PATENT DOCUMENTS

| | | | | |
|---|---|---|---|---|
| 5,372,672 | A | | 12/1994 | Seifert et al. |
| 5,434,796 | A | | 7/1995 | Weininger |
| 5,472,672 | A | | 12/1995 | Brennan |
| 5,529,756 | A | | 6/1996 | Brennan |
| 5,571,902 | A | | 11/1996 | Ravikumar et al. |
| 5,574,656 | A | | 11/1996 | Agrafiotis et al. |
| 5,703,792 | A | | 12/1997 | Chapman |
| 5,880,972 | A | | 3/1999 | Horlbeck |
| 5,888,738 | A | | 3/1999 | Hendry |
| 6,090,620 | A | * | 7/2000 | Fu et al. |

FOREIGN PATENT DOCUMENTS

| | | |
|---|---|---|
| WO | WO 89/12694 | 12/1989 |

OTHER PUBLICATIONS

McKnight et al., Immunogenetics 30, 145–147 (1989).*

Chen et al., Proc. Natl. Acad. Sci. USA, vol. 82, pp. 7284–7288 (Nov. 1995).*

PCT International Search Report dated Jul. 7, 1999, 6 pages.

Czarnik, A.W. et al., (eds.), *A Practical Guide to Combinatorial Chemistry*, American Chemical Society, Washington, DC, 1997, Chs. 2, 13, 14, 17–47 and 357–412.

Braddock et al., "Blocking of Tat–dependent HIV–1 RNA modification by an inhibitor of RNA polymerase II processivity," *Nature*, 1991, 350, 439–441.

Corey, E.J. et al., "Computer–Assisted Analysis in Organic Synthesis," *Science*, 1985, 228, 408–418.

Crain et al., "Applications of Electrospray Ionization Mass Spectrometry to Structural Studies of Oligonucleotides and RNA," *Books of Abstracts*, 207th ACS National Meeting, Mar. 13–17, 1994, Abstract No. 99, 3 pages.

Ramezani et al., "Comparative Analysis of Five Highly Conserved Target Sites Within the HIV–1 RNA for Their Susceptibility to Hammerhead Ribozyme–Mediated Cleavage In Vitro and In Vivo," *Antisense & Nucl. Acid Drug Develop.*, 1996, 6, 229–235.

Rotstein, S.H. et al., "GroupBuild: A Fragment–Based Method for *De Novo* Drug Design," *J. Med. Chem.*, 1993, 36, 1700–1710.

Sannes–Lowery, K.A. et al., "HIV–1 Tat Peptide Binding to TAR RNA by Electrospray Ionization Mass Spectrometry," *Anal. Chem.*, 1997, 69, 5130–5135.

Stryer, L. (ed.), *Biochemistry*, Third Edition, W.H. Freeman and Company, New York, 1975, 86–88 and 91–95.

Adams, M.D. et al., "Initial assessment of human gene diversity and expression patters based upon 83 million nucleotides of cDNA sequence," *Nature*, 1995, 377(Supp. 28), 3–17.

Bruice, T.W. et al., "Control of Complexity Constraints on Combinatorial Screening for Preferred Oligonucleotide Hybridization Sites on Structured RNA," *Biochem.*, 1997, 36, 5004–5019.

Chen, S.J. et al., "A viral long terminal repeat in the interleukin 2 gene of a cell line that constitutively produces interleukin 2," *Proc. Natl. Acad. Sci. USA*, 1985, 82, 7284–7288.

Devos, R. et al., "Molecular cloning of human interleukin 2 cNDA and its expression in *E. coli*," *Nucl. Acids Res.*, 1983, 11(13), 4307–4323.

Draper, D.E., "Protein–RNA Recognition in a Highly Conserved Ribosomal Domain Targeted by Thiazole Antibiotics," *The Many Faces of RNA*, 1998, 8, 113–125.

Efrat, S. et al., "Kinetics of induction and molecular size of mRNAs encoding human interleukin–2 and γ–interferon," *Nature*, 1982, 297, 236–239.

Jäschke, A., "Catalysis of Organic Reactions by RNA—Strategies for the Selection of Catalytic RNAs," *The Many Faces of RNA*, 1998, 12, 179–190.

(Continued)

*Primary Examiner*—Karen A. Lacourciere
(74) *Attorney, Agent, or Firm*—Isis Patent Department; Cozen O'Connor, P.C.

(57) ABSTRACT

Methods for the identification of compounds which modulate, either inhibit or stimulate, biomolecules are provided. Nucleic acids, especially RNAs are preferred substrates for such modulation. The present methods are particularly powerful in that they provide novel combinations of techniques which give rise to compounds, usually "small" organic compounds, which are highly potent modulators of RNA and other biomolecular activity. In accordance with preferred aspects of the invention, very large numbers of compounds may be tested essentially simultaneously to determine whether they are likely to interact with a molecular interaction site and modulate the activity of the biomolecule. Pharmaceuticals, veterinary drugs, agricultural chemicals, industrial chemicals, research chemicals and many other beneficial compounds may be identified in accordance with embodiments of this invention.

4 Claims, 88 Drawing Sheets

OTHER PUBLICATIONS

Maniatis, T. et al. (eds.), *Molecular Cloning: A Laboratory Manual*, 1982, 405–410.
Naora, H. et al., "Mechanisms Regulating the mRNA Levels of Interleukin–5 and Two Other Coordinately Expressed Lymphokines in the Murine T Lymphoma EL4.23," *Blood*, 1994, 83(12), 3620–3628.
Polisky, B., "Progress towards Therapeutic Application of SELEX–derived Aptamers," *The Many Faces of RNA*, 1998, 11, 161–177.
Przybylski, M. et al., "Mass spectrometric approaches to molecular characterization of protein–nucleic acid interactions," *Toxicology Letts.*, 1995, 82/83, 567–575.
Ryan, P.C. et al., "Thermodynamics of Protein–RNA Recognition in a Highly Conserved Region of the Large–Subunit Ribosomal RNA," *Biochem.*, 1989, 28, 9949–9956.
Abagyan et al., "ICM—A Method for Protein Modeling and Design: Applications to Docking and Structure Prediction from the Distorted Native Conformation", *J. Comp. Chem.*, 1994, 15(5), 488–506.
Addess et al., "Structure and Dynamics of the Iron Responsive Element RNA: Implications for Binding of the RNA by Iron Regulatory Binding Proteins", *J. Mol. Biol.*, 1997, 274, 72–83.
Amster, "Fourier Transform Mass Spectrometry", *J. Mass Spectrom.*, 1996, 31, 1325–1337.
An et al., "New Piperazinyl Polyazacyclophane Scaffolds, Libraries and Biological Activities," *Bioorg. Med. Chem. Lett.*, 1998, 8, 2345–2350.
Anderegg et al., "Mass Spectrometric Characterization of a Protein—Ligand Interaction", *J. Am. Chem. Soc.*, 1995, 117, 1374–1377.
Atherton et al., in *Solid Peptide Synthesis: A Practical Approach*, IRL Press, Oxford, UK, 1989, 135.
Baca et al., "Direct Observation of a Ternary Complex between the Dimeric Enzyme HIV–1 Protease and a Substrate–Based Inhibitor", *J. Am. Chem. Soc.*, 1992, 114, 3992–3993.
Baczynskyj et al., "Application of Thermally Assisted Electrospray Ionization Mass Spectrometry for Detection of Noncovalent Complexes of Bovine Serum Albumin with Growth Hormone Releasing Factor and Other Biologically Acitve Peptides", *Rapid Commun. Mass Spectrom.*, 1994, 8, 280–286.
Bayer et al., "Analysis of Double–Stranded Oligonucleotides by Electrospray Mass Spectrometry", *Anal. Chem.*, 1994, 66, 3858–3863.
Benson et al., "GenBank", *Nucl. Acids Res.*, 1998, 26(1), 1–7.
Berson et al., "General Principles of Radioimmunoassay", *Clin. Chim. Acta*, 1968, 22, 51–66.
Biemann, K., "Mass Spectrometry of Peptides and Proteins", *Ann. Rev. Biochem.*, 1992, 61, 977–1010.
Bowers, M.T. et al., "Mass Spectrometry: Recent Advances and Future Directions," *J. Phys. Chem.*, 1996, 100, 12897–12910.
Brown, J.W., "Phylogenetic analysis of RNA structure on the Macintosh computer", *CABIOS Commun.*, 1991, 7(3), 391–393.
Bruce et al., "Bio–Affinity Characterization Mass Spectrometry", *Rapid Commun. Mass Spectrom.*, 1995, 9, 644–650.
Bruins et al., "Ion Spray Interface for Combined Liquid Chromatography/Atmospheric Pressure Ionization Mass Spectrometry", *Anal. Chem.*, 1987, 59, 2642–2646.
Bryan, "Mechanisms of Action of Aminoglycoside Antibiotics", in *New Dimensions in Antimicrobial Therapy*, Root, R.K. et al. (eds.), Churchill Livingstone, New York, 1984, vol. 1, Ch. 2, 17–36.
Burlingame, A.L. et al., "Mass Spectrometry," *Anal. Chem.*, 1998, 70, 647R–716R.
Busman et al., "Observation of Large Multimers in the Electrsopray Ionization Mass Spectrometry of Peptides", *Rapid Commun. Mass Spectrom.*, 1994, 8, 211–216.
Cai et al., "Capillary electrohoresis—mass spectrometry", *J. Chromatogr.*, 1995, 703, 667–692.
Cain et al., "Solution structure of a DNA hairpin and its disulfide cross–linked analog", *Nucl. Acids Res.*, 1995, 23(12), 2153–2160.
Casey et al., "Iron–Responsive Elements: Regulatory RNA Sequences that Control mRNA Levels and Translation," *Science*, 1988, 240, 924–928.
Cedergren et al., "Modeling the Tertiary Structure of RNA" in *RNA Struacture and Function*, Cold Spring Harbor Laboratory Press, 1988, 37–75.
Chattopadhyaya et al., "X–ray structure of a DNA hairpin molecule", *Nature*, 1988, 334, 175–179.
Chen et al., "Structure–Based Discovery of Ligands Targeted to the RNA Double Helix", *Biochem.*, 1997, 36, 11402–11407.
Chen et al., "Spectroscopic recognition of guanine dimeric hairpin quadruplexes by a carbocyanine dye", *Proc. Natl. Acad. Sci.*, 1996, 93, 2635–2639.
Cheng et al., "Using Electrospray Ionization FTICR Mass Spectrometry to Study Competitive Binding of Inhibitors to Carbonic Anhydrase", *J. Am. Chem. Soc.*, 1995, 117, 8859–8860.
Cheng et al., "Direct measurement of oligonucleotide binding stoichiometry of gene V protein by mass spectrometry", *Proc. Natl. Acad. Sci USA*, 1996, 93, 7022–7027.
Cheng et al., "Electrospray Ionization with High Performance Fourier Transform Ion Cyclotron Resonance Mass Spectrometry for the Study of Noncovalent Biomolecular Complexes", in *Techniques in Protein Chemistry*, 1996, vol. 7, 13–22.
Cheong et al., "Solution structure of an unusually stable RNA hairpin, 5'GGAC(UUCG)GUCC", *Nature*, 1990, 346, 680–682.
Cohen et al., "Probing the solution structure of the DNA–binding protein Max by a combination of proteolysis and mass spectrometry", *Protein Sci.*, 1995, 4, 1088–1099.
Chu et al., "Affinity Capillary Electrophoresis", *Acc. Chem. Res.*, 1995, 25, 461–468.
Chu et al., "Using Affinity Capillary Electrophoresis to Identify the Peptide in a Peptide Library that Binds Most Tightly to Vancomycin", *J. Org. Chem.*, 1993, 58, 648–652.
Chu et al., "Affinity Capillary Electrophoresis—Mass Spectrometry for Screening Combinatorial Libraries", *J. Am. Chem. Soc.*, 1996, 118, 7827–7835.
Crain et al., "Applications of mass spectrometry to the characterization of oligonucleotides and nucleic acids", *Curr. Opin. Bioetechnol.*, 1998, 9, 25–34.
De Stasio et al., "Mutations in 16S ribosomal RNA disrupt antibiotic—RNA interactions", *EMBO J.*, 1989, 8, 1213–1216.
Doktycz et al., "Accumulation and Storage of Ionized Duplex DNA Molecules in a Quadrupole Ion Trap", *Anal. Chem.*, 1994, 66, 3416–3422.

Dunayevskiy et al., "Mass Spectrometric Identification of Ligands Selected from Combinatorial Libraries Using Gel Filtration", *Rapid Commun. Mass Spectrom.*, 1997, 11, 1178–1184.
Duret et al., "HOVERGEN: a database of homologous vertebrate genes," *Nucl. Acids Res.*, 1994, 22(12), 2360–2365.
Ecker et al., "Combinatorial Drug Discovery: Which Methods Will Produce the Greatest Value", *Biotech.*, 1995, 13, 351–360.
Erie et al., "A Monte Carlo Method for Generating Structures of Short Single–Stranded DNA Sequences", *Biopolymers*, 1993, 33, 75–105.
Erickson et al., "Macromolecular X–Ray Crystallography and NMR as Tools for Structure–based Drug Design", *Ann. Rep. Med. Chem.*, 1992, vol. 27, Ch. 29, 271–289.
Feng et al., "Analysis of Antibodies and Other Large Glycoproteins in the Mass Range of 150 000200 000 Da by Electrsopray Ionization Mass Spectrometry", *Anal. Chem.*, 1992, 64, 2090–2095.
Feng et al., "HIV–1 *tat trans*–activation requires the loop sequence within *tar*", *Nature*, 1988, 334, 165–167.
Filikov et al., "Structure–based design of ligands for protein basic domains: Application to the HIV–1 Tat protein", *J. Comp.–Aided Molec. Design*, 1998, 12, 229–240.
Fitzgerald, M. et al., "Probing the oligomeric structure of an enzyme by electrospray ionization time–of–flight mass spectrometry", *Proc. Natl. Acad. Sci. USA*, 1996, 93, 6851–6856.
Fourmy et al., "Paromomycin Binding Induces a Local Conformational Change in the A–site of 16 S rRNA", *J. Mol. Biol.*, 1998, 277, 333–345.
Fourmy et al., "Structure of the A Site of *Escherichia coli* 16S Ribosomal RNA Complexed with an Aminoglycoside Antibiotic", *Science*, 1996, 274, 1367–1371.
Gale et al., "Characterization of Noncovalent Complexes Formed between Minor Groove Binding Molecules and Duplex DNA by Electrospray Ionization—Mass Spectrometry", *J. Am. Soc. Mass Spectrometry*, 1995, 6, 1154–1164.
Gale et al., "Observation of Duplex DNA–Drug Noncovalent Complexes by Electrospray Ionization Mass Spectrometry", *J. Am. Chem. Soc.*, 1994, 116, 6027–6028.
Ganem et al., "Detecting Noncovalent Complexes of Biological Macromolecules: New Applications of Ion–Spray Mass Spectrometry", *ChemTracts–Org. Chem.*, 1993, 6, 1–22.
Ganem et al., "Detection of Oligonucleotide Duplex Forms by Ion–Spray Mass Spectrometry", *Tetra. Lett.*, 1993, 34(9), 1445–1448.
Ganguly et al., "Studies of the *Ras*–GDP and *Ras*–GTP Noncovalent Complexes by Electrospray Mass Spectrometry", *Tetrahedron*, 1993, 49(36), 7985–7996.
Gao et al., "Screening Derivatized Peptide Libraries for Tight Binding Inhibitors to Carbonic Anyhydrase II by Electrospray Ionization–Mass Spectrometry", *J. Med. Chem.,* 1996, 39, 1949–1955.
Gautheret et al., "Inferring the conformation of RNA base pairs and triples from patterns of sequence variation", *Nucl. Acids Res.*, 1997, 25(8), 1559–1564.
Gautheret et al., "G U base pairing motifs in ribosomal RNA", *RNA*, 1995, I, 807–814.
Gautheret et al., "Identification of Base–triples in RNA using Comparative Sequence Analysis", *J. Mol. Biol.*, 1995, 248. 27–43.
Gdaniec et al., "Iron Regulatory Element and Internal Loop/Bulge Structure for Ferritin mRNA Studied by Cobalt(III) Hexammine Binding, Molecular Modeling, and NMR Spectroscopy", *Biochem.*, 1998, 37, 1505–1512.
Glover et al., "Sequencing of Oligonucleotides Using High Performance Liquid Chromatography and Electrospray Mass Spectrometry", *Rapid Commun. Mass Spectrom.*, 1995, 9, 897–901.
Goodlett et al., "Direct Observation of a DNA Quadruplex by Electrospray Ionization Mass Spectrometry", *Biol. Mass Spectrom.*, 1993, 22, 181–183.
Greig et al., "Measurement of Macromolecular Binding Using Electrospray Mass Spectrometry. Determiniation of Dissocation Constants for Oligonucleotide—Serum Albumin Complexes", *J. Am. Chem. Soc.*, 1995, 117, 10765–10766.
Grens et al., "The 5'– and 3'–Untranslated Regions of Ornithine Decarboxylase mRNA Affect the Translational Efficiency," *J. Biol. Chem.*, 1990, 265(20), 11810–11816.
Griffey et al., "Detection of base pair mismatches in duplex DNA and RNA oligonucleotides using electrospray mass spectrometry", *Proc. SPIE–Int. Soc. Opt. Eng.,* 1997, 2985, 82–86.
Gschwend et al.,"Orientational sampling and rigid–body minimization in molecular docking revisited: On–the–fly optimization and degeneracy removal", *J. Compt.–Aided Mol. Des.,* 1996, 10, 123–132.
Gutell, "Collection of small subunit (16S– and 16S–like) ribosomal RNA structures: 1994", *Nucl. Acids Res.*, 1994, 22(17), 3502–3507.
Gutell, "Collection of small subunit (16S– and 16S–like) ribosomal RNA structures", *Nucl. Acids Res.,* 1993, 21(13), 3051–3054.
Gutell, "A compilation of large subunit (23S and 23S–like) ribosomal RNA structures: 1993", *Nucl. Acids Res.,* 1993, 21(13), 3055–3074.
Henion et al., "Mass Spectrometric Investigations of Drug–Receptor Interactions", *Ther. Drug Monitoring,* 1993, 15(6), 563–569.
Hillenkamp et al., "Matrix–Assisted Laser Desorption/Ionization Mass Spectrometry of Biopolymers", *Anal. Chem.*, 1991, 63(24). 1193A–1202A.
Hu et al., "Determining Calcium–binding Stoichiometry and Cooperativity of Parvalbumin and Calmodulin by Mass Spectrometry", *J. Mass Spectrom.*, 1995, 30, 1076–1082.
Huang et al., "Packed–Capillary Liquid Chromatography/Ion–Spray Tandem Mass Spectrometry Determination of Biomolecules", *Anal. Chem.*, 1991, 63, 732–739.
Huang et al., "LC/MS and LC/MS/MS Determination of Protein Tryptic Digests", *J. Am. Soc. Mass Spectrom.*, 1990, 1(2), 158–165.
Jefson, "Applications of NMR Spectroscopy to Protein Structure Determination", *Ann. Rep. Med. Chem.*, 1988, vol. 23, Ch. 28, 275–283.
Jensen et al., "Mass Spectrometric Characterization of UV–Crosslinked Protein–Nucleic Acid Complexes", *42nd ASMS Conf. On Mass Spectrom. and Allied Topics,* 1994, 923.
Jensen et al., "Direct Observation of UV–crosslinked Protein–Nucleic Acid Complexes by Matrix–assisted Laser Desorption Ionization Mass Spectrometry", *Rapid Commun. Mass Spectrom.*, 1993, 7, 496–501.

Jones, "A Graphics Model Building and Refinement System for Macromolecules", *J. Appl. Crystallogr.*, 1978, 11, 268–272.

Jonsson et al., "Real–Time Biospecific Interaction Analysis Using Surface Plasmon Resonance and a Sensor Chip Technology", *Biotech.,* 1991, 11(5), 620–627.

Jorgensen et al., "Direct Determination of Solution Binding Constants for Noncovalent Complexes between Bacterial Cell Wall Peptide Analogues and Vancomycin Group Antibiotics by Electrospray Ionization Mass Spectrometry", *Anal. Chem.*, 1998, 70, 4427–4432.

Karlsson et al., "Kinetic analysis of monoclonal antibody–antigen interactions with a new biosensor based analytical system", *J. Immunol. Methods,* 1991, 145, 229–240.

Kassel et al., "Direct Coupling of an Automated 2–Dimensional Microcolumn Affinity Chromatography–Capillary HPLC System with Mass Spectrometry for Biomolecular Analysis", in *Techniques in Protein Chemistry*, J. Crabb (ed.), Academic Press, San Diego, 1995, Ch. VI, 39–46.

Knight et al., "Electrospray Ionization Mass Spectrometry as a Mechanistic Tool: Mass of Human Leucocyte Elastase and a β–Lactam–Derived E–I Complex", *Biochem.*, 1993, 32, 2031–2035.

Köster, H. et al., "A Strategy for rapid and efficient DNA sequencing by mass spectrometry,", *Nature Biotechnology*, 1996, 14, 1123–1128.

Kozak, "Structural Features in Eukaryotic mRNAs That Modulate the Initiation of Translation", *J. Biol. Chem.,* 1991, 266(30), 19867–19870.

Kuntz et al., "Structure–Based Molecular Design", *Acc. Chem. Res.,* 1994, 27(5), 117–123.

Kuntz et al., "A Geometric Approach to Macromolecule–Ligand Interactions", *J. Mol. Biol.,* 1982, 161, 269–288.

Laferriere et al., "An RNA pattern matching program with enhanced performance and portability", *Comput. Appl. Biosci.*, 1994, 10(2), 211–212.

Lane et al., "SPARC Is a Source of Copper–binding Peptides that Stimulate Angiogenesis", *J. Cell Biol.,* 1994, 125(4), 929–943.

Li et al., "Mass Spectrometric Studies on Noncovalent Dimers of Leucine Zipper Peptides", *J. Am. Chem. Soc.,* 1993, 115, 8409–8413.

Light–Wahl et al., "Observation of a Small Oligonucleotide Duplex by Electrospray Ionization Mass Spectrometry", *J. Am. Chem. Soc.,* 1993, 115, 803–804.

Light–Wahl et al., "Observation of the Noncovalent Quaternary Associations of Proteins by Electrospray Ionization Mass Spectrometry", *J. Am. Chem. Soc.,* 1994, 116, 5271–5278.

Light–Wahl et al., "Collisionally Activated Dissociation and Tandem Mass Spectrometry of Intact Hemoglobin β–Chain Variant Proteins with Electrospray Ionization", *Biol. Mass Spectrom.*, 1993, 22, 112–120.

Lim et al., "Recognition of Cell–wall Peptide Ligands by Vancomycin Group Antibiotics: Studies Using Ion Spray Mass Spectrometry", *J. Mass Spectrom.,* 1995, 30, 708–714.

Little et al., "Rapid Sequencing of Oligonucleotides by High–Resolution Mass Spectrometry", *J. Am. Chem. Soc.,* 1994, 116, 4893–4897.

Little et al., "Sequencing 50–mer DNAs Using Electrospray Tandem Mass Spectrometry and Complementary Fragmentation Methods", *J. Am. Chem. Soc.,* 1995, 17, 6783–6784.

Little et al., "Infrared Multiphoton Dissociation of Large Multiply Charged Ions for Biomolecule Sequencing", *Anal. Chem.,* 1994, 66, 2809–2815.

Little et al., "Verification of 50– to 100–mer DNA and RNA sequences with high–resolution mass spectrometry", *Proc. Natl. Acad. Sci. USA*, 1995, 92, 2318–2322.

Lodmell et al., "Genetic and comparative analyses reveal an alternative secondary structure in the region of nt 912 *Escherichia coli* 16S rRNA", *Proc. Natl. Acad. Sci. USA*, 1995, 92, 10555–10559.

Loo, "Studying Noncovalent Protein Complexes by Electrospray Ionization Mass Spectrometry", *Mass Spectrometry Reviews*, 1997, 16, 1–23.

Loo, "Bioanalytical Mass Spectrometry: Many Flavors to Choose", *Bioconjugate Chem.*, 1995, 6, 644–665.

Loo, "Observation of Large Subunit Protein Complexes by Electrospray Ionization Mass Spectrometry", *J. Mass. Spectrom.*, 1995, 30, 180–183.

Loo et al., "Use of Electrospray Ionization Mass Spectrometry to Probe Antisense Peptide Interactions", *Biol. Mass Spectrom.*, 1994, 23, 6–12.

Loo et al. "Interaction of Angiotensin Peptides and Zinc Metal Ions Probed by Electrospray Ioniztion Mass Spectrometry", *J. Am. Soc. Mass Spectrom.*, 1994, 5(11), 959–965.

Major et al., "Reproducing the three–dimensional structure of a tRNA molecule from structural constraints", *Proc. Natl. Acad. Sci.*, 1993, 90, 9408–9412.

Marshall et al., "Fouriere Transform Ion Cyclotron Resonance Mass Spectrometry: The Teenage Years", *Anal. Chem.*, 1991, 63(4). A215–A229.

Marshall et al., "Fourier Transform Ion Cyclotron Resonance Mass Spectrometry: A Primer", *Mass Spectrom. Rev.*, 1998, 17, 1–35.

Martin, F. et al., "The gene for histone RNA hairpin binding protein is located on human chromosome 4 and encodes a novel type of RNA binding protein", *EMBO J.*, 1997, 16(4), 769–778.

McLuckey et al., "Tandem Mass Spectrometry of Small, Multiply Charged Oligonucleotides", *J. Am. Soc. Mass Spectrom.*, 1992, 3(1), 60–70.

McLuckey et al., "Decompositions of Mulitply Charged Oligonucleotide Anions", *J. Am. Chem. Soc.,* 1993, 115, 12085–12095.

McMartin et al., "QXP: Powerful, rapid computer algorithms for structure–based drug design," *J. Comput.–Aided Mol. Design.* 1997, 11, 333–334.

Meng et al., "Automated Docking with Grid–Based Energy Evaluation", *J. Comp. Chem.*, 1992, 13(4), 505–524.

Miyaguchi et al., "An antibiotic motif of an RNA fragment derived from the A–site–related region of *Escherichia coli* 16A rRNA", *Nucl. Acids Res.*, 1996, 24(19), 3700–3706.

Moras et al., "Crystal structure of yeast tRNA", *Nature*, 1980, 288, 669–674.

Mueller et al., "A New Model for the Three–dimensional Folding of *Escherichia coli* 16S Ribosomal RNA. I. Fitting the RNA to a 3D Electron Microscopic Map at 20 Å", *J. Mol. Biol.*, 1997, 271, 524–544.

Nelson et al., "Mass Determination of Human Immunoglobulin IgM Using Matrix–assisted Laser Desorption/Ionization Time–of–flight Mass Spectrometry", *Rapid Commun. Mass Spectrom.*, 1994, 8, 627–631.

Ni et al., "Interpretation of Oligonucleotide Mass Spectra for Determination of Sequence Using Electrospray Ionization and Tandem Mass Spectrometry", *Anal. Chem.*, 1996, 68, 1989–1999.

Nordhoff et al., "Direct Mass Spectrometric Sequencing of Low–picomole Amounts of Oligodeoxynuclotides with up to 21 Bases by Matric–assisted Laser Desorption/Ionization Mass Spectrometry", *J. Mass Spectrom.*, 1995, 30, 99–112.

Owen et al., "Noncoding 3' sequences of the transferrin receptor gene are required for mRNA regulation by iron," *EMBO J.*, 1987, 6(5), 1287–1293.

Pain, "Initiation of protein synthesis in eukaryotic cells", *Eur. J. Biochem.*, 1996, 236, 747–771.

Phillipe et al., "Target Site of *Escherichia coli* Ribosomal Protein S15 on its Messenger RNA: Conformation and Interaction with the Protein", *J. Mol. Biol.,* 1990, 211, 415–426.

Pieles et al., "Matrix–assisted laser desorption inioization time–of–flight mass spectrometry: a powerful tool for the mass and sequence analysis of natural and modified oligonucleotides", *Nucl. Acid Res.*, 1993, 21(14), 3191–3196.

Quigley et al., "Yeast phenylalanine transfer RNA: atomic coordinates and torsion angles", *Nucl. Acids Res.*, 1975, 2(12), 2329–2341.

Raghunathan et al., "Conformational Feasibility of a Hairpin with Two Purines in the Loop. 5'–d–GGTAC*IAGTA*CC–3'", *Biochem.*, 1991, 30, 782–788.

Recht et al., "RNA Sequence Determinants for Aminoglycoside Binding to an A–site rRNA Model Oligonucleotide", *J. Mol. Biol.*, 1996, 262, 421–436.

Rossomando et al., "Identification of Tyr–185 as the site of tyrosine autophosphorylation of recombinant mitogen–activated protein kinase $p42^{mapk}$", *Proc. Natl. Acad. Sci USA*, 1992, 89, 5779–5783.

Shaler et al., "Analysis of Enzymatic DNA Sequencing Reactions by Matrix–assisted Laser Desorption/Ionization Time–of–flight Mass Spectrometry", *Rapid Commun. Mass Spectrom.*, 1995, 9, 942–947.

Shen et al., "RNA structure at high resolution", *FASEB J.*, 1995, 9, 1023–1033.

Smith et al., "The Observation of NOn–covalent Interactions in Solution by Electrospray Ionization Mass Spectrometry: Promise, Pitfalls and Prognosis", *J. Biol. Mass Spectrum.*, 1993, 22, 493–501.

Smith et al., "New Developments in Biochemical Mass Spectrometry: Electrospray Ionization", *Anal. Chem.*, 1990, 62, 882–899.

Smith et al., "New mass spectrometric methods for the study of noncovalent associations of biopolymers", *Chem. Soc. Rev.*, 1997, 26, 191–202.

Son, "The Structure and Regulations of Histone Genes," *Saenghwahak Nyusu*, 1993, 13(2), 64–70.

Standart et al., "Regulation of translation by specific protein/mRNA interactions", *Biochimie*, 1994, 76, 867–879.

Sternberg et al., "Display of peptides and protiens on the surface of bacteriophage λ", *Proc. Natl. Acad. Sci. USA*, 1995, 92, 1609–1613.

Sutton et al., "TIGR Assembler: A New Tood for Assembling Large Shotgun Sequencing Projects", *Genome Science & Tech.*, 1995, 1(1), 9–19.

Thompson et al., "CLUSTAL W: improving the sensitivity of progressive multiple sequence alignment through sequence weighting, position–specific gap penalties and weight matrix choice", *Nucl. Acids Res.*, 1994, 22(22), 4673–4680.

Tung, "A Computational Approach to Modeling Nucleic Acid Hairpin Structures", *Biophysical J.*, 1997, 72, 876–885.

Udenfriend et al., "Scintillation Proximity Assay: A Sensitive and Continuous Isotopic Methods for Monitoring Ligand/Receptor and Antigen/Antibody Interactions", *Anal. Biochem.*, 1987, 161, 494–500.

Valegard et al., "Crystal structure of an RNA bacteriophage coat protein—operator complex", *Nature*, 1994, 371, 623–626.

Varani et al., "The Structure of the Human Immunodeficiency Virus Type–1 TAR RNA Reveals Principles of RNA Recognition by Tat Protein", *J. Mol. Biol.*, 1995, 253, 313–332.

Wang et al., "Specificity of Aminoglycoside Binding to RNA Constructs Derived from the 16S rRNA Decoding Region and the HIV–RRE Activator Region", *Biochem.*, 1997, 36, 768–779.

Westhof et al., "Computer–Aided Structural Biochemistry of Ribonucleic Acids", in *Theoretical Biochemistry and Molecular Biophysics*, Beveridge and Lavery (eds.), Adenine, NY, 1991, 399–409.

Westhof et al., "Three–dimensional working model of M1 RNA, the catalytic RNA subunit of ribonuclease P from *Escherichia coli*", *Proc. Natl. Acad. Sci.*, 1994, 91, 5133–5137.

Wilson, "Computers Customize Combinatorial Libraries", *C&EN*, Apr. 17, 1998, 31–37.

Wincott et al., "Synthesis, deprotection, analysis and purification of RNA and ribozymes", *Nucl. Acids Res.*, 1995, 23(14), 2677–2684.

Winger et al., "High–Resolution Accurate Mass Measurements of Biomolecules Using a New Electrospray Ionization Ion Cyclotron Resonance Mass Spectrometer", *J. Am. Soc. Mass Spectrom.*, 1993, 4(7), 566–577.

Witherell et al., "Specific Interaction between RNA Phage Coat Proteins and RNA", *Prog. Nucl. Acids Res. Mol. Biol.*, 1991, 40, 185–220.

Witkowska et al., "Mass Spectrometric Analysis of a Native Zinc–Finger Structure: The Glucocorticoid Receptor DNA Binding Domain", *J. Am. Chem. Soc.*, 1995, 117(12), 3319–3324.

Woese et al., "Evidence for several higher order structural elements in ribosomal RNA", *Proc. Natl. Acad. Sci. USA*, 1989, 86, 3119–3122.

Woese et al., "Secondary structure model for bacterial 16S ribosomal RNA: phylogenetic, enzymatic and chemical evidence", *Nucl. Acids Res.*, 1980, 8(10), 2275–2293.

Wong et al., "Specificity of aminoglycoside antibiotics for the A–site of the decoding region of ribosomal RNA", *Chem. Biol.*, 1998, 5(7), 397–406.

Zehner et al., "RNA–protein interactions within the 3' untranslated region of vimentin mRNA," *Nucl. Acids Res.*, 1997, 25(16), 3362–3370.

* cited by examiner

IRE
Stem-loop Model

H1 S1 H2 S2 H2 H1

H1 3:3 NNN:NNN
S1 1 C
H2 5:5 NNNNN:NNNNN
S2 6 CAGNGN

W2
M0

<u>IRE String descriptor</u>

This descriptor allows for
- a wobble (W) of 2
- no mismatches.
- N can be any nucleotide
- H refers to the stem region
- S refers to the single stranded region.

| | HUMAN PIG | HAMSTER MOUSE RAT | CHICKEN | TROUT SALMON | XENOPUS FROG | FLY | MOSQUITO |
|---|---|---|---|---|---|---|---|
| HUMAN PIG | No | No | Yes | Yes | Yes | No | No |
| HAMSTER MOUSE RAT | | No | Yes | Yes | Yes | No | No |
| CHICKEN | | | No | Yes | Yes | No | No |
| TROUT SALMON | | | | No | Yes | Yes | Yes |
| XENOPUS FROG | | | | | No | Yes | Yes |
| FLY | | | | | | No | Yes |
| MOSQUITO | | | | | | | No |

Compound CI
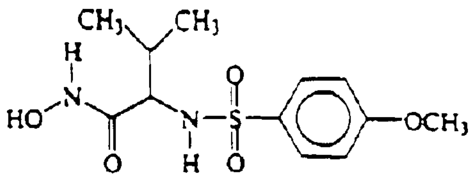
$C_{12}H_{18}N_2O_5S$
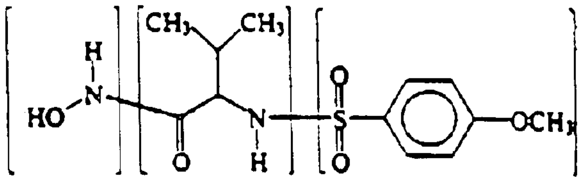
| | $F_i$ | $F_{ii}$ | $F_{iii}$ |
|---|---|---|---|
| Molecular formula | $H_2NO$ | $C_5H_9NO$ | $C_7H_7O_3S$ |
Figure 14

Addition of fragments to yield compounds
Table
| Fragment Identifier | Structure | Name | Molecular formula | Other |
|---|---|---|---|---|
| $F_i$ |  | Hydroxylamine | $H_2NO$ | ... |
| $F_{ii}$ | 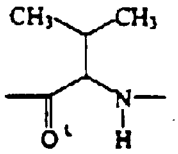 | Amino acid | $C_5H_9NO$ | ... |
| $F_{iii}$ | 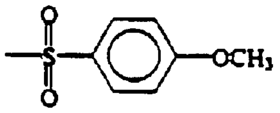 | Sulfonyl | $C_7H_2O_3S$ | ... |
Figure 15

| Reagents | Identifier | Name | Properties |
|---|---|---|---|
|  or 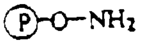 | $R_i$ | Hydroxylamine | ... |
| 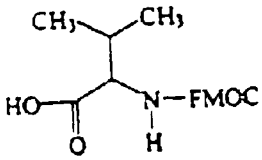 | $R_{ii}$ | FMOC blocked amino acid | ... |
| 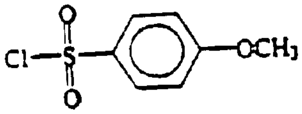 | $R_{iii}$ | Sulfonylchloride | ... |
 = Solid support
Figure 16

Transformation
$T_i$ 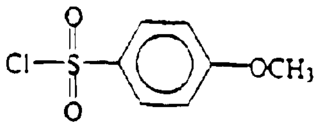 Reagent $R_i$
reaction conditions alpha
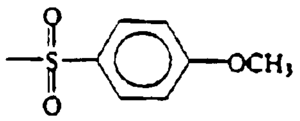 Fragment $F_i$
$T_{ii}$ 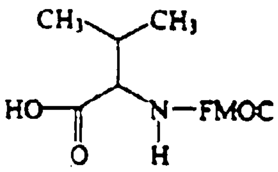 Reagent $R_{ii}$
reaction conditions beta
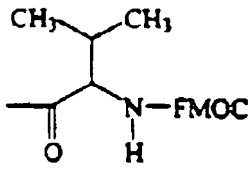 Fragment $F_{ii}$
$T_{iii}$ 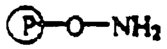 Reagent $R_{iii}$
reaction conditions gamma
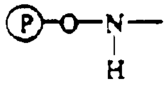 Fragment $F_{iii}$
(P) = Solid support
Figure 17

Common Fragment / Different Reagents and Transformations

Reagent X

Transformation A

Common Product Fragment

Transformation B

Reagent Y

Common Fragment / Different Reagents and Transformations

Common Reagent

Common reagent Z

Symbolic addition of fragments to yield compound
| Symbolic Structure | Symbolic Identifier | Molecular formula |
|---|---|---|
| **Fragment** | | |
|   | $F_{i'}$ | $C_uH_vN_w$ ... |
|   | $F_{ii'}$ | $C_uH_vN_w$ ... |
| 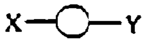  | $F_{iii'}$ | $C_uH_vN_w$ ... |
| **Compound** | | |
| 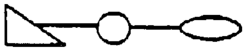 | CI' | $C_uH_vN_w$ ... |
Molecular formula $F_{i'}$
\+
Molecular formula $F_{ii'}$
\+
Molecular formula $F_{iii'}$
= Molecular formula CI'
Figure 20

Symbolic Reagent Table
| Identifier | Name | Structure | Molecular formula |
| --- | --- | --- | --- |
| R1 | xxx |  | xxx |
| R2 | ... |  | ... |
| R3 | ... |  | ... |
| R4 | ... |  | ... |
| R5 | ... | 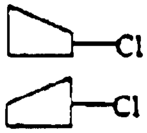 | ... |
| R6 | ... | 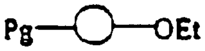 | ... |
| R7 | ... |  | ... |
| R8 | ... |  | ... |
| R9 | ... | 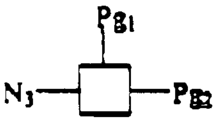 | ... |
| R10 | ... | 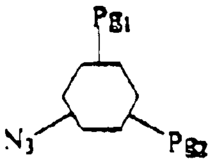 | ... |
Figure 21

Symbolic Fragment Table
| Identifier | Symbolic Structure | Molecular formula | Molecular Weight |
|---|---|---|---|
| F1 |  | xxx | xxx |
| F2 |  | ... | ... |
| F3 |  | ... | ... |
| F4 | 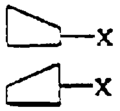 | ... | ... |
| F5 |  | ... | ... |
| F6 |  | ... | ... |
| F7 | 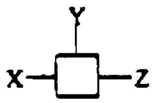 | ... | ... |
| F8 | 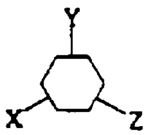 | ... | ... |
Figure 22

Symbolic Transformation Table
| Identifier | | Symbolic Reactions | Reagent |
|---|---|---|---|
| T1 | F1 |  R1 | conditions α |
| T2 | F2 |  R2 | conditions β |
| T3 | F3 | 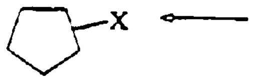 R3 | conditions α |
| T4 | F3 | 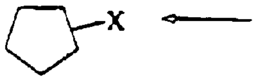 R4 | conditions α |
| T5 | F4 | 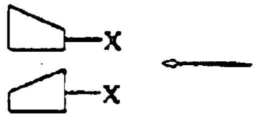 R5 | conditions α |
| T6 | F5 |  R6 | conditions ε |
| T7 | F5 |  R7 | conditions α |
| T8 | F6 |  R8 | conditions α |
| T9 | F7 | 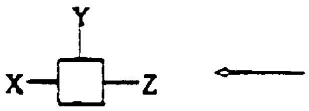 R9 | conditions γ |
| T10 | F8 | 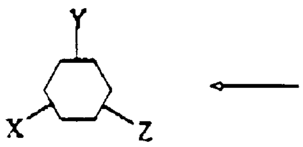 R10 | conditions γ |
Figure 23

Single Compounds and Mixtures

P = synthetic path
F = fragment
C = compound
CF = complex fragment
M = mixture

Mixture 2

M2

Mixture 3

Mixture 4 (continued)

16 compounds

Tracking Table for Compound C1

(a) By Fragments:

| n | n+1 | n+2 |
|---|---|---|
| F7 | | |
| | F2 | |
| | F1 | |
| | F5 | |
| | | F3 |

(b) By Transformations:

Synthesis Path 1

| n | n+1 | n+2 |
|---|---|---|
| T9 | | |
| | T2 | |
| | T1 | |
| | T6 | |
| | | T3 |

Synthesis Path 2

| n | n+1 | n+2 |
|---|---|---|
| T9 | | |
| | T2 | |
| | T1 | |
| | T7 | |
| | | T3 |

Synthesis Path 3

| n | n+1 | n+2 |
|---|---|---|
| T9 | | |
| | T2 | |
| | T1 | |
| | T6 | |
| | | T4 |

Synthesis Path 4

| n | n+1 | n+2 |
|---|---|---|
| T9 | | |
| | T2 | |
| | T1 | |
| | T7 | |
| | | T4 |

Figure 28

Tracking Table

Tracking M2

Step 1

| n | n+1 | n+2 |
|---|---|---|
| T9 | | |

Step 2

| n | n+1 | n+2 |
|---|---|---|
| T9 | | |
| | T2 | |

Step 3

| n | n+1 | n+2 |
|---|---|---|
| T9 | | |
| | T2 | |
| | T1 | |

Step 4

| n | n+1 | n+2 |
|---|---|---|
| T9 | | |
| | T2 | |
| | T1 | |
| | T7 | |

Step 5

| n | n+1 | n+2 |
|---|---|---|
| T9 | | |
| | T2 | |
| | T1 | |
| | T7 | |
| | | T4 |

C1

Step 1

| n | n+1 | n+2 |
|---|---|---|
| T10 | | |

Step 2

| n | n+1 | n+2 |
|---|---|---|
| T10 | | |
| | T2 | |

Step 3

| n | n+1 | n+2 |
|---|---|---|
| T10 | | |
| | T2 | |
| | T1 | |

Step 4

| n | n+1 | n+2 |
|---|---|---|
| T10 | | |
| | T2 | |
| | T1 | |
| | T7 | |

Step 5

| n | n+1 | n+2 |
|---|---|---|
| T10 | | |
| | T2 | |
| | T1 | |
| | T7 | |
| | | T4 |

Tracking Table

Tracking M3

Synthesis of hydroxamic acids from alcohol resin

Synthesis of hydroxamic acids from hydroxylamine resin

| ACD Code | Structure | Calc. ΔG of binding (kcal/mole) | $IC_{50}$ (μM) |
|---|---|---|---|
| 00001199 | 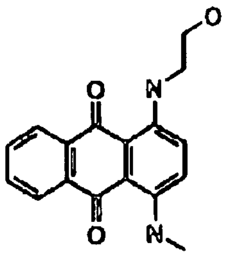 | -5.1 | < 2 |
| 00192509 | 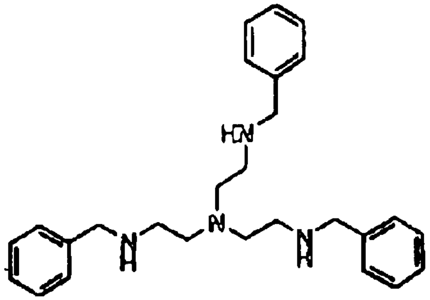 | -8.5 | < 2 |
| 00003934 | 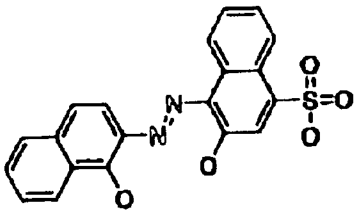 | -5.1 | < 50 |
Figure 37

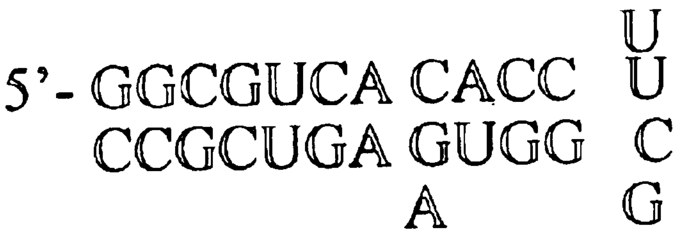
16S A Site rRNA
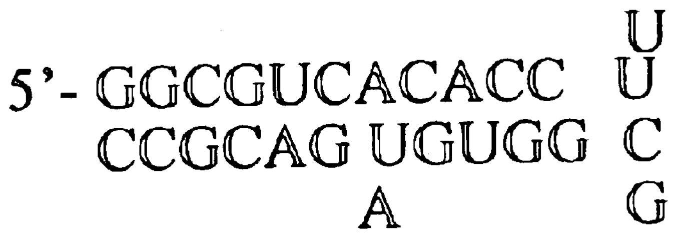
Control RNA
Figure 40

MS Fragmentation of DNA:RNA duplexes

Figure 57

Score: 165.0

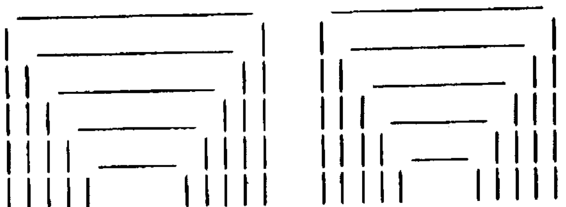

| | |
|---|---|
| NNUNNNNGAUNCUUUNNGUAAGCCCNANGNGNNNNAAANNNNNN | Consensus |
| -UUUUAAGAUUCUUUUUGUAAGCCCUACGGGCU-UAAAAAUUCA | gi\|163204\|M12791 |
| -UUUUAAGAUUCUUUUUGUAAGCCCUAGGCGUGCUAAAAACUC- | gi\|304313\|L19402 |
| -UUUAAAGAUUCUUUUUGUAAGCCCCAAGGGCUCAAAAAUGUU- | gi\|198302\|K02797 |
| -UUUAAAGAUUCUUUUUGUAAGCCCCAAGGGCUCAAAAAUGUU- | gi\|204909\|M22899 |
| CUUUUAAGAUUCUUUU-GUAAGCCCUAAGGGCUCUAAAAUGGU- | gi\|3450973\|AF082496 |
| -UUUUAUGAUUCUUUUUGUAAGCCCUAGGGGCUCUAAAAUGGU- | gi\|33808\|X01586 |
| -AUAUUUGAUCCUUUCUGUAAGCCCUACGGGCUCAAAAUGUAC- | gi\|3087784\|AJ224516 |

MASS of 60-Member Ibis Library Against 16S A-site RNA

MASS of 60-member Library against 16S A-site Model

FT-ICR MS of Starting Library

Figure 62

Compound Identification from a 60-member Combinatorial library with MASS

| | |
|---|---|
| Complex $M_{meas}$ | 9320.300±.009 Da |
| RNA $M_{meas}$ | 8922.189±.009 |
| ΔM | 398.111±.009 Da |

| | |
|---|---|
| $C_{15}H_{16}N_4O_2F_6$ | 398.117 Da |
| ~~$C_{19}H_{22}N_6O_4$~~ | ~~398.163~~ |

Figure 63

Elemental Composition Constraints

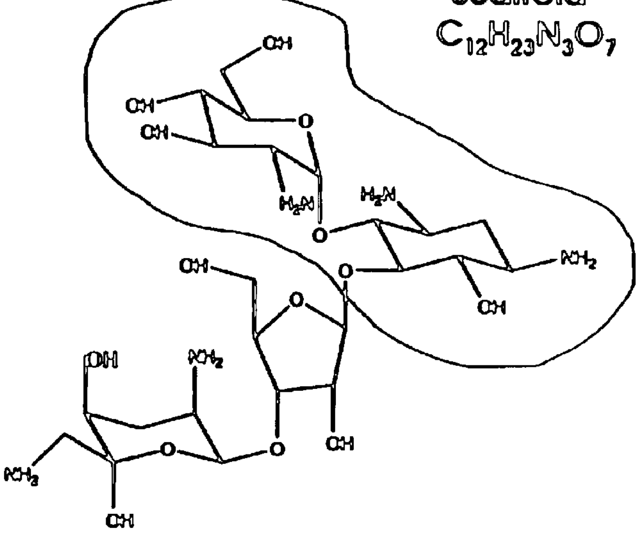

"Scaffold"
$C_{12}H_{23}N_3O_7$

Measured Mass: 615.2969
Mass Tolerance: 1.0 ppm
Charge: 0

| Element | Min. atoms | Max. atoms |
|---|---|---|
| $^{12}C$ | 12 | 30 |
| $^{1}H$ | 23 | 60 |
| $^{16}O$ | 7 | 20 |
| $^{14}N$ | 3 | 20 |

Possible Elemental Compositions:

| Calc. Mass (amu) | Error (ppm) | Molecular Formula |
|---|---|---|
| ~~615.296291~~ | ~~0.98~~ | ~~$^{16}O_4\ ^{14}N_{19}\ ^{12}C_{21}\ ^{1}H_{33}$~~ |
| 615.296298 | 0.98 | $^{16}O_9\ ^{14}N_{12}\ ^{12}C_{22}\ ^{1}H_{39}$ |
| 615.296305 | 0.97 | $^{16}O_{14}\ ^{14}N_5\ ^{12}C_{23}\ ^{1}H_{45}$ |
| ~~615.296808~~ | ~~0.15~~ | ~~$^{16}O_{15}\ ^{14}N_{17}\ ^{12}C_8\ ^{1}H_{41}$~~ |
| ~~615.296815~~ | ~~0.14~~ | ~~$^{16}O_{20}\ ^{14}N_{10}\ ^{12}C_9\ ^{1}H_{47}$~~ |

Further constrain by elemental composition of "letters"

unintended products...

MASS $K_d$ determination for 16S-Paromomycin

MASS Protection Assay

MS/MS of 16S 27-mer extensive fragmentation observed at weak linkages

MS/MS of 16S 27-mer + Paromomycin significant protection from fragmentation due to paromomycin binding

MASS Protection Assay

Eukaryotic and Prokaryotic A-Sites

Aminoglycoside antibiotics bind to
A-site of decoding region in 16S RNA

Human
18S A-site

E. coli
16S A-site

Δ MW = 15.011 Da

Neutral Mass Tag Does Not Affect Ligand Binding

Simultaneous Screening of 16S A-site and 18S A-site Model RNAs Against Aminoglycoside Mixture

| nr | name | apex | start | stop | height | area |
|---|---|---|---|---|---|---|
| 1 | 16628-1.-4 | 1783.710 | 1783.635 | 1783.834 | 14.55 | 1.63 |
| 2 | 16628-1.-3 | 1783.909 | 1783.834 | 1783.972 | 60.04 | 5.15 |
| 3 | 16628-1.-2 | 1784.109 | 1784.021 | 1784.184 | 115.60 | 11.14 |
| 4 | 16628-1.-1 | 1784.308 | 1784.233 | 1784.383 | 167.34 | 15.89 |
| 5 | 16628-1.0 | 1784.508 | 1784.433 | 1784.620 | 133.94 | 14.74 |
| 6 | 16628-1.1 | 1784.707 | 1784.620 | 1784.795 | 136.60 | 13.38 |
| 7 | 16628-1.2 | 1784.907 | 1784.795 | 1784.982 | 82.63 | 8.56 |
| 8 | 16628-1.3 | 1785.107 | 1785.032 | 1785.219 | 57.81 | 5.21 |
| 9 | 16628-1.4 | 1785.306 | 1785.232 | 1785.369 | 32.31 | 2.65 |
| 10 | 16628-1.5 | 1785.506 | 1785.456 | 1785.569 | 17.67 | 1.12 |
| 11 | 16628.10019.-4 | 1906.974 | 1906.874 | 1907.031 | 12.63 | 1.00 |
| 12 | 16628.10019.-3 | 1907.173 | 1907.045 | 1907.273 | 22.54 | 2.11 |
| 13 | 16628.10019.-2 | 1907.373 | 1907.287 | 1907.444 | 33.86 | 2.91 |
| 14 | 16628.10019.-1 | 1907.572 | 1907.458 | 1907.701 | 34.87 | 3.30 |
| 15 | 16628.10019.0 | 1907.772 | 1907.701 | 1907.843 | 20.93 | 1.55 |
| 16 | 16628.10019.1 | 1907.972 | 1907.900 | 1908.043 | 21.03 | 1.55 |
| 17 | 16628.10019.2 | 1908.157 | 1908.086 | 1908.271 | 10.97 | 0.90 |
| 18 | 16628.-4 | 2229.874 | 2229.679 | 2230.029 | 27.51 | 4.87 |
| 19 | 16628.-3 | 2230.146 | 2230.029 | 2230.263 | 111.72 | 16.23 |
| 20 | 16628.-2 | 2230.380 | 2230.263 | 2230.516 | 225.18 | 32.39 |
| 21 | 16628.-1 | 2230.633 | 2230.516 | 2230.770 | 280.66 | 40.90 |
| 22 | 16628.0 | 2230.887 | 2230.770 | 2231.023 | 287.24 | 41.95 |
| 23 | 16628.1 | 2231.140 | 2231.023 | 2231.257 | 242.23 | 34.17 |

Figure 76

SEQUENCE LISTING

<160> NUMBER OF SEQ ID NOS: 97

<210> SEQ ID NO 1
<211> LENGTH: 24
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(12)
<223> OTHER INFORMATION: N is any nucleotide
<221> NAME/KEY: misc_feature
<222> LOCATION: (14)..(15)
<223> OTHER INFORMATION: N is any nucleotide
<221> NAME/KEY: misc_feature
<222> LOCATION: (17)..(24)
<223> OTHER INFORMATION: N is any nucleotide

<400> SEQUENCE: 1
nnnncnnnnn nnunnannnn nnnn 24

<210> SEQ ID NO 2
<211> LENGTH: 31
<212> TYPE: RNA
<213> ORGANISM: Artificial Sequence
<220> FEATURE:
<223> OTHER INFORMATION: Novel Sequence

<400> SEQUENCE: 2
uuuacaacau aaucuaguuu acagaaaaau c 31

<210> SEQ ID NO 3
<211> LENGTH: 48
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (44)..(45)
<223> OTHER INFORMATION: N is any nucleotide
<221> NAME/KEY: misc_feature
<222> LOCATION: (48)..(48)
<223> OTHER INFORMATION: N is any nucleotide

<400> SEQUENCE: 3
nnnnanaugg gnnnucacan nuancugugu uccuauggaa acunnuun 48

<210> SEQ ID NO 4
<211> LENGTH: 45
<212> TYPE: RNA
<213> ORGANISM: Artificial Sequence
<220> FEATURE:

-continued

<223> OTHER INFORMATION: Novel Sequence

<400> SEQUENCE: 4
uaggauaugg gucacacuua ucuguguucc uauggaaacu auuug 45

<210> SEQ ID NO 5
<211> LENGTH: 44
<212> TYPE: RNA
<213> ORGANISM: Artificial Sequence
<220> FEATURE:
<223> OTHER INFORMATION: Novel Sequence

<400> SEQUENCE: 5
uaggagaugg gggucacacu uacuguguuc cuauggaaac uuug 44

<210> SEQ ID NO 6
<211> LENGTH: 45
<212> TYPE: RNA
<213> ORGANISM: Artificial Sequence
<220> FEATURE:
<223> OTHER INFORMATION: Novel Sequence

<400> SEQUENCE: 6
uaggagaugg ggggucacac uuacuguguu ccuaugaaac uuuug 45

<210> SEQ ID NO 7
<211> LENGTH: 30
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(8)
<223> OTHER INFORMATION: N is any nucleotide
<221> NAME/KEY: misc_feature
<222> LOCATION: (14)..(15)
<223> OTHER INFORMATION: N is any nucleotide
<221> NAME/KEY: misc_feature
<222> LOCATION: (18)..(18)
<223> OTHER INFORMATION: N is any nucleotide

<400> SEQUENCE: 7
augggnnnuc acannuancu guguuccuau 30

<210> SEQ ID NO 8
<211> LENGTH: 27
<212> TYPE: RNA
<213> ORGANISM: Artificial Sequence
<220> FEATURE:
<223> OTHER INFORMATION: Novel Sequence

<400> SEQUENCE: 8
augggucaca cuuaucugug uuccuau 27

<210> SEQ ID NO 9
<211> LENGTH: 28
<212> TYPE: RNA
<213> ORGANISM: Artificial Sequence
<220> FEATURE:
<223> OTHER INFORMATION: Novel Sequence

<400> SEQUENCE: 9
auggggguca cacuuacugu guuccuau 28

<210> SEQ ID NO 10
<211> LENGTH: 29
<212> TYPE: RNA

-continued

<213> ORGANISM: Artificial Sequence
<220> FEATURE:
<223> OTHER INFORMATION: Novel Sequence

<400> SEQUENCE: 10
augggggguc acacuuacug uguuccuau 29

<210> SEQ ID NO 11
<211> LENGTH: 17
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (5)..(6)
<223> OTHER INFORMATION: N is any nucleotide
<221> NAME/KEY: misc_feature
<222> LOCATION: (10)..(10)
<223> OTHER INFORMATION: N is any nucleotide

<400> SEQUENCE: 11
caagnnuuun uagcuug 17

<210> SEQ ID NO 12
<211> LENGTH: 18
<212> TYPE: RNA
<213> ORGANISM: Artificial Sequence
<220> FEATURE:
<223> OTHER INFORMATION: Novel Sequence

<400> SEQUENCE: 12
caagcauuug uagcuugu 18

<210> SEQ ID NO 13
<211> LENGTH: 18
<212> TYPE: RNA
<213> ORGANISM: Artificial Sequence
<220> FEATURE:
<223> OTHER INFORMATION: Novel Sequence

<400> SEQUENCE: 13
caagcguuug uagcuugu 18

<210> SEQ ID NO 14
<211> LENGTH: 18
<212> TYPE: RNA
<213> ORGANISM: Artificial Sequence
<220> FEATURE:
<223> OTHER INFORMATION: Novel Sequence

<400> SEQUENCE: 14
caagcauuua uagcuugu 18

<210> SEQ ID NO 15
<211> LENGTH: 18
<212> TYPE: RNA
<213> ORGANISM: Artificial Sequence
<220> FEATURE:
<223> OTHER INFORMATION: Novel Sequence

<400> SEQUENCE: 15
caagcauuug uagcuugu 18

<210> SEQ ID NO 16
<211> LENGTH: 62
<212> TYPE: RNA
<213> ORGANISM: Artificial Sequence -continued
<220> FEATURE:
<223> OTHER INFORMATION: Novel Sequence
<221> NAME/KEY: misc_feature
<222> LOCATION: (21)..(21)
<223> OTHER INFORMATION: N is any nucleotide
<221> NAME/KEY: misc_feature
<222> LOCATION: (34)..(34)
<223> OTHER INFORMATION: N is any nucleotide
<221> NAME/KEY: misc_feature
<222> LOCATION: (37)..(38)
<223> OTHER INFORMATION: N is any nucleotide
<221> NAME/KEY: misc_feature
<222> LOCATION: (41)..(42)
<223> OTHER INFORMATION: N is any nucleotide
<221> NAME/KEY: misc_feature
<222> LOCATION: (44)..(44)
<223> OTHER INFORMATION: N is any nucleotide
<221> NAME/KEY: misc_feature
<222> LOCATION: (46)..(46)
<223> OTHER INFORMATION: N is any nucleotide
<221> NAME/KEY: misc_feature
<222> LOCATION: (48)..(50)
<223> OTHER INFORMATION: N is any nucleotide
<221> NAME/KEY: misc_feature
<222> LOCATION: (54)..(54)
<223> OTHER INFORMATION: N is any nucleotide
<221> NAME/KEY: misc_feature
<222> LOCATION: (57)..(57)
<223> OTHER INFORMATION: N is any nucleotide
<221> NAME/KEY: misc_feature
<222> LOCATION: (60)..(60)
<223> OTHER INFORMATION: N is any nucleotide

<400> SEQUENCE: 16
uauuuauuua aauauuuaaa nuuuauauuu auunuunnau nnangnunnn cuancunuun 60
ua 62

<210> SEQ ID NO 17
<211> LENGTH: 62
<212> TYPE: RNA
<213> ORGANISM: Artificial Sequence
<220> FEATURE:
<223> OTHER INFORMATION: Novel Sequence

<400> SEQUENCE: 17
uauuuauuua aauauuuaaa uuuuauauuu auuguugaau guaugguuug cuaccuauug 60
ua 62

<210> SEQ ID NO 18
<211> LENGTH: 32
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (4)..(4)
<223> OTHER INFORMATION: N is any nucleotide
<221> NAME/KEY: misc_feature
<222> LOCATION: (17)..(17)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (24)..(25)
<223> OTHER INFORMATION: N is any nucleotide
<221> NAME/KEY: misc_feature
<222> LOCATION: (27)..(27)
<223> OTHER INFORMATION: N is any nucleotide
<221> NAME/KEY: misc_feature
<222> LOCATION: (29)..(29)
<223> OTHER INFORMATION: N is any nucleotide
<221> NAME/KEY: misc_feature -continued
<222> LOCATION: (31)..(32)
<223> OTHER INFORMATION: N is any nucleotide

<400> SEQUENCE: 18
aaanuuuaua uuuauunuun naunnangnu nn 32

<210> SEQ ID NO 19
<211> LENGTH: 32
<212> TYPE: RNA
<213> ORGANISM: Artificial Sequence
<220> FEATURE:
<223> OTHER INFORMATION: Novel Sequence

<400> SEQUENCE: 19
aaauuuuaua uuuauuguug aauguauggu uu 32

<210> SEQ ID NO 20
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(2)
<223> OTHER INFORMATION: N is any nucleotide
<221> NAME/KEY: misc_feature
<222> LOCATION: (4)..(10)
<223> OTHER INFORMATION: N is any nucleotide
<221> NAME/KEY: misc_feature
<222> LOCATION: (15)..(15)
<223> OTHER INFORMATION: N is any nucleotide
<221> NAME/KEY: misc_feature
<222> LOCATION: (17)..(20)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (29)..(29)
<223> OTHER INFORMATION: N is any nucleotide
<221> NAME/KEY: misc_feature
<222> LOCATION: (31)..(33)
<223> OTHER INFORMATION: N is any nucleotide
<221> NAME/KEY: misc_feature
<222> LOCATION: (35)..(36)
<223> OTHER INFORMATION: N is any nucleotide
<221> NAME/KEY: misc_feature
<222> LOCATION: (38)..(45)
<223> OTHER INFORMATION: N is any nucleotide

<400> SEQUENCE: 20
nnunnnnnnn gaucnunnnn gauncuuunu nnnannccnn nnnnn 45

<210> SEQ ID NO 21
<211> LENGTH: 45
<212> TYPE: RNA
<213> ORGANISM: Artificial Sequence
<220> FEATURE:
<223> OTHER INFORMATION: Novel Sequence

<400> SEQUENCE: 21
uauaaauaug gaucuuuuau gauucuuuuu guaagcccua ggggc 45

<210> SEQ ID NO 22
<211> LENGTH: 45
<212> TYPE: RNA
<213> ORGANISM: Artificial Sequence
<220> FEATURE:
<223> OTHER INFORMATION: Novel Sequence

<400> SEQUENCE: 22

-continued gauaaauaug gaucuuuaaa gauucuuuuu guaagcccca agggc 45

<210> SEQ ID NO 23
<211> LENGTH: 29
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(3)
<223> OTHER INFORMATION: N is any nucleotide
<221> NAME/KEY: misc_feature
<222> LOCATION: (7)..(7)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (22)..(22)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (26)..(26)
<223> OTHER INFORMATION: N is any nucleotide
<221> NAME/KEY: misc_feature
<222> LOCATION: (28)..(29)
<223> OTHER INFORMATION: N is any nucleotide

<400> SEQUENCE: 23
nnngauncuu unnguaagcc cnangngnn 29

<210> SEQ ID NO 24
<211> LENGTH: 29
<212> TYPE: RNA
<213> ORGANISM: Artificial Sequence
<220> FEATURE:
<223> OTHER INFORMATION: Novel Sequence

<400> SEQUENCE: 24
uaugauucuu uuuguaagcc cuaggggcu 29

<210> SEQ ID NO 25
<211> LENGTH: 29
<212> TYPE: RNA
<213> ORGANISM: Artificial Sequence
<220> FEATURE:
<223> OTHER INFORMATION: Novel Sequence

<400> SEQUENCE: 25
aaagauucuu uuuguaagcc ccaagggcu 29

<210> SEQ ID NO 26
<211> LENGTH: 29
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(12)
<223> OTHER INFORMATION: N is any nucleotide
<221> NAME/KEY: misc_feature
<222> LOCATION: (15)..(15)
<223> OTHER INFORMATION: N is any nucleotide
<221> NAME/KEY: misc_feature
<222> LOCATION: (18)..(29)
<223> OTHER INFORMATION: N is any nucleotide

<400> SEQUENCE: 26

-continued nnnnnnnnnn nnugncunnn nnnnnnnnn 29

<210> SEQ ID NO 27
<211> LENGTH: 29
<212> TYPE: RNA
<213> ORGANISM: Artificial Sequence
<220> FEATURE:
<223> OTHER INFORMATION: Novel Sequence

<400> SEQUENCE: 27
ugauaaacua auugccucac auugucacu 29

<210> SEQ ID NO 28
<211> LENGTH: 28
<212> TYPE: RNA
<213> ORGANISM: Artificial Sequence
<220> FEATURE:
<223> OTHER INFORMATION: Novel Sequence

<400> SEQUENCE: 28
gauaaacuua auugucucuc gucacuga 28

<210> SEQ ID NO 29
<211> LENGTH: 28
<212> TYPE: RNA
<213> ORGANISM: Artificial Sequence
<220> FEATURE:
<223> OTHER INFORMATION: Novel Sequence

<400> SEQUENCE: 29
ugauauuacu cugucuuucc ccagggcg 28

<210> SEQ ID NO 30
<211> LENGTH: 28
<212> TYPE: RNA
<213> ORGANISM: Artificial Sequence
<220> FEATURE:
<223> OTHER INFORMATION: Novel Sequence

<400> SEQUENCE: 30
gagacccaaa ucugucucac aaugaaac 28

<210> SEQ ID NO 31
<211> LENGTH: 19
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(19)
<223> OTHER INFORMATION: N is any nucleotide

<400> SEQUENCE: 31
nnnnnnnnnn nnnnnnnnn 19

<210> SEQ ID NO 32
<211> LENGTH: 19
<212> TYPE: RNA
<213> ORGANISM: Artificial Sequence
<220> FEATURE:
<223> OTHER INFORMATION: Novel Sequence

<400> SEQUENCE: 32
aaucugaaug agaaugccu 19

<210> SEQ ID NO 33

-continued

<211> LENGTH: 19
<212> TYPE: RNA
<213> ORGANISM: Artificial Sequence
<220> FEATURE:
<223> OTHER INFORMATION: Novel Sequence

<400> SEQUENCE: 33
auugccauaa gguucuacu 19

<210> SEQ ID NO 34
<211> LENGTH: 19
<212> TYPE: RNA
<213> ORGANISM: Artificial Sequence
<220> FEATURE:
<223> OTHER INFORMATION: Novel Sequence

<400> SEQUENCE: 34
ccacugaagg agcaaggcu 19

<210> SEQ ID NO 35
<211> LENGTH: 27
<212> TYPE: RNA
<213> ORGANISM: Artificial Sequence
<220> FEATURE:
<223> OTHER INFORMATION: Novel Sequence

<400> SEQUENCE: 35
ggcgucacac cuucggguga agucgcc 27

<210> SEQ ID NO 36
<211> LENGTH: 27
<212> TYPE: RNA
<213> ORGANISM: Artificial Sequence
<220> FEATURE:
<223> OTHER INFORMATION: Novel Sequence
<221> NAME/KEY: misc_feature
<223> OTHER INFORMATION: chimeric nucleic acid
<221> NAME/KEY: misc_feature
<222> LOCATION: (7)..(7)
<223> OTHER INFORMATION: a= deoxyadenosine
<221> NAME/KEY: misc_feature
<222> LOCATION: (20)..(21)
<223> OTHER INFORMATION: a= deoxyadenosine

<400> SEQUENCE: 36
ggcgucacac cuucggguga agucgcc 27

<210> SEQ ID NO 37
<211> LENGTH: 27
<212> TYPE: RNA
<213> ORGANISM: Artificial Sequence
<220> FEATURE:
<223> OTHER INFORMATION: Novel Sequence

<400> SEQUENCE: 37
ggcgucacac cuuccgcuga agugggc 27

<210> SEQ ID NO 38
<211> LENGTH: 27
<212> TYPE: RNA
<213> ORGANISM: Artificial Sequence
<220> FEATURE:
<223> OTHER INFORMATION: Novel Sequence

<400> SEQUENCE: 38
ggcgucacac cuuccgcaga ugugggc 27

-continued

<210> SEQ ID NO 39
<211> LENGTH: 28
<212> TYPE: DNA
<213> ORGANISM: Artificial Sequence
<220> FEATURE:
<223> OTHER INFORMATION: Novel Sequence

<400> SEQUENCE: 39
cgcttgggag tctcgcgaac cgtcagag 28

<210> SEQ ID NO 40
<211> LENGTH: 28
<212> TYPE: DNA
<213> ORGANISM: Artificial Sequence
<220> FEATURE:
<223> OTHER INFORMATION: Novel Sequence

<400> SEQUENCE: 40
cgcttggcag tctcgcgaac cgtcagag 28

<210> SEQ ID NO 41
<211> LENGTH: 28
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: MS Fragmentation of DNA:RNA duplexes

<400> SEQUENCE: 41
agcttagcag tctcucgaac cgucagag 28

<210> SEQ ID NO 42
<211> LENGTH: 28
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: MS Fragmentation of DNA:RNA duplexes

<400> SEQUENCE: 42
agcttgccag tctcucgaac cgucagag 28

<210> SEQ ID NO 43
<211> LENGTH: 28
<212> TYPE: DNA
<213> ORGANISM: Artificial Sequence
<220> FEATURE:
<223> OTHER INFORMATION: Novel Sequence
<221> NAME/KEY: misc_feature
<223> OTHER INFORMATION: MS Fragmentation of DNA:RNA duplexes

<400> SEQUENCE: 43
agcttggcag tctcucgaac cgucagag 28

<210> SEQ ID NO 44
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(2)
<223> OTHER INFORMATION: N is any nucleotide
<221> NAME/KEY: misc_feature
<222> LOCATION: (4)..(7)
<223> OTHER INFORMATION: N is any nucleotide
<221> NAME/KEY: misc_feature -continued
<222> LOCATION: (11)..(11)
<223> OTHER INFORMATION: N is any nucleotide
<221> NAME/KEY: misc_feature
<222> LOCATION: (16)..(17)
<223> OTHER INFORMATION: N is any nucleotide
<221> NAME/KEY: misc_feature
<222> LOCATION: (26)..(26)
<223> OTHER INFORMATION: N is any nucleotide
<221> NAME/KEY: misc_feature
<222> LOCATION: (28)..(28)
<223> OTHER INFORMATION: N is any nucleotide
<221> NAME/KEY: misc_feature
<222> LOCATION: (30)..(30)
<223> OTHER INFORMATION: N is any nucleotide
<221> NAME/KEY: misc_feature
<222> LOCATION: (32)..(35)
<223> OTHER INFORMATION: N is any nucleotide
<221> NAME/KEY: misc_feature
<222> LOCATION: (39)..(44)
<223> OTHER INFORMATION: N is any nucleotide

<400> SEQUENCE: 44
nnunnnngau ncuuunngua agcccnangn gnnnnaaann nnnn 44

<210> SEQ ID NO 45
<211> LENGTH: 42
<212> TYPE: RNA
<213> ORGANISM: Artificial Sequence
<220> FEATURE:
<223> OTHER INFORMATION: Novel Sequence

<400> SEQUENCE: 45
uuuuaagauu cuuuuuguaa gcccuacggg cuuaaaaauu ca 42

<210> SEQ ID NO 46
<211> LENGTH: 42
<212> TYPE: RNA
<213> ORGANISM: Artificial Sequence
<220> FEATURE:
<223> OTHER INFORMATION: Novel Sequence

<400> SEQUENCE: 46
uuuuaagauu cuuuuuguaa gcccuaggcg ugcuaaaaac uc 42

<210> SEQ ID NO 47
<211> LENGTH: 42
<212> TYPE: RNA
<213> ORGANISM: Artificial Sequence
<220> FEATURE:
<223> OTHER INFORMATION: Novel Sequence

<400> SEQUENCE: 47
uuuaaagauu cuuuuuguaa gccccaaggg cucaaaaaug uu 42

<210> SEQ ID NO 48
<211> LENGTH: 42
<212> TYPE: RNA
<213> ORGANISM: Artificial Sequence
<220> FEATURE:
<223> OTHER INFORMATION: Novel Sequence

<400> SEQUENCE: 48
uuuaaagauu cuuuuuguaa gccccaaggg cucaaaaaug uu 42

<210> SEQ ID NO 49
<211> LENGTH: 42
<212> TYPE: RNA
<213> ORGANISM: Artificial Sequence
<220> FEATURE:

-continued

<223> OTHER INFORMATION: Novel Sequence

<400> SEQUENCE: 49
cuuuuaagau ucuuuuguaa gcccuaaggg cucuaaaaug gu 42

<210> SEQ ID NO 50
<211> LENGTH: 42
<212> TYPE: RNA
<213> ORGANISM: Artificial Sequence
<220> FEATURE:
<223> OTHER INFORMATION: Novel Sequence

<400> SEQUENCE: 50
uuuuaugauu cuuuuuguaa gcccuagggg cucuaaaaug gu 42

<210> SEQ ID NO 51
<211> LENGTH: 42
<212> TYPE: RNA
<213> ORGANISM: Artificial Sequence
<220> FEATURE:
<223> OTHER INFORMATION: Novel Sequence

<400> SEQUENCE: 51
auauuugauc cuuucuguaa gcccuacggg cucaaaaugu ac 42

<210> SEQ ID NO 52
<211> LENGTH: 24
<212> TYPE: RNA
<213> ORGANISM: Artificial Sequence
<220> FEATURE:
<223> OTHER INFORMATION: Novel Sequence

<400> SEQUENCE: 52
uaaggaggug auaucaccuc cuua 24

<210> SEQ ID NO 53
<211> LENGTH: 23
<212> TYPE: RNA
<213> ORGANISM: Artificial Sequence
<220> FEATURE:
<223> OTHER INFORMATION: Novel Sequence

<400> SEQUENCE: 53
cugcuucaac agugcuugga cgg 23

<210> SEQ ID NO 54
<211> LENGTH: 23
<212> TYPE: RNA
<213> ORGANISM: Artificial Sequence
<220> FEATURE:
<223> OTHER INFORMATION: Novel Sequence

<400> SEQUENCE: 54
cugcuucaac agugcuugaa cgg 23

<210> SEQ ID NO 55
<211> LENGTH: 23
<212> TYPE: RNA
<213> ORGANISM: Artificial Sequence
<220> FEATURE:
<223> OTHER INFORMATION: Novel Sequence

<400> SEQUENCE: 55
cugcgucaac agugcuugga cgg 23

-continued

<210> SEQ ID NO 56
<211> LENGTH: 23
<212> TYPE: RNA
<213> ORGANISM: Artificial Sequence
<220> FEATURE:
<223> OTHER INFORMATION: Novel Sequence

<400> SEQUENCE: 56
uugcuucaac agugauugaa cgg 23

<210> SEQ ID NO 57
<211> LENGTH: 23
<212> TYPE: RNA
<213> ORGANISM: Artificial Sequence
<220> FEATURE:
<223> OTHER INFORMATION: Novel Sequence

<400> SEQUENCE: 57
uugcuucaac aguguuugaa cgg 23

<210> SEQ ID NO 58
<211> LENGTH: 23
<212> TYPE: RNA
<213> ORGANISM: Artificial Sequence
<220> FEATURE:
<223> OTHER INFORMATION: Novel Sequence

<400> SEQUENCE: 58
cuucugcgcc agugugugua aag 23

<210> SEQ ID NO 59
<211> LENGTH: 23
<212> TYPE: RNA
<213> ORGANISM: Artificial Sequence
<220> FEATURE:
<223> OTHER INFORMATION: Novel Sequence

<400> SEQUENCE: 59
cuucugugcc aguguguaua aag 23

<210> SEQ ID NO 60
<211> LENGTH: 46
<212> TYPE: RNA
<213> ORGANISM: Artificial Sequence
<220> FEATURE:
<223> OTHER INFORMATION: Novel Sequence

<400> SEQUENCE: 60
ggacgcuacu cuguuuacca gguucgccaa ggcagaugac gcgucc 46

<210> SEQ ID NO 61
<211> LENGTH: 15
<212> TYPE: RNA
<213> ORGANISM: Artificial Sequence
<220> FEATURE:
<223> OTHER INFORMATION: Novel Sequence

<400> SEQUENCE: 61
acugcggccg cugaa 15

<210> SEQ ID NO 62
<211> LENGTH: 27
<212> TYPE: RNA
<213> ORGANISM: Artificial Sequence
<220> FEATURE:
<223> OTHER INFORMATION: Novel Sequence -continued

<400> SEQUENCE: 62
ggcgucacac cuucggguga agucgcc 27

<210> SEQ ID NO 63
<211> LENGTH: 12
<212> TYPE: RNA
<213> ORGANISM: Artificial Sequence
<220> FEATURE:
<223> OTHER INFORMATION: Novel Sequence

<400> SEQUENCE: 63
caccuucggg ug 12

<210> SEQ ID NO 64
<211> LENGTH: 27
<212> TYPE: RNA
<213> ORGANISM: Artificial Sequence
<220> FEATURE:
<223> OTHER INFORMATION: Novel Sequence

<400> SEQUENCE: 64
ggcgucgcua cuucgguaaa agucgcc 27

<210> SEQ ID NO 65
<211> LENGTH: 23
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(11)
<223> OTHER INFORMATION: N is any nucleotide
<221> NAME/KEY: misc_feature
<222> LOCATION: (13)..(14)
<223> OTHER INFORMATION: N is any nucleotide
<221> NAME/KEY: misc_feature
<222> LOCATION: (16)..(23)
<223> OTHER INFORMATION: N is any nucleotide

<400> SEQUENCE: 65
nnnncnnnnn nunnannnnn nnn 23

<210> SEQ ID NO 66
<211> LENGTH: 47
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (43)..(44)
<223> OTHER INFORMATION: N is any nucleotide
<221> NAME/KEY: misc_feature
<222> LOCATION: (47)..(47)
<223> OTHER INFORMATION: N is any nucleotide

<400> SEQUENCE: 66

-continued nnnnanaugg gnnnucacan nuacuguguu ccuauggaaa cunnuun 47

<210> SEQ ID NO 67
<211> LENGTH: 46
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (43)..(43)
<223> OTHER INFORMATION: N is any nucleotide
<221> NAME/KEY: misc_feature
<222> LOCATION: (46)..(46)
<223> OTHER INFORMATION: N is any nucleotide

<400> SEQUENCE: 67
nnnnanaugg gnnnucacan nuacuguguu ccuauggaaa cunuun 46

<210> SEQ ID NO 68
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 68
nnnnanaugg gnnnucacan nuacuguguu ccuauggaaa cuuun 45

<210> SEQ ID NO 69
<211> LENGTH: 47
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide -continued
<221> NAME/KEY: misc_feature
<222> LOCATION: (24)..(24)
<223> OTHER INFORMATION: N is any nucleotide
<221> NAME/KEY: misc_feature
<222> LOCATION: (44)..(44)
<223> OTHER INFORMATION: N is any nucleotide
<221> NAME/KEY: misc_feature
<222> LOCATION: (47)..(47)
<223> OTHER INFORMATION: N is any nucleotide

<400> SEQUENCE: 69
nnnnanaugg gnnnucacan nuancugugu uccuauggaa acunuun 47

<210> SEQ ID NO 70
<211> LENGTH: 46
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(14)
<223> OTHER INFORMATION: N is any nucleotide
<221> NAME/KEY: misc_feature
<222> LOCATION: (20)..(21)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (46)..(46)
<223> OTHER INFORMATION: N is any nucleotide

<400> SEQUENCE: 70
nnnnanaugg gnnnucacan nuancugugu uccuauggaa acuuun 46

<210> SEQ ID NO 71
<211> LENGTH: 47
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (23)..(23)
<223> OTHER INFORMATION: N is any nucleotide
<221> NAME/KEY: misc_feature
<222> LOCATION: (43)..(44)
<223> OTHER INFORMATION: N is any nucleotide
<221> NAME/KEY: misc_feature
<222> LOCATION: (47)..(47)
<223> OTHER INFORMATION: N is any nucleotide

<400> SEQUENCE: 71
nnnnanaugg gnnucacann uancuguguu ccuauggaaa cunnuun 47

<210> SEQ ID NO 72

-continued

<211> LENGTH: 46
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (42)..(43)
<223> OTHER INFORMATION: N is any nucleotide
<221> NAME/KEY: misc_feature
<222> LOCATION: (46)..(46)
<223> OTHER INFORMATION: N is any nucleotide

<400> SEQUENCE: 72
nnnnanaugg gnnucacann uacuguguuc cuauggaaac unnuun 46

<210> SEQ ID NO 73
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (42)..(42)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 73
nnnnanaugg gnnucacann uacuguguuc cuauggaaac unuun 45

<210> SEQ ID NO 74
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (44)..(44)

-continued

<223> OTHER INFORMATION: N is any nucleotide

<400> SEQUENCE: 74
nnnnanaugg gnnucacann uacuguguuc cuauggaaac uuun 44

<210> SEQ ID NO 75
<211> LENGTH: 46
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (23)..(23)
<223> OTHER INFORMATION: N is any nucleotide
<221> NAME/KEY: misc_feature
<222> LOCATION: (43)..(43)
<223> OTHER INFORMATION: N is any nucleotide
<221> NAME/KEY: misc_feature
<222> LOCATION: (46)..(46)
<223> OTHER INFORMATION: N is any nucleotide

<400> SEQUENCE: 75
nnnnanaugg gnnucacann uancuguguu ccuauggaaa cunuun 46

<210> SEQ ID NO 76
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (19)..(20)
<223> OTHER INFORMATION: N is any nucleotide
<221> NAME/KEY: misc_feature
<222> LOCATION: (23)..(23)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 76
nnnnanaugg gnnucacann uancuguguu ccuauggaaa cuuun 45

<210> SEQ ID NO 77
<211> LENGTH: 46
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide -continued
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)
<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (22)..(22)
<223> OTHER INFORMATION: N is any nucleotide
<221> NAME/KEY: misc_feature
<222> LOCATION: (42)..(43)
<223> OTHER INFORMATION: N is any nucleotide
<221> NAME/KEY: misc_feature
<222> LOCATION: (46)..(46)
<223> OTHER INFORMATION: N is any nucleotide

<400> SEQUENCE: 77
nnnnanaugg gnucacannu ancuguguuc cuauggaaac unnuun 46

<210> SEQ ID NO 78
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)
<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (41)..(42)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 78
nnnnanaugg gnucacannu acuguguucc uauggaaacu nnuun 45

<210> SEQ ID NO 79
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)
<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (41)..(41)
<223> OTHER INFORMATION: N is any nucleotide
<221> NAME/KEY: misc_feature
<222> LOCATION: (44)..(44)
<223> OTHER INFORMATION: N is any nucleotide -continued

<400> SEQUENCE: 79
nnnnanaugg gnucacannu acuguguucc uauggaaacu nuun 44

<210> SEQ ID NO 80
<211> LENGTH: 43
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)
<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (43)..(43)
<223> OTHER INFORMATION: N is any nucleotide

<400> SEQUENCE: 80
nnnnanaugg gnucacannu acuguguucc uauggaaacu uun 43

<210> SEQ ID NO 81
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)
<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (22)..(22)
<223> OTHER INFORMATION: N is any nucleotide
<221> NAME/KEY: misc_feature
<222> LOCATION: (42)..(42)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 81
nnnnanaugg gnucacannu ancuguguuc cuauggaaac unuun 45

<210> SEQ ID NO 82
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (12)..(12)

-continued

<223> OTHER INFORMATION: N is any nucleotide
<221> NAME/KEY: misc_feature
<222> LOCATION: (18)..(19)
<223> OTHER INFORMATION: N is any nucleotide
<221> NAME/KEY: misc_feature
<222> LOCATION: (22)..(22)
<223> OTHER INFORMATION: N is any nucleotide
<221> NAME/KEY: misc_feature
<222> LOCATION: (44)..(44)
<223> OTHER INFORMATION: N is any nucleotide

<400> SEQUENCE: 82
nnnnanaugg gnucacannu ancuguguuc cuauggaaac uuun 44

<210> SEQ ID NO 83
<211> LENGTH: 45
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (21)..(21)
<223> OTHER INFORMATION: N is any nucleotide
<221> NAME/KEY: misc_feature
<222> LOCATION: (41)..(42)
<223> OTHER INFORMATION: N is any nucleotide
<221> NAME/KEY: misc_feature
<222> LOCATION: (45)..(45)
<223> OTHER INFORMATION: N is any nucleotide

<400> SEQUENCE: 83
nnnnanaugg gucacannua ncuguguucc uauggaaacu nnuun 45

<210> SEQ ID NO 84
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (40)..(41)
<223> OTHER INFORMATION: N is any nucleotide
<221> NAME/KEY: misc_feature
<222> LOCATION: (44)..(44)
<223> OTHER INFORMATION: N is any nucleotide

<400> SEQUENCE: 84
nnnnanaugg gucacannua cuguguuccu auggaaacun nuun 44

<210> SEQ ID NO 85
<211> LENGTH: 43
<212> TYPE: RNA
<213> ORGANISM: Artificial Sequence
<220> FEATURE:
<223> OTHER INFORMATION: Novel Sequence -continued
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (40)..(40)
<223> OTHER INFORMATION: N is any nucleotide
<221> NAME/KEY: misc_feature
<222> LOCATION: (43)..(43)
<223> OTHER INFORMATION: N is any nucleotide

<400> SEQUENCE: 85
nnnnanaugg gucacannua cuguguuccu auggaaacun uun 43

<210> SEQ ID NO 86
<211> LENGTH: 42
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (42)..(42)
<223> OTHER INFORMATION: N is any nucleotide

<400> SEQUENCE: 86
nnnnanaugg gucacannua cuguguuccu auggaaacuu un 42

<210> SEQ ID NO 87
<211> LENGTH: 44
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (21)..(21)
<223> OTHER INFORMATION: N is any nucleotide
<221> NAME/KEY: misc_feature
<222> LOCATION: (41)..(41)
<223> OTHER INFORMATION: N is any nucleotide
<221> NAME/KEY: misc_feature
<222> LOCATION: (44)..(44)
<223> OTHER INFORMATION: N is any nucleotide

<400> SEQUENCE: 87
nnnnanaugg gucacannua ncuguguucc uauggaaacu nuun 44

<210> SEQ ID NO 88
<211> LENGTH: 43
<212> TYPE: RNA
<213> ORGANISM: Artificial Sequence -continued
<220> FEATURE:
<223> OTHER INFORMATION: Novel Sequence
<221> NAME/KEY: misc_feature
<222> LOCATION: (1)..(4)
<223> OTHER INFORMATION: N is any nucleotide
<221> NAME/KEY: misc_feature
<222> LOCATION: (6)..(6)
<223> OTHER INFORMATION: N is any nucleotide
<221> NAME/KEY: misc_feature
<222> LOCATION: (17)..(18)
<223> OTHER INFORMATION: N is any nucleotide
<221> NAME/KEY: misc_feature
<222> LOCATION: (21)..(21)
<223> OTHER INFORMATION: N is any nucleotide
<221> NAME/KEY: misc_feature
<222> LOCATION: (43)..(43)
<223> OTHER INFORMATION: N is any nucleotide

<400> SEQUENCE: 88
nnnnanaugg gucacannua ncuguguucc uauggaaacu uun 43

<210> SEQ ID NO 89
<211> LENGTH: 29
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(8)
<223> OTHER INFORMATION: N is any nucleotide
<221> NAME/KEY: misc_feature
<222> LOCATION: (14)..(15)
<223> OTHER INFORMATION: N is any nucleotide

<400> SEQUENCE: 89
augggnnnuc acannuacug uguuccuau 29

<210> SEQ ID NO 90
<211> LENGTH: 29
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(7)
<223> OTHER INFORMATION: N is any nucleotide
<221> NAME/KEY: misc_feature
<222> LOCATION: (13)..(14)
<223> OTHER INFORMATION: N is any nucleotide
<221> NAME/KEY: misc_feature
<222> LOCATION: (17)..(17)
<223> OTHER INFORMATION: N is any nucleotide

<400> SEQUENCE: 90
augggnnuca cannuancug uguuccuau 29

<210> SEQ ID NO 91
<211> LENGTH: 28
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(7)
<223> OTHER INFORMATION: N is any nucleotide
<221> NAME/KEY: misc_feature
<222> LOCATION: (13)..(14)
<223> OTHER INFORMATION: N is any nucleotide

<400> SEQUENCE: 91
augggnnuca cannuacugu guuccuau 28

-continued

<210> SEQ ID NO 92
<211> LENGTH: 28
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide
<221> NAME/KEY: misc_feature
<222> LOCATION: (16)..(16)
<223> OTHER INFORMATION: N is any nucleotide

<400> SEQUENCE: 92
augggnucac annuancugu guuccuau 28

<210> SEQ ID NO 93
<211> LENGTH: 27
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (6)..(6)
<223> OTHER INFORMATION: N is any nucleotide
<221> NAME/KEY: misc_feature
<222> LOCATION: (12)..(13)
<223> OTHER INFORMATION: N is any nucleotide

<400> SEQUENCE: 93
augggnucac annuacugug uuccuau 27

<210> SEQ ID NO 94
<211> LENGTH: 27
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (11)..(12)
<223> OTHER INFORMATION: N is any nucleotide
<221> NAME/KEY: misc_feature
<222> LOCATION: (15)..(15)
<223> OTHER INFORMATION: N is any nucleotide

<400> SEQUENCE: 94
augggucaca nnuancugug uuccuau 27

<210> SEQ ID NO 95
<211> LENGTH: 26
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (11)..(12)
<223> OTHER INFORMATION: N is any nucleotide

<400> SEQUENCE: 95
augggucaca nnuacugugu uccuau 26

<210> SEQ ID NO 96
<211> LENGTH: 44
<212> TYPE: RNA
<213> ORGANISM: Artificial Sequence
<220> FEATURE:
<223> OTHER INFORMATION: Novel Sequence -continued

```
<221> NAME/KEY: misc_feature
<222> LOCATION: (1)..(2)
<223> OTHER INFORMATION: N is any nucleotide
<221> NAME/KEY: misc_feature
<222> LOCATION: (4)..(10)
<223> OTHER INFORMATION: N is any nucleotide
<221> NAME/KEY: misc_feature
<222> LOCATION: (15)..(15)
<223> OTHER INFORMATION: N is any nucleotide
<221> NAME/KEY: misc_feature
<222> LOCATION: (17)..(20)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (29)..(29)
<223> OTHER INFORMATION: N is any nucleotide
<221> NAME/KEY: misc_feature
<222> LOCATION: (31)..(33)
<223> OTHER INFORMATION: N is any nucleotide
<221> NAME/KEY: misc_feature
<222> LOCATION: (35)..(35)
<223> OTHER INFORMATION: N is any nucleotide
<221> NAME/KEY: misc_feature
<222> LOCATION: (38)..(44)
<223> OTHER INFORMATION: N is any nucleotide

<400> SEQUENCE: 96

nnunnnnnnn gaucnunnnn gauncuuunu nnnanccnnn nnnn                   44


<210> SEQ ID NO 97
<211> LENGTH: 43
<212> TYPE: RNA
<213> ORGANISM: Artificial Sequence
<220> FEATURE:
<223> OTHER INFORMATION: Novel Sequence
<221> NAME/KEY: misc_feature
<222> LOCATION: (1)..(2)
<223> OTHER INFORMATION: N is any nucleotide
<221> NAME/KEY: misc_feature
<222> LOCATION: (4)..(10)
<223> OTHER INFORMATION: N is any nucleotide
<221> NAME/KEY: misc_feature
<222> LOCATION: (15)..(15)
<223> OTHER INFORMATION: N is any nucleotide
<221> NAME/KEY: misc_feature
<222> LOCATION: (17)..(20)
<223> OTHER INFORMATION: N is any nucleotide
<221> NAME/KEY: misc_feature
<222> LOCATION: (24)..(24)
<223> OTHER INFORMATION: N is any nucleotide
<221> NAME/KEY: misc_feature
<222> LOCATION: (29)..(29)
<223> OTHER INFORMATION: N is any nucleotide
<221> NAME/KEY: misc_feature
<222> LOCATION: (31)..(33)
<223> OTHER INFORMATION: N is any nucleotide
<221> NAME/KEY: misc_feature
<222> LOCATION: (37)..(43)
<223> OTHER INFORMATION: N is any nucleotide

<400> SEQUENCE: 97

nnunnnnnnn gaucnunnnn gauncuuunu nnnaccnnnn nnn                    43
```

MOLECULAR INTERACTION SITES OF INTERLEUKIN-2 RNA AND METHODS OF MODULATING THE SAME

FIELD OF THE INVENTION

The present invention relates to the identification of compounds which modulate, either inhibit or stimulate, biomolecules. Nucleic acids, especially RNA are preferred substrates for such modulation and all such substrates are denominated "targets" for such action. The present methods are particularly powerful in that they provide novel combinations of techniques which give rise to compounds, usually "small" organic compounds, which are highly potent modulators of RNA and other biomolecular activity. Very large numbers of compounds may be tested in silico to determine whether they are likely to interact with a molecular interaction site and, hence, modulate the activity of the biomolecule. Pharmaceuticals, veterinary drugs, agricultural chemicals, industrial chemicals, research chemicals and many other beneficial compounds may be identified in accordance with embodiments of this invention. In particular, the present invention relates to identification of molecular interaction sites of interleukin-2.

BACKGROUND OF THE INVENTION

Recent advances in genomics, molecular biology, and structural biology have highlighted how RNA molecules participate in or control many of the events required to express proteins in cells. Rather than function as simple intermediaries, RNA molecules actively regulate their own transcription from DNA, splice and edit mRNA molecules and tRNA molecules, synthesize peptide bonds in the ribosome, catalyze the migration of nascent proteins to the cell membrane, and provide fine control over the rate of translation of messages. RNA molecules can adopt a variety of unique structural motifs, which provide the framework required to perform these functions.

"Small" molecule therapeutics, which bind specifically to structured RNA molecules, are organic chemical molecules which are not polymers. "Small" molecule therapeutics include the most powerful naturally-occurring antibiotics. For example, the aminoglycoside and macrolide antibiotics are "small" molecules that bind to defined regions in ribosomal RNA (rRNA) structures and work, it is believed, by blocking conformational changes in the RNA required for protein synthesis. Changes in the conformation of RNA molecules have been shown to regulate rates of transcription and translation of mRNA molecules.

An additional opportunity in targeting RNA for drug discovery is that cells frequently create different mRNA molecules in different tissues that can be translated into identical proteins. Processes such as alternative splicing and alternative polyadenylation can create transcripts that are unique or enriched in particular tissues. This provides the opportunity to design drugs that bind to the region of RNA unique in a desired tissue, including tumors, and not affect protein expression in other tissues, or affect protein expression to a lesser extent, providing an additional level of drug specificity generally not achieved by therapeutic targeting of proteins.

RNA molecules or groups of related RNA molecules are believed by Applicants to have regulatory regions that are used by the cell to control synthesis of proteins. The cell is believed to exercise control over both the timing and the amount of protein that is synthesized by direct, specific interactions with mRNA. This notion is inconsistent with the impression obtained by reading the scientific literature on gene regulation, which is highly focused on transcription. The process of RNA maturation, transport, intracellular localization and translation are rich in RNA recognition sites that provide good opportunities for drug binding. Applicants' invention is directed to finding these regions for RNA molecules in the human genome as well as in other animal genomes and prokaryotic genomes.

Combinatorial chemistry is a recent addition to the toolbox of chemists and represents a field of chemistry dealing with the synthesis of a large number of chemical entities. This is generally achieved by condensing a small number of reagents together in all combinations defined by a given reaction sequence. Advances in this area of chemistry include the use of chemical software tools and advanced computer hardware which has made it possible to consider possibilities for synthesis in orders of magnitude greater than the actual synthesis of the library compounds. The concept of "virtual library" is used to indicate a collection of candidate structures that would theoretically result from a combinatorial synthesis involving reactions of interest and reagents to effect those reactions. It is from this virtual library that compounds are selected to be actually synthesized.

Project Library (MDL Information Systems, Inc., San Leandro, Calif.) is said to be a desktop software system which supports combinatorial research efforts. (*Practical Guide to Combinatorial Chemistry*, A. W. Czarnik and S. H. DeWitt, eds., 1997, ACS, Washington, D.C.) The software is said to include an information-management module for the representation and search of building blocks, individual molecules, complete combinatorial libraries, and mixtures of molecules, and other modules for computational support for tracking mixture and discrete-compound libraries.

Molecular Diversity Manager (Tripos, Inc., St. Louis, Mo.) is said to be a suite of software modules for the creation, selection, and management of compound libraries. (*Practical Guide to Combinatorial Chemistry*, A. W. Czarnik and S. H. DeWitt, eds., 1997, ACS, Washington, D.C.) The LEGION and SELECTOR modules are said to be useful in creating libraries and characterizing molecules in terms of both 2-dimensional and 3-dimensional structural fingerprints, substituent parameters, topological indices, and physicochemical parameters.

Afferent Systems (San Francisco, Calif.) is said to offer combinatorial library software that creates virtual molecules for a database. It is said to do this by virtually reacting precursor molecules and selecting those that could be actually synthesized (Wilson, C&EN, Apr. 27, 1998, p.32).

While only Project Library and Molecular Diversity Manager are available commercially, these products do not provide facilities to efficiently track reagents and synthesis conditions employed for the introduction of fragments into the desired compounds being generated. Further, these products are unable to track mixtures of compounds that are generated by the introduction of multiple fragments by the use of multiple reagents. Therefore, it is desirable to have available methods for handling mixtures of compounds, as well as methods for the tracking of chemical reactions or transformations utilized in the synthesis of individual compounds and mixtures thereof.

Combinatorial chemistry is a recent addition to the toolbox of chemists and represents a field of chemistry dealing with the synthesis of a large number of chemical entities. This is generally achieved by condensing a small number of reagents together in all combinations defined by a given reaction sequence. Advances in this area of chemistry include the use of chemical software tools and advanced computer hardware which has made it possible to consider possibilities for synthesis in orders of magnitude greater than the actual synthesis of the library compounds. The concept of "virtual library" is used to indicate a collection of candidate structures that would theoretically result from a combinatorial synthesis involving reactions of interest and reagents to effect those reactions. It is from this virtual library that compounds are selected to be actually synthesized.

Project Library (MDL Information Systems, Inc., San Leandro, Calif.) is said to be a desktop software system which supports combinatorial research efforts. (*Practical Guide to Combinatorial Chemistry*, A. W. Czarnik and S. H. DeWitt, eds., 1997, ACS, Washington, D.C.) The software is said to include an information-management module for the representation and search of building blocks, individual molecules, complete combinatorial libraries, and mixtures of molecules, and other modules for computational support for tracking mixture and discrete-compound libraries.

Molecular Diversity Manager (Tripos, Inc., St. Louis, Mo.) is said to be a suite of software modules for the creation, selection, and management of compound libraries. (*Practical Guide to Combinatorial Chemistry*, A. W. Czarnik and S. H. DeWitt, eds., 1997, ACS, Washington, D.C.) The LEGION and SELECTOR modules are said to be useful in creating libraries and characterizing molecules in terms of both 2-dimensional and 3-dimensional structural fingerprints, substituent parameters, topological indices, and physicochemical parameters.

Afferent Systems (San Francisco, Calif.) is said to offer combinatorial library software that creates virtual molecules for a database. It is said to do this by virtually reacting precursor molecules and selecting those that could be actually synthesized (Wilson, C&EN, Apr. 27, 1998, p.32).

While only Project Library and Molecular Diversity Manager are available commercially, these products do not provide facilities to efficiently track the reagents employed for the introduction of fragments into the desired compounds being generated. Further, these products are unable to track mixtures of compounds that are generated by the introduction of multiple fragments by the use of multiple reagents. Therefore, it is desirable to have available methods for handling mixtures of compounds, as well as methods for the tracking of chemical reactions or transformations utilized in the synthesis of individual compounds and mixtures thereof.

The selection of compounds for synthesis and screening is a critical step in any drug discovery process. This is particularly true for combinatorial chemistry-based discovery strategies, where a very much larger number of compounds can be conceived than can be prepared in a reasonable time frame. Computational chemistry methods have been applied to find the "best" sets of compounds for screening. One strategy optimizes the chemical "diversity" in a library in order to increase the likelihood of finding a hit with biological activity in a screen against a macromolecular target of unknown structure.

Targeting nucleic acids has been recognized as a valid strategy for interference with biological pathways and the treatment of disease. In this regard, both deoxyribonucleic acids (DNA) and ribonucleic acids (RNA) have been the target of numerous therapeutic strategies. A wide variety of "small" molecules, oligomers and oligonucleotides have been shown to possess binding affinity for nucleic acids. The vast majority of experience in interfering with nucleic acid function has been via the specific binding of ligands to a particular base, base pair, and/or primary sequence of bases in the nucleic acid target. Some compounds have also demonstrated a composite specificity that arises from recognition and interactions with both the primary and secondary structural features of the nucleic acid, such as preferential binding to A-T base pairs in the DNA minor groove, with little or no binding to corresponding RNA sequences.

Exploiting the knowledge of the three-dimensional structure of biological targets is a promising strategy from a drug design and discovery standpoint. This has been demonstrated by the design and development of numerous drugs and drug candidates targeted to proteins involved in various pathophysiological pathways. While three dimensional structures of proteins have been widely determined by techniques such as X-ray crystallography, molecular modeling and NMR, nucleic acid targets have been difficult to study. The literature reveals few three dimensional structures of biologically active RNA, including a tRNA, said to have been determined via X-ray crystallography. Quigley, et al., *Nucleic Acids Res.,* 1975, 2, 2329; and Moras, et al., *Nature* (*London*), 1980, 288, 669. The difficulties associated with proper crystallization and study of nucleic acids by X-ray methods along with the increasing number of biologically important small RNAs have increased the need for new structure determination and drug discovery strategies for such targets.

Many approaches to predicting RNA structure have been discussed in the scientific literature. Essentially, these involve sequencing and genomic analysis of nucleic acids, such as RNA, as a first step to establish the primary sequence structure and potential folded structures of the target. A second step entails definition of structural constraints such as base pairing and long range interactions among bases based on information derived from cross-linking, biochemical and genetic structure-function studies. This information, together with modeling and simulation software, has allowed scientists to predict three dimensional models of RNA and DNA. While such models may not be as powerful as X-ray crystal structures, they have been useful in ascertaining some structural features and structure-function relationships.

An understanding of the structural features of specific motifs in nucleic acids, especially hairpins, loops, helices and double helices, has been found to be useful in gaining molecular insights. For example, a hairpin motif comprising a double helical stem and a single-stranded loop is believed to be one of the simplest yet most important structural element in nucleic acids. Such hairpin structures are proposed to be nucleation sites and serve as major building blocks for the folded three dimensional structure of RNAs. Shen, et al., *FASEB J.,* 1995, 9, 1023. Hairpins are also involved in specific interactions with a variety of proteins to regulate gene expression. Feng, et al., *Nature,* 1988, 334, 165, Witherell, et al., *Prog. Nucleic Acid Res. Mol Biol.,* 1991, 40, 185, and Phillipe, et al., *J. Mol. Biol.,* 1990, 211, 415. Nucleic acid hairpin structures have therefore been widely studied by NMR, molecular modeling techniques such as constrained molecular dynamics and distance geometry (Cheong, et al., *Nature,* 1990, 346, 680 and Cain, et al., *Nuc. Acids Res.,* 1995, 23, 2153), X-ray crystallography (Valegard, et al., *Nature,* 1994, 371, 623 and Chattopadhyaya, et al., *Nature,* 1988, 334, 175), and theoretical methods (Tung, *Biophysical J.,* 1997, 72, 876, Erie, et al., *Biopolymers,* 1993, 33, 75, and Raghunathan, et al., *Biochemistry,* 1991, 30, 782.

The determination of potential three dimensional structures of nucleic acids and their attendant structural motifs affords insights into areas such as the study of catalysis by RNA, RNA-RNA interactions, RNA-nucleic acid interactions, RNA-protein interactions, and the recognition of small molecules by nucleic acids. Four general approaches to the generation of model three dimensional structures of RNA have been demonstrated in the literature. All of these employ sophisticated molecular modeling and computational algorithms for the simulation of folding and tertiary interactions within target nucleic acids, such as RNA. Westhof and Altman (*Proc. Natl. Acad. Sci.,* 1994, 91, 5133) have described the generation of a three-dimensional working model of M1 RNA, the catalytic RNA subunit of RNase P from *E. coli* via an interactive computer modeling protocol. Leveraging the significant body of work in the area of cryo-electron microscopy (cryo-EM) and biochemical studies on ribosomal RNAs, Mueller and Brimacombe (*J. Mol. Biol.,* 1997, 271, 524) have constructed a three dimensional model of *E. coli* 16S Ribosomal RNA. A method to model nucleic acid hairpin motifs has been developed based on a set of reduced coordinates for describing nucleic acid structures and a sampling algorithm that equilibriates structures using Monte Carlo (MC) simulations (Tung, *Biophysical J,* 1997, 72, 876, incorporated herein by reference in its entirety). MC-SYM is yet another approach to predicting the three dimensional structure of RNAs using a constraint-satisfaction method. Major, et al., *Proc. Natl. Acad. Sci.,* 1993, 90, 9408. The MC-SYM program is an algorithm based on constraint satisfaction that searches conformational space for all models that satisfy query input constraints, and is described in, for example, Cedergren, et al., *RNA Structure And Function,* 1998, Cold Spring Harbor Lab. Press, p.37–75. Three dimensional structures of RNA are produced by that method by the stepwise addition of nucleotide having one or several different conformations to a growing oligonucleotide model.

Westhof and Altman (*Proc. Natl. Acad. Sci.,* 1994, 91, 5133) have described the generation of a three-dimensional working model of M1 RNA, the catalytic RNA subunit of RNase P from *E. coli* via an interactive computer modeling protocol. This modeling protocol incorporated data from chemical and enzymatic protection experiments, phylogenetic analysis, studies of the activities of mutants and the kinetics of reactions catalyzed by the binding of substrate to M1 RNA. Modeling was performed for the most part as described in the literature. Westhof, et al., in "Theoretical Biochemistry and Molecular Biophysics," Beveridge and Lavery (eds.), Adenine, N.Y., 1990, 399. In general, starting with the primary sequence of M1 RNA, the stem-loop structures and other elements of secondary structure were created. Subsequent assembly of these elements into a three dimensional structure using a computer graphics station and FRODO (Jones, *J. Appl. Crystallogr.,* 1978, 11, 268) followed by refinement using NUCLIN-NUCLSQ afforded a RNA model that had correct geometries, the absence of bad contacts, and appropriate stereochemistry. The model so generated was found to be consistent with a large body of empirical data on M1 RNA and opens the door for hypotheses about the mechanism of action of RNase P. However, the models generated by this method are less well resolved that the structures determined via X-ray crystallography.

Mueller and Brimacombe (*J. Mol. Biol.,* 1997, 271, 524) have constructed a three dimensional model of *E. coli* 16S ribosomal RNA using a modeling program called ERNA-3D. This program generates three dimensional structures such as A-form RNA helices and single-strand regions via the dynamic docking of single strands to fit electron density obtained from low resolution diffraction data. After helical elements have been defined and positioned in the model, the configurations of the single strand regions is adjusted, so as to satisfy any known biochemical constraints such as RNA-protein cross-linking and foot-printing data.

A method to model nucleic acid hairpin motifs has been developed based on a set of reduced coordinates for describing nucleic acid structures and a sampling algorithm that equilibriates structures using Monte Carlo (MC) simulations. Tung, *Biophysical J.,* 1997, 72, 876, incorporated herein by reference. The stem region of a nucleic acid can be adequately modeled by using a canonical duplex formation. Using a set of reduced coordinates, an algorithm that is capable of generating structures of single stranded loops with a pair of fixed ends was created. This allows efficient structural sampling of the loop in conformational space. Combining this algorithm with a modified Metropolis Monte Carlo algorithm afforded a structure simulation package that simplifies the study of nucleic acid hairpin structures by computational means.

Knowledge and mastery of the foregoing techniques is assumed to be part of the ordinary skill in the art. There has been a long-felt need in the art to provide methods for improved determination of the three-dimensional structure of important regulatory and other elements in nucleic acids, especially RNA. It is also been greatly desired to achieve improved knowledge about the nature of interactions between ligands and potential ligands or nucleic acids, especially RNA. The present invention is directed towards satisfaction of these objectives.

The process of drug discovery is changing at a fast pace because of the rapid progress and evolution of a number of technologies that impact this process. Drug discovery has evolved from what was, several decades ago, essentially random screening of natural products, into a scientific process that not only includes the rational and combinatorial design of large numbers of synthetic molecules as potential bioactive agents, such as ligands, agonists, antagonists, and inhibitors, but also the identification, and mechanistic and structural characterization of their biological targets, which may be polypeptides, proteins, or nucleic acids. These key areas of drug design and structural biology are of tremendous importance to the understanding and treatment of disease. However, significant hurdles need to be overcome when trying to identify or develop high affinity ligands for a particular biological target. These include the difficulty surrounding the task of elucidating the structure of targets and targets to which other molecules may be bound or associated, the large numbers of compounds that need to be screened in order to generate new leads or to optimize existing leads, the need to dissect structural similarities and dissimilarities between these large numbers of compounds, correlating structural features to activity and binding affinity, and the fact that small structural changes can lead to large effects on biological activities of compounds.

Traditionally, drug discovery and optimization have involved the expensive and time-consuming, and therefore slow, process of synthesis and evaluation of single compounds bearing incremental structural changes. When using natural products, the individual components of extracts had to be painstakingly separated into pure constituent compounds prior to biological evaluation. Further, all compounds had to he carefully analyzed and characterized prior to in vitro screening. These screens typically included evaluation of candidate compounds for binding affinity to their target, competition for the ligand binding site, or efficacy at the target as determined via inhibition, cell proliferation, activation or antagonism end points. Considering all these facets of drug design and screening that slow the process of drug discovery, a number of approaches to alleviate or remedy these matters, have been implemented by those involved in discovery efforts.

One way in which the drug discovery process is being accelerated is by the generation of large collections, libraries, or arrays of compounds. The strategy of discovery has moved from selection of drug leads from among compounds that are individually synthesized and tested to the screening of large collections of compounds. These collections may be from natural sources (Sternberg et al., Proc. Natl. Acad. Sci. USA, 1995, 92, 1609–1613) or generated by synthetic methods such as combinatorial chemistry (Ecker and Crooke, Bio/Technology, 1995, 13, 351–360 and U.S. Pat. No. 5,571,902, incorporated herein by reference). These collections of compounds may be generated as libraries of individual, well-characterized compounds synthesized, e.g. via high throughput, parallel synthesis or as a mixture or a pool of up to several hundred or even several thousand molecules synthesized by split-mix or other combinatorial methods. Screening of such combinatorial libraries has usually involved a binding assay to determine the extent of ligand-receptor interaction (Chu et al., J. Am. Chem. Soc., 1996, 118, 7827–35). Often the ligand or the target receptor is immobilized onto a surface such as a polymer bead or plate. Following detection of a binding event, the ligand is released and identified. However, solid phase screening assays can be rendered difficult by non-specific interactions.

Whether screening of combinatorial libraries is performed via solid-phase, solution methods or otherwise, it can be a challenge to identify those components of the library that bind to the target in a rapid and effective manner and which, hence, are of greatest interest. This is a process that needs to be improved to achieve ease and effectiveness in combinatorial and other drug discovery processes. Several approaches to facilitating the understanding of the structure of biopolymeric and other therapeutic targets have also been developed so as to accelerate the process of drug discovery and development. These include the sequencing of proteins and nucleic acids (Smith, in Protein Sequencing Protocols, Humana Press, Totowa, N.J., 1997; Findlay and Geisow, in Protein Sequencing: A Practical Approach, IRL Press, Oxford, 1989; Brown, in DNA Sequencing, IRL Oxford University Press, Oxford, 1994; Adams, Fields and Venter, in Automated DNA Sequencing and Analysis, Academic Press, San Diego, 1994). These also include elucidating the secondary and tertiary structures of such biopolymers via NMR (Jefson, Ann. Rep. in Med. Chem., 1988, 23, 275; Erikson et al., Ann. Rep. in Med. Chem., 1992, 27, 271-289), X-ray crystallography (Erikson et al., Ann. Rep. in Med. Chem., 1992, 27, 271–289) and the use of Computer algorithms to attempt the prediction of protein folding (Copeland, in Methods of Protein Analysis: A Practical Guide to Laboratory Protocols, Chapman and Hall, New York, 1994; Creighton, in Protein Folding, W. H. Freeman and Co., 1992). Experiments such as ELISA (Kemeny and Challacombe, in ELISA and other Solid Phase Immunoassays: Theoretical and Practical Aspects; Wiley, N.Y., 1988) and radioligand binding assays (Berson et al., Clin. Chim. Acta, 1968, 22, 51–60; Chard, in "An Introduction to Radioimmunoassay and Related Techniques," Elsevier press, Amsterdam/N.Y., 1982), the use of surface-plasmon resonance (Karlsson, Michaelsson and Mattson, J. Immunol. Methods, 1991, 145, 229; Jonsson et al., Biotechniques, 1991, 11, 620), and scintillation proximity assays (Udenfriend et al., Anal. Biochem., 1987, 161, 494–500) are being used to understand the nature of the receptor-ligand interaction.

All of the foregoing paradigms and techniques are now available to persons of ordinary skill in the art and their understanding and mastery is assumed herein.

Likewise, advances have occurred in the chemical synthesis of compounds for high-throughput biological screening. Combinatorial chemistry, computational chemistry, and the synthesis of large collections of mixtures of compounds or of individual compounds have all facilitated the rapid synthesis of large numbers of compounds for ill vitro screening. Despite these advances, the process of drug discovery and optimization entails a sequence of difficult steps. This process can also be an expensive one because of the costs involved at each stage and the need to screen large numbers of individual compounds. Moreover, the structural features of target receptors can be elusive.

One step in the identification of bioactive compounds involves the determination of binding affinity of test compounds for a desired biopolymeric or other receptor, such as a specific protein or nucleic acid combination thereof. For combinatorial chemistry, with its ability to synthesize, or isolate from natural sources, large numbers of compounds for ill vitro biological screening, this challenge is magnified. Since combinatorial chemistry generates large numbers of compounds or natural products, often isolated as mixtures, there is a need for methods which allow rapid determination of those members of the library or mixture that are most active or which bind with the highest affinity to a receptor target.

From a related perspective, there are available to the drug discovery scientist a number of tools and techniques for the structural elucidation of biologically interesting targets, for the determination of the strength and stoichiometry of target-ligand interactions, and for the determination of active components of combinatorial mixtures.

Techniques and instrumentation are available for the sequencing of biological targets such as proteins and nucleic acids (e.g. Smith, in Protein Sequencing Protocols, 1997 and Findlay and Geisow, in Protein Sequencing: A Practical Approach, 1989) cited previously. While these techniques are useful, there are some classes and structures of biopolymeric target that are not susceptible to such sequencing efforts, and, in any event, greater convenience and economy have been sought. Another drawback of present sequencing techniques is their inability to reveal anything more than the primary structure, or sequence, of the target.

While X-ray crystallography is a very powerful technique that can allow for the determination of some secondary and tertiary structure of biopolymeric targets (Erikson et al., Ann. Rep. in Med. Chem., 1992, 27, 271–289), this technique can be an expensive procedure and very difficult to accomplish. Crystallization of biopolymers is extremely challenging, difficult to perform at adequate resolution, and is often considered to be as much an art as a science. Further confounding the utility of X-ray crystal structures in the drug discovery process is the inability of crystallography to reveal insights into the solution-phase, and therefore the biologically relevant, structures of the targets of interest.

Some analysis of the nature and strength of interaction between a ligand (agonist, antagonist, or inhibitor) and its target can be performed by ELISA (Kemeny and Challacombe, in ELISA and other Solid Phase Immunoassays: 1988), radioligand binding assays (Berson et al., Clin. 1968, Chard, in "An Introduction to Radioimmunoassay and Related Techniques," 1982), surface-plasmon resonance (Karlsson et al., 1991, Jonsson et al., Biotechniques, 1991), or scintillation proximity assays (Udenfriend et al., Anal. Biochem., 1987), all cited previously. Thc radioligand binding assays are typically useful only when assessing the competitive binding of the unknown at the biding site for that of the radioligand and also require the use of radioactivity. The surface-plasmon resonance technique is more straight forward to use, but is also quite costly. Conventional biochemical assays of binding kinetics, and dissociation and association constants are also helpful in elucidating the nature of the target-ligand interactions.

When screening combinatorial mixtures of compounds, the drug discovery scientist will conventionally identify an active pool, deconvolute it into its individual members via resynthesis, and identify the active members via analysis of the discrete compounds. Current techniques and protocols for the study of combinatorial libraries against a variety of biologically relevant targets have many shortcomings. The tedious nature, high cost, multi-step character, and low sensitivity of many of the above-mentioned screening technologies are shortcomings of the currently available tools. Further, available techniques do not always afford the most relevant structural information —the structure of a target in solution, for example. Instead they provide insights into target structures that may only exist in the solid phase. Also, the need for customized reagents and experiments for specific tasks is a challenge for the practice of current drug discovery and screening technologies. Current methods also fail to provide a convenient solution to the need for deconvolution and identification of active members of libraries without having to perform tedious re-syntheses and re-analyses of discrete members of pools or mixtures.

Therefore, methods for the screening and identification of complex chemical libraries especially combinatorial libraries are greatly needed such that one or more of the structures of both the target and ligand, the site of interaction between the target and ligand, and the strength of the target-ligand interaction can be determined. Further, in order to accelerate drug discovery, new methods of screening combinatorial libraries are needed to provide ways for the direct identification of the bioactive members from a mixture and to allow for the screening of multiple biomolecular targets in a single procedure. Straightforward methods that allow selective and controlled cleavage of biopolymers, while also analyzing the various fragments to provide structural information, would be of significant value to those involved in biochemistry and drug discovery and have long been desired. Also, it is preferred that the methods not be restricted to one type of biomolecular target, but instead be applicable to a variety of targets such as nucleic acids, peptides, proteins and oligosaccharides.

Accordingly, it is a principal object of the invention to identify molecular interaction sites in nucleic acids, especially RNA. A further object of the invention is to identify secondary structural elements in RNA which are highly likely to give rise to significant therapeutic, regulatory, or other interactions with "small" molecules and the like. Identification of tissue-enriched unique structures in RNA is another objective of the present invention.

It is another objective of the present invention to provide improved characterization of interactions between RNA and other nucleic acids and ligands or potential ligands therefor.

A further object of the invention is to compare molecular interaction sites of RNA with compounds proposed for interaction therewith.

In accordance with preferred embodiments of the present invention, the comparison of molecular interaction sites of RNA with compounds is achieved through comparison of numerical representations of the three-dimensional structure of the molecular interaction site with the three dimensional structure of the ligands in a fashion such that such interactions can be compared as to quality.

Another object of the present invention is the preparation of hierarchies of ligands ranked or ordered in accordance with in accordance with their ability to interact with molecular interaction sites of RNA and other nucleic acid targets.

Yet another object of the present invention is the establishment of databases of the numerical representations of three-dimensional structures of molecular interaction sites of nucleic acids and three-dimensional structures of libraries of ligands. Such databases libraries provide powerful tools for the elucidation of structure and interactions of molecular interaction sites with potential ligands and predictions thereof.

A principal object of the present invention is to provide novel methods for the determination of the structure of biomolecular targets and ligands that interact with them and to ascertain the nature and sites of such interactions.

A further object of the invention is to determine the structural features of biomolecular targets such as peptides, proteins, oligonucleotides, and nucleic acids such as the primary sequence, the secondary and folded structures of biopolymers, and higher order tertiary and quaternary structures of biomolecules that result from intramolecular and intermolecular interactions.

Yet another object of the invention is to determine the site(s) and nature of interaction between a biomolecular target aid a binding ligand or ligands. The binding ligand may be a "small" molecule, a biomolecule such as a peptide, oligonucleotide or oligosaccharide, a natural product, or a member of a combinatorial library.

A further object of the invention is to determine the relative binding affinity or dissociation constant of ligands that bind to biopolymer targets. Preferably, this gives rise to a determination of relative binding affinities between a biopolymer such as an RNA/DNA target and ligands e.g. members of combinatorially synthesized libraries.

A further object of the invention is to determine the absolute binding affinity or dissociation constant of ligands that bind to biopolymer targets.

A still further object of the present invention is to provide a general method for the screening of combinatorial libraries comprising individual compounds or mixtures of compounds against a biomolecular target such as a nucleic acid, so as to determine which components of the library bind to the target.

An additional object of the present invention is to provide methods for the determination of the molecular weight and structure of those members of a combinatorial library that bind to a biomolecular target.

Yet another object of the invention is to provide methods for screening multiple targets such as nucleic acids, proteins, and other biomolecules and oligomers simultaneously against a combinatorial library of compounds.

A still further object of the invention is to ascertain the specificity and affinity of compounds, especially "small" organic molecules to bind to or interact with molecular interaction sites of biological molecules, especially nucleic acids such as RNA. Such molecules may be and preferably do form ranked hierarchies of ligands and potential ligands for the molecular interaction sites, ranked in accordance with predicted or calculated likelihood of interaction with such sites.

Another object of the present invention is to alleviate the problem of peak overlap in mass spectra generated from the analysis of mixtures of screening targets and combinatorial or other mixtures of compounds. In a preferred embodiment, the invention provides methods to solve the problems of mass redundancy in combinatorial or other mixtures of compounds, and also provides methods to solve the problem of mass redundancy in the mixture of targets being screened.

A further object of the invention is to provide methods for determining the binding specificity of a ligand for a target in comparison to a control. The present invention facilitates the determination of selectivity, the identification of non-specific effects and the elimination of non-specific ligands from further consideration for drug discovery efforts.

SUMMARY OF THE INVENTION

The invention is directed to identification of novel drugs, agricultural chemicals, industrial chemicals and the like which operate through the modulation of biomolecules, especially RNAs. A number of procedures and protocols are preferably integrated to provide powerful drug and other biologically useful compound identification.

Applicants' invention is directed to methods of identifying secondary structures in eukaryotic and prokaryotic RNA molecules termed "molecular interaction sites." Molecular interaction sites are small, preferably less than 70 nucleotides, preferably less than 50 nucleotides, alternatively less than 30 nucleotides, independently folded, functional subdomains contained within a larger RNA molecule. Applicants' methods preferably comprise a family of integrated processes that analyze nucleic acid, preferably RNA, sequences and predict their structure and function. Applicants' methods preferably comprise processes that execute subroutines in sequence, where the results of one process are used to trigger a specific course of action or provide numerical or other input to other steps. Preferably, there are decision points in the processes where the paths taken are determined by expert processes that make decisions without detailed, real-time human intervention. Automation of the analysis of RNA sequences provides the ability to identify regulatory sites at the rate that RNA sequences become available from genomic sequence databases and otherwise. The invention can be used, for example, to identify molecular interaction sites in connection with central nervous system (CNS) disease, metabolic disease, pain, degenerative diseases of aging, cancer, inflammatory disease, cardiovascular disease and many other conditions. Applicants' invention can also be used, for example, to identify molecular interaction sites, which are absent from eukaryotes, particularly humans, which can serves as sites for "small" molecule binding with concomitant modulation, either augmenting or diminishing, of the RNA of prokaryotic organisms. Human toxicity can, thus, he avoided in the treatment of viral, bacterial or parasitic disease.

The present invention preferably identifies molecular interaction sites in a target nucleic acid by comparing the nucleotide sequence of the target nucleic acid with the nucleotide sequences of a plurality of nucleic acids from different taxonomic species, identifying at least one sequence region which is effectively conserved among the plurality of nucleic acids and the target nucleic acid, determining whether the conserved region has secondary structure, and, for conserved regions having secondary structure, identifying the secondary structures.

The present invention is also directed to databases relating to molecular interaction sites, in eukaryotic and prokaryotic RNA. The databases are obtained by comparing the nucleotide sequence of the target nucleic acid with the nucleotide sequences of a plurality of nucleic acids from different taxonomic species, identifying at least one sequence region which is conserved among the plurality of nucleic acids and the target nucleic acid, determining whether the conserved region has secondary structure, and for the conserved regions having secondary structure, identifying the secondary structures, and compiling a group of such secondary structures.

The present invention is also directed to oligonucleotides comprising a molecular interaction site that is present in the RNA of a selected organism and in the RNA of at least one additional organism, wherein the molecular interaction site serves as a binding site for at least one molecule which, when bound to the molecular interaction site, modulates the expression of the RNA in the selected organism.

The present invention is also directed to oligonucleotides comprising a molecular interaction site that is present in prokaryotic RNA and in at least one additional prokaryotic RNA, wherein the molecular interaction site serves as a binding site for at least one molecule, when bound to the molecular interaction site, modulates the expression of the prokaryotic RNA.

The present invention also concerns pharmaceutical compositions comprising an oligonucleotide having a molecular interaction site that is present in prokaryotic RNA and in at least one additional prokaryotic RNA, wherein the molecular interaction site serves as a binding site for at least one "small" molecule. Such molecule, when bound to the molecular interaction site, modulates the expression of the prokaryotic RNA. A pharmaceutical carrier is also preferably included.

The present invention also provides pharmaceutical compositions comprising an oligonucleotide comprising a molecular interaction site that is present in the RNA of a selected organism and in the RNA of at least one additional organism. The molecular interaction site serves as a binding site for at least one molecule that, when bound to the molecular interaction site, modulates the expression of the RNA in the selected organism, and a pharmaceutical carrier.

Ultimately, the methods of the present invention identify the physical structures present in a target nucleic acid which are of great importance to an organism in which the nucleic acid is present. Such structures—called molecular interaction sites—are capable of interacting with molecular species to modify the nature or effect of the nucleic acid. This may be exploited therapeutically as will be appreciated by persons skilled in the art. Such structures may also be found in the nucleic acid of organisms having great importance in agriculture, pollution control, industrial biochemistry, and otherwise. Accordingly, pesticides, herbicides, fungicides, industrial organisms such as yeast, bacteria, viruses, and the like, and biocatalytic systems may be benefitted hereby.

In accordance with the present invention, there are provided methods for the generation of virtual combinatorial libraries of small molecules. These library molecules or members are generated in silico. Library members of larger molecular weight, such as those that are polymeric in nature, may also be generated using the methods of the present invention.

The present invention further provides methods for tracking and maintaining in databases, the fragments, reagents and unique combinations of these used for the in silico generation of the library members. Methods for interfacing the information necessary for the generation of libraries in silico, as instructions designed to direct the actual synthesis of the library members on an instrument such as a parallel array synthesizer, are also provided in the present invention.

The present invention also provides methods for the in silico docking of the library members to identified target molecules. According to these methods, individual library members are allowed to bind to the desired target molecule in order to identify those library members that demonstrate high affinity binding to the targets.

In accordance with the present invention, there are provided methods for the generation of virtual combinatorial libraries of small molecules. These library molecules or members are generated in silico. Library members of larger molecular weight, such as those that are polymeric in nature, may also be generated using the methods of the present invention.

The present invention further provides methods for tracking and maintaining in databases, the fragments, reagents and unique combinations of these used for the in silico generation of the library members. Methods for interfacing the information necessary for the generation of libraries in silico, as instructions designed to direct the actual synthesis of the library members on an instrument such as a parallel array synthesizer, are also provided in the present invention.

The present invention is also directed to methods of identifying compounds which bind to a molecular interaction site of a nucleic acid comprising providing a numerical representation of the three-dimensional structure of the molecular interaction site and providing a compound data set comprising numerical representations of the three dimensional structures of a plurality of organic compounds. The numerical representation of the molecular interaction site is then compared with members of the compound data set to generate a hierarchy of organic compounds ranked in accordance with the ability of the organic compounds to form physical interactions with the molecular interaction site.

The present invention is also directed to data sets comprising the numerical representations of the three dimensional structures of molecular interaction sites and to the numerical representations of the three dimensional structure of a plurality of organic compounds.

The present invention is directed to methods of identifying compounds which bind to a molecular interaction site of nucleic acids. They comprise providing a numerical representation of the three dimensional structure of the molecular interaction site, providing a compound data set comprising numerical representations of the three-dimensional structures of a plurality of organic compounds, comparing the numerical representation of the molecular interaction site with members of the compound data set to generate a hierarchy of organic compounds which is ranked in accordance with the ability of the organic compounds to form physical interactions with the molecular interaction site.

One aspect of the invention is a method to determine the structure of biomolecular targets such as nucleic acids using mass spectrometry. The method provides not only the primary, sequence structure of nucleic acid targets, but also information about the secondary and tertiary structure of nucleic acids, RNA and DNA, including mismatched base pairs, loops, bulges, kinks, and stem structures. This can be accomplished in accordance with one embodiment by incorporating deoxynucleotide residues or other modified residues into an oligoribonucleotide at specific sites followed by selective cleavage of these hybrid RNA/DNA nucleic acids in a mass spectrometer. It has now been found that electrospray ionization of the nucleic acid, cleavage of the nucleic acid, and subsequent tandem $MS^n$ spectrometry affords a pattern of fragments that is indicative of the nucleic acid sequence and structure. Cleavage is dependent on the sites of incorporation of the deoxynucleotide or other foreign residues and the secondary structure of the nucleic acid. This method therefore provides mass spectral data that identifies the sites and types of secondary structure present in the sequence of nucleic acids.

When the present methods are performed on a mixture of the biomolecular target and a ligand or molecule that binds to the target, it is possible to ascertain both the extent of interaction and the location of this interaction between ligand and biomolecule. The binding of the ligand to the biomolecule protects the binding site on the biomolecule from facile cleavage during mass spectrometry. Therefore, comparison of ESI-$MS^n$ mass spectra generated, using this method, for RNA/DNA in the presence and the absence of a binding ligand or drug reveals the location of binding. This altered cleavage pattern is clearly discerned in the mass spectrum and correlated to the sequence and structure of the nucleic acid. Thus, the absolute binding affinity of the test ligand can be determined by the methods of the present invention. Comparison of the abundance of the nucleic acid-ligand noncovalent complex ion to the abundance of a similar complex ion generated from a standard compound (such as paromomycin for the 16S RNA A site) whose binding affinity is known, allows for the determination of relative binding affinity of the test ligand.

The methods of this invention can be used for the rapid screening of large collections of compounds. It is also possible to screen mixtures of large numbers of compounds that are generated via combinatorial or other means. When a large mixture of compounds is exposed to a biomolecular target, such as a nucleic acid, a small fraction of ligands may exhibit some binding affinity to the nucleic acid. The actual number of ligands that may be detected as binders is based on the concentration of the nucleic acid target, the relative concentrations of the components of the combinatorial mixture, and the absolute and relative binding affinities of these components. The method is capable of separating different noncovalent complexes, using techniques such as selective ion trapping, or accumulation and analyzing each complex for the structure and identity of the bound ligand using collisionally activated dissociation or $MS^n$ experiments. The methods of this invention, therefore, can not only serve as methods to screen combinatorial libraries for molecules that bind to biomolecular targets, but can also provide, in a straightforward manner, the structural identity of the bound ligands. In this manner, any mass redundancy in the combinatorial library does not pose a problem, as the methods can provide high resolution molecular masses and also able to discern differences between the different structures of ligands of identical molecular mass using tandem methods.

In accordance with preferred embodiments, a target biomolecule such as an RNA having a molecular interaction site, is presented with one or more ligands or suspected ligands for the interaction site under conditions such that interaction or binding of the ligand to the molecular interaction site can occur. The resulting complex, which may be of one or even hundreds of individual complexes of ligands with the RNA or other biomolecule, is then subjected to mass spectrometric evaluation in accordance with the invention. "Preparative" mass spectrometry can isolate individual complexes which can then be fragmented under controlled conditions within the mass spectrometric environment for subsequent analysis. In this way, the nature and degree, or absolute binding affinity, of binding of the ligands to the molecular interaction site can be ascertained. Identification of specific, strong binding ligands can be made and those selected for use either as therapeutics, agricultural, industrial or other chemicals, or the same used as lead compounds for subsequent modification into improved forms for such uses.

A further application of the present invention is the use of mass spectrometric methods for the simultaneous screening of multiple biomolecular targets against combinatorial libraries or mixtures of compounds. This rather complex screening procedure is made possible by the combined power of the mass spectrometric methods used and the way in which the screening is performed. When screening multiple target nucleic acids, for example, mass redundancy is a concern, especially if two or more targets are of similar sequence composition or mass. This problem is alleviated by the present invention, by using special mass modifying, molecular weight tags on the different nucleic acid targets being studied. These mass modifying tags are typically large molecular weight, non-ionic polymers including but not limited to, polyethylene glycols, polyacrylamides and dextrans, that are available in many different sizes and weights, and which may be attached at one or more of many different possible sites on nucleic acids. Thus similar nucleic acid targets may be differentially tagged and now be readily differentiated, in the mass spectrum, from one another by their distinctly different mass to charge ratios (m/z signals). Using the methods of this invention, screening efforts can be significantly accelerated because multiple targets can now be screened simultaneously against mixtures of large numbers of compounds.

Another related advantage of the methods of this invention is the ability to determine the specificity of binding interactions between a new ligand and a biomolecular target. By simultaneously screening a target nucleic acid, for example, and one or more control nucleic acids against a combinatorial library or a specific ligand, it is possible to ascertain, using the methods of this invention, whether the ligand binds specifically to only the target nucleic acids, or whether the binding observed with the target is reproduced with control nucleic acids and is therefore non-specific.

The methods of the invention are applicable to the study of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides, nucleic acids or oligonucleotides. The mass spectrometric techniques which can be used in the methods of the invention include, but are not limited to, $MS^n$, collisionally activated dissociation (CAD) and collisionally induced dissociation (CID) and infrared multiphoton dissociation (IRMPD). A variety of ionization techniques may be used including, but not limited to, electrospray, MALDI and FAB. The mass detectors used in the methods of this invention include, but are not limited to, FTICR, ion trap, quadrupole, magnetic sector, time of flight (TOF), Q-TOF, and triple quadrupole. The methods of this invention may also use "hyphenated" techniques such as, but not limited to, LC/MS and CE/MS, all as described more fully hereinafter.

While there are a number of ways to characterize binding between molecular interaction sites and ligands, such as for example, organic compounds, preferred methodologies are described in U.S. Ser. Nos. 09/076,440, 09/076,405, 09/076,447, 09/076,206, 09/076,214, and 09/076,404, each of which was filed oil May 12, 1998 and each assigned to the assignee of this invention. All of the foregoing applications are incorporated by reference herein in their entirety.

BRIEF DESCRIPTION OF THE DRAWINGS

FIG. 14 shows a compound, compound C1, dissected into its constituent fragments;

FIG. 15 shows the various identifying characteristics of the fragments comprising compound C1;

FIG. 16 shows the various identifying characteristics of the reagents used to introduce the corresponding fragments comprising compound C1;

FIG. 17 is a list of transformations that link the fragments and reagents associated with the generation of compound C1;

FIG. 20 shows the symbolic addition of fragments yielding a symbolic compound, compound C1';

FIG. 21 is a symbolic reagent table;

FIG. 22 is a symbolic fragment table;

FIG. 23 is a symbolic transformation table;

FIG. 28 shows tables for tracking compound C1 by the fragments added and or transformations performed;

FIG. 30 shows tables for tracking mixture M2 by the transformations performed.

FIG. 37 shows the target RNA for 4.5S-P48.

FIG.40 shows the sequence and structure of the 27-mer RNA target corresponding to the 16S rRNA A-site. SEQ ID NO:37 (top) and SEQ ID NO:38 bottom are shown.

FIG. 57 shows a representative Dome structure view of region 3 of IL-23' UTR. SEQ ID NO:44, SEQ ID NO:45, SEQ ID NO:46, SEQ ID NO:47, SEQ ID NO:48, SEQ ID NO:49, SEQ ID NO:50, and SEQ ID NO:51 are shown top to bottom, respectively.

FIG. 62 depicts high resolution ESI-FTICR spectrum of the library used in FIGS. 60 and 61.

FIG. 63 depicts use of exact mass measurements and elemental constraints to determine the elemental composition of an exemplary "unknown" binding ligand.

FIG. 76 depicts data tabulated and stored in a relational database.

As will be appreciated, the present invention provides for the identification of molecules having the ability to modulate RNA and other biomolecules. Novel combinations of procedures provide extraordinary power and versatility to the present methods. While it is preferred in some embodiments to integrate a number of processes developed by the assignee of the present application as will be set forth more fully herein, it should be recognized that other methodologies may be integrated herewith to good effect. Thus, while it is greatly advantageous to determine molecular binding sited on RNAs and other molecules in accordance with the teachings of this invention, the interactions of ligands and libraries of ligands with RNA and other molecules identified as being of interest may greatly benefit from other aspects of this invention. All such combinations are within the spirit of the invention.

In accordance with preferred embodiments, particular structural elements in eukaryotic and prokaryotic nucleic acid, molecular interaction sites, are identified. Thus, the present invention is directed to methods of identifying particular structural elements in eukaryotic and prokaryotic nucleic acid, especially RNA molecules, which can interact with other molecules to effect modulation of the RNA. "Modulation" refers to augmenting or diminishing RNA activity or expression. The present invention is outlined in flowchart form in FIG. 1. The structural elements in eukaryotes and prokaryotes are referred to as "molecular interaction sites." These elements contain secondary structure, that is, have three-dimensional form capable of undergoing interaction with "small" molecules and otherwise, and are expected to serve as sites for interacting with "small" molecules, oligomers such as oligonucleotides, and other compounds in therapeutic and other applications.

Figure 1:
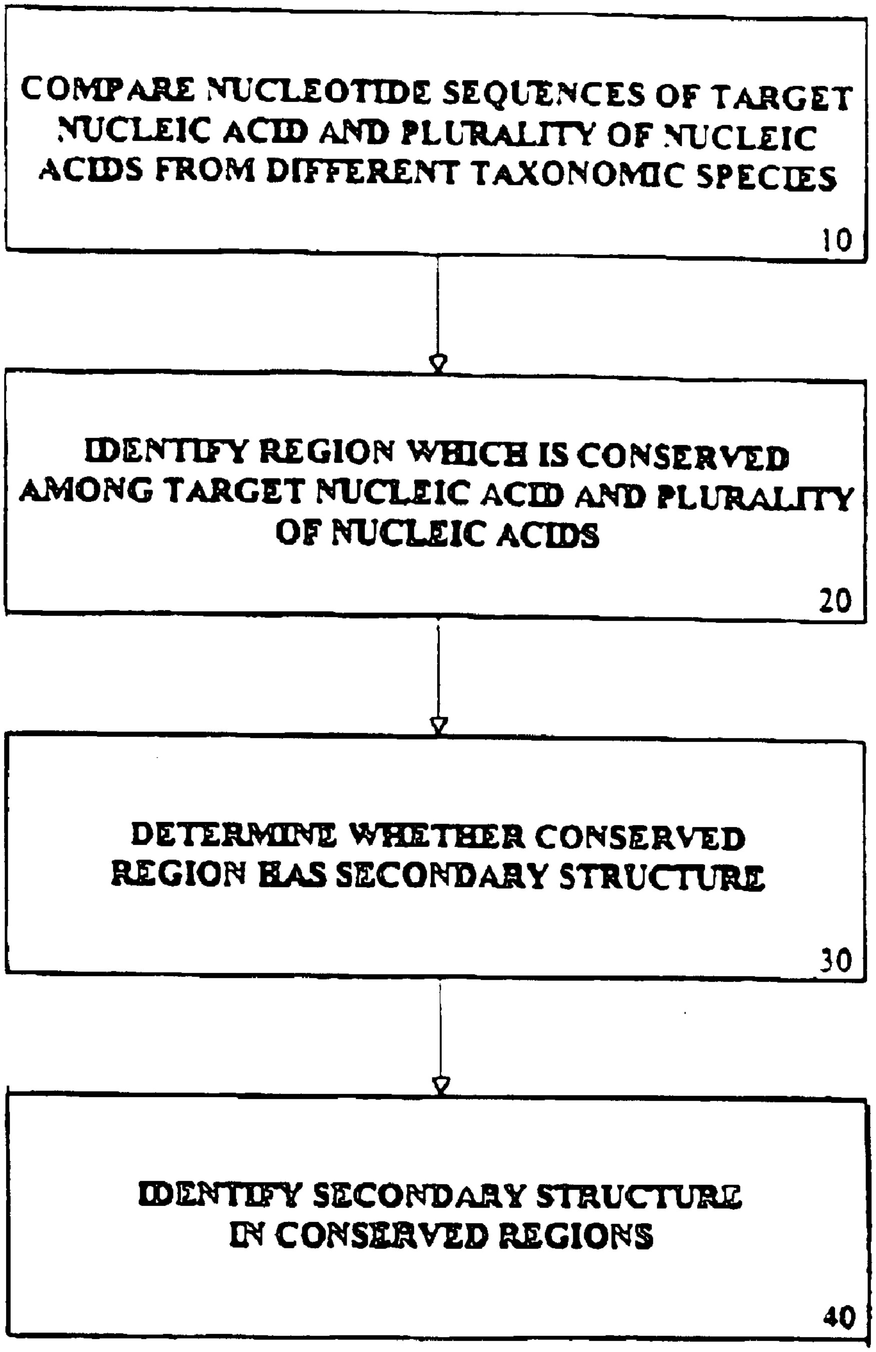
FIG. 1 illustrates a flowchart comprising one preferred set of method steps for identifying molecular interaction sites in eukaryotic and prokaryotic RNA.

Referring to FIG. 1, preferred steps for identifying molecular interaction sites in target nucleic acids are shown in the flow diagram. The nucleotide sequence of the target nucleic acid is compared with the nucleotide sequences of a plurality of nucleic acids from different taxonomic species, 10. The target nucleic acid may be present in eukaryotic cells or prokaryotic cells, the target nucleic acid may be bacterial or viral as well as belonging to a "higher" organism such as human. Any type of nucleic acid can serve as a target nucleic acid. Preferred target nucleic acids include, but are not limited to, messenger RNA (mRNA), pre-messenger RNA (pre-mRNA), transfer RNA (tRNA), ribosomal RNA (rRNA), or small nuclear RNA (snRNA). Initial selection of a particular target nucleic acid can be based upon any functional criteria. Nucleic acids known to be important during inflammation, cardiovascular disease, pain, cancer, arthritis, trauma, obesity, Huntingtons, neurological disorders, or other diseases or disorders, for example, are exemplary target nucleic acids.

Nucleic acids known to be involved in pathogenic genomes such as, for example, bacterial, viral and yeast genomes are exemplary prokaryotic nucleic acid targets. Pathogenic bacteria, viruses and yeast are well known to those skilled in the art. Exemplary nucleic acid targets are shown in Table 1. Applicants' invention, however, is not limited to the targets shown in Table 1 and it is to be understood that the present invention is believed to be quite general.

TABLE 1

Exemplary RNA Targets

| Protein | RNA Target | GenBank # | Therapeutic |
|---|---|---|---|
| 46 kD protein | 3'-UTR stemloop in vimentin mRNA | X56134 | cancer |
| unknown-cGMP regulated | 5'-UTR of Asialoglycoprotein receptor mRNA | m10058 | cancer |
| unknown | unknown | m11025 | unknown |
| unknown insulin regulated protein | 3'-UTR of E-selectin mRNA | unknown | inflammation |
| 30 kD protein | 3'-UTR of lipoprotein lipase mRNA | m15856 | obesity |

TABLE 1-continued

Exemplary RNA Targets

| Protein | RNA Target | GenBank # | Therapeutic |
|---|---|---|---|
| unknown | 3'-UTR of NR2A subunit of NMDA receptor | U09002 | trauma, paid, AD |
| histone binding protein (HBP) | 3'-UTR of histone mRNA + paralogs | x57129 | cancer |
| unknown | 3'-UTR of p53 mRNA | x02469 | cancer |
| p53 | 5'-UTR of mdm2 oncogene mRNA | u39736 | cancer |
| unknown | 5'-UTR of interleukin 1 type receptor (1L-1R1) | m27492 | inflammation |
| none | 5'-UTR of muscle acylphosphatase mRNA | x84195 | musculoskeletal disease |
| ribosomal proteins | 5'-UTR of c-myc in multiple myeloma | V00568 | cancer |
| unknown | 5'-UTR of Huntingtons disease gene | | Huntingtons |
| unknown | 5'-UTR of angiotensin AqT | p30556 | cardiovascular disease |
| unknown | zip code sequence in ARC mRNA | d87468 | unknown |
| L-4 | 5'-UTR of L4 ribosomal protein | d23660 | cancer |
| L-32 | 5'-UTR of L32 ribosomal protein | x03342 | cancer |
| unknown | TCTP, translationally controlled tumor protein | x16064 | cancer |
| unknown | 3'-UTR of B-F1-ATPase | d00022 | cancer |
| PU family of proteins, FBF binding factor | 3'-UTR of fem-3 in *C. elegans* | X64962 | unknown |
| unknown | 3'-UTR of myocyte enhancer factor 2 MEF2A | x68505 | metabolic |
| unknown | 5'-UTR of glucose transporter mRNA GLUTI | k03195 | diabetes |
| 48 kD reticulocyte protein | 3'-UTR of 15-lipoxygenase | M23892 | inflammation |
| La protein | 5'-UTR of ribosomal RNA proteins | | cancer |
| unknown | translational regulation of IL-2 | S82692 | inflammation |
| unknown | 3'-UTR of CaMKlla mRNA in neurons | u81554 | CNS |
| bicoid (bcd) | BRE 3'-UTR fragment mRNA encoding cad protein | M21069 | under development |
| 48/50 kD protein | 3'-UTR structure protamines 1 | Y00443 | cancer |
| translin (human) TB-RBP (mouse) | protamine 1 mRNA (human testes specific) | Y00443 | cancer |
| translin (human) TB-RBP (mouse) | protamine 2 mRNA | X07862 | unknown |
| translin (human) TB-RBP (mouse) | transition protein mRNA | x14474 | cancer |
| translin (human) TB-RBP (mouse) | Tau mRNA | m13577 | cancer |
| translin (human) TB-RBP (mouse) | myelin basic protein mRNA | x07948 | cancer |
| p75 | 3'-UTR of ribonucleotide reductase R2 | x59618 | cancer |
| 39 kD poly C protein | alpha globin | v00493 | cancer |
| unknown | beta protein | v00497 | metabolic |
| human teratocarcinoma protein p40 | Line-1 mRNA | | cancer, metabolic |
| RPL32 | 5'-UTR hairpin structure in RPL32 | | cancer |
| Y-box proteins | family of transcription factor mRNAs with a Y-box sequence | | cancer |
| telomerase protein | telomerase RNA | AF015950 | cancer |
| ferritin, transferrin | IREs, internal loops in mRNA encoding ferritin and transferrin | | inflammation |
| ribosomal proteins | 5'-UTR of PDGF2/c-sis mRNA | M12873 | inflammation |

TABLE 1-continued

Exemplary RNA Targets

| Protein | RNA Target | GenBank # | Therapeutic |
|---|---|---|---|
| zip code for localization | 3'-UTR of beta actin | | cancer |
| unknown insulin regulated protein | 5'-UTR of ornithine decarboxylase mRNA | x55362 | cancer |
| ribosomal proteins | ornithine decarboxylase antizyme | | cancer |
| unknown | FGF-5 | | inflammation |
| DFR protein factor | 3'-UTR TGE elements in the human oncogene GLI | X07384 | cancer |
| DFR protein factor | 3'-UTR tra-2 of *C. elegans* | | unknown |
| viral capsid protein | 3'-UTR of alfalfa mosaic virus RNA3 | | unknown |
| unknown | BRE Bruno response element in 3'-UTR of drosophila oskar mRNA | | cancer |
| unknown | NRE nanose response element | | cancer |
| unknown | repeated element | | inflammation |
| U1A RDB protein | U1 snRNA | | inflammation |
| CD40 | | X60592 | inflammation |
| IGF-R | | X04434<br>M24599 | inflammation |
| A1 adenosine receptor | | X68485 | cardiovascular |
| B7-1 | | M27533 | inflammation |
| B7-2 | | | imflammation |
| cyclophilin B | | M60857<br>M60457<br>M63573 | inflammation |
| cyclophilin C | | S71018 | transplantation |
| FKBP51 | | | transplantation |
| Th1 cytokines IFN γ | | | inflammation |
| Th1 cytokines IL-12 | | U03187 | inflammation |
| NF-kappa B | | | cancer |
| ICAM-1 | | X06990 | inflammation |
| L-selectin | | X16150 | inflammation |
| VCAM-1 | | M30257 | inflammation |
| Alpha 4 integrin | | X16983<br>X15356 | inflammation |
| Beta 7 | | U34971 | inflammation |
| MadCAM-1 | | U43628 | inflammation |
| PECAM-1 | | M28526 | inflammation |
| LFA-1 | | Y00796 | inflammation |
| TACE | | | inflammation |
| LFA-3 | | X06296<br>Y00636 | inflammation |
| CD-18 | | | inflammation |
| ICAM-3 | | X69819 | inflammation |
| ICAM-2 | | X15606 | inflammation |
| CD11a | | M87662 | inflammation |
| protein kinase C-α | | | cancer |
| protein kinase C-β | | X52479 | cancer |
| protein kinase C-δ | | | cancer |
| protein kinase C-ε | | Z22521 | cancer |
| protein kinase C-h | | X65293 | cancer |
| protcin kinase C-m | | M55284 | cancer |
| protein kinase C-ζ | | | cancer |
| unknown | | Z15108 | unknown |
| unknown | ornithine decarboxylase mRNA | X55362 | cancer |
| unknown | IL-2 mRNA | X01586 | inflammation |
| unknown | IL-4 | M13982 | inflammation |

Additional nucleic acid targets may be determined independently or can be selected from publicly available prokaryotic and eukaryotic genetic databases known to those skilled in the art. Preferred databases include, for example, Online Mendelian Inheritance in Man (OMIM), the Cancer Genome Anatomy Project (CGAP), GenBank, EMBL, PIR, SWISS-PROT, and the like. OMIM, which is a database of genetic mutations associated with disease, was developed, in part, for the National Center for Biotechnology Information (NCBI). OMIM is publicly available through the Internet at the world wide web at, for example, ncbi.nlm.nih.gov/Omim/. CGAP, which is an interdisciplinary program to establish the information and technological tools required to decipher the molecular anatomy of a cancer cell. CGAP is publicly available through the Internet at the world wide web at, for example, ncbi.nlm.nih.gov/ncicgap/. Some of these databases may contain complete or partial nucleotide sequences. In addition, nucleic acid targets can also be selected from private genetic databases. Alternatively, nucleic acid targets can be selected from available publications or can be determined especially for use in connection with the present invention.

After a nucleic acid target is selected or provided, the nucleotide sequence of the nucleic acid target is determined and then compared to the nucleotide sequences of a plurality of nucleic acids from different taxonomic species. In one embodiment of the invention, the nucleotide sequence of the nucleic acid target is determined by scanning at least one genetic database or is identified in available publications. Preferred databases known and available to those skilled in the art include, for example, the Expressed Gene Anatomy Database (EGAD) and Unigene-Homo Sapiens database (Unigene), GenBank, and the like. EGAD contains a non-redundant set of human transcript (HT) sequences and is publicly available through the Internet at the world wide web at, for example, tigr.org/tdb/egad/egad.html. Unigene is a system for automatically partitioning GenBank sequences into a non-redundant set of gene-oriented clusters. Each Unigene cluster contains sequences that represent a unique gene, as well as related information such as the tissue types in which the gene has been expressed and map location.

In addition, Unigene contains hundreds of thousands of novel expressed sequence tag (EST) sequences. Unigene is publicly available through the Internet at the world wide web at, for example, ncbi.nlm.nih.gov/UniGene/. These databases can be used in connection with searching programs such as, for example, Entrez, which is known and available to those skilled in the art, and the like. Entrez is publicly available through the Internet at the world wide web at, for example, ncbi.nlm.nih.gov/Entrez. Preferably, the most complete nucleic acid sequence representation available from various databases is used. The GenBank database, which is known and available to those skilled in the art, can also be used to obtain the most complete nucleotide sequence. GenBank is the NIH genetic sequence database and is an annotated collection of all publicly available DNA sequences. GenBank is described in, for example, Nuc. Acids Res., 1998, 26, 1–7, which is incorporated herein by reference in its entirety, and can be accessed by those skilled in the art through the Internet at the world wide web at, for example, ncbi.nlm.nih.gov/Web/Genbank/index.html. Alternatively, partial nucleotide sequences of nucleic acid targets can be used when a complete nucleotide sequence is not available.

In another embodiment of the present invention, the nucleotide sequence of the nucleic acid target is determined by assembling a plurality of overlapping expressed sequence tags (ESTs). The EST database (dbEST), which is known and available to those skilled in the art, comprises approximately one million different human mRNA sequences comprising from about 500 to 1000 nucleotides, and various numbers of ESTs from a number of different organisms. dbEST is publicly available through the Internet at the world wide web at, for example, ncbi.nlm.nih.gov/dbEST/index.html. These sequences are derived from a cloning strategy that uses cDNA expression clones for genome sequencing. ESTs have applications in the discovery of new genes, mapping of genomes, and identification of coding regions in genomic sequences. Another important feature of EST sequence information that is becoming rapidly available is tissue-specific gene expression data. This can be extremely useful in targeting selective gene(s) for therapeutic intervention. Since EST sequences are relatively short, they must be assembled in order to provide a complete sequence. Because every available clone is sequenced, it results in a number of overlapping regions being reported in the database.

Figure 2:
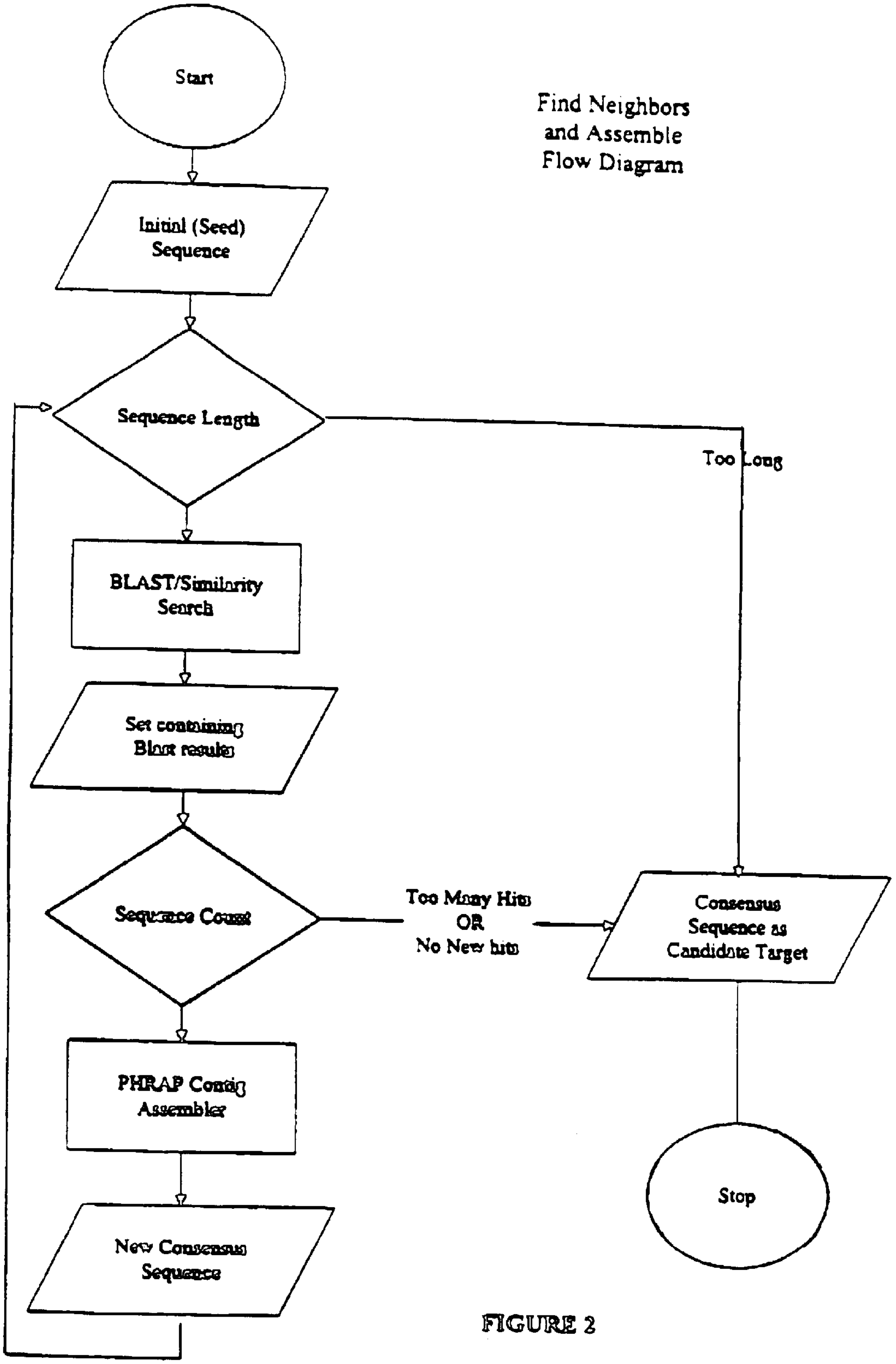
FIG. 2 is a flowchart describing a preferred set of procedures in the Find Neighbors And Assemble ESTBlast protocol.

Assembly of overlapping ESTs extended along both the 5' and 3' directions results in a full-length "virtual transcript." The resultant virtual transcript may represent an already characterized nucleic acid or may be a novel nucleic acid with no known biological function. The Institute for Genomic Research (TIGR) Human Genome Index (HGI) database, which is known and available to those skilled in the art, contains a list of human transcripts. TIGR is publicly available through the Internet at the world wide web at, for example, tigr.org/. The transcripts were generated in this manner using TIGR-Assembler, an engine to build virtual transcripts and which is known and available to those skilled in the art. TIGR-Assembler is a tool for assembling large sets of overlapping sequence data such as ESTs, BACs, or small genomes, and can be used to assemble eukaryotic or prokaryotic sequences. TIGR-Assembler is described in, for example, Sutton, et al., *Genome Science & Tech.,* 1995, 1, 9–19, which is incorporated herein by reference in its entirety, and is publicly available through the Internet via file transfer program at, for example tigr.org/pub.software/TIGRassembler. In addition, GLAXO-MRC, which is known and available to those skilled in the art, is another protocol for constructing virtual transcripts. In addition, "Find Neighbors and Assemble EST Blast" protocol, which runs on a UNIX platform, has been developed by Applicants to construct virtual transcripts. Preferred steps in the Find Neighbors and Assemble EST Blast protocol is described in the flowchart set forth in FIG. 2. PHRAP is used for sequence assembly within Find Neighbors and Assemble EST Blast. PHRAP is publicly available through the Internet at, for example, chimera.biotech.washington.edu/uwgc/tools/phrap.htm. One skilled in the art can construct source code to carry out the preferred steps set forth in FIG. 2.

The nucleotide sequence of the nucleic acid target is compared to the nucleotide sequences of a plurality of nucleic acids from different taxonomic species. A plurality of nucleic acids from different taxonomic species, and the nucleotide sequences thereof, can be found in genetic databases, from available publications, or can be determined especially for use in connection with the present invention. In one embodiment of the invention, the nucleic acid target is compared to the nucleotide sequences of a plurality of nucleic acids from different taxonomic species by performing a sequence similarity search, an ortholog search, or both, such searches being known to persons of ordinary skill in tile art.

The result of a sequence similarity search is a plurality of nucleic acids having at least a portion of their nucleotide sequences which are homologous to at least an 8 to 20 nucleotide region of the target nucleic acid, referred to as the window region. Preferably, the plurality of nucleotide sequences comprise at least one portion which is at least 60% homologous to any window region of the target nucleic acid. More preferably, the homology is at least 70%. More preferably, the homology is at least 80%. Most preferably, the homology is at least 90%. For example, the window size, the portion of the target nucleotide to which the plurality of sequences are compared, can be from about 8 to about 20, preferably 10–15, most preferably about 11–12, contiguous nucleotides. The window size can be adjusted accordingly. A plurality of nucleic acids from different taxonomic species is then preferably compared to each likely window in the target nucleic acid until all portions of the plurality of sequences is compared to the windows of the target nucleic acid. Sequences of the plurality of nucleic acids from different taxonomic species which have portions which are at least 60%, preferably at least 70%, more preferably at least 80%, or most preferably at least 90% homologous to any window sequence of the target nucleic acid are considered as likely homologous sequences.

Sequence similarity searches can be performed manually or by using several available computer programs known to those skilled in the art. Preferably, Blast and Smith-Watermnan algorithms, which are available and known to those skilled in the art, and the like can be used. Blast is NCBI's sequence similarity search tool designed to support analysis of nucleotide and protein sequence databases. Blast is publicly available through the Internet at the world wide web at, for example, ncbi.nlm.nih.gob/BLAST/. The GCG Package provides a local version of Blast that can be used either with public domain databases or with any locally available searchable database. GCG Package v.9.0 is a commercially available software package that contains over 100 interrelated software programs that enables analysis of sequences by editing, mapping, comparing and aligning them. Other programs included in the GCG Package include, for example, programs which facilitate RNA secondary structure predictions, nucleic acid fragment assembly, and evolutionary analysis. In addition, the most prominent genetic databases (GenBank, EMBL, PIR, and SWISS-PROT) are distributed along with the GCG Package and are fully accessible with the database searching and manipulation programs. GCG is publicly available through the Internet at the world wide web at, for example, gcg.com/. Fetch is a tool available in GCG that can get annotated GenBank records based on accession numbers and is similar to Entrez. Another sequence similarity search can be performed with GeneWorld and GeneThesaurus from Pangea. GeneWorld 2.5 is an automated, flexible, high-throughput application for analysis of polynucleotide and protein sequences. GeneWorld allows for automatic analysis and annotations of sequences. Like GCG, GeneWorld incorporates several tools for homology searching, gene finding, multiple sequence alignment, secondary structure prediction, and motif identification. GeneThesaurus 1.0 tm is a sequence and annotation data subscription service providing information from multiple sources, providing a relational data model for public and local data.

Another alternative sequence similarity search can be performed, for example, by BlastParse. BlastParse is a PERL script running on a UNIX platform that automates the strategy described above. BlastParse takes a list of target accession numbers of interest and takes each one through the preferred processes described in the flowchart set forth in FIG. 3. BlastParse parses all the GenBank fields into "tab-delimited" text that can then be saved in a "relational database" format for easier search and analysis, which provides flexibility. The end result is a series of completely parsed GerLBank records that can be easily sorted, filtered, and queried against, as well as an annotations-relational database.

Another toolkit capable of doing sequence similarity searching and data manipulation is SEALS, also from NCBI. This tool set is written in perl and C and can run on any computer platform that supports these languages. It is publicly available through the Internet at the world wide web at, for example, ncbi.nlm.nih.gov/Walker/SEALS/. This toolkit provides access to Blast2 or gapped blast. It also includes a tool called tax_collector which, in conjunction with a tool called tax_break, parses the output of Blast2 and returns the identifier of the sequence most homologous to the query sequence for each species present. Another useful tool is feature2fasta which extracts sequence fragments from an input sequence based on the annotation. An exemplary use for this tool is to create sequence files containing the 5' untranslated region of a cDNA sequence.

Figure 3:
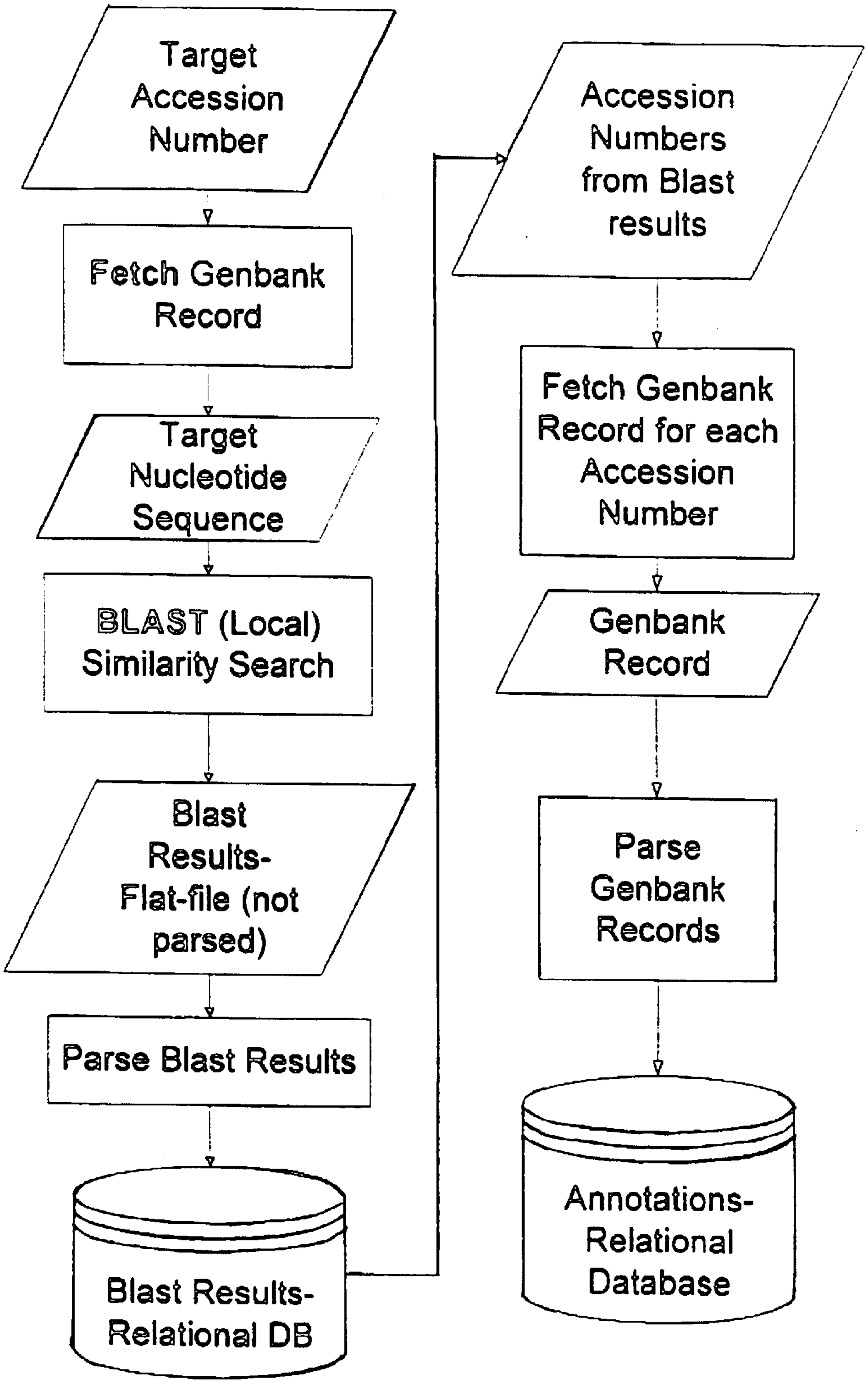
FIG. 3 is a flowchart describing preferred steps in the BlastParse protocol.

Preferably, the plurality of nucleic acids from different taxonomic species which have homology to the target nucleic acid, as described above in the sequence similarity search, are further delineated so as to find orthologs of the target nucleic acid therein. An ortholog is a term defined in gene classification to refer to two genes in widely divergent organisms that have sequence similarity, and perform similar functions within the context of the organism. In contrast, paralogs are genes within a species that occur due to gene duplication, but have evolved new functions, and are also referred to as isotypes. Optionally, paralog searches can also be performed. By performing an ortholog search, an exhaustive list of homologous sequences from diverse organisms is obtained. Subsequently, these sequences are analyzed to select the best representative sequence that fits the criteria for being an ortholog. An ortholog search can be performed by programs available to those skilled in the art including, for example, Compare. Preferably, an ortholog search is performed with access to complete and parsed GenBank annotations for each of the sequences. Currently, the records obtained from GenBank are "flat-files", and are not ideally suited for automated analysis. Preferably, the ortholog search is performed using a Q-Compare program. Preferred steps of the Q-Compare protocol are described in the flowchart set forth in FIG. 4. The Blast Results-Relation database, depicted in FIG. 3, and the Annotations-Relational database, depicted in FIG. 3, are used in the Q-Compare protocol, which results in a list of ortholog sequences to compare in the interspecies sequence comparisons programs described below.

The above-described similarity searches provide results based on cut-off values, referred to as e-scores. E-scores represent the probability of a random sequence match within a given window of nucleotides. The lower the e-score, the better the match. One skilled in the art is familiar with e-scores. The user defines the e-value cut-off depending upon the stringency, or degree of homology desired, as described above. In embodiments of the invention where prokaryotic molecular interaction sites are identified, it is preferred that any homologous nucleotide sequences that are identified be non-human.

In another embodiment of the invention, the sequences required are obtained by searching ortholog databases. One such database is Hovergen, which is a curated database of vertebrate orthologs. Ortholog sets may be exported from this database and used as is, or used as seeds for further sequence similarity searches as described above. Further searches may be desired, for example, to find invertebrate orthologs. Hovergen is publicly available through the Internet via file transfer program at, for example, pbil.univ-lyon1.fr/pub/hovergen/. A database of prokaryotic orthologs, COGS, is available and can be used interactively through the Internet at the world wide web at, for example, ncbi.nlm.nih.gov/COG/.

In another embodiment of the present invention, the nucleotide sequences of a plurality of nucleic acids from different taxonomic species are compared to the nucleotide sequence of the target nucleic acid by performing a sequence similarity search using dbEST, or the like, and constructing virtual transcripts. Using EST information is useful for two distinct reasons. First, the ability to identify orthologs for human genes in evolutionarily distinct organisms in GenBank database is limited. As more effort is directed towards identifying ESTs from these evolutionarily distinct organisms, dbEST is likely to be a better source of ortholog information.

Second, the attempt to sequence human genome is less than 10% complete. Thus, it is likely that the human dbEST will provide more information for identifying primary targets as the sequence of the human genome nears completion. EST sequences are short and need to be assembled to be used. Preferably, a sequence similarity search is performed using Smith-Waterman algorithms, as described above, under high stringency against dbEST excluding human sequences. Because dbEST contains sequencing errors, including insertions and deletions, in order to accurately search for new sequences, the search method used should allow for these gaps. Because every available clone is sequenced, it results in a number of overlapping regions being reported in the database. A full-length or partial "virtual transcript" for non-human RNAs is constructed by a process whereby overlapping EST sequences arc extended along both the 5' and 3' directions, until a "full-length" transcript is obtained. In another embodiment of the invention, a chimeric virtual transcript is constructed.

The resultant virtual transcript may represent an already characterized RNA molecule or could be a novel RNA molecule with no known biological function. As described above, TIGR HG1 database makes available an engine to build virtual transcripts called TIGR-Assembler. GLAXO-MRC and GeneWorld from Pangea provide for construction of virtual transcripts as well. As described above, Find Neighbors and Assemble EST Blast can also be used to build virtual transcripts.

Referring to FIG. 1, after the orthologs or virtual transcripts described above are obtained through either the sequence similarity search or the ortholog search, at least one sequence region which is conserved among the plurality of nucleic acids from different taxonomic species and the target nucleic acid is identified, 20. Interspecies sequence comparisons can be performed using numerous computer programs which are available and known to those skilled in the art. Preferably, interspecies sequence comparison is performed using Compare, which is available and known to those skilled in the art. Compare is a GCG tool that allows pair-wise comparisons of sequences using a window/stringency criterion. Compare produces an output file containing points where matches of specified quality are found. These can be plotted with another GCG tool, DotPlot.

Figure 4:
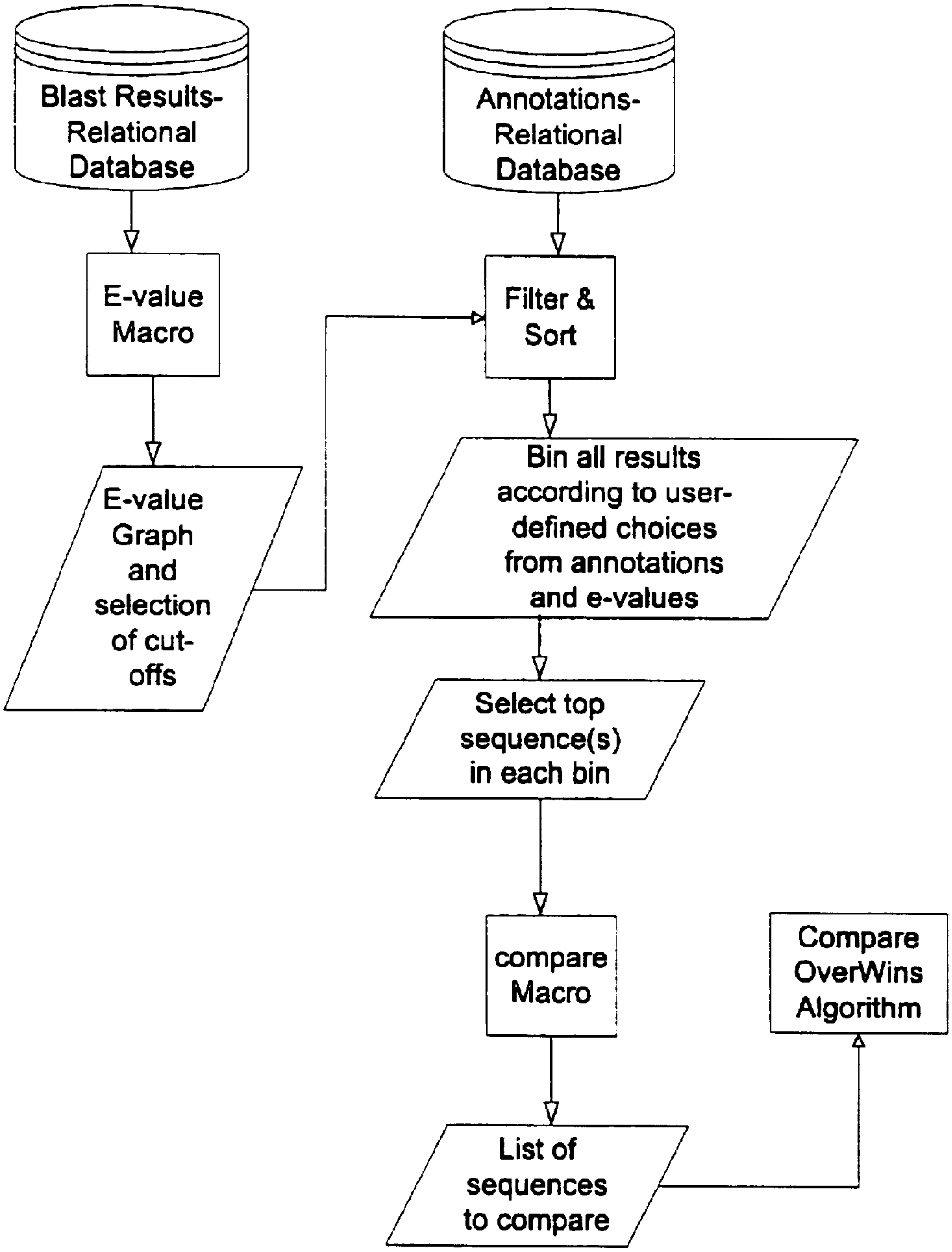
FIG. 4 is a flowchart describing preferred steps in the Q-Compare protocol.
Figure 5A:
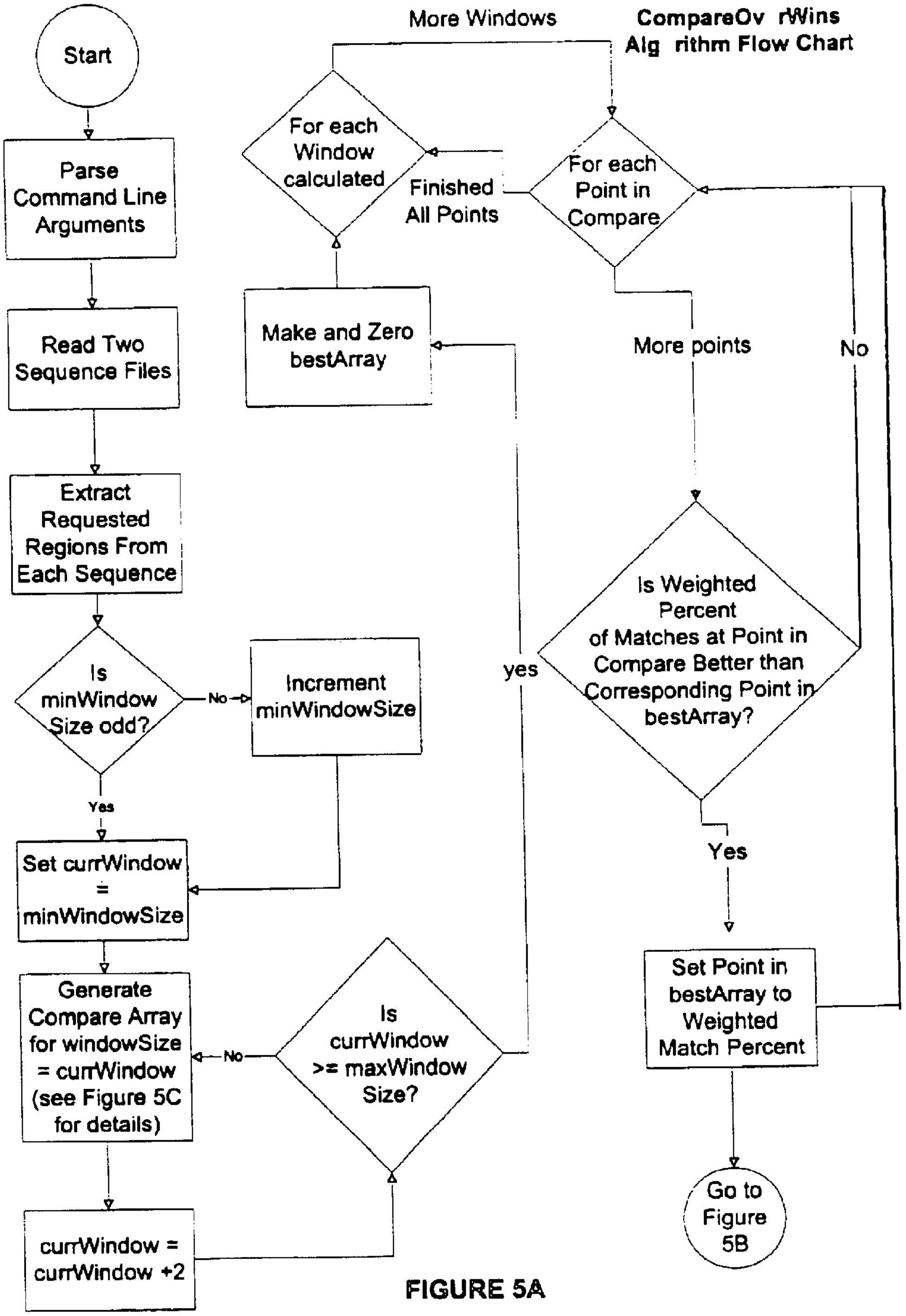
FIGS. 5A, 5B, 5C and 5D illustrate flowcharts describing preferred steps in the CompareOverWins protocol.
Figure 5B:
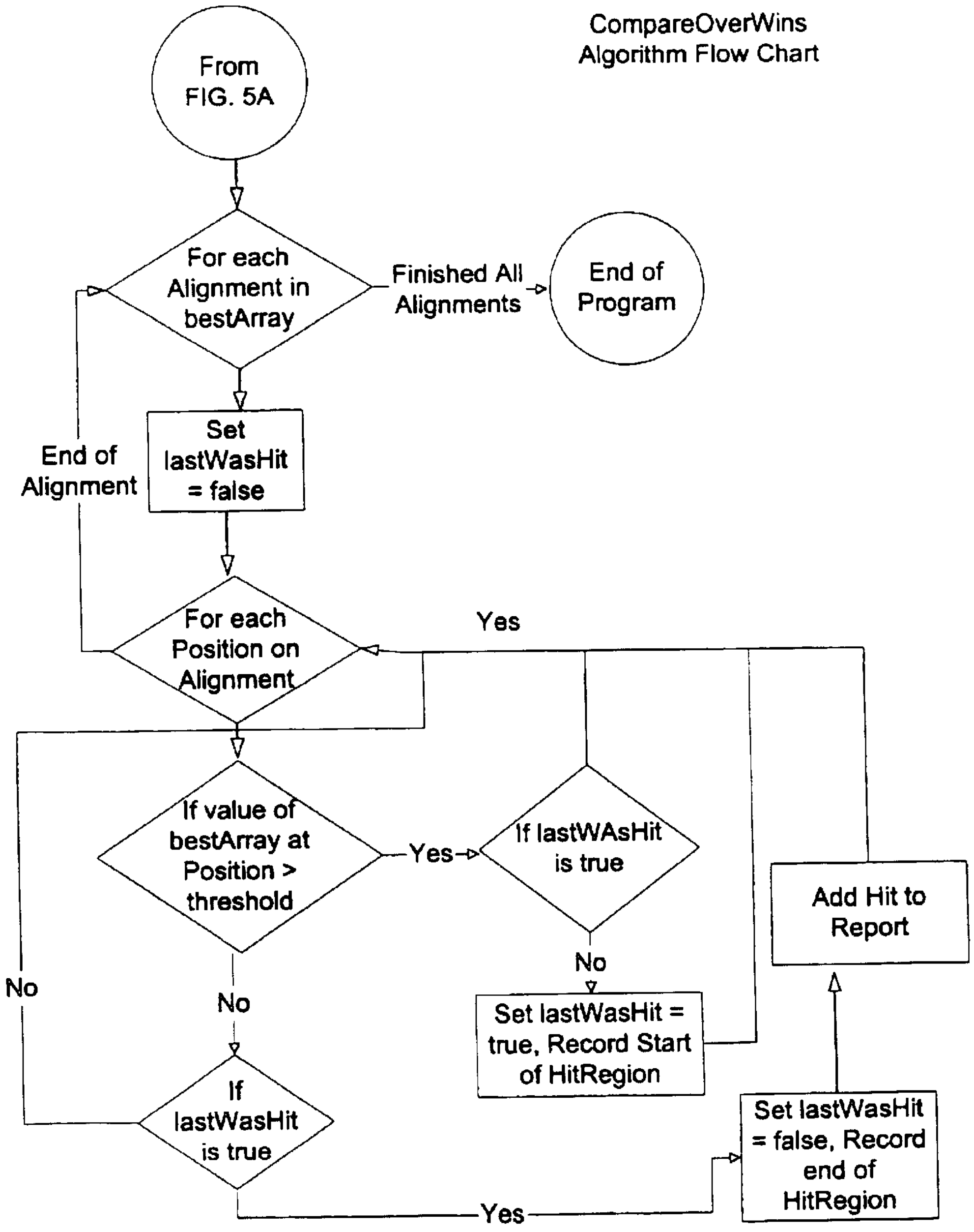
Figure 5C:
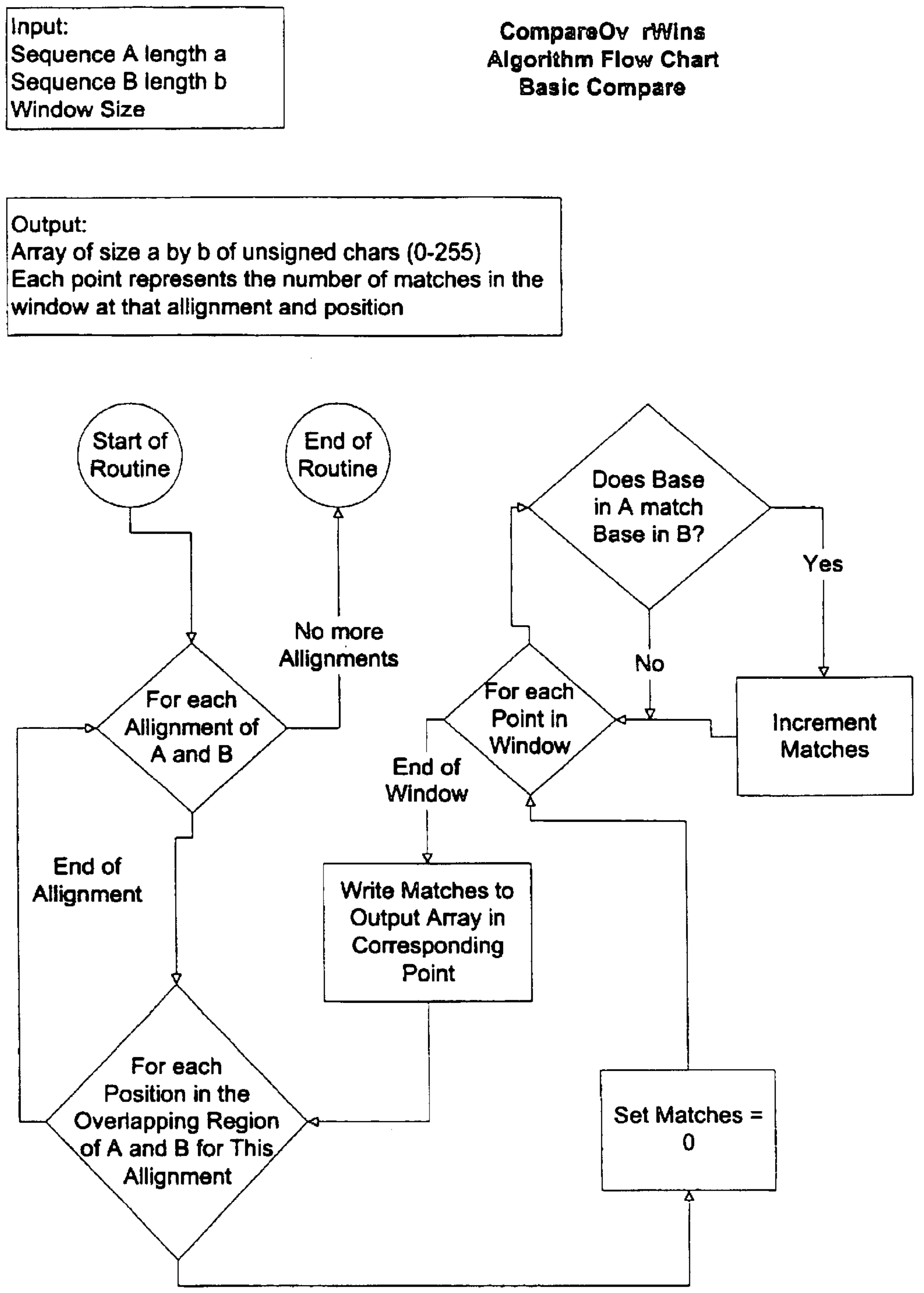

Alternatively, the identification of a conserved sequence region is performed by interspecies sequence comparisons using the ortholog sequences generated from Q-Compare in combination with CompareOverWins, as described above. Preferably, the list of sequences to compare, i.e., the ortholog sequences, generated from Q-Compare, as described in FIG. 4, is entered into the CompareOverWins algorithm. Preferred steps in the CompareOverWins are described in FIGS. 5A, 5B, and 5C. Preferably, interspecies sequence comparisons are performed by a pair-wise sequence comparison in which a query sequence is slid over a window on the master target sequence. Preferably, the window is from about 9 to about 99 contiguous nucleotides.

Figure 6:
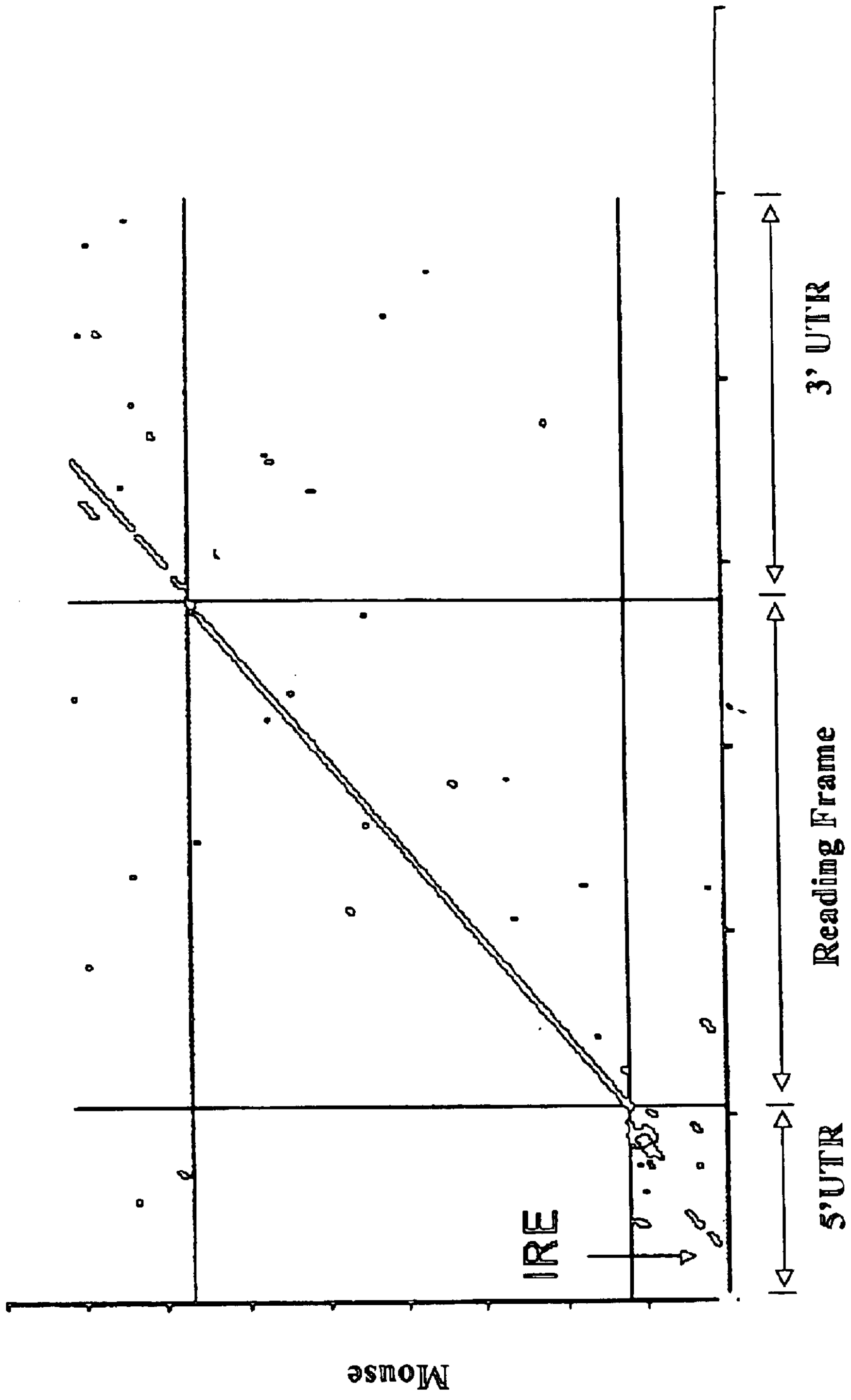
FIG. 6 is representative scatter plot of an interspecies sequence comparison between mouse and human for a ferritin RNA.

Sequence homology between the window sequence of the target nucleic acid and the query sequence of any of the plurality of nucleic acid sequences obtained as described above, is preferably at least 60%, more preferably at least 70%, more preferably at least 80%, and most preferably at least 90%. The most preferable method of choosing the threshold is to have the computer automatically try all thresholds from 50% to 100% and choose a threshold based a metric provided by the user. One such metric is to pick the threshold such that exactly n hits are returned, where n is usually set to 3. This process is repeated until every base on the query nucleic acid, which is a member of the plurality of nucleic acids described above, has been compared to every base on the master target sequence. The resulting scoring matrix can be plotted as a scatter plot. Based on the match density at a given location, there may be no dots, isolated dots, or a set of dots so close together that they appear as a line. The presence of lines, however small, indicates primary sequence homology. A representative scatter plot of such interspecies sequence comparison is depicted in FIG. 6. Sequence conservation within nucleic acid molecules, particularly the UTRs of RNA, in divergent species is likely to be an indicator of conserved regulatory elements that are also likely to have a secondary structure. The results of the interspecies sequence comparison can be analyzed using MS Excel and visual basic tools in an entirely automated manner as known to those skilled in the art.

Referring to FIG. 1, after at least one region that is conserved between the nucleotide sequence of the nucleic acid target and the plurality of nucleic acids from different taxonomic species, preferably via the orthologs, is identified, the conserved region is analyzed to determine whether it contains secondary structure, 30. Determining whether the identified conserved regions contain secondary structure can be performed by a number of procedures known to those skilled in the art. Determination of secondary structure is preferably performed by self complementarity comparison, alignment and covariance analysis, secondary structure prediction, or a combination thereof.

In one embodiment of the invention, secondary structure analysis is performed by alignment and covariance analysis. Numerous protocols for alignment and covariance analysis are known to those skilled in the art. Preferably, alignment is performed by ClustalW, which is available and known to those skilled in the art. ClustalW is a tool for multiple sequence alignment that, although not a part of GCG, can be added as an extension of the existing GCG tool set and used with local, sequences. ClustalW is publicly available through the Internet at, for example, dot.imgen.bcm.tmc.edu:9331/multialign/Options/clustalw.html. ClustalW is also described in Thompson, et al., *Nuc. Acids Res.,* 1994, 22, 4673–4680, which is incorporated herein by reference in its entirety. These processes can be scripted to automatically use conserved UTR regions identified in earlier steps. Seqed, a UNIX command line interface available and known to those skilled in the art, allows extraction of selected local regions from a larger sequence. Multiple sequences from many different species can be clustered and aligned for further analysis.

In a preferred embodiment of the invention, the output of all possible pair-wise CompareOverWindows comparisons are compiled and aligned to a reference sequence using a program called AlignHits. A diagram of the operation of this program is given in FIG. 5D.

This program could be reproduced by one skilled in the art. A preferred purpose of this program is to map all hits made in pair-wise comparisons back to the position on a reference sequence. This method combining CompareOverWindows and AlignHits provides more local alignments (over 20–100bases) than any other algorithm. This local alignment is required for the structure finding routines described later such as covariation or RevComp. This algorithm writes a fasta file of aligned sequences. As shown, the algorithm does not correct single base insertions or deletions. This is usually accomplished by putting the output through ClustalW described elsewhere. It is important to differentiate this from using ClustalW by itself, without CompareOverWindows and AlignHits.

Covariation is a process of using phylogenetic analysis of primary sequence information for consensus secondary structure prediction. Covariation is described in the following references, each of which is incorporated herein by reference in their entirety: Gutell, et al., "Comparative Sequence Analysis Of Experiments Performed During Evolution" In Ribosomal RNA Group I Introns, Green, Ed., Austin:Landes, 1996; Gautheret, et al., *Nuc. Acids Res.,* 1997, 25, 1559–1564; Gautheret, et al., *RNA,* 1995, 1, 807–814; Lodmell, et al., *Proc. Natl. Acad. Sci. USA,* 1995, 92, 10555–10559; Gautheret, et al., *J. Mol. Biol.,* 1995, 248, 27–43; Gutell, *Nuc. Acids Res.,* 1994, 22, 3502–3517; Gutell, *Nuc. Acids Res.,* 1993, 21, 3055–3074; Gutell, *Nuc. Acids Res.,* 1993, 21, 3051–3054; Woese, *Proc. Natl. Acad. Sci. USA,* 1989, 86, 3119–3122; and Woese, et al., *Nuc. Acids Res.,* 1980, 8, 2275–2293. Preferably, covariance software is used for covariance analysis. Preferably, Covariation, a set of programs for the comparative analysis of RNA structure from sequence alignments, is used. Covariation uses phylogenetic analysis of primary sequence information for consensus secondary structure prediction. Covariation is publicly available through the Internet at the world wide web at, for example mbio.ncsu.edu/RNaseP/info/programs/programs.html. A complete description of a version of the program has been published (Brown, J. W. 1991 Phylogenetic analysis of RNA structure on the Macintosh computer. CABIOS7:391–393). The current version is v4.1, which can perform various types of covariation analysis from RNA sequence alignments, including standard covariation analysis, the identification of compensatory base-changes, and mutual information analysis. The program is well-documented and comes with extensive example files. It is compiled as a stand-alone program; it does not require Hypercard (although a much smaller 'stack' version is included). This program will run in any Macintosh environment running MacOS v7.1 or higher. Faster processor machines (68040 or PowerPC) is suggested for mutual information analysis or the analysis of large sequence alignments.

In another embodiment of the invention, secondary structure analysis is performed by secondary structure prediction. There are a number of algorithms that predict RNA secondary structures based on thermodynamic parameters and energy calculations. Preferably, secondary structure prediction is performed using either M-fold or RNA Structure 2.52. M-fold is publicly available through the Internet at the world wide web at, for example, ibc.wustl.edu/-zuker/ma/form2.cgi or can be downloaded for local use on UNIX platforms. M-fold is also available as a part of GCG package. RNA Structure 2.52 is a windows adaptation of the M-fold algorithm and is publicly available through the Internet at, for example, 128.151.176.70/RNAstructure.html.

Figure 7:
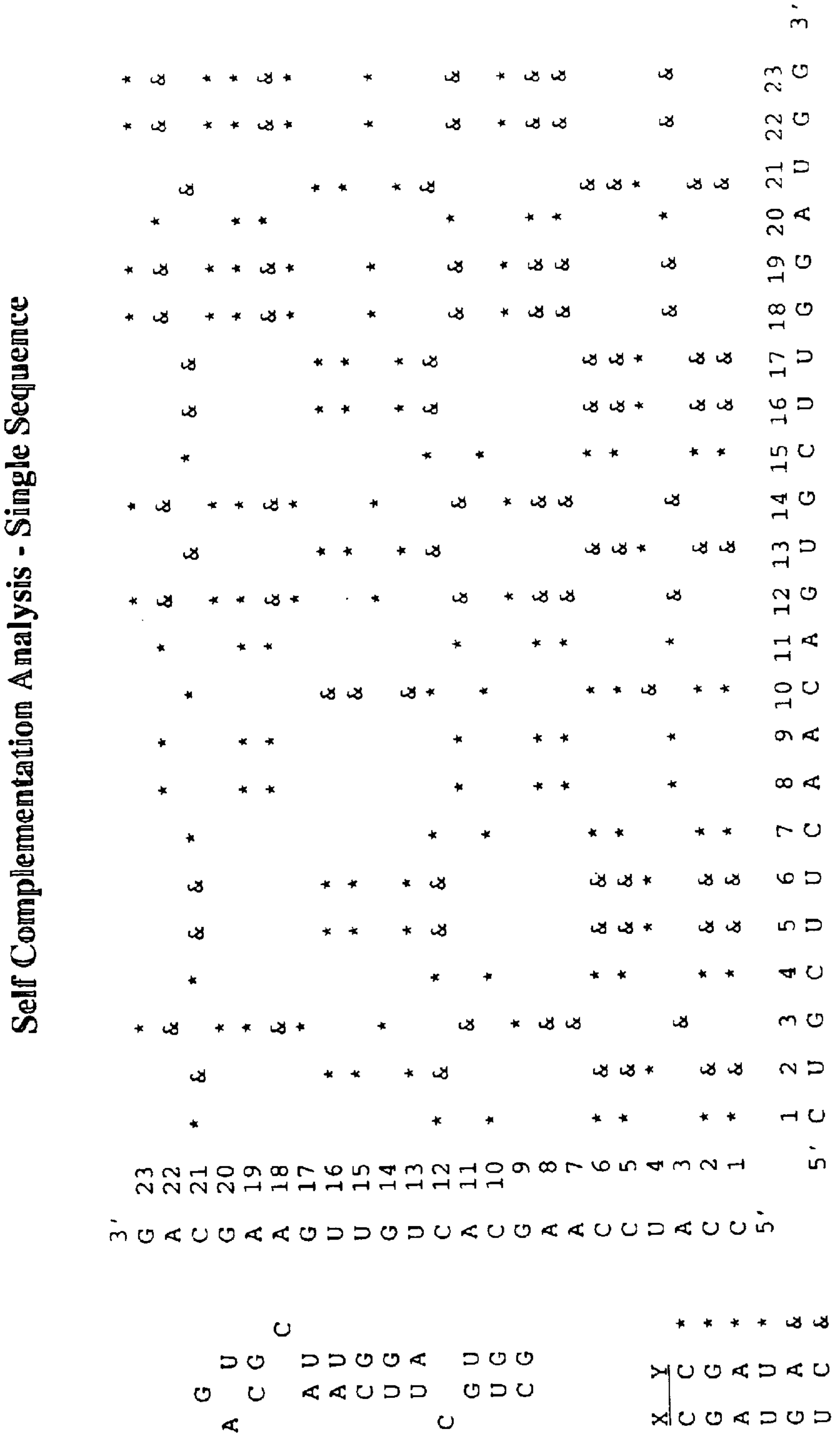
FIG. 7 shows an example of self complementation analysis of a single sequence.
Figure 8:
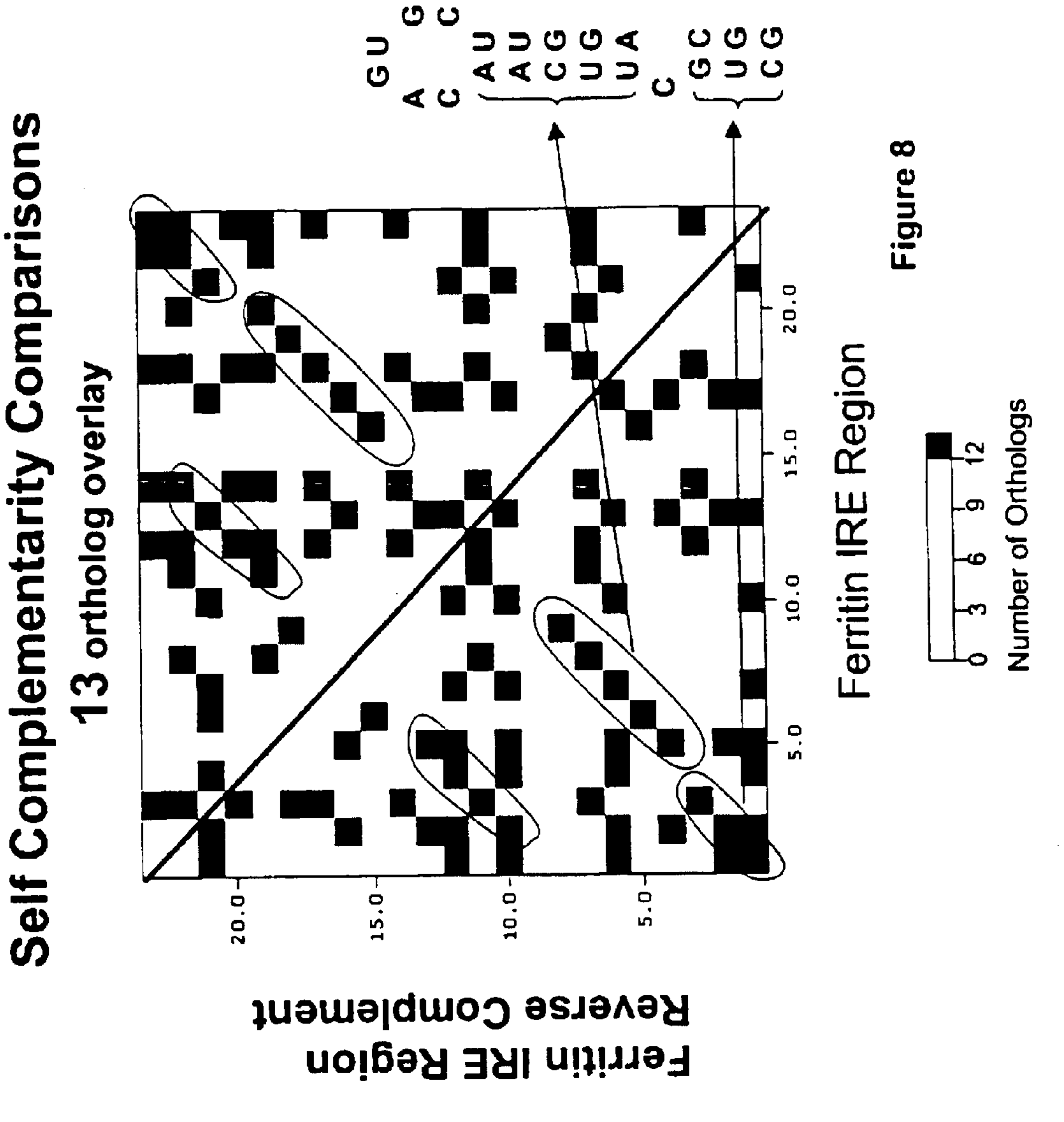
FIG. 8 shows an overlay of self-complementarity plots of certain orthologs, and selection for the most repetitive pattern in each, resulting in a minimal number of possible folded configurations as depicted in the diagonal strings of blocks.

In another embodiment of the invention, secondary structure analysis is performed by self complementarity comparison. Preferably, self complementarity comparison is performed using Compare, described above. More preferably, Compare can be modified to expand the pairing matrix to account for G-U or U-G basepairs in addition to the conventional Watson-Crick G-C/C-G or A-U/U-A pairs. Such a modified Compare program (modified Compare) begins by predicting all possible base-pairings within a given sequence. As described above, a small but conserved region, preferably a UTR, is identified based on primary sequence comparison of a series of orthologs. In modified Compare, each of these sequences is compared to its own reverse complement. FIG. 7 depicts an exemplary self complementarity analysis. Allowable base-pairings include Watson-Crick A-U, G-C pairing and non-canonical G-U pairing. An overlay of such self complementarity plots of all available orthologs, and selection for the most repetitive pattern in each, results in a minimal number of possible folded configurations. FIG. 8 shows an exemplary overlay. These overlays can then used in conjunction with additional constraints, including those imposed by energy considerations described above, to deduce the most likely secondary structure.

Figure 53:
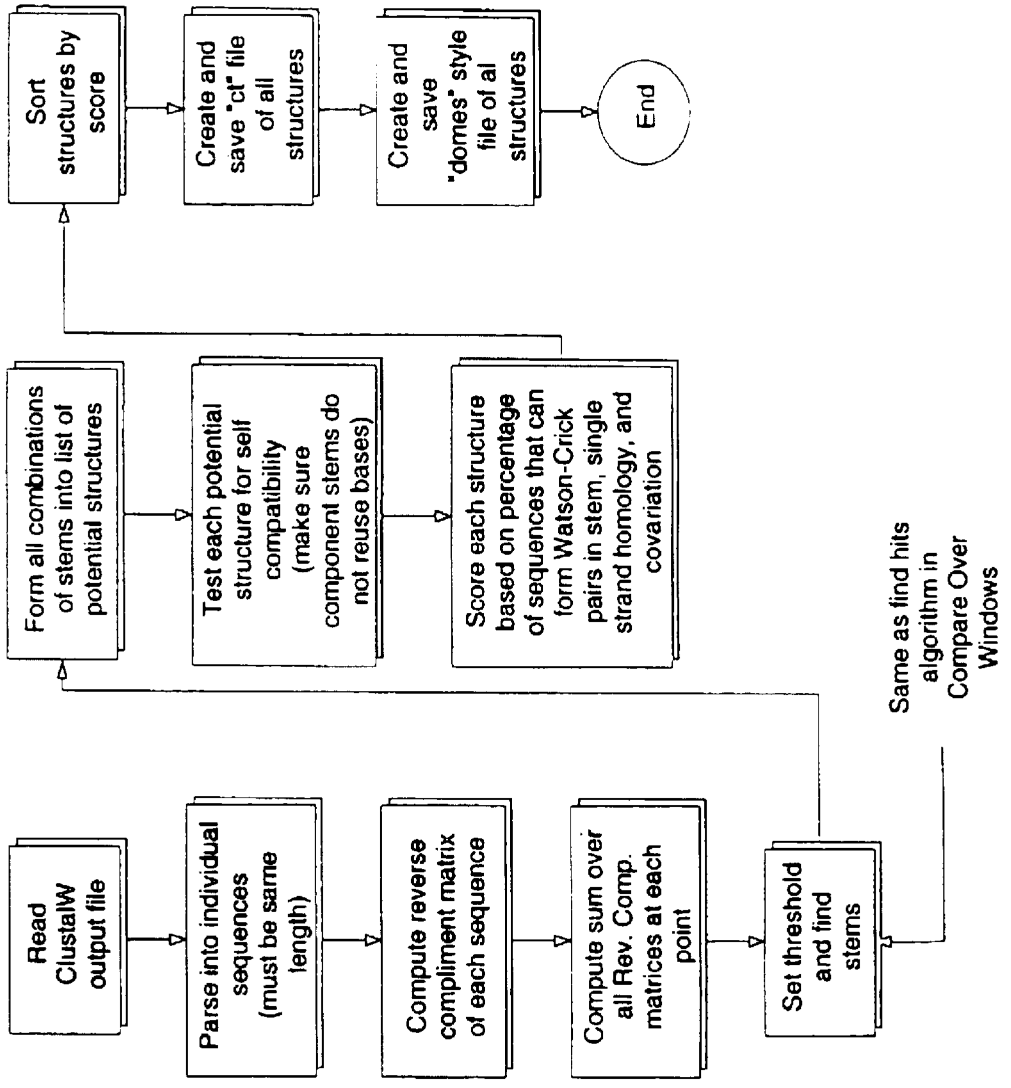
FIG. 53 shows a representative block diagram of a program called RevComp.
Figure 54:
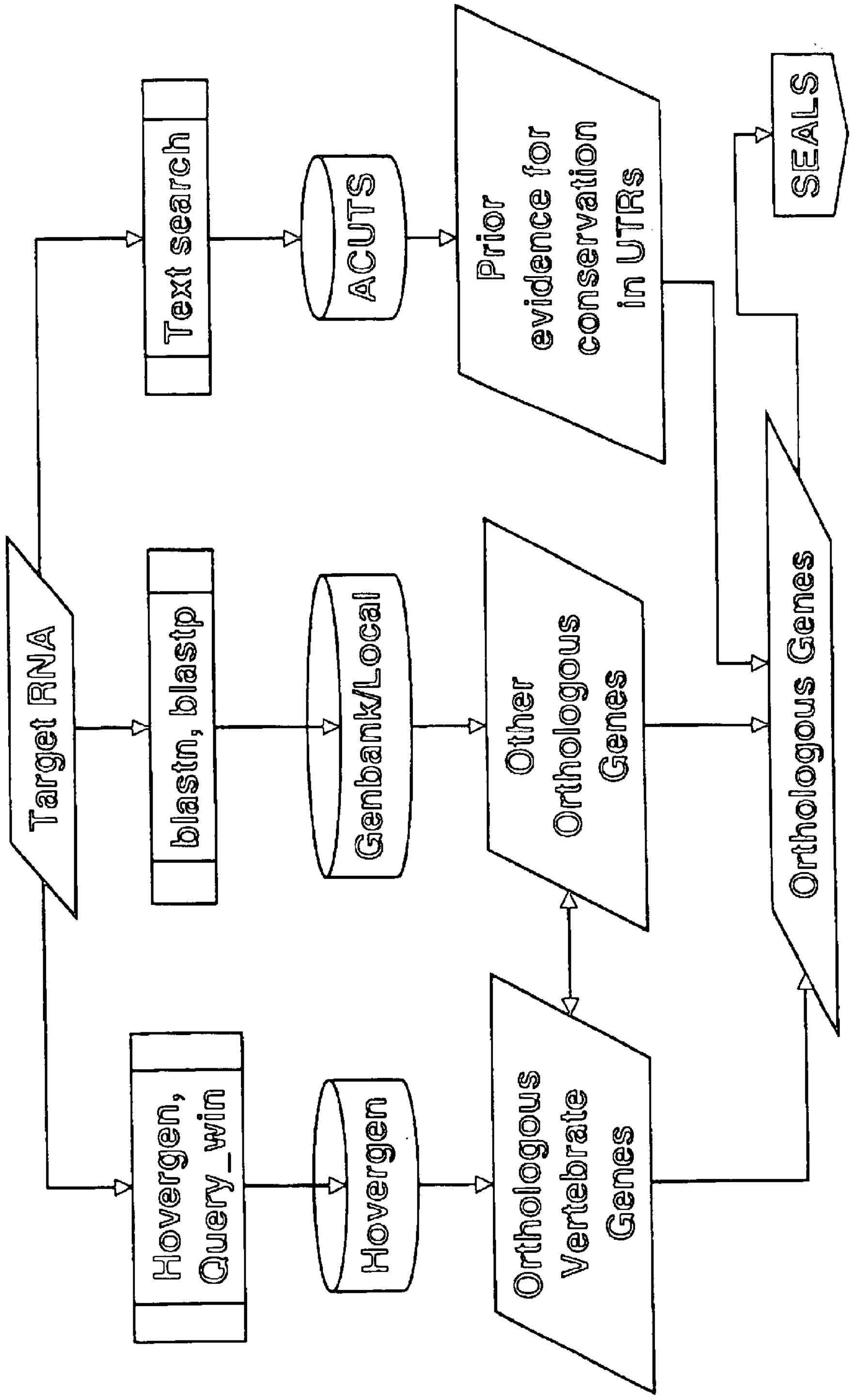
FIG. 54 shows a representative flow chart showing preferred steps of a preferred database search strategy for ortholog finding.

In another preferred embodiment of the invention, the output of AlignHits is read by a program called RevComp. A block diagram of this program is shown in FIG. 53. This program could be reproduced by one skilled in the art. A preferred purpose of this program is to use base pairing rules and ortholog evolution to predict RNA secondary structure. RNA secondary structures are composed of single stranded regions and base paired regions, called stems. Since structure conserved by evolution is searched, the most probable stem for a given alignment of ortholog sequences is the one which could be formed by the most sequences. Possible stem formation or base pairing rules is determined by, for example, analyzing base pairing statistics of sterns which have been determined by other techniques such as NMR. The output of RevComp is a sorted list of possible structures, ranked by the percentage of ortholog set member sequences which could form this structure. Because this approach uses a percentage threshold approach, it is insensitive to noise sequences. Noise sequences are those that either not true orthologs, or sequences that made it into the output of AlignHits due to high sequence homology even though they do not represent an example of the structure which is searched. A very similar algorithm is implemented using Visual basic for Applications (VBA) and Microsoft Excel to be run on PCs, to generate the reverse complement matrix view for the given set of sequences.

A result of the secondary structure analysis described above, whether performed by alignment and covariance, self complementarity analysis, secondary structure predictions, such as using M-fold or otherwise, is the identification of secondary structure in the conserved regions among the target nucleic acid and the plurality of nucleic acids from different taxonomic species, 40. Exemplary secondary structures that may be identified include, but are not limited to, bulges, loops, stems, hairpins, knots, triple interacts, cloverleafs, or helices, or a combination thereof. Alternatively, new secondary structures may be identified.

In another embodiment of the invention, once the secondary structure of the conserved region has been identified, as described above, at least one structural motif for the conserved region having secondary structure is identified. These structural motifs correspond to the identified secondary structures described above. For example, analysis of secondary structure by self complementation may provide one type of secondary structure, whereas analysis by M-fold may provide another secondary structure. All the possible secondary structures identified by secondary structure analysis described above are, thus, represented by a family of structural motifs.

Once the secondary structure(s) of the target nucleic acids, as well as the secondary structures of nucleic acids from different taxonomic species, have been identified, further nucleic acids can be identified by searching on the basis of structure, rather than by primary nucleotide sequence, as described above. Additional nucleic acids which have secondary structure similar or identical to the secondary structure found as described above can be identified by constructing a family of descriptor elements for the structural motifs described above, and identifying other nucleic acids having secondary structures corresponding to the descriptor elements. The combination of any or all of the nucleic acids having secondary structure can be compiled into a database. The entire process can be repeated with a different target nucleic acid to generate a plurality of different secondary structure groups which can be compiled into the database. Thus, databases of molecular interaction sites can be compiled by performing by the invention described herein.

Figure 9:
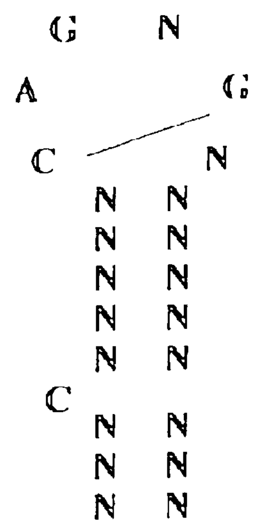
FIG. 9 shows an exemplary descriptor.

After the hypothetical structure motifs are determined from the secondary structure analysis described above, a family of structure descriptor elements is constructed. Preferably, the structural motifs described above are converted into a family of descriptor elements. An exemplary descriptor element is shown in FIG. 9. One skilled in the art is familiar with construction of descriptors. Structure descriptors are described in, for example, Laferrierc, et al., *Comput. Appl. Biosci.,* 1994, 10, 211–212, incorporated herein by reference in its entirety. A different structure descriptor element is constructed for each of the structural motifs identified from the secondary structure analysis. Briefly, the secondary structure is converted to a generic text string, such as shown in FIG. 9. For novel motifs, further biochemical analysis such as chemical mapping or mutagenesis may be needed to confirm structure predictions. Descriptor elements may be defined to have various stringency.

For example, referring to FIG. 9, the region termed H1, which comprises the first region of the stem, can be described as NNN:NNN, which contemplates any complementary base pairing including G-C, C-G, A-U, and U-A. The H1 region may also be designated so as to include only C-G or A-U, etc., base pairing. In addition, the descriptor elements can be defined to allow for a wobble. Thus, descriptor elements can be defined to have any level of stringency desired by the user. Applicants' invention, thus, is also directed to a database comprising different descriptor elements.

After a family of structure descriptor elements is constructed, nucleic acids having secondary structure which correspond to the structure descriptor elements are identified.

Preferably, nucleic acids having secondary structure which correspond to the structure descriptor elements are identified by searching at least one database, performing clustering and analysis, identifying orthologs, or a combination thereof. Thus, the identified nucleic acids have secondary structure which falls within tile scope of te secondary structure defined by the descriptor elements. Thus, the identified nucleic acids have secondary structure identical to nearly identical, depending on the stringency of the descriptor elements, to the target nucleic acid.

In one embodiment of the invention, nucleic acids having secondary structure which correspond to the structure descriptor elements are identified by searching at least one database. Any genetic database can be searched. Preferably, the database is a UTR database, which is a compilation of the untranslated regions in messenger RNAs. A UTR database is publicly available through the Internet via file transfer program at area.ba.cnr.it/pub/embnet/database/utr/. Preferably the database is searched using a computer program, such as, for example, Rnamot, a UNIX-based motif searching tool available from Daniel Gautheret. Each "new" sequence that has the same motif is then queried against public domain databases to identify additional sequences. Results are analyzed for recurrence of pattern in UTRs of these additional ortholog sequences, as described below, and a database of RNA secondary structures is built. One skilled in the art is familiar with Rnamot. Briefly, Rnamot takes a descriptor string, such as the one shown in FIG. 9, and searches any Fasta format database for possible matches. Descriptors can be very specific, to match exact nucleotide(s), or can have built-in degeneracy. Lengths of the stem and loop can also be specified. Single stranded loop regions can have a variable length. G-U pairings are allowed and can be specified as a wobble parameter. Allowable mismatches can also be included in the descriptor definition. Functional significance is assigned to the motifs if their biological role is known based on previous analysis. Known regulatory regions such as Iron Response Element have been found using this technique (see, Example 1 below). In embodiments of the invention in which a database containing prokaryotic molecular interaction sites is compiled, it is preferable to refrain from searching human sequences or, alternatively, discarding human sequences when found.

In another embodiment of the invention, the nucleic acids identified by searching databases such as, for example, searching a UTR database using Rnamot, are clustered and analyzed so as to determine their location within the genome. The results provided by Rnamot simply identify sequences containing the secondary structure but do not give any indication as to the location of the sequence in the genome. Clustering and analysis is preferably performed with ClustalW, as described above.

In another embodiment of the invention, after clustering and analysis is performed as described above, orthologs are identified as described above. However, in contrast to the orthologs identified above, which were solely identified on the basis of their primary nucleotide sequences, these new orthologous sequences are identified on the basis of structure using tile nucleic acids identified using Rnamot. Identification of orthologs is preferably performed by BlastParse or Q-Compare, as described above. In embodiments of the invention in which a database containing prokaryotic molecular interaction sites is compiled, it is preferable to refrain from finding human orthologs or, alternatively, discarding human orthologs when found.

After nucleic acids having secondary structures which correspond to the structure descriptor elements are identified, any or all of the nucleotide sequences can be compiled into a database by standard compiling protocols known to those skilled in the art. One database may contain eukaryotic molecule interaction sites and another database may contain prokaryotic molecule interaction sites The present invention is also directed to oligonucleotides comprising a molecular interaction site that is present in the RNA of a selected organism and in the RNA of at least one preferably several additional organisms. The nucleotide sequence of the oligonucleotide is selected to provide the secondary structure of the molecular interaction sites described above. The nucleotide sequence of the oligonucleotide is preferably the nucleotide sequence of the target nucleic acids described above. Alternatively, the nucleotide sequence is preferably the nucleotide sequence of nucleic acid from a plurality of different taxonomic species which also contain the molecular interaction site. The molecular interaction site serves as a binding site for at least one molecule which, when bound to the molecular interaction site, modulates the expression of the RNA in the selected organism.

The present invention is also directed to oligonucleotides comprising a molecular interaction site that is present in a prokaryotic RNA and in at least one additional prokaryotic RNA, wherein the molecular interaction site serves as a binding site for at least one molecule which, when bound to the molecular interaction site, modulates the expression of the prokaryotic RNA. The additional organism is selected from all eukaryotic and prokaryotic organisms and cells but is not the same organism as the selected organism. Oligonucleotides, and modifications thereof, are well known to those skilled in the art. The oligonucleotides of the invention can be used, for example, as research reagents to detect, for example, naturally occurring molecules which bind the molecular interaction sites. The oligonucleotides of the invention can also be used as decoys to compete with naturally-occurring molecular interaction sites within a cell for research, diagnostic and therapeutic applications. Molecules which bind to the molecular interaction site modulate, either by augmenting or diminishing, the expression of the RNA. The oligonucleotides can also be used in agricultural, industrial and other applications.

The present invention is also directed to pharmaceutical compositions comprising the oligonucleotides described above in combination with a pharmaceutical carrier. A "pharmaceutical carrier" is a pharmaceutically acceptable solvent, diluent, suspending agent or any other pharmacologically inert vehicle for delivering one or more nucleic acids to an animal, and are well known to those skilled in the art. The carrier may be liquid or solid and is selected, with the planned manner of administration in mind, so as to provide for the desired bulk, consistency, etc., when combined with the other components of a pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The present invention is directed to computational methods employed for the in silico design and synthesis of combinatorial libraries of small molecules. The library members are generated in silico. The present invention also encompasses methods for tracking and storing the information generated during the in silico creation of library members into relational databases for later access and use. For the purposes of this specification, in silico refers to the creation in a computer memory, i.e., on a silicon or other like chip. Stated otherwise in silico means "virtual."

According to the methods of the present invention, each compound or library member is dissected into its component or constituent parts referred to as fragments. Thus each compound that is generated is considered to be comprised of constituent fragments such that the sum of the molecular formulas of each of the fragments when added together totals the molecular formula of the compound generated. This dissection can be done in a variety of ways using chemical intuition. Thus a variety of components of fragments may be identified, each of which lend themselves to readily available reagents or reactions to generate diverse compounds. Further, each fragment is associated with at least one reagent, which represents the necessary chemical to be used to introduce that desired fragment into the compound being generated in silico. Dissection of compounds is based on the ease of synthesis of the reagents, commercial availability of the reagents, or a combination of both. Each of the fragments and reagents are stored in a relational database and are described in terms of identifying characteristics in the database. A fragment may be available from a variety of starting materials or reaction schemes. So when a library is being generated, which entails building a database, the fragments used in building that library can be stored in the database using the corresponding set of reagents and reaction conditions. When another library is to be generated, the fragment information stored in the database is now available for use in the generation of the new library of compounds. Similarly, when a third library is being generated, an even greater quantity of fragment, reagent, and reaction information is available in the database. Thus the methods of the present invention represent a dynamic method of building a database associated with building libraries of compounds. Initial library generation requires database input for fragments, reagents and transformations necessary for desired library. As tile database grows, however, an increasing number of fragments and reagents are available in the database, which simplifies the generation of subsequent libraries of compounds and makes for more routine combinatorial synthetic efforts which can be accomplished with increasing ease and efficacy. Fragments that are recorded in the database may be defined using identifying characteristics. Identifying characteristics defining fragments include a structural representation (as a 2-dimensional or 3-dimensional file), name, molecular weight, molecular formula, and attachment points or nodes (which denote sites of attachment or linkage of the fragment to other fragments of the compound being generated iii silico). For the purpose of describing this invention, 2-dimensional representations are used, which are further simplified by the use of symbolic representations without reference to any particular chemical entities. The symbolic representations as used herein merely shows how fragments can be tracked to further the methods of the present invention. Other identifying characteristics may also be added to the database. Any characteristic that is desired to be tracked may be included ill the database, including biological data, chemical reactivity rates, or other physical or chemical properties. Further, a fragment may also be created by modifying a reagent, and such modifications can be added to the database in terms of changes made to the reagent structure. Some of the identifying characteristics associated with any fragment may be common to those of the corresponding reagent. The related fragment thus created can then be stored in the relational database.

Identifying characteristics defining reagents include a structural representation, name, molecular weight, molecular formula, and source, such as a commercial source or a unique compound defined by the user. In case of a commercial source for the reagent, a catalog number or a link to a web page can be provided. Some commonalities may exist between the identifying characteristics associated with a reagent anti those associated with the related fragment.

Further, in accordance with the present invention, a compound is the sum of various transformations. Transformation is the nomenclature attributed according to the present invention to a chemical synthesis. A transformation is a 1:1 link between a fragment and a reagent. Thus each transformation describes a unique conversion of a reagent into the corresponding fragment as introduced into a compound. When the compound being generated in silico is broken down into its component fragments, and the corresponding reagents have been identified, each fragment is linked to the corresponding reagent in a 1:1 relationship in order to describe a transformation. Thus, according to the present invention, a transformation may be viewed as the source of a fragment, thereby linking that fragment to a particular synthetic method or reaction. This description of a transformation according to the methods of the present invention also includes any auxiliary reagents or conditions used to effect the reaction denoted by the transformation, such as temperature and pressure requirements, catalysts, activators, solvents, or other additives.

Each combination of a fragment and reagent in a 1:1 link comprises a different transformation. Therefore, each transformation is unique The present invention allows the tracking of fragments in terms of the reaction or transformation in which those fragments are introduced into the compounds of the library. Thus the database describes not only the compounds generated in terms of their constituent fragments, but also in terms of the synthetic pathways to produce those compounds, i.e. the related transformations to generate the library compounds. In this manner, a user of the present invention can generate a virtual library of compounds by simply selecting the fragments desired. Alternately, a user can also generate the compounds by selecting the chemical pathways required for actual synthesis of the compounds. This is accomplished by selecting the appropriate transformation associated with the generation of the desired compounds. Here, the user uses intuition or an in silico expert system to assist in selecting those transformations that are expected to allow generation or synthesis of the desired compounds. Each of the transformations created in silico is stored in the relational database and described in terms of identifying characteristics. Identifying characteristics defining transformations include the fragment, the reagent, and any auxiliary reagent or conditions necessary to effect the conversion of the reagent into the fragment as incorporated into the compound.

For example, consider in FIG. 14 the in silico generation of compound CI according to the methods of the present invention. As shown in FIG. 14, upon dissection of CI (molecular formula of $C_{12}H_{18}N_2O_5S_i$), its constituent fragments can be denoted as F, (molecular formula of $H_2NO$), $F_{ii}$ (molecular formula of $C_5H_9NO$), and $F_{iii}$ (molecular formula of $C_7H_7O_3S$). $F_i$ can also be a hydroxylamine moiety linked to a solid support, i.e. P—O—NH, wherein P is a solid support. The sum of the molecular formulas of each of the fragments totals the molecular formula of compound CI.

As shown in FIG. 15, each of the fragments, $F_i$, $F_{ii}$, and $F_{iii}$, are stored in a relational database, and are described in terms of identifying characteristics including a structural representation (which may be 2-dimensional or 3-dimensional), an identifier or name, molecular formula and attachment points or nodes which signify sites on the fragment which are linked to other fragments in compound CI. Other information such as molecular weight can also be associated with the fragment in the database.

As shown in FIG. 16, each of the corresponding reagents ($R_i$, $R_{ii}$, and $R_{iii}$) are also stored in the relational database, and described in terms of identifying characteristics. Identifying characteristics used to define the reagents include a structural representation, and identifier or name and molecular formula. As with the fragment, other associated information such as molecular weight and source (such as a commercial source verses user-supplied, amount on hand, special handling, etc.) can also be stored in database in association with the individual reagents.

Next, each of the transformations associated with the in silico generation of compound CI are also stored in the relational database. As shown in FIG. 17, transformation $T_i$ links reagent $R_i$ with fragment $F_i$, $T_{ii}$ links $R_{ii}$ with $F_{ii}$, and $T_{iii}$ links $R_{iii}$ with $F_{iii}$ in a 1:1 relationship. Also, associated with each transformation is the necessary reation condition, so that transformation $T_i$ is associated with reaction condition alpha, $T_{ii}$ with reaction condition beta, and $T_{iii}$ with reaction condition gamma. In the case of transformation $T_{iii}$, reagent $R_{iii}$ may be a hydroxylamine attached to a solid support so that fragment $F_{iii}$ can be represented as a hydroxylamine moiety attached to a solid support.

Figure 18:
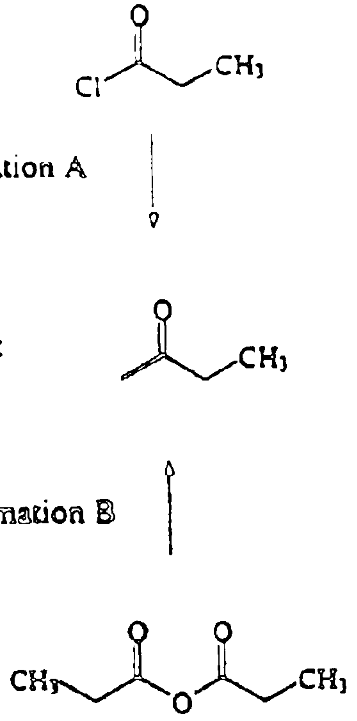
FIG. 18 is a schematic for the introduction of a common fragment using two different reagents.

While each fragment may be arrived at or generated by a unique corresponding reagent, the present invention also encompasses common fragments that may be generated via two or more reagents, so that two or more transformations can lead to the same fragment. As shown in FIG. 18, the common fragment $CH_3—CH_2—C(=O)—$ may be arrived at via transformation A, which employs reagent X (an acid chloride), $CH_3—CH_2—C(=O)Cl$. The common fragment can also be introduced into a compound being generated in silico via transformation B, which employs reagent Y (an acid anhydride), $CH_3—CH_2—C(=O)—O—C(=O)—CH_2—CH_3$. Therefore, in accordance with the methods of the present invention, a common fragment can be introduced into the compound via two or more different reagents, and thus via two or more distinct transformations.

Figure 19A:
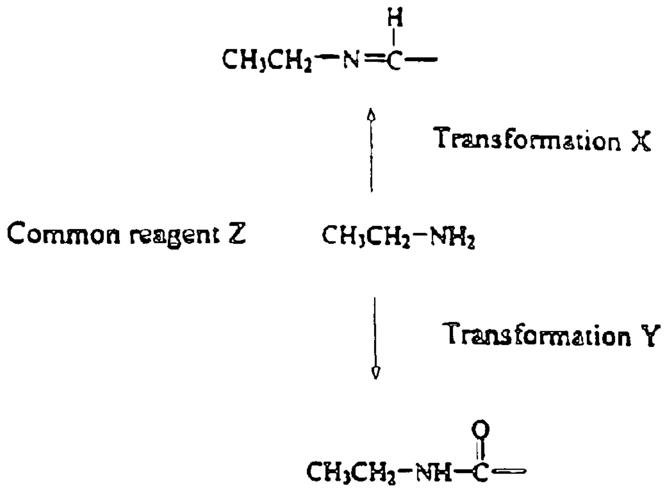
FIG. 19A is a schematic for the use of a single reagent for the introduction of two different fragments into a compound.

Alternately, a common reagent may be employed to effect two or more conversions forming two or more different fragments. This then represents two or more different transformations associated with different conditions. For example, as shown in FIG. 19A, common reagent Z, $CH_3—CH_2—NH_2$, can be employed to introduce an alkene fragment into the compound under conditions favoring Schiff's base formation. This represents transformation X. The same common reagent Z, however, can also be employed to introduce an amide fragment into the compound by using a different set of conditions, constituting transformation Y. Thus, a common reagent can introduce two or more different fragments into final compounds being generated in silico, and can he associated with two or more transformations depending upon the conditions associated with each of those transformations.

Figure 19B:
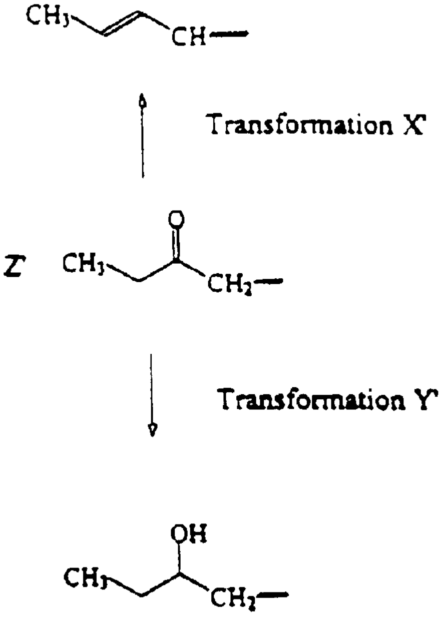
FIG. 19B is a schematic showing the use of a common reagent for the introduction of a common fragment into the compound which can further be converted into two different fragments within the compound generated.

Additionally, once a fragment has been introduced into a compound, it can be further modified and converted into yet another fragment without effecting any other chemical changes within the compound formed. As an example, shown in FIG. 19B, consider common reagent Z', $CH_3—CH, —C(=O)CH_2—Cl$. Common reagent Z' corresponds to a fragment having the structure $CH_3—CH_2—C(=O)CH_2—$. Common reagent Z' may be used to introduce an alkene fragment into the final compound, representing transformation X', under conditions favoring reduction and dehydration. Common reagent Z', however, can also be used to introduce a hydroxyalkyl fragment into the final compound under conditions favoring reduction. This represents transformation Y'.

The present invention may be described more generally, in terms of symbolic representations. Symbolic representations are used to describe the methods of the present invention because such representations are not limited to any particular chemistry. Symbolic representations merely denote the manner of using the present invention with multiple chemical entities. Each symbol used in the representations describing the present invention may represent one compound or multiple compounds because the present invention is not limited to tracking a single compound, but may be used to track a vast variety of compounds that can be generated.

FIG. 20 shows the symbolic addition of fragments which yields compound C1'. The fragments have structures $F_i$, $F_{ii}$, and $F_{iii}$ that are added sequentially to yield compound C1'. Structures $F_i$, $F_{ii}$, and $F_{iii}$, are symbolic representations of the fragments that constitute compound C1'. These fragments can be stored in the relational database with the corresponding identifying characteristics for each of them, including the structural representation, name, molecular formula, and attachment sites or nodes. A visual inspection of compounds C1 and C1'°revels the commonality between the chemical compound C1 and the symbolic representation of a compound C1' as well as the chemical structure of the fragments and the symbolic structure of the fragments.

A symbolic reagent table is shown in FIG. 21. Reagents R1 to R10 can be described in terms of their structure, name, molecular formula, molecular weight, and source as well as other information that might be desired to be associated with the reagents. R3 and R4 are two different reagents, but may be used to introduce the same fragment into a compound. This depends upon the reaction conditions used as reagent R3 is used in a transformation associated with one set of conditions, while reagent R4 is used in another transformation associated with a different set of conditions. Also, reagent R5 is comprised of a mixture of two reagents or components. These may be (R)- and (S)-stereoisomers, D- and L-isomers, or may be two completely different reagents. While R5 here is represented as a mixture of only two reagents or components, it will be recognized by the art-skilled that thc methods of the present invention may be practiced using a mixture of two or more reagents. Typical reagent mixtures used in constructing libraries might have four, five or more individual reagent constituting the mixture.

FIG. 22 shows a symbolic fragment table. Fragments F1 to F8 are stored in the relational database with identifying characteristics that include a structural representation, name, molecular weight, molecular formula, and attachment sites or nodes. This table depicts symbolic representations of the various fragments that are introduced into the compounds of the library by the use of reagents symbolized in FIG. 21. Thus it can be seen that fragment F1 can be introduced into the compound by employing reagent R1. In fragment F1, X is an identifier for an attachment site. This indicates that X is the site at which F1 attaches to another fragment in a compound. Similarly, fragment F2 may be introduced into a compound (attaching at its X site) by employing reagent R2.

Fragment F3, however, can be introduced into the compound by the use of either reagent R3 or R4. This allows for selection in the choice of the reagent used, and also allows for the consideration of the compatibility of the chemistries involved in the introduction of other fragments into the compound. Next, fragment F4 (which is a mixture of fragments) can be introduced via the use of reagent R5, which is a mixture of reagents, as shown in FIG. 21.

Fragment F5 has two attachment sites, indicating that other fragments can attach at sites X and Y when F5 has been incorporated into a compound. The presence of two attachment sites indicates that two attachments may be undertaken to build a compound when dealing with F5. Here again, as before, F5 can be introduced into the compound using either of reagents R6 or R7, depending upon the reaction conditions used and the chemistries involved when introducing other fragments to build the compound.

Fragments F7 and F8 can be introduced into a compound being created in silico by employing reagents R9 and R10, respectively. Both these fragments have three attachment sites, indicating that three attachments to other fragments can occur when using these fragments to build a compound in silico. While fragments F7 and F8 have three attachment sites, it is recognized by the art-skilled that more than three attachment sites may be present in a fragment, allowing for more attachments to the fragment upon introduction into a compound (with the use of an appropriate reagent).

With the fragment and reagent tables in place in the relational database, a transformation table is created in accordance with the methods of the present invention, by linking a fragment with a reagent to form a unique transformation. FIG. 23 shows a symbolic transformation table where a fragment is linked to a reagent in a 1:1 relationship. The identifying characteristics describing each transformation include a 1:1 link (a one to one link) between a fragment and a reagent, and the reaction conditions which include, solvent, concentration, temperature and pressure requirements, or auxiliary reagents necessary to effect the introduction of the fragment into the compound by using an appropriate reagent. Auxiliary reagents include catalysts, activators, acids, bases or other chemicals or additives necessary to effect the fragment introduction described. For example a base can always be added with an alkyl halide to scavenge the acid generated with use of the alkyl halide.

As seen in FIG. 23, transformation T1 links fragment F1 with reagent R1. T1 also specifies the reaction conditions (a) associated with this 1:1link. Similarly, T2 links F2 with R2 under conditions A. Transformations T3 and T4 are each unique transformations despite being associated with a common fragment, F3: Transformation T3 links common fragment F3 with reagent R3 under conditions a, while transformation T4 links the common fragment F3 with another reagent, R4, under the different conditions, conditions δ. For example reagent R3 might be an alkyl chloride while R4 might be an alkyl iodide. While these reagents are similar (they are both alkyl halides), they might be used under different reaction conditions. Use of different reagents to effect the introduction of the same fragment into the compound being generated in silico represents two unique transformations. This indicates two distinct or unique synthetic ways of introducing the same fragment into the compound. Depending upon the totality of the chemical steps involved in synthesizing the compound, one transformation may be preferred over other transformations that introduce the same fragment into the compound.

Transformation T5 links fragment F4 with reagent R5. R5 is a mixture of reagents, such as (R)- and (S)-stereoisomers, D- and L-isomers, or two or more different reagents. As a result, use of R5 leads to the introduction of a mixture of fragments F4 into the compound. The art-skilled will recognize that the multiple reagents in R5 are selected such that they are capable of being mixed together, do not react with each other, and react under similar reaction conditions. For example, R5 may be comprised of a mixture of acid halides. These do not react with each other, but do react similarly with a nucleophile under similar conditions. It is also recognized by the art-skilled that a reagent is not limited to only one or two components or constituent reagents, but in fact may comprise of two, three, four, five or more reagents or components.

When using a mixture of reagents, each of the individual component reagents may have different chemical reactivity rates. If a correction is not made for this, this could result in their products being unequally represented in the product compounds. This is solved by adjusting the concentration of each reagent in the reaction mixture relative to the other reagents in the mixture such that the relative rates are the same. This is effected by comparing to the reactivity of each of the reagents to a chosen standard reagent. The standardized reactivity rates can then be used to adjust the concentration of each constituent reagent in the reagent mixture to compensate for the varied reaction rates. Thus a mixture of reagents with different reaction rates may be used in one reagent mixture to still generate equivalent quantities of the desired compounds in the library.

Transformations T6 and T7 are similar to transformations T3 and T4 except that conditions identifying each of these transformations are different. Transformation T6 links fragment F5 with reagent R6 under conditions e, while transformation T7 links the same fragment F5 with a different reagent R7 under different conditions (condition a). As the conditions associated with transformations T6 and T7 are different, this allows selection of compatible chemistries with other fragments during any particular synthesis being used. This is a very useful and very important consideration in actually synthesizing real libraries. When it is desired to introduce fragment F5 into tile compound, the actual chemistries used to build the compound can be initially be considered in selecting transformation T6 or T7, and thus reagents R6 or R7. This is in direct opposition to any chemical database generator that only considers the compound structure not the actual chemistries necessary to build a compound.

Transformations T9 and T 10 link fragment F7 with reagent R9 and fragment F8 with reagent R10, respectively. Both transformations are identified to be associated with reaction conditions g. Fragments F7 and F8 have three attachment sites, but it is recognized that these fragments may have more than three attachment sites, thereby increasing the complexity of the compounds generated, and increasing the number of rounds that may be employed to attach other fragments. For the three sites illustrated, if three sets of different reagent mixtures each have five reagents in the set are used, then 125 compounds will be generated for fragment F7 and a further 125 compounds will be generated for fragment F8.

Figure 24:
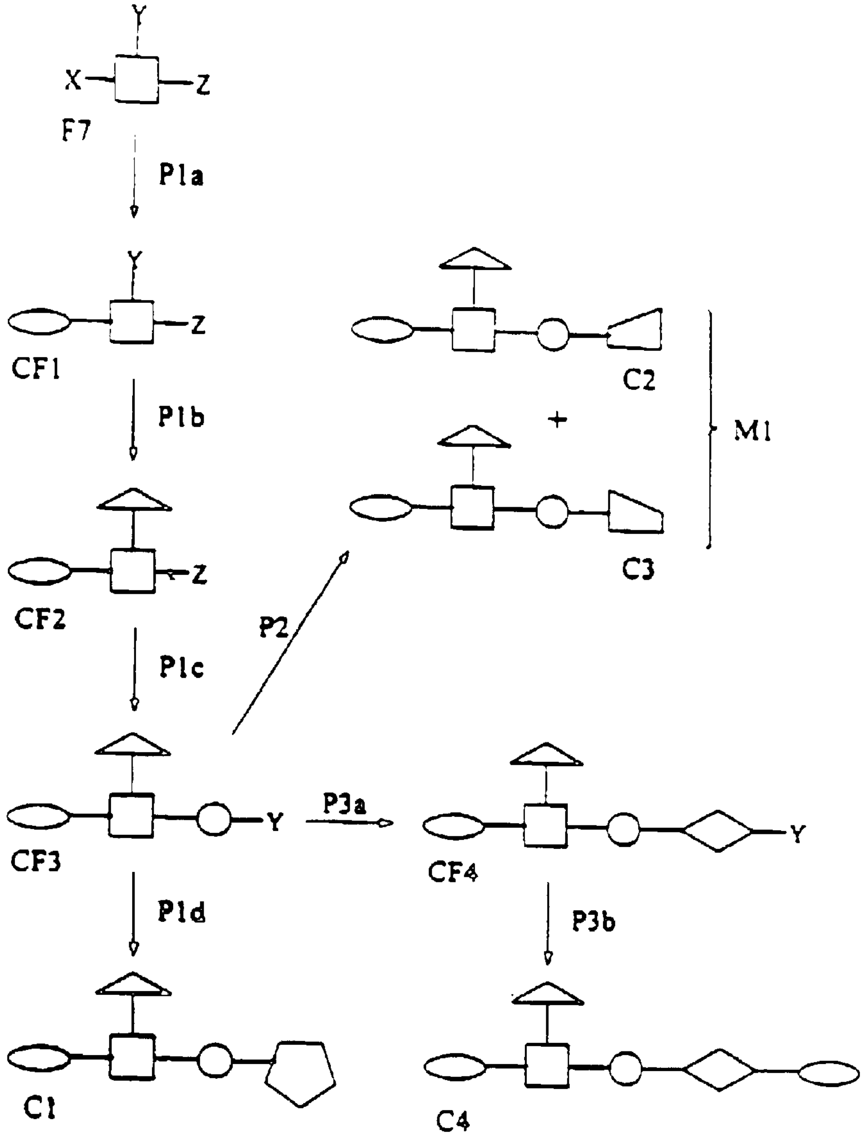
FIG. 24 shows the generation of individual compounds, compounds C1 and C4, and a mixture, mixture M1.
Figure 25:
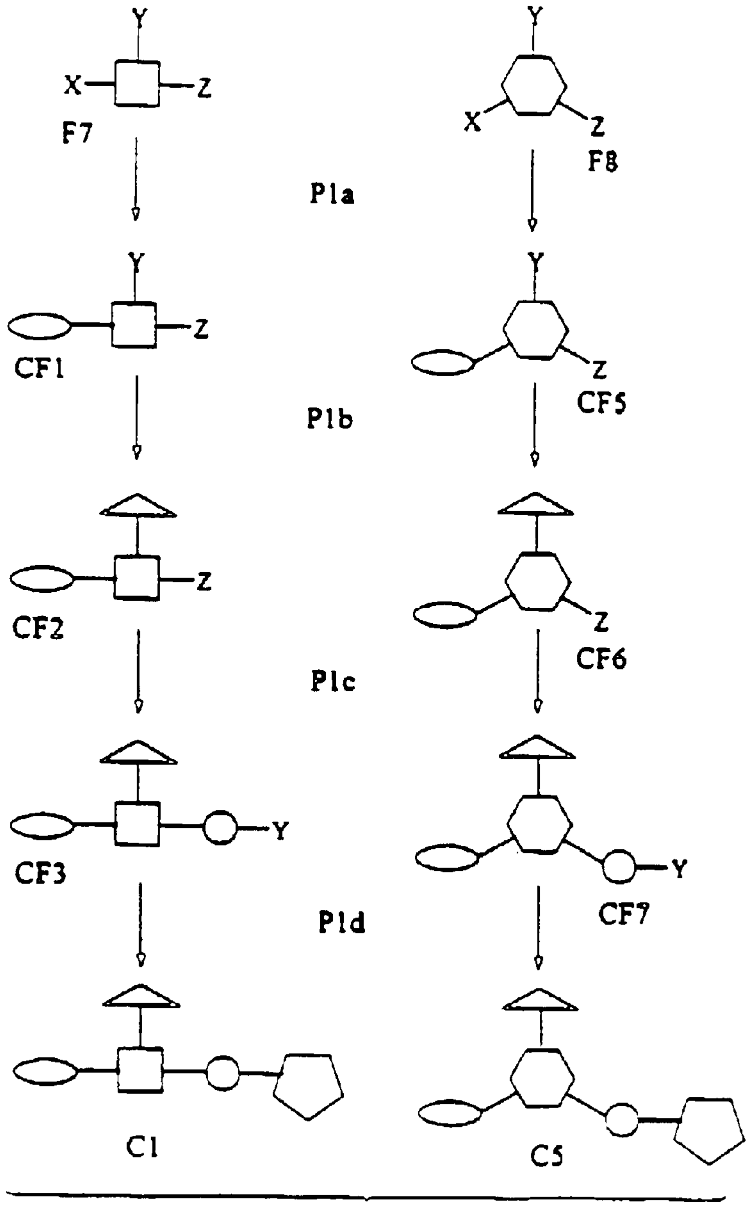
FIG. 25 shows the generation of further mixture, mixture M2.

The methods of the present invention may be used to generate single compounds or mixtures of compounds. A mixture comprises two or more compounds and may involve the use of two or more reagents (thus introduction of two or more fragments) at the outset of library generation, introduction of a mixture of reagents (thus a mixture of fragments) at a subsequent stage of library generation, or a combination of both such techniques. FIGS. 24 and 25 illustrate this aspect of the present invention.

As shown in FIG. 24, the methods of the present invention may be used to generate single compounds such as C1 and C4, or may also be used to generate a mixture of compounds, M1, comprising compounds C2 and C3. Library generation commences with selecting fragment F7 (with three attachment sites), in the first round (i.e. round n). In the second synthesis round (i.e. round n+1), F7 is combined with fragment F2, constituting synthetic pathway P1 a, and resulting in the formation of complex fragment CF1. F7 possesses three attachment sites (i.e. X, Y and Z). Thus round n+1 will not be complete until each of X, Y and Z have been used, if desired, to attach other fragments to. Stepping around each of X, Y and Z, and attaching fragments to these sites, occurs in that sequential order. Once sites X, Y and Z of the fragment selected in the first synthesis round (i.e. round n) have been exhausted, stepping around the attachment sites present in the next added fragment constitutes the next synthesis round (i.e. the third synthesis round, or round n+2). Here again, when all desired attachment sites on this fragment have been used, that particular synthesis round is complete. This attachment iteration around the desired and available attachment sites of the fragments added continues until the desired compounds have been generated.

As shown in FIG. 24, CF1 is next subjected to synthetic pathway P1 b wherein fragment F1 is introduced into CF1, thereby forming complex fragment CF2. CF2 is then subjected to synthetic pathway P1c wherein fragment F5 is added to CF2, leading to the formation of complex fragment CF3. This completes synthesis round n+1 (i.e. the second round of fragment introduction, or synthesis, to build the compound). As fragment F5 has two attachment sites, CF3 has an available attachment site (i.e. site Y). Introduction of fragments to this site (Y site) constitutes synthesis round n+2 (i.e. the third round) because all the desired attachment sites on the previously added fragment have been exhausted. Next, CF3 is subjected to synthetic pathway P2 wherein fragment F4 is introduced into CF3 at attachment site Y. As F4 is a mixture of two components, a mixture (M1) of two compounds, C2 and C3, is generated.

A single compound, however, may also be generated using the present scheme of fragment introduction. Thus, compound C1 can be generated by subjecting CF3 to synthetic pathway P1d wherein CF3 is combined with fragment F3, which attaches to site Y in CF3. The introduction of fragment F3 into CF3 constitutes the third synthesis round (i.e. round n+2), leading to the generation of C1.

Alternately, CF3 can be subjected to synthetic pathway P3a wherein fragment F6 is introduced into CF3 to form CF4. This represents the third synthesis round (i.e. round n+2). CF4 has one more available attachment site (i.e. site Y) to which fragment F2 may be attached via synthetic pathway P3b. This leads to the generation of compound C4 which is a compound of increased complexity because of the number of attachment sites on the chosen fragments and synthetic pathways employed. The addition of fragment F6 to CF4 constitutes the third synthesis round (i.e. round n+2). Addition of fragment F2 to CF4 represents the fourth synthesis round, or round n+3, because P3b involves addition of a fragment (fragment F2) onto a site (i.e. site Y in CF4) which has been generated by adding fragment F6 to CF3, thus exhausting the available attachment sites on the previously added fragment in CF4 (i.e. fragment F5). That is, the addition of fragment F6 completed round n+2 (or the third synthesis round) because F6 attached to the last available attachment site on CF3 (i.e. site Y in CF3).

For the reactions effected at path P1c in FIG. 24, a single fragment (F5) can be added to CF2 via use of either reagents R6 or R7 (as thus via the transformations associated with R6 and R7). While these additions are represented as two unique transformations for the purpose of tracking in the database on the invention, these additions in effect perform the same chemical conversion. Thus, the simultaneous tracking of compounds generated according to the methods of the invention is useful not only in working with virtual libraries of compounds, but also provide the user with a choice of synthetic pathways along which the compounds can be actually synthesized. This tracking aspect of the present invention is, therefore, a novel and unique way to account for the fragments being introduced, the related transformations (or reactions) associated with the fragments, and the alternate transformations that lead to the introduction of a common fragment into the desired compounds. The present invention allows not only the tracking of individual compounds that are generated by the use of multiple reagents, but also allows for the simultaneous tracking of multiple compounds that are generated via multiple transformations.

While the methods described herein represent the tracking aspects of the invention in terms of symbolic representations or tables, it is recognized by the art-skilled that a variety of computer algorithmic codes and techniques may be employed for the individual or simultaneous tracking aspects described above.

The present invention further provides methods for the one-pot generation of mixtures of compounds by commencing the library generation using different starting fragments in a one-pot fashion. One-pot generation or synthesis of compounds refers to the formation of multiple compounds in a single reaction vessel (i.e. one pot). This is possible if compatible chemistries are selected. Examples of such single vessels include but are not limited to multiple well plates, e.g. a 96-well plate, reactions flasks, e.g. a 25 mL flask, or even an industrial reactor. The reactions, or transformations, are performed in one vessel regardless of the size of the reaction vessel. The concept of one-pot synthesis is irrelevant to the generation of virtual libraries of compounds as these virtual libraries are merely generated in silico. The concept of one-pot synthesis becomes relevant, however, when the actual synthesis of libraries of compounds is to be undertaken. Thus the compounds can be tracked separately for compound building in order to generate distinct chemical structures, however, they can be group together for synthesis allowing them to be made in the same "pot."

An example of a one-pot synthesis was shown in FIG. 24 with the addition of the complex reagent R5 to form mixture M1. A further one-pot synthesis is shown in FIG. 25, where a further mixture of compounds is generated. Mixture M2 comprising compounds C1 and C5 can be generated by starting with fragments F7 and F8 in the first synthesis round (i.e. round n). Each of these fragments have three attachment sites onto which other fragments can be introduced. As a result, subjecting the two fragments to synthetic pathway p1a wherein F7 and F8 are combined with fragment F5 at site X, results in the one-pot formation of complex fragments CF1 and CF5. CF1 and CF5 are next subjected to synthetic pathway P1b wherein fragment F1 is introduced into CF1 and CF5 at site Y, thereby forming complex fragments CF2 and CF6. CF2 and CF6 are next subjected to synthetic pathway P1c wherein fragment F5 is introduced into these complex fragments at site Z, forming CF3 and CF7. This completes the second synthetic round (i.e. round n+1). As fragment FS contains two attachment sites, after introduction into CF3 and CF7, there is still available an attachment site (i.e. site Y) for further introduction of another fragment. Thus CF3 and CF7 are converted to a mixture (M2) of compounds C1 and C5 via synthetic pathway P1d wherein CF3 and CF7 are combined with fragment F3 which attaches to the Y site on fragment F5 in CF3 and CF7.

The introduction of fragment F3 at site Y in CF3 and CF7 represents the third synthetic round (i.e. round n+2).

Figure 26:
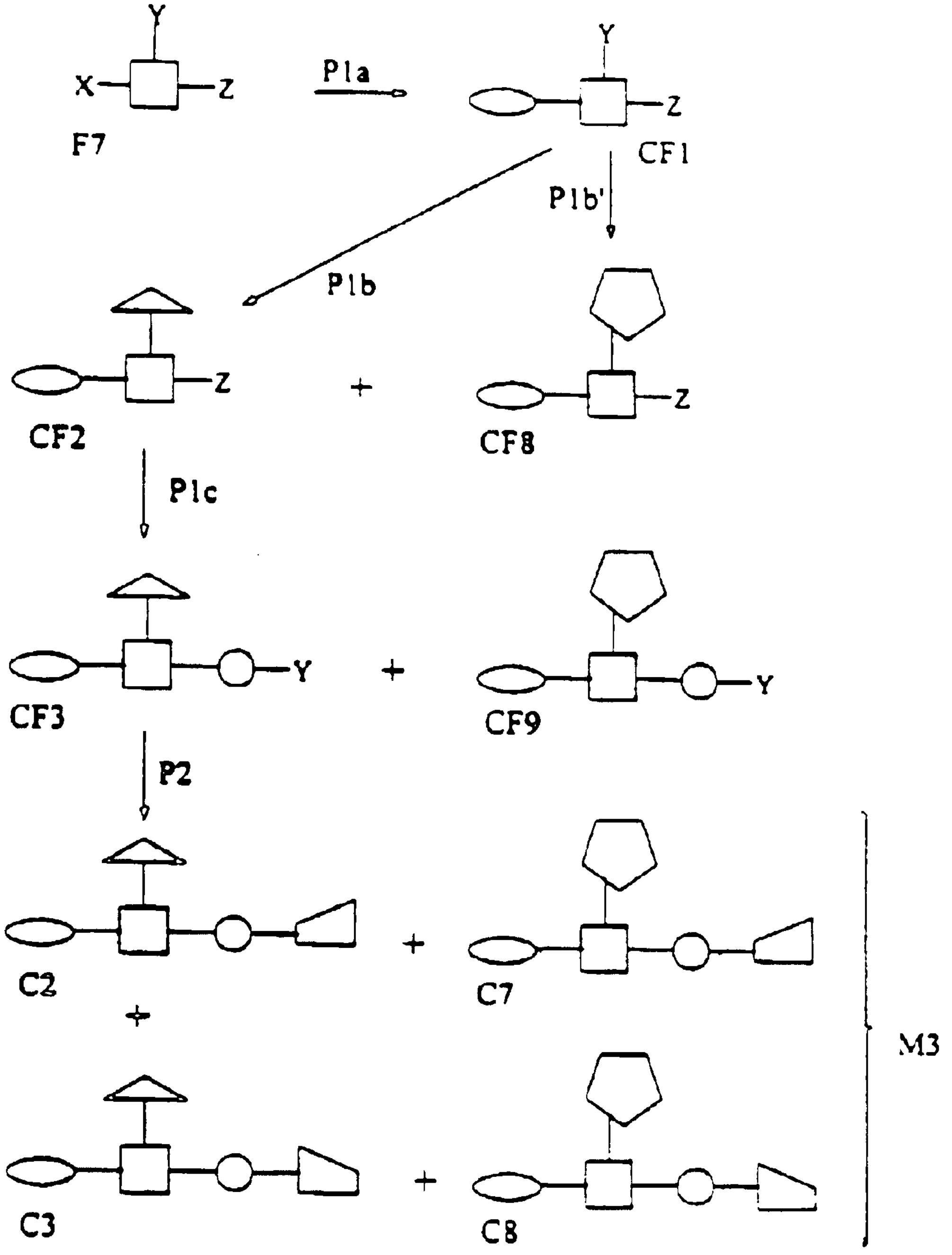
FIG. 26 shows the generation of an additional mixture, mixture M3.

Yet another symbolic example of the one-pot generation of mixtures of compounds, in accordance with the present invention, is shown in FIG. 26. In silico generation of compounds commences with the selection of fragment F7, which has three sites of attachment (X, Y, and Z). This represents the first synthesis round (i.e. round n). Next, F7 is subjected to synthetic pathway P1a wherein F7 is combined with fragment F2. F2 attaches to site X on fragment F7, forming complex fragment CF1. At this stage, CF1 is subjected to two synthetic pathways, P1b and P1b'. P1b employs fragment F1 which is introduced onto site Y on CF1, thereby forming complex fragment CF2, while P1b' employs fragment F3 which is introduced onto site Y on CF1, thereby forming complex fragment CF8. Thus a mixture of complex fragments (CF2 and CF8) are formed. Both fragments, F 1 and F3 can be introduced together (such as from a single reagent bottle when actual synthesis is being undertaken) for the one-pot generation of compounds if the chemistries associated with introduction of these fragments into the compounds are compatible. If not, these fragments can be introduced separately. Next, CF2 and CF8 are subjected to synthetic pathway P1 wherein both complex fragments are combined with fragment F5 which attaches to site Z on CF2 and CF8, thereby forming complex fragments CF3 and CF9. The formation of CF3 and CF9 completes the second synthesis round (i.e. round n+1). As fragment F5 has two sites of attachment, site Y is still available for attachment to another fragment. Therefore, CF3 is subjected to synthetic pathway P3 wherein CF3 is combined with fragment F4. Introduction of F4 represents the third synthesis round (i.e. round n+2). F4 is a mixture of fragments (and introduced by adding a mixture of reagents), as shown in FIG. 22. As a result, synthetic pathway P2 leads to the generation of compounds C2 and C3. Simultaneously, CF9 combines with fragment F4, via synthetic pathway P2', leading to the generation of compounds C7 and C8. Thus mixture M3 is formed comprising compounds C2, C3, C7 and C8.

Figure 27A:
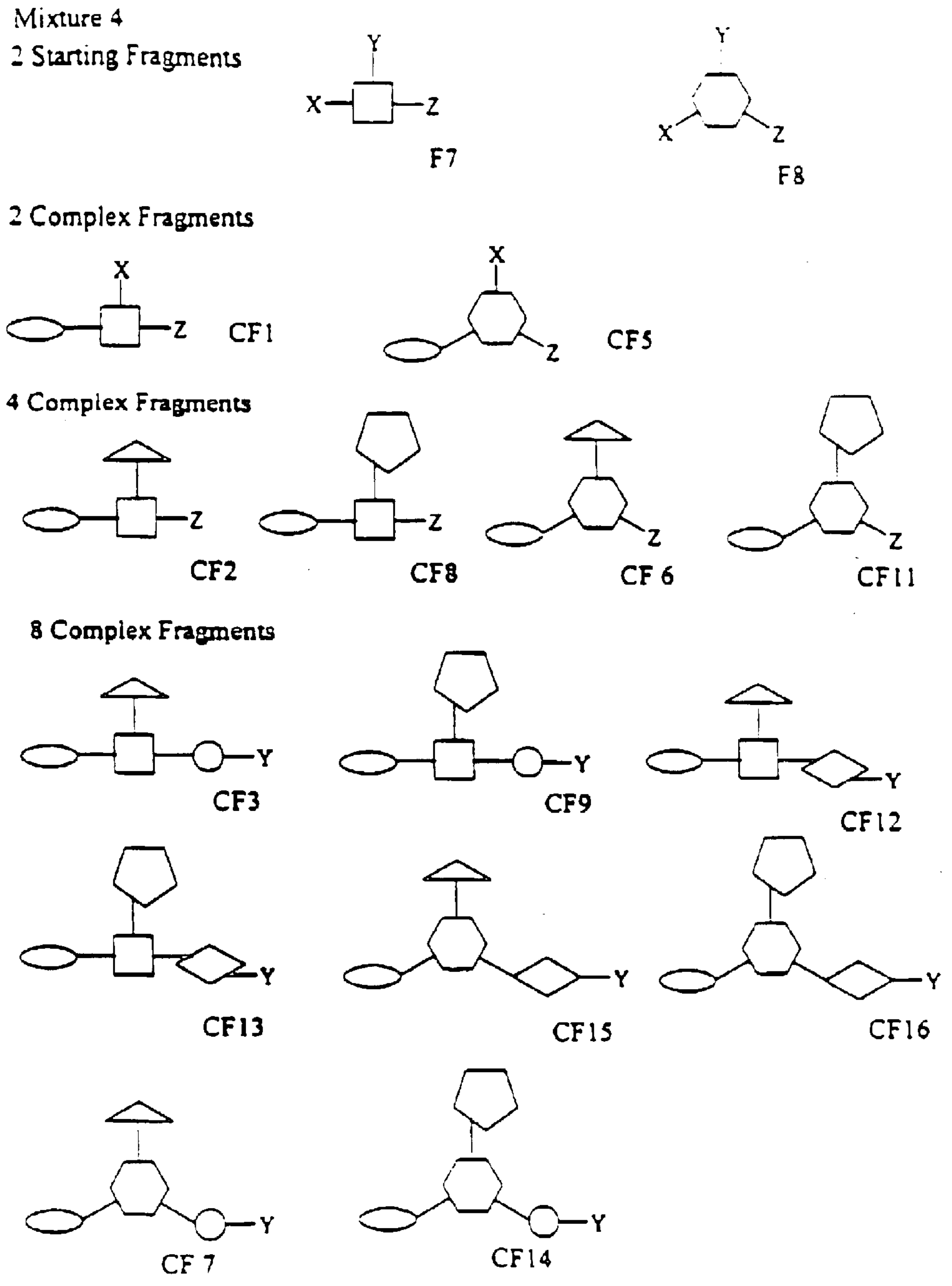
FIGS. 27A and 27B show the generation of an additional mixture, mixture M4.
Figure 27B:
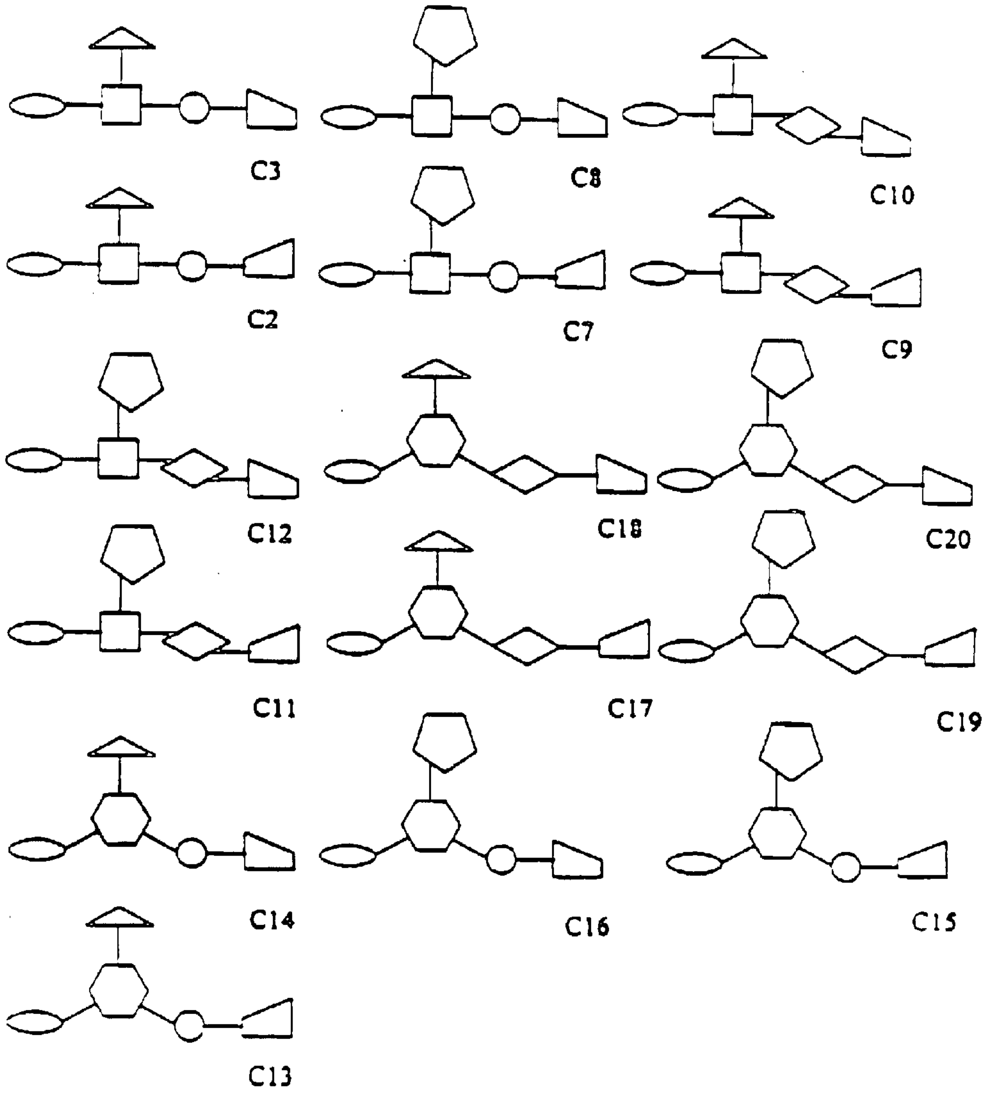

The present invention also provides methods for the generation of increasingly complex mixtures of compounds. An example is shown in FIGS. 27A and 27B where mixture M4 is generated and comprises sixteen compounds. The compounds in mixture M4 can be generated by starting with fragments F7 and F8 in the first synthesis round (i.e. round n). These fragments can then be combined with fragment F2, which is introduced at site X in each of F7 and F8, forming complex fragment CF1 and CF5. Following this, a mixture of fragments F1 and F3 are introduced into CF1 and CF5 at site Y of these complex fragments, leading to the formation of four complex fragments, CF2, CF6, CF8 and CF11. These complex fragments are next combined with a mixture of fragments F5 and F6. Both F5 and F6 have two attachment sites such that site X on FS and F6 attaches to site Z on CF2, CF6, CF8 and CF11 forming a mixture of eight complex fragments, CF3, CF7, CF9, CF12, CF13, CF14, CF15 and CF16. This completes the second synthesis round (i.e. round n+1). As fragments F5 and F6 have two attachment sites, X and Y, the abovementioned eight complex fragments have one more available attachment site (i.e. site Y) onto which another fragment may be introduced. Attachment of a fragment to site Y on these eight complex fragments represents the third synthesis round (i.e. round n+2). Next, fragment F4 is introduced into CF3, CF7, CF9, CF12, CF13, CF14, CF15 and CF16. As fragment F4 is a mixture of two constituent fragments, sixteen compounds are generated: C2, C3, C7, C8, C9, C10, C11, C12, C13, C14, C15, C16, C17, C18, C19 and C20. Thus it can be seen that by using multiple fragments in a one-pot fashion and combining with mixtures of fragments, mixtures of compounds of increasing complexity can he generated. The example in FIGS. 27A and 27B shows sixteen unique compounds being generated as mixture M4 when the library is generated by starting with two fragments. It is recognized by the art-skilled that if the library generation is commenced with more than two fragments or multiple fragments are added to the same precursor fragment, even more complex mixtures of compounds can be generated.

The present invention also provides methods for keeping track of fragment addition in the various synthesis rounds.

This system of accounting is accomplished by tabulation of the synthesis rounds which are correlated with addition of fragments. While for the purposes of illustration of the invention, a tabulation method of tracking fragment addition is described herein, it will be recognized by the art-skilled that other algorithms, algorithmic codes, computer readable mediums and various software coding techniques know to those skilled in the computer arts may be used for such tracking. The tables tracking fragment addition can be used to produce structural representations of compounds and create virtual libraries where actual synthesis of the compounds is not desired. Tables tracking transformations, however, can be used to synthesize compounds by selecting the appropriate transformations, and in the case of multiple transformations, selecting the preferable transformations to introduce the required fragment into the compounds being synthesized.

FIG. 28 is descriptive of compound C1 in terms of the fragments added in each synthesis round. The first synthesis round (i.e. round n) commences with the selection of fragment F7. This is followed by the sequential addition of fragments F2, F1 and F5 in the second synthesis round (i.e. round n+1). Finally, compound C1 is generated by the addition of fragment F3 in the third synthesis round (i.e. round n+2). The compounds thus generated can be stored as a 2-dimensional virtual library, or may be converted to a 3-dimensional virtual library that can be used for in silico docking to desired target molecules.

For the generation of virtual libraries of compounds and for docking the library members onto target molecules, it suffices to add compounds to the relational database in terms of its fragments to track the addition of fragments in the various synthetic rounds. However, when the actual synthesis of desired compounds of a library is to be undertaken, it becomes necessary to specify the actual synthetic steps, reagents, solvents, concentrations, auxiliary compounds needed and other various synthetic factors in order to effect such an actual synthesis of real chemical compounds. Such synthetic steps, reagents, solvents, concentrations and auxiliary compounds are, in fact, incorporated in to the above described transformations. Thus by employing the concept of transformations, the present invention provides methods to track the compounds generated not only in terms of the fragments added but as well as the synthetic parameters necessary for each synthesis round.

FIG. 28 also shows the generation of compound C1 in terms of the various transformations employed in the synthesis rounds. Four synthesis pathways lead to the synthesis of compound C1 because of the availability of multiple transformations that can introduce tile same fragment into tile compound being synthesized. Thus, as seen in FIG. 28, selection of fragment F7 constitutes transformation T9 in the first synthesis round (i.e. round n). This is followed by the addition of fragment F2 which is achieved by employing transformation T2. Next, fragment F1 is added via transformation T1. Fragment F5, however, may be added by employing either reagent R6 via transformation T6 along synthesis paths 1 and 3, or reagent R7 via transformation T7 along synthesis paths 2 and 4. Similarly, the final fragment F3 can be added by using either reagent R3 via transformation T3 along synthesis paths 1 and 2, or reagent R4 via transformation T4 along synthesis paths 3 and 4. Thus FIG. 28 shows that compound C1 can be actually synthesized via one of four different synthetic schemes which can be tracked or tabulated and accounted for using the methods of the present invention. Each of the four tables is completely descriptive of each of the four synthetic pathways for the preparation of C1. Thus, a user of the present invention has available all the alternate pathways of performing the same reaction (i.e. introducing the same fragment), and can select the preferable or most appropriate synthetic route to preparing the desired compounds.

Figure 29:
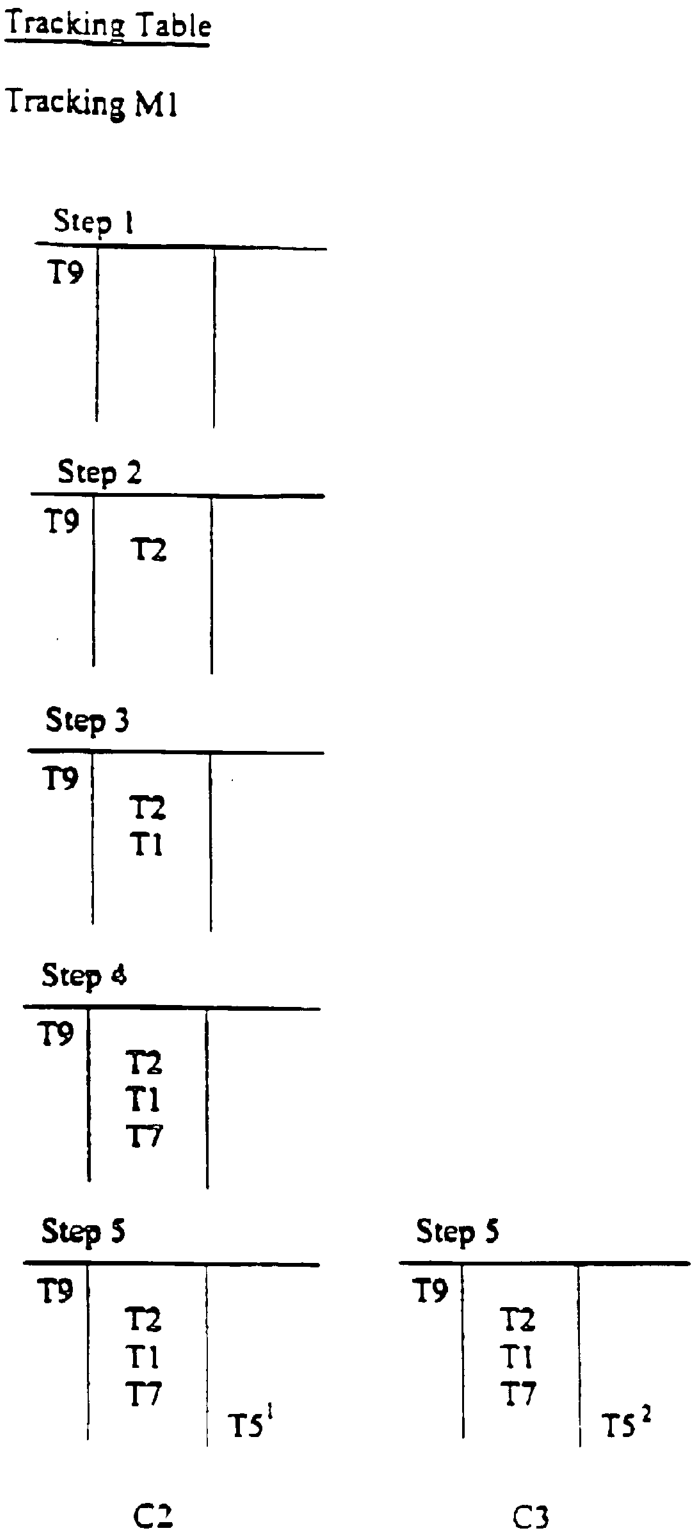
FIG. 29 shows tables for tracking mixture M1 by the transformations performed.

FIG. 29 shows a similar transformation tracking table for compounds C2 and C3 in mixture M1. Synthesis of compounds C2 and C3 commences with selection of fragment F7 which represents transformation T9 (step 1 in FIG. 29) in the first synthesis round (i.e. round n). Next, F7 is combined with fragment F2 via transformation T2 in the second synthesis round (i.e. round n+) (step 2). In the same round, fragment F1, via transformation T1, and fragment F5, via transformation T7 are added sequentially (steps 3 and 4). Finally, fragment F4 is added in the third synthesis round (i.e. round n+2). As F4 is a mixture of two constituent fragments (because of two constituent reagents), the table is duplicated at this stage (step 5) to account for the different synthetic ways in which transformation T5 may be accomplished (i.e. $T5^1$ and $T5^2$). Step 5 represents compounds C2 and C3. Thus it can be seen that, in accordance with the present invention, whenever there is more than one reagents associated with a particular transformation, the table is duplicated as many times as there are such reagents.

FIG. 30 shows a transformation tracking table for compounds C1 and C5 in mixture M3. As the synthesis commences with two fragments, F7 and F8, tracking begins with two parallel tables (step 1 in FIG. 30). In the first synthesis round (i.e. round n), F7 is selected via transformation T9, while F8 is selected via transformation T10. The second synthesis round (i.e. round n+1) commences at step 2 with the introduction of fragment F2 via transformation T2. In step 3, transformation T1 introduces fragment F1 into the compound. In step 4, transformation T7 introduces fragment F5. This completes the second synthesis round (i.e. round n+1). Finally, in the third synthesis round (i.e. round n+2), transformation T4 is used to introduce fragment F3 (at step 5) producing mixture M2 comprising compounds C1 and C5. In this example, the tables are duplicated early in the synthetic scheme because of the use of a mixture of fragments F7 and F8 at the outset.

Figure 31:
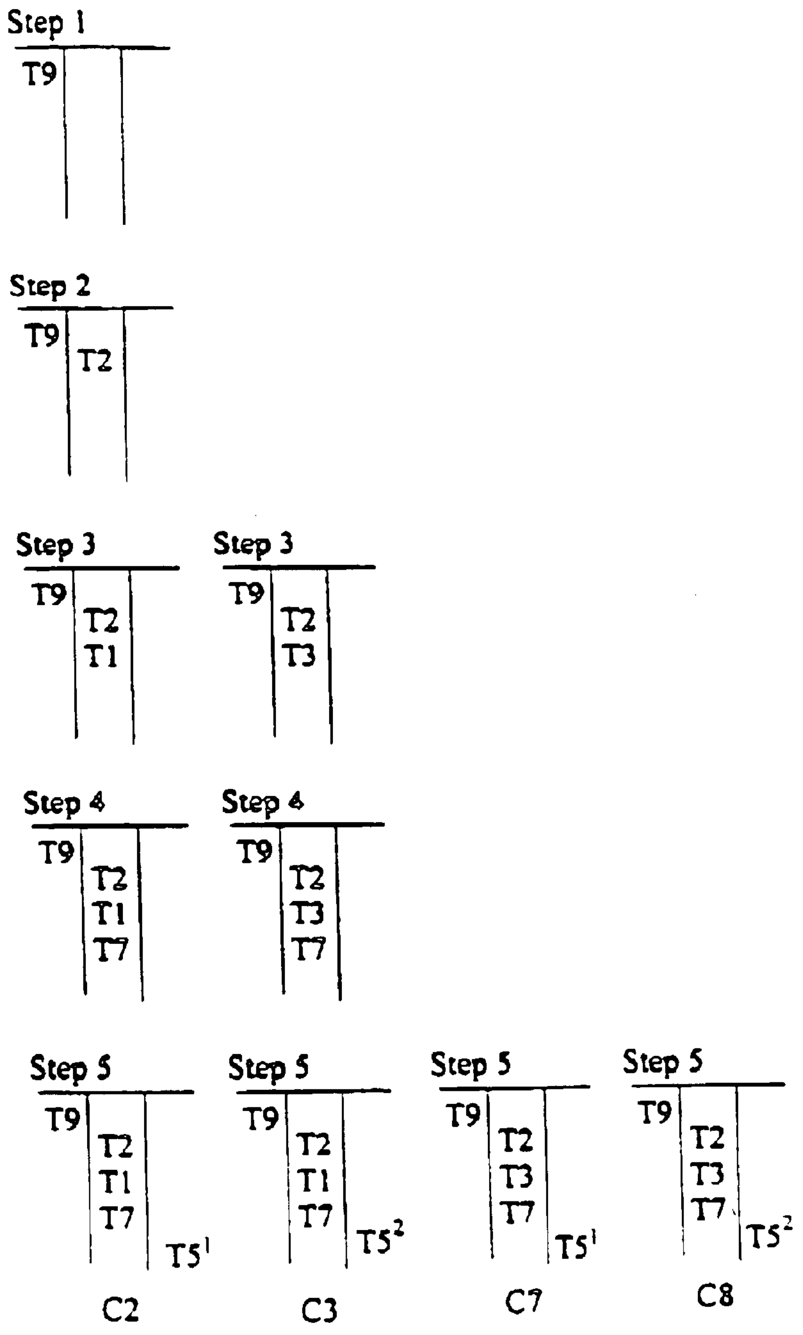
FIG. 31 shows tables for tracking mixture M3 by the transformations performed.

The transformation tracking table for compounds C2, C3, C7 and C8 of mixture M3 are shown in FIG. 31. The synthesis of these compounds commences with the first synthesis round (i.e. round n) in which fragment F7 is selected. This represents transformation T9 (shown in step 1 in FIG. 31). Step 2 in FIG. 31 depicts the second synthesis round (i.e. round n+1) and involves the addition of fragment F2 via transformation T2. While steps 1 and 2 involve single transformations each, step 3 involves two different transformations because two different fragments are being introduced into the compounds through the use of two different reagents. Therefore, at step 3 the table is twice duplicated because two different reagents are being employed to introduce two different fragments via two different transformations. In step 3, transformation T1 is used to introduce fragment F1 while transformation T3 is used to introduce fragment F3. The second synthesis round (i.e. round n+1) is completed at step 4 with transformation T7 which introduces fragment F5. In the final synthesis round (i.e. the third round or round n+2), transformation T5 is used to introduce fragment F4. As F4 is a mixture of two constituent fragments, each table at step 5 is twice duplicated for transformations T5' and T52 which represent each of the constituent fragments of F4.

These figures represent merely one manner in which the various fragments, reagents and transformations may be tracked during the generation or synthesis of single compounds or mixtures of compounds. It will, however, be recognized by the art-skilled that various other algorithm schemes may be employed to track and account for the fragments being introduced via transformations when compounds are being generated in silico.

The library members or compounds generated according to the methods of the present invention can be converted into three-dimensional representations using commercially available software. Next, the compounds, in their three-dimensional structures can be docked onto identified targets, also represented as three-dimensional structures.

Docking of these library members (or ligands) entails the in silico binding of the members to desired target molecules. A variety of theoretical and computational methods are known in the literature to study and optimize the interactions of small molecules with biological targets such as proteins and nucleic acids. These structure-based drug design tools have been very useful in modeling the interactions of proteins with small molecule ligands and in optimizing these interactions. Typically this type of study was performed when the structure of the protein receptor was known by querying individual small molecules, one at a time, against this receptor. Usually these small molecules had either been co-crystallized with the receptor, were related to other molecules that had been co-crystallized or were molecules for which some body of knowledge existed concerning their interactions with the receptor. A significant advance in this area was the development of a software program called DOCK that allows structure-based database searches to find and identify the interactions of known molecules to a receptor of interest (Kuntz et al., *Acc. Chem. Res.,* 1994, 27, 117; Gschwend and Kuntz, *J. Compt.-Aided Mol. Des.,* 1996, 10, 123). DOCK allows the screening of molecules, whose 3D structures have been generated in silico, but for which no prior knowledge of interactions with the receptor is available. DOCK, therefore, provides a tool to assist in discovering new ligands to a receptor of interest. DOCK can thus be used for docking the compounds prepared according to the methods of the present invention to desired target molecules.

The DOCK program has been applied to protein targets and the identification of ligands that bind to them. The DOCK software program consists of several modules, including SPHGEN (Kuntz et al., *J. Mol. Biol.,* 1982, 161, 269) and CHEMGRID (Meng el al., *J. Comput. Chem.,* 1992, 13, 505). SPHGEN generates clusters of overlapping spheres that describe the solvent-accessible surface of the binding pocket within the target receptor. Each cluster represents a possible binding site for small molecules. CHEMGRID precalculates and stores in a grid file the information necessary for force field scoring of the interactions between binding molecule and target. The scoring function approximates molecular mechanics interaction energies and consists of van der Waals and electrostatic components. DOCK uses the selected cluster of spheres to orient ligands molecules in the targeted site on the receptor. Each molecule within a previously generated 3D database is tested in thousands of orientations within the site, and each orientation is evaluated by the scoring function. Only that orientation with the best score for each compound so screened is stored in the output file. Finally, all compounds of the database are ranked in order of their scores and a collection of the best candidates may then be screened experimentally.

Using DOCK, ligands have been identified for certain protein targets. Recent efforts in this area have resulted in reports of the use of DOCK to identify and design small molecule ligands that exhibit binding specificity for nucleic acids such as RNA double helices. While RNA plays a significant role in many diseases such as AIDS, viral and bacterial infections, few studies have been made on small molecules capable of specific RNA binding. Compounds possessing specificity for the RNA double helix, based on the unique geometry of its deep major groove, were identified using the DOCK methodology (Chen et al., *Biochemistry,* 1997, 36, 11402; Kuntz et al., *Acc. Chem. Res.,* 1994, 27, 117). Using a recent X-ray structure for r(UAAGGAGGUGAU).r(AUCACCUCCUUA) (SEQ ID NO:52) as the model structure for the A-form RNA duplex, DOCK identified several aminoglycosides as candidate ligands, characterized by shape complementarity to the RNA groove. Binding experiments then revealed that one of these aminoglycosides not only bound preferentially to RNA over B-form DNA but also that the ligand binds in the targeted RNA major groove. Recently, the application of DOCK to the problem of ligand recognition in DNA quadruplexes has also been reported (Chen et al., *Proc. Natl. Acad. Sci.,* 1996, 93, 2635).

Programs such as DOCK typically assume knowledge of the conformation of the bound ligand and use a rigid conformation for a given ligand in molecular docking studies to arrive at structures of ligand-receptor complexes (which is a prerequisite for computing binding energies). Most ligands, however, possess a number of rotatable bonds, thus increasing the complexity of the calculation. Docking of flexible ligands would be desirable but requires one to search an enormous amount of conformational space. For example, the study of an aminoglycoside antibiotic (paromomycin) bound to 16S A-site RNA target, would constitute a search space of ~$10^{30}$ possible solutions.

QXP is a method that permits flexible ligand docking calculations (McMartin, C. and Bohacek, R. S., *J. Comput.-Aided Mole Design,* 1997, 11, 333). In this method, full conformational searches on flexible ligands are carried out. QXP search algorithms employ the Monte Carlo perturbation technique with energy minimization in Cartesian space. An additional fast search step is introduced between the initial perturbation and energy minimization. This method is also presently preferred for use herein.

As yet there has been no report of the evaluation of virtual libraries against RNA targets. Certain reports of the generation of virtual libraries are available from the standpoint of library design, generation, and screening against protein targets. Likewise, some efforts in the area of generating RNA models have been reported in the literature. However, there are no reports on the use of structure-based design approaches to query virtual libraries against three-dimensional models of RNA structure so as to identify ligands, such as small molecules, oligonucleotides or other nucleic acids, that bind to such targets. The present invention provides a solution to this problem by allowing the building of three-dimensional models of RNA structure, the building of virtual libraries of ligands, including small molecules, polymeric compounds, oligonucleotides and other nucleic acids, screening of such virtual libraries against RNA targets in silico, scoring and identifying the best potential binders from such libraries, and finally, synthesizing such molecules in a combinatorial fashion and testing them experimentally to identify new ligands for such targets.

The methods of the present invention aid in the drug discovery process by allowing the identification of those library members which bind with high affinity to the target molecules and, therefore, represent molecules that may be actually synthesized and developed as lead drug candidates.

The libraries as described above as well as libraries created by other means, can be synthesized on various automated synthesizers. For illustrative purposes, the synthesizer utilized for synthesis of above described libraries, is a variation of the synthesizer described in U.S. Pat. Nos. 5,472,672 and 5,529,756, the entire contents of which are herein incorporated by reference. The synthesizer described in those patents was modified to include movement in along the Y axis in addition to movement along the X axis. As so modified, a 96-well array of compounds can be synthesized by the synthesizer. The synthesizer can further include temperature control and the ability to maintain an inert atmosphere during all phases of a synthesis. The reagent array delivery format employs orthogonal X-axis motion of a matrix of reaction vessels and Y-axis motion of an array of reagents. Each reagent has its own dedicated plumbing system to eliminate the possibility of cross-contamination of reagents and line flushing and/or pipette washing. This in combined with a high delivery speed obtained with a reagent mapping system allows for the extremely rapid delivery of reagents. This further allows long and complex reaction sequences to be performed in an efficient and facile manner.

Software, as described below utilized in conjunction with the synthesizer allows the straightforward programming of the parallel synthesis of a large number of compounds. The software utilizes a general synthetic procedure in the form of a command (.cmd) file, which calls upon certain reagents to be added to certain wells via lookup in a sequence (.seq) file. The bottle position, flow rate, and concentration of each reagent is stored in a lookup table (.tab) file. Thus, once a synthetic method is outlined, a plate of compounds is made by permutating a set of reagents, and writing the resulting output to a text file. The text file is input directly into the synthesizer and used for the synthesis of the plate of compounds. The synthesizer can be interfaced with a relational database allowing data output related to the synthesized compounds to be registered in a highly efficient manner.

The .seq, .cmd and .tab files are built or constructed and once constructed, are stored in an appropriate database. The .cmd file is a synthesis file. This file can be built fresh to reflect a completely new set of machine commands reflecting a set of chemical synthesis steps (as for instance the above describe transformations) or it can modify an existing file stored in a database by editing a stored File. The .cmd files are built using a word processor and a command set of instructions as outlined below.

In a like manner to the building the .cmd files, tab files are built to reflect the necessary reagents used in the automatic synthesizer for the particular chemistries necessary for the library of desired compounds. Thus for each of a set of these chemistries, a .tab file is built and stored in the database. As with the .cmd files, an existing .tab file can be edited for use in constructing a further .tab file.

Both the .cmd files and the tab files are linked together for later retrieval from the database. Linking can be as simple as using like file names to associate a .cmd file to its appropriate .tab file, e.g., syntheses.cmd is linked to syntheses.tab by use of the same preamble in their names.

Figure 32:
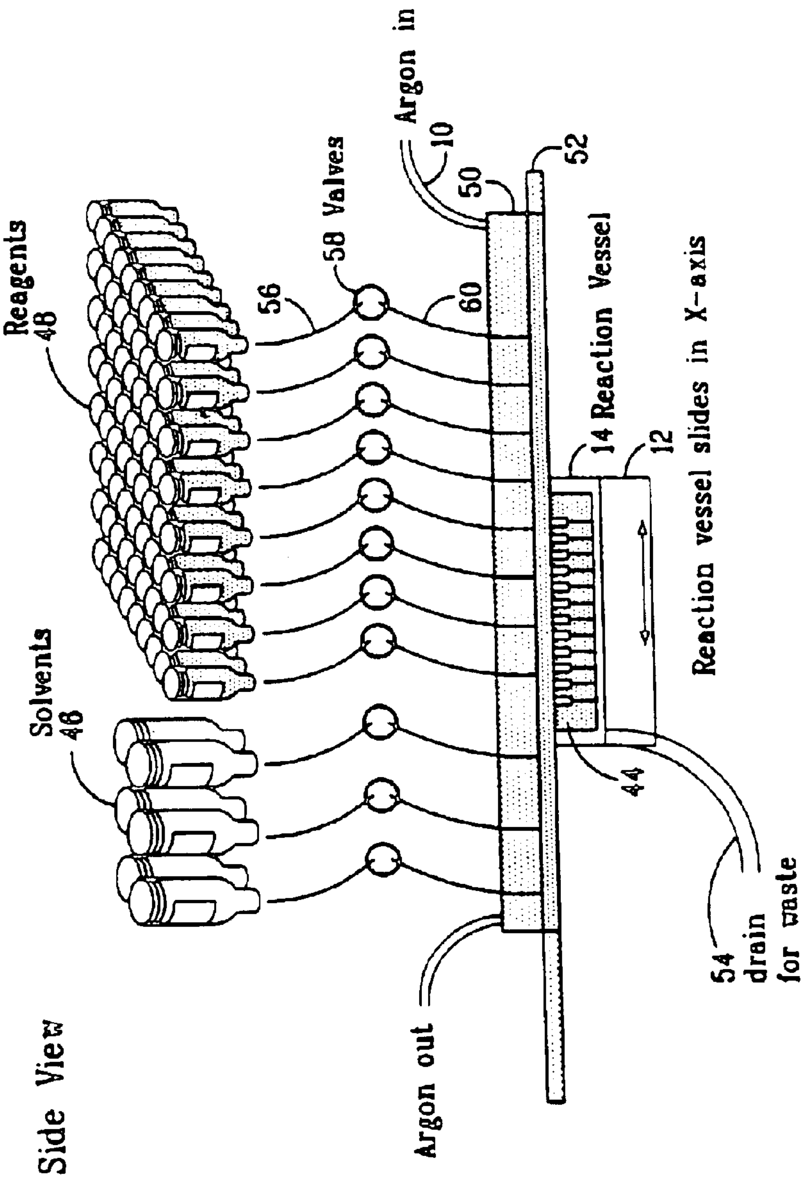
FIG. 32 is a pictorial elevation view of an apparatus used to robotically synthesize compound.
Figure 33:
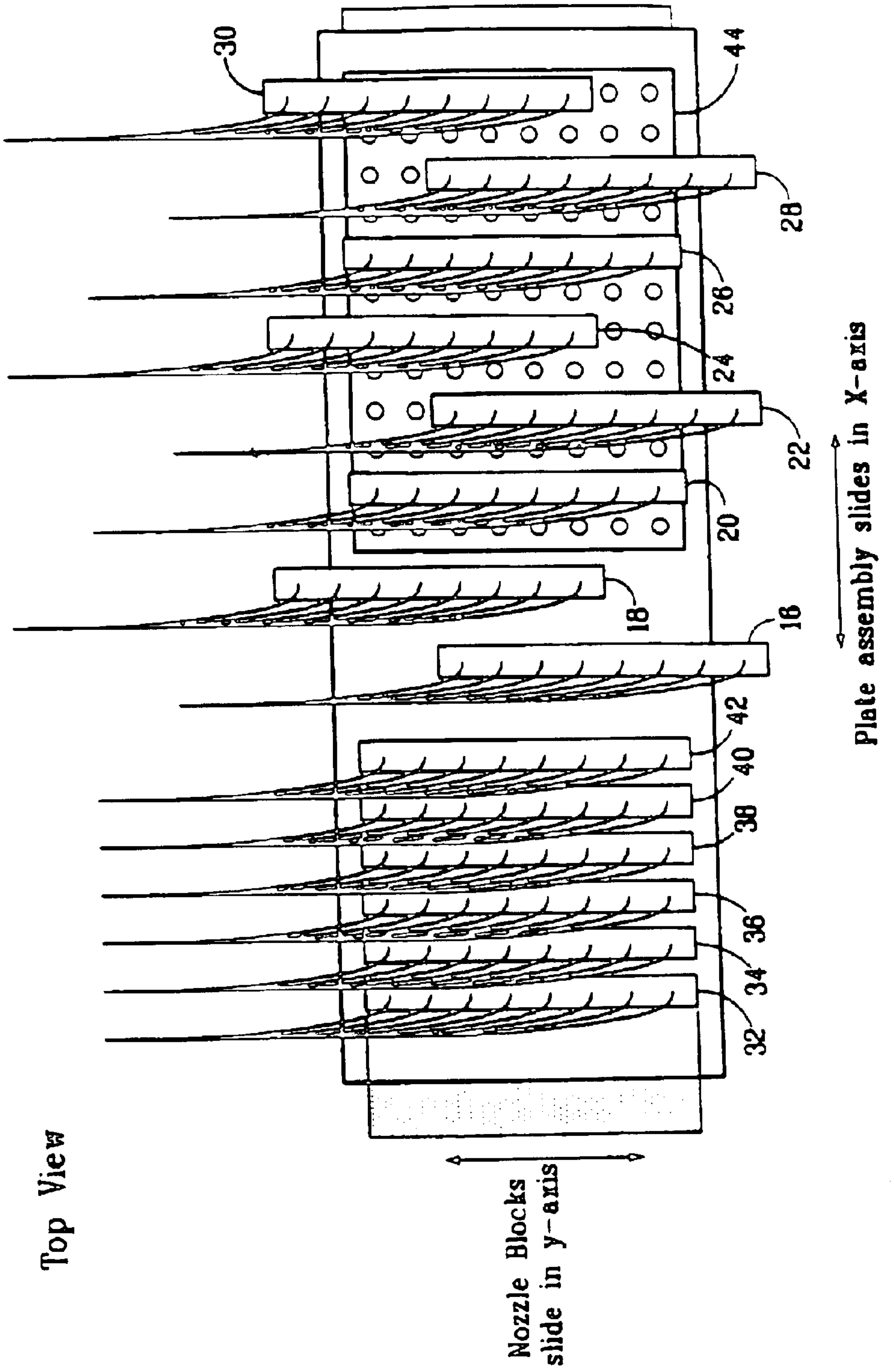
FIG. 33 is a pictorial plan view of an apparatus used to robotically synthesize compounds.

The automated, multi-well parallel array synthesizer employs a reagent array delivery format, in which each reagent utilized has a dedicated plumbing system. As seen in FIGS. 32 and 33, an inert atmosphere 10 is maintained during all phases of a synthesis. Temperature is controlled via a thermal transfer plate 12, which holds an injection molded reaction block 14. The reaction plate assembly slides in the X-axis direction, while eight nozzle blocks (16, 18, 20, 22, 24, 26, 28 and 30) holding the reagent lines slide in the Y-axis direction, allowing for the extremely rapid delivery of any of 64 reagents to 96 wells. In addition, there are six banks of fixed nozzle blocks (32, 34, 36, 38, 40 and 42) which deliver the same reagent or solvent to eight wells at once, for a total of 72 possible reagents. In synthesizing compounds for screening, the target reaction vessels, a 96 well plate 44 (a 2-dimensional array), moves in one direction along the X axis, while the series of independently controlled reagent delivery nozzles (16, 18, 20, 22, 24, 26, 28 and 30) move along the Y-axis relative to the reaction vessel 46. As the reaction plate 44 and reagent nozzles (16, 18, 20, 22, 24, 26, 28 and 30) can be moved independently at the same time, this arrangement facilitated the extremely rapid delivery of up to 72 reagents independently to each of the 96 reaction vessel wells.

The system software allows the straightforward programming of the synthesis of a large number of compounds by supplying the general synthetic procedure in the form of the command file to call upon certain reagents to be added to specific wells via lookup in the sequence file with the bottle position, flow rate, and concentration of each reagent being stored in the separate reagent table file. Compounds can be synthesized on various scales ranging from small, as for example a 200 nmole scale, to larger scales, as for example a 10 μmole scale (3–5 mg). The resulting crude compounds are generally >80% pure, and are utilized directly for high throughput screening assays. Alternatively, prior to use the plates can be subjected to quality control to ascertain their exact purity. Use of the synthesizer, results in a very efficient means for the parallel synthesis of compounds for screening.

The software inputs accept tab delimited text files from any text editor. A typical command file, a .cmd file, is shown in Example 5, Table 3. A typical sequence file, a seq files, is shown in Example 5, Table 4, and a typical reagent file, a tab file, is shown in Example 5, Table 5. Typically some of the wells of the 96 well plate may be left empty (depending on the number of compounds in the individual synthesis) or some of the well may have compounds that will serve as standards for comparison or analytical purposes.

Prior to loading reagents, moisture sensitive reagent lines are purged with argon at 10 for 20 minutes. Reagents are dissolved to appropriate concentrations and installed on the synthesizer. Large bottles, collectively identified as 46 in FIG. 32 (containing 8 delivery lines) are used for wash solvents and the delivery of general activators, cleaving reagents and other reagents that may be used in multiple wells during any particular synthesis. Small septa bottles, collectively identified as 48 in FIG. 32, are utilized to contain individual reagent compounds. This allows for anhydrous preparation and efficient installation of multiple reagents by using needles to pressurize the bottle, and as a delivery path. After all reagents are installed, the lines are primed with reagent, flow rates measured, then entered into the reagent table (.tab file). A dry resin loaded plate is removed from vacuum and installed in the machine for the synthesis.

The modified 96 well polypropylene plate 44 is utilized as the reaction vessel. The working volume in each well is approximately 700 μl. The bottom of each well is provided with a pressed-fit 20 μm polypropylene frit and a long capillary exit into a lower collection chamber as is illustrated in FIG. 5 of the above referenced U.S. Pat. No. 5,372,672. The solid support for use in holding the growing Compounds during synthesis is loaded into the wells of the synthesis plate 44 by pipetting the desired volume of a balanced density slurry of the support suspended in an appropriate solvent, typically an acetonitrile-methylene chloride mixture. Reactions can be run on various scales as for instance the above noted 200 nmole and 10 μmol scales. Various supports can be utilized for synthesis. Particularly useful supports include medium loading polystyrene-PEG supports such as TentaGel™ or ArgoGel™.

As seen in FIG. 33, the synthesis plate is transported back and forth in the X-direction under an array of 8 moveable banks (16, 18, 20, 22, 24, 26, 28 and 30) of 8 nozzles (64 total) in the Y-direction, and 6 banks (32, 34, 36, 38, 40 and 42) of 48 fixed nozzles, so that each well can receive the appropriate amounts of reagents and/or solvents from any reservoir (large bottle or smaller septa bottle). A sliding balloon-type seal 50 surrounds this nozzle array and joins it to the reaction plate headspace 52. A slow sweep of nitrogen or argon 20 at ambient pressure across the plate headspace is used to preserve an anhydrous environment.

The liquid contents in each well do not drip out until the headspace pressure exceeds the capillary forces on the liquid in the exit nozzle. A slight positive pressure in the lower collection chamber can be added to eliminate residual slow leakage from filled wells, or to effect agitation by bubbling inert gas through the suspension. In order to empty the wells, the headspace gas outlet valve is closed and the internal pressure raised to about 2 psi. Normally, liquid contents are blown directly to waste 54. However, a 96 well microtiter plate can be inserted into the lower chamber beneath the synthesis plate in order to collect the individual well eluent for spectrophotometric monitoring of reaction progress and yield.

The basic plumbing scheme for the machine is the gas-pressurized delivery of reagents. Each reagent is delivered to the synthesis plate through a dedicated supply line, collectively identified at 56, solenoid valve collectively identified at 58 and nozzle, collectively identified at 60. Reagents never cross paths until they reach the reaction well. Thus, no line needs to be washed or flushed prior to its next use and there is no possibility of cross-contamination of reagents. The liquid delivery velocity is sufficiently energetic to thoroughly mix the contents within a well to form a homogeneous solution, even when employing solutions having drastically different densities. With this mixing, once reactants are in homogeneous solution, diffusion carries the individual components into and out of the solid support matrix where the desired reaction takes place. Each reagent reservoir can be plumbed to either a single nozzle or any combination of up to 8 nozzles. Each nozzle is also provided with a concentric nozzle washer to wash the outside of the delivery nozzles in order to eliminate problems of crystallized reactant buildup due to slow evaporation of solvent at the tips of the nozzles. The nozzles and supply lines can be primed into a set of dummy wells directly to waste at any time.

The entire plumbing system is fabricated with Teflon tubing, and reagent reservoirs are accessed via syringe needle/septa or direct connection into the higher capacity bottles. The septum vials 48 are held in removable 8-bottle racks to facilitate easy setup and cleaning. The priming volume for each line is about 350 μl. The minimum delivery volume is about 2 μl, and flow rate accuracy is ±5%. The actual amount of material delivered depends on a timed flow of liquid. The flow rate for a particular solvent will depend on its viscosity and wetting characteristics of the Teflon tubing. The flow rate (typically 200–350 μl per see) is experimentally determined, and this information is contained in the reagent table setup file.

Heating and cooling of the reaction block 14 is effected utilizing a recirculating heat exchanger plate 12, similar to that found in PCR thermocyclers, that nests with the polypropylene synthesis plate 44 to provide good thermal contact. The liquid contents in a well can be heated or cooled at about 10° C. per minute over a range of +5 to +80° C., as polypropylene begins to soften and deform at about 80° C. For temperatures greater than this, a non-disposable synthesis plate machined from stainless steel or monel with replaceable frits might be utilized.

The hardware controller is designed around a set of three 1 MHZ 86332 chips. This controller is used to drive the single X-axis and 8 Y-axis stepper motors as well as provide the timing functions for a total of 154 solenoid valves. Each chip has 16 bidirectional timer I/O and 8 interrupt channels in its timer processing unit (TPU). These are used to provide the step and direction signals, and to read 3 encoder inputs and 2 limit switches for controlling up to three motors per chip. Each 86332 chip also drives a serial chain of 8 UNC5891A darlington array chips to provide power to 64 valves with msec resolution. The controller communicates with the Windows software interface program running on a PC via a 19200 Hz serial channel, and uses an elementary instruction set to communicate valve_number and time_open, and motor_number and position_data.

The three components of the software program that run the array synthesizer, the generalized procedure or command (.cmd) file which specifics the synthesis instructions to be performed, the sequence (.seq) file which specifies the scale of the reaction and the order in which variable groups will be added to the core synthon, and the reagent table (.tab) file which specifies the name of a chemical, its location (bottle number), flow rate, and concentration are utilized in conjunction with a basic set of command instructions.

The basic set of command instructions are:

ADD

IF {block of instructions} END_IF

REPEAT {block of instructions} END_REPEAT

PRIME, NOZZLE_WASH

WAIT, DRAIN

LOAD, REMOVE

NEXT_SEQUENCE

LOOP_BEGIN, LOOP_END

The ADD instruction has two forms, and is intended to have the look and feel of a standard chemical equation. Reagents are specified to be added by a molar amount if the number proceeds the name identifier, or by an absolute volume in micro liters if the number follows the identifier. The number of reagents to be added is a parsed list, separated by the '+' sign. For variable reagent identifiers, the key word, <seq>, means look in the sequence table for the identity of the reagent to be added, while the key word, <act>, means add the reagent which is associated with that particular <seq>. Reagents are delivered in the order specified in the list.

Thus:

```
ADD ACN 300
        means: Add 300 µl of the named reagent ACN to each well of active
        synthesis
ADD <seq> 300
        means: If the sequence pointer in the .seq file is to a reagent in the list
        of reagents, independent of scale, add 300 µl of that particular reagent
        specified for that well.
ADD 1.1 PYR + 1.0 <seq> + 1.1 <act1>
        means: If the sequence pointer in the .seq file is to a reagent in the list
        of acids in the Class ACIDS__1, and PYR is the name of pyridine, and
        ethyl chloroformate is defined in the .tab file to activate the class,
        ACIDS__1, then this instruction means:
        Add      1.1 equiv. pyridine
                 1.0 equiv. of the acid specified for that well and
                 1.1 equiv. of the activator, ethyl chloroformate
    The IF command allows one to test what type of reagent is specified in the <seq>
variable and process the succeeding block of commands accordingly.
    Thus:
ACYLATION                {the procedure name}
        BEGIN
                 IF CLASS = ACIDS__1
                     ADD 1.0 <seq> + 1.1 <act1> + 1.1 PYR
                     WAIT 60
                 ENDIF
                 IF CLASS = ACIDS__2
                     ADD 1.0 <seq> + 1.2 <act1> + 1.2 TEA
                 ENDIF
                 WAIT 60
                 DRAIN 10
        END
```

means: Operate on those wells for which reagents contained in the Acid__1 class are specified, WAIT 60 sec, then operate on those wells for which reagents contained in the Acid__2 class are specified, then WAIT 60 sec longer, then DRAIN the whole plate. Note that the Acid__I group has reacted for a total of 120 sec, while the $Acid_{13}$ 2 group has reacted for only 60 sec.

The REPEAT command is a simple way to execute the same block of commands multiple times.

Thus:

```
WASH__1                  {the procedure name}
        BEGIN
                 REPEAT 3
                     ADD ACN 300
                     DRAIN 15
                 END__REPEAT
        END
```

means: repeats the add acetonitrile and drain sequence for each well three times.

The PRIME command will operate either on specific named reagents or on nozzles which will be used in the next associated <seq>operation. The µ1 amount dispensed into a prime port is a constant that can be specified in a config.dat file.

The NOZZLE__WASH command for washing the outside of reaction nozzles free from residue due to evaporation of reagent solvent will operate either on specific named reagents or on nozzles which have been used in the preceding associated <seq>operation. The machine is plumbed such that if any nozzle in a block has been used, all the nozzles in that block will be washed into the prime port.

The WAIT and DRAIN commands are by seconds, with the drain command applying a gas pressure over the top surface of the plate in order to drain the wells.

The LOAD and REMOVE commands are instructions for the machine to pause for operator action.

The NEXT__SEQUENCE command increments the sequence pointer to the next group of substituents to be added in the sequence file.

The general form of a seq file entry is the definition:

Well__No Well__ID Scale Sequence

The sequence information is conveyed by a series of columns, each of which represents a variable reagent to be added at a particular position. The scale (µmole) variable is included so that reactions of different scale can be run at the same time if desired. The reagents are defined in a lookup table (the .tab file), which specifies the name of the reagent as referred to in the sequence and command files, its location (bottle number), flow rate, and concentration. This information is then used by the controller software and hardware to determine both the appropriate slider motion to position the plate and slider arms for delivery of a specific reagent, as well as the specific valve and time required to deliver the appropriate reagents. The adept classification of reagents allows the use of conditional IF loops from within a command file to perform addition of different reagents differently during a 'single step' performed across 96 wells simultaneously. Reagents can be group according to "class." Thus all for a particular synthesis that utilizes a fragment that is based on amino acids, the class "AMINO__ACIDS" can be created. The special class ACTIVATORS defines certain reagents that always get added with a particular class of reagents (for example Betaine utilized to activate the class AMINO__ACIDS).

The general form of the tab file is the definition:

Class Bottle Reagent Name Flow__rate Conc.

The LOOP__BEGIN and LOOP__END commands define the block of commands which will continue to operate until a NEXT__SEQUENCE command points past the end of the longest list of reactants in any well.

Not included in the command set is a MOVE command. For all of the above commands, if any plate or nozzle movement is required, this is automatically executed in order to perform the desired solvent or reagent delivery operation. This is accomplished by the controller software and hardware, which determines the correct nozzle(s) and well(s) required for a particular reagent addition, then synchronizes the position of the requisite nozzle and well prior to adding the reagent.

A MANUAL mode is also utilized in which the synthesis plate and nozzle blocks can be 'homed' or moved to any position by the operator, the nozzles primed or washed, the various reagent bottles depressurized or washed with solvent, the chamber pressurized, etc. The automatic COMMAND mode can be interrupted at any point, MANUAL commands executed, and then operation resumed at the appropriate location. The sequence pointer can be incremented to restart a synthesis anywhere within a command file.

The compounds to be synthesized can be rearranged or grouped for optimization of synthesis. Such grouping can be effected based on any parameter that will result in optimization of synthesis. One such factor considers the fragment of the compounds that are directly linked to the supporting resin. If the same fragment is to be utilized multiple times, it can be joined to the support in a batch wise manner and aliquots of this batch synthesis then loaded into the individual wells of the plate prior to start of the synthesis. Another parameter is by positioning like compounds near each other. By grouping like fragments near each other, machine movements are conserved and in doing so, overall synthesis lime is shortened.

In utilizing the multi well format for compound synthesis, for each compound to be synthesized, an aliquot of a solid support bearing the proper first fragment thereon can be added to the well for synthesis. Thus prior to loading the sequence of compounds to be synthesized in the seq File, they are sorted by this fragment. Based on that sorting, all of compounds having similar first fragments are positioned together in adjacent wells on the plate. Thus in loading the fragment-bearing solid support into the synthesis wells, machine movements are conserved. In a further method of preparing compounds, only the solid support is added to the wells and the first fragment is then linked to the solid support as the first synthetic step. The seq file is appropriately modified to reflect that the first segment is to be added.

Once sorted into types, the position of the compounds on the synthesis plates is specified by the creation of a seq file as described above. The .seq file is associated with the respective .cmd and tab files needed for synthesis of the particular chemistries specified for the compounds by retrieval of the .cmd and tab files a database. These files are then input into the multi well synthesizer for compound synthesis. Upon completion of synthesis, for shipping, storage or other handling purposes, the plates can be lyophilized at this point if desired. Upon lyophilization, each well contains the compounds located therein as a dry compound.

Figure 34:
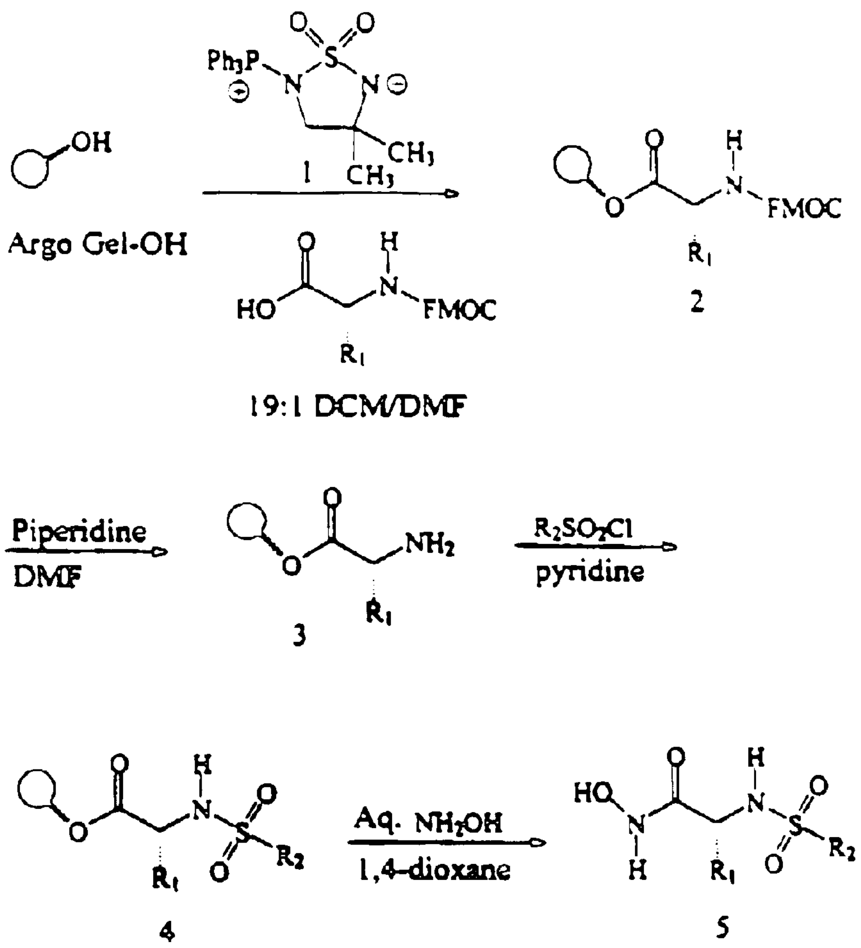
FIG. 34 is a first synthetic reaction scheme for preparing a library of compounds.
Figure 35:
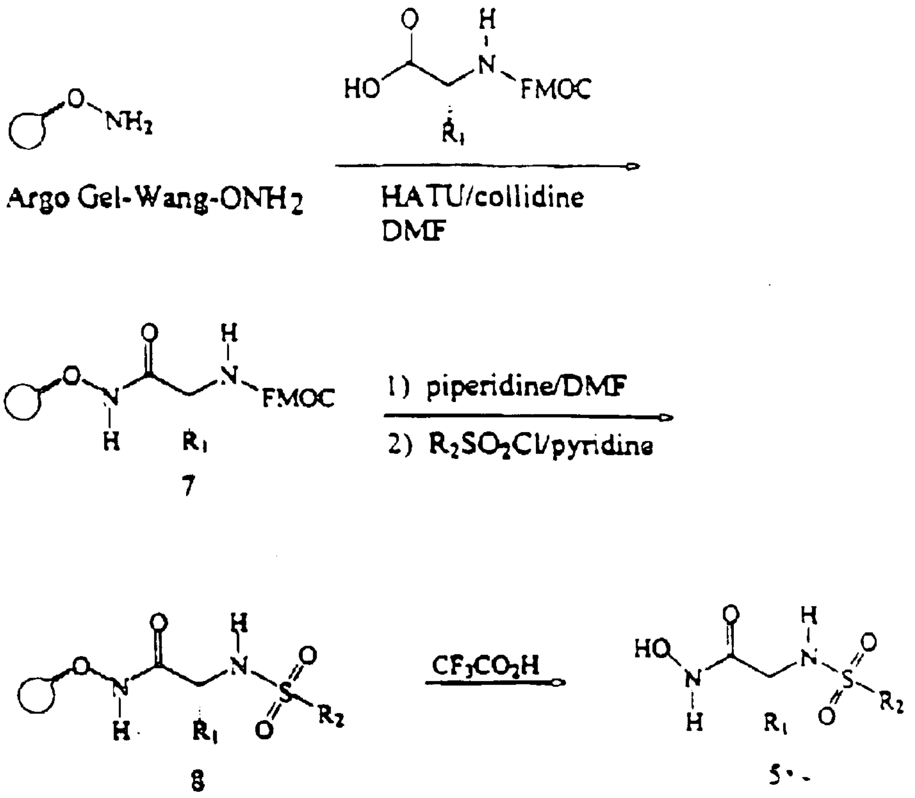
FIG. 35 is a second synthetic reaction scheme for preparing the library of compounds of FIG. 34.

To illustrate a preferred embodiment of the invention, a synthetic was effected utilizing the methods of the invention to generate a small library (~1200) of discreet hydroxamic acids. The total library is shown in Table 2 below. Two distinct chemical pathways were utilized for the automated synthesis of the illustrative library of hydroxamic acid compounds. These are shown in FIGS. 34 and 35. Each pathway had its own advantages.

The illustrative hydroxamic library compounds generally correspond in structure to compound C1 of FIG. 14, formed from a hydroxylamine fragment, a valine fragment (the amino acid fragment) and a sulfonyl-4-methoxybenzene fragment (the sulfonyl fragment) of FIG. 15. They differ from one another with respect to their amino acid fragment and their sulfonyl fragment. They have in common their hydroxylamine fragment. Compound C1 directly corresponds (they are one in the same) to compound a-x of Table 2. These compounds further corresponds to symbolic compound C1'.

For illustrative purposes to demonstrate complex chemical structures and mixtures, the symbolic tables shown in the FIGS. 28, 29, 30, and 31 describe certain complex symbolic structures and thus equally complex chemical structures. Compared to these complex structures and mixtures, compound C1'is less complex, however, its construction embodies the same principles as used to describe the structures of those figures. Since it embodies the same principles, one can construct a similar table for compound C1'. Thus in round n it would have the fragment Fi', in round n+1 the fragment Fii' and in round n+2, the fragment Fiii'. A transformation table can likewise be constructed listing Ti in round n, Tii in round n+1 and Tiii in round n+2. This information is then used to instruct the automated synthesizer to prepare the actual library.

In constructing the illustrative hydroxamic library utilizing the synthetic pathway of FIG. 35, the first fragment, the hydroxylamine fragment is the same in all members of the library. Therefore, for ease of synthesis, it is added already attached to a solid support to wells in a synthesis plate. This reduces the complexity of the synthesis by a factor of "one fragment" and in turn reduce the number of rounds by one of synthesis that must be effected on the synthesizer. In essence this eliminates the round n as described in the tables of FIGS. 28, 29, 30 and 31.

As described above, the general form of a seq file entry was:

Well_No Well_ID Scale Sequence where the "Sequence" information was conveyed by a series of columns. Since the round n transformation has been generalized for each well on the plate by adding the hydroxyl amine fragment attached to a solid support, only two Sequence columns are necessary to describe the synthesis, one for the round n+1 showing the amino acid reagent used and one for the round n+2 showing the sulfonyl reagent used. Each "Sequence" column corresponds to a reagent which is a member of a transformation represented in the tracking tables. This reagent is linked by the one to one relationship specified by the transformation to its resulting fragment.

Various algorithms, as will be evident to those skilled in the computer programing arts, could be utilized to convert the information contained withing the tracking tables described above into the format suitable for synthesis utilizing the parallel array synthesizer described herein. One preferred way to accomplish this is by looking up the transformation required for each particular round of synthesis for each compound or group of compounds in the tracking table. The appropriate complex or single reagent is then written to a software file in a format such that each reagent utilized for the transformation indicated in the tracking table at the appropriate synthesis round corresponds to a single column entry in the seq file. The compounds or groups of compounds stored in the database and their location in the reaction vessel in which they are synthesized are then linked by the Well_ID field of the seq file, which is assigned by the database. Thus, having described the compounds by their transformations allows for facile construction of the .seq file need for synthesis. This is illustrated by the synthesis files for the parallel array synthesizer detailed above, but the process is equally applicable to any suitable programmable chemical synthesis apparatus.

In a like manner the general form of the tab file was:

Class Bottle Reagent Name Flow Rate Conc.

Here complex or single reagents can be specified in the "Reagent Name" as defined by the bottle the reagent or mixture of reagents is located. Whether it was a single reagent or a complex reagent mixture specified by a particular transformation, that information is carried over to the synthesizer instructions by the appropriate entry in the tab file for that reagent. As for the .seq file creation, the information in the transformation tracking table can be readily converted to a .tab file. Each complex or single reagent called for in the synthesis is given a line entry in the .tab file. Additionally, the single reagent components of complex reagents may be specified in a comments section of the tab file to facilitate preparation of complex reagents. The appropriate conditions for the specified reagent as indicated in the corresponding transformation are also written to the proscribed field in the tab file. Additionally, associated reagents for accomplishing the specified transformation (such as activators, bases, scavangers, coupling reagents, etc.) may also be written to the .tab file as appropriate. In the synthesis of the illustrative hydroxamic acid library, the activator named "betaine" is associated with the transformation attaching the amino acid to solid support. It is placed in the tab file, along with a modifier specifying which reagents it is associated. As a result of having described the compounds by their transformations, construction of the .tab file need for synthesis is facilitate. This is illustrated by the synthesis files for the parallel array synthesizer detailed herein, but the process is equally applicable to any suitable programmable chemical synthesis apparatus.

As the complexity of the fragments for the compounds in a library increases as for instances steps P1a, P1b, P1c, P1c and P3b of FIG. 24, they in turn require more column entries the "Sequence" portion of .seq. However, if complexity is achieved by using mixtures of reagents that are used in unison, as for instances step P2 of FIG. 24, this is controlled by locating them in a single reagent bottle as specified by the tab file.

In reference again to the illustrative hydoxamic acid library of Table 2, the first method of synthesis, illustrated in FIG. 34, entails derivatizing commercially available ArgoGel-OH™ (which has an PEG based alcohol as the reactive functional group) with an FMOC-amino acid via a modified Mitsunobu reaction employing the sulfonamide betaine 1 as the activating species. This reaction proceeded to essentially 100% completion (by FMOC) in several hours, and has the advantage over other loading procedure (symmetric anhydride/DMAP) of eliminating the potential for racemization of the amino acid. It also requires less equivalents, as one equivalent of amino acid is not wasted due to the formation of a symmetric anhydride, and the potential for FMOC loss is minimized. The resin bound ester 2 was next deprotected, then sulfonylated using a sulfonyl chloride in pyridine. The yield of the Mitsunobu loading step was measured by collecting the washes from the FMOC deprotection, followed by spectrophotometric determination of the amount released in a 96 well plate reader. This information was then written to a data file for import into a database, which allows a yield estimate of the synthesized compounds. It was found that cleavage of the ester 4 with hydroxylamine in 1,4-dioxane (50% aqueous $NH_2OH$ diluted to 4 M final $NH_2OH$ concentration with 1,4-dioxane) generally proceeded to completion overnight at room temperature to provide the desired hydroxamic acids 5. A small amount (10–20%) of the corresponding carboxylic acid resulted from competitive hydrolysis for hindered amino acids such as valine, even when anhydrous hydroxylamine was employed. Several hindered amino acids and electron deficient sulfonyl chlorides failed completely with this method as indicated in Table 2 below.

The procedure has the advantage that orthogonal deprotection and cleavage strategies can be employed, allowing standard peptide acid labile side chain protection (t-butyl based, trityl, PMC, etc.) to be used on the amino acid component. This allows isolation of product free from side chain protection by-products in the case of commonly used trityl and sulfonyl based protection of histidine, arginine, glutamine, and asparagine. Thus, the resin bound ester 4 can be treated with anhydrous TFA for 4 h on the instrument, resulting in complete side chain deprotection. If cleaned of TFA immediately after synthesis, the instrument, including lines and valves were unaffected by the extreme conditions. The support could then be washed and the product 5 cleaved from support using the standard methodology. This synthesis was accomplished very readily on the automated parallel array synthesizer, using a very simple command file, which functions as a 'general procedure'. Representative command, sequence and tab files are detailed in the Example 5 below to illustrate the synthesis.

The second method utilized the acid labile Wang based hydroxylamine support 6 (FIG. 35) to circumvent the minor problem of competitive hydrolysis, and the failure of electron deficient sulfonyl chlorides. The resin was prepared in an analogous manner to the procedure described by Atheron et al., *Solid Peptide Synthesis: A Practical Approach*; IRL Press: Oxford, UK 1989: p 135 employing an initial Mitsunobu reaction of ArgoGel-Wang™ resin with N-hydroxyphthalimide, followed by deprotection with methylhydrazine to afford 6 in quantitative yield by gel-phase $^{13}C$ NMR. The hydroxylamine resin was then acylated with an FMOC-amino acid utilizing standard peptide coupling methodology to provide 7, which was deprotected then sulfonylated as before to provide resin bound hydroxamic acid 8. This material was efficiently cleaved from the resin with TFA containing $Et_3SiH$ (5% v/v) as a scavenger to provide compounds 5.

A molecular interaction site is a region of a nucleic acid which has secondary structure. Preferably, the molecular interaction site is conserved between a plurality of different taxonomic species. The nucleic acid can be either eukaryotic or prokaryotic. The nucleic acid is preferably mRNA, pre-mRNA, tRNA, rRNA, or snRNA. The RNA can be viral, fungal, parasitic, bacterial, or yeast. Preferably, the molecular interaction site is present in a region of an RNA which is highly conserved among a plurality of taxonomic species. In accordance with some preferred embodiments of this invention, it will be appreciated that the biomolecules having a molecular interaction site or sites, especially RNAs, may be derived from a number of sources. Thus, such RNA targets can be identified by any means, rendered into three dimensional representations and employed for the identification of compounds which can interact with them to effect modulation of the RNA.

The three dimensional structure of a molecular interaction site, preferably of an RNA, can be manipulated as a numerical representation. Computer software that provides one skilled in the art with the ability to design molecules based oil the chemistry being performed and on available reaction building blocks is commercially available. Software packages from companies such as, for example, Tripos (St. Louis, Mo.), Molecular Simulations (San Diego, Calif.), MDL Information Systems (San Leandro, Calif.) and Chemical Design (NJ) provide means for computational generation of structures. These software products also provide means for evaluating and comparing computationally generated molecules and their structures. In silico collections of molecular interaction sites can be generated using the software from any of the above-mentioned vendors and others which are or may become available A set of structural constraints for the molecular interaction site of the RNA can be generated from biochemical analyses such as, for example, enzymatic mapping and chemical probes, and from genomics information such as, for example, covariance and sequence conservation. Information such as this can be used to pair bases in the stem or other region of a particular secondary structure. Additional structural hypotheses can be generated for noncanonical base pairing schemes in loop and bulge regions. A Monte Carlo search procedure can sample the possible conformations of the RNA consistent with the program constraints and produce three dimensional structures.

Reports of the generation of three dimensional, in silico representations are available from the standpoint of library design, generation, and screening against protein targets. Likewise, some efforts in the area of generating RNA models have been reported in the literature. However, there are no reports on the use of structure-based design approaches to query in silico representations of organic molecules, "small" molecules, oligonucleotides or other nucleic acids, with three dimensional, in silico, representations of RNA structures. The present invention preferably employs computer software that allows the construction of three dimensional models of RNA structure, the construction of three dimensional, in silico representations of a plurality of organic compounds, "small" molecules, polymeric compounds, oligonucleotides and other nucleic acids, screening of such in silico representations against RNA molecular interaction sites in silico, scoring and identifying the best potential binders from the plurality of compounds, and finally, synthesizing such compounds in a combinatorial fashion and testing them experimentally to identify new ligands for such targets.

In preferred embodiments of the invention, an automated computational search algorithm, such as those described above, is used to predict all of the allowed three dimensional molecular interaction site structures, preferably from RNA, which are consistent with the biochemical and genomic constraints specified by the user. Based e.g. on their root-mean-squared deviation values, these structures are clustered into different families. A representative member or members of each family can be subjected to further structural refinement via molecular dynamics with explicit solvent and cations.

Structural enumeration and representation by these software programs is typically done by drawing molecular scaffolds and substituents in two dimensions. Once drawn and stored in the computer, these molecules may be rendered into three dimensional structures using algorithms present within the commercially available software. Preferably, MC-SYM is used to create three dimensional representations of the molecular interaction site. The rendering of two dimensional structures of molecular interaction sites into three dimensional models typically generates a low energy conformation or a collection of low energy conformers of each molecule. The end result of these commercially available programs is the conversion of a nucleic acid sequence containing a molecular interaction site into families of similar numerical representations of the three dimensional structures of the molecular interaction site. These numerical representations form an ensemble data set.

The three dimensional structures of a plurality of compounds, preferably "small" organic compounds, can be designated as a compound data set comprising numerical representations of the three dimensional structures of the compounds. "small" molecules in this context refers to non-oligomeric organic compounds. Two dimensional structures of compounds can be converted to three dimensional structures, as described above for the molecular interaction sites, and used for querying against three dimensional structures of the molecular interaction sites. The two dimensional structures of compounds can be generated rapidly using structure rendering algorithms commercially available. The three dimensional representation of the compounds which are polymeric in nature, such as oligonucleotides or other nucleic acids structures, may be generated using the literature methods described above. A three dimensional structure of "small" molecules or other compounds can be generated and a low energy conformation can be obtained from a short molecular dynamics minimization. These three dimensional structures can be stored in a relational database. The compounds upon which three dimensional structures are constructed can be proprietary, commercially available, or virtual.

In some preferred embodiments of the invention, a compound data set comprising numerical representations of the three dimensional structure of a plurality of organic compounds is provided by, for example, Converter (MSI, San Diego) from two dimensional compound libraries generated by, for example, a computer program modified from a commercial program. Other suitable databases can be constructed by converting two dimensional structures of chemical compounds into three dimensional structures, as described above. The software is described in greater detail elsewhere in this U.S. Application. The end result is the conversion of a two dimensional structure of organic compounds into numerical representations of the three dimensional structures of a plurality of organic compounds. These numerical representations are presented as a compound data set.

After both the numerical representations of the three-dimensional structure of the molecular interaction sites and the compound data set comprising numerical representations of the three dimensional structures of a plurality of organic compounds are obtained, the numerical representations of the molecular interaction sites are compared with members of the compound data set to generate a hierarchy of the organic compounds. The hierarchy is ranked in accordance with the ability of the organic compounds to form physical interactions with the molecular interaction site. Preferably, the comparing is carried out seriatim upon the members of the compound data set. In accordance with some embodiments, the comparison can be performed with a plurality of molecular interaction sites at the same time.

A variety of theoretical and computational methods are known by those skilled in the art to study and optimize the interactions of "small" molecules or organic compounds with biological targets such as nucleic acids. These structure-based drug design tools have been very useful in modeling the interactions of proteins with small molecule ligands and in optimizing these interactions. Typically this type of study has been performed when the structure of the protein receptor was known by querying individual small molecules, one at a time, against this receptor. Usually these small molecules had either been co-crystallized with the receptor, were related to other molecules that had been co-crystallized or were molecules for which some body of knowledge existed concerning their interactions with the receptor. A significant advance in this area was the development of a software program called DOCK that allows structure-based database searches to find and identify molecules that are expected to bind to a receptor of interest. Kuntz, et al., *Acc. Chem. Res.,* 1994, 27, 117, and Gschwend and Kuntz, *J. Compt.-Aided Mol. Des.,* 1996, 10, 123. DOCK 4.0 is commercially available from the Regents of the University of California. Equivalent programs are also comprehended in the present invention. DOCK allows the screening of a large collection of molecules whose three dimensional structures have been generated in silico, i.e., in computer readable format, but for which no prior knowledge of interactions with the ligands is available. DOCK, therefore, is a significant tool to the process of discovering new ligands to a molecule of interest and is presently preferred for use herein.

The DOCK program has been widely applied to protein targets and the identification of ligands that bind to them. Typically, new classes of molecules that bind to known targets have been identified, and later verified by in vitro experiments. The DOCK software program consists of several modules, including SPHGEN (Kuntz, et al., *J. Mol. Biol.,* 1982, 161, 269) and CHEMGRID (Meng, et al., *J. Compost. Chem.,* 1992, 13, 505). SPHGEN generates clusters of overlapping spheres that describe the solvent-accessible surface of the binding pocket within the target receptor. Each cluster represents a possible binding site for small molecules. CHEMGRID precalculates and stores in a grid file the information necessary for force field scoring of the interactions between binding molecule and target. The scoring function approximates molecular mechanics interaction energies and consists of van der Waals and electrostatic components. DOCK uses the selected cluster of spheres to orient ligands molecules in the targeted site on the receptor. Each molecule within a previously generated three dimensional database is tested in thousands of orientations within the site, and each orientation is evaluated by the scoring function. Only that orientation with the best score for each compound so screened is stored in the output file. Finally, all compounds of the database are ranked in a hierarchy in order of their scores and a collection of the best candidates may then be screened experimentally.

Using DOCK, numerous ligands have been identified for a variety of protein targets. Recent efforts in this area have resulted in reports of the use of DOCK to identify and design small molecule ligands that exhibit binding specificity for nucleic acids such as RNA double helices. While RNA plays a significant role in many diseases such as AIDS, viral and bacterial infections, few studies have been made on small molecules capable of specific RNA binding. Compounds possessing specificity for the RNA double helix, based on the unique geometry of its deep major groove, were identified using the DOCK methodology. Chen, et al., *Biochemistry,* 1997, 36, 11402 and Kuntz, et al., *Acc. Client. Res.,* 1994, 27, 117. Recently, the application of DOCK to the problem of ligand recognition in DNA quadruplexes has been reported. Chen, et al., *Proc. Natl. Acad. Sci.,* 1996, 93, 2635.

Preferably, individual compounds are designated as tool files, for example, and combined into a collection of in silico representations using an appropriate chemical structure program or equivalent software. These two dimensional mol files are exported and converted into three dimensional structures using commercial software such as Converter (Molecular Simulations Inc., San Diego) or equivalent software, as described above. Atom types suitable for use with a docking program such as DOCK or QXP are assigned to all atoms in the three dimensional mol file using software such as, for example, Babel, or with other equivalent software.

A low-energy conformation of each molecule is generated with software such as Discover (MSI, San Diego). An orientation search is performed by bringing each compound of the plurality of compounds into proximity with the molecular interaction site in many orientations using DOCK or QXP. A contact score is determined for each orientation, and the optimum orientation of the compound is subsequently used. Alternatively, the conformation of the compound can be determined from a template conformation of the scaffold determined previously.

The interaction of a plurality of compounds and molecular interaction sites is examined by comparing the numerical representations of the molecular interaction sites with members of the compound data set. Preferably, a plurality of compounds such as those generated by a computer program or otherwise, is compared to the molecular interaction site and undergoes random "motions" among the dihedral bonds of the compounds. Preferably about 20,000 to 100,000 compounds are compared to at least one molecular interaction site. Typically, 20,000 compounds are compared to about five molecular interaction sites and scored. Individual conformations of the three dimensional structures are placed at the target site in many orientations. Moreover, during execution of the DOCK program, the compounds and molecular interaction sites are allowed to be "flexible" such that the optimum hydrogen bonding, electrostatic, and van der Waals contacts can be realized. The energy of the interaction is calculated and stored for 10–15 possible orientations of the compounds and molecular interaction sites. QXP methodology allows true flexibility in both the ligand and target and is presently preferred.

The relative weights of each energy contribution are updated constantly to insure that the calculated binding scores for all compounds reflect the experimental binding data. The binding energy for each orientation is scored on the basis of hydrogen bonding, van der Waals contacts, electrostatics, solvation/desolvation, and the quality of the fit. The lowest-energy van der Waals, dipolar, and hydrogen bonding interactions between the compound and the molecular interaction site are determined, and summed. In preferred embodiments, these parameters can be adjusted according to the results obtained empirically. The binding energies for each molecule against the target are output to a relational database. The relational database contains a hierarchy of the compounds ranked in accordance with the ability of the compounds to form physical interactions with the molecular interaction site. The higher ranked compounds are better able to form physical interactions with the molecular interaction site.

In a preferred embodiment, the highest ranking, i.e., the best fitting compounds, are selected for synthesis. In preferred embodiments of the invention, those compounds which are likely to have desired binding characteristics based on binding data are selected for synthesis. Preferably the highest ranking 5% are selected for synthesis. More preferably, the highest ranking 10% are selected for syntheses. Even more preferably, the highest ranking 20% are selected for synthesis. The synthesis of the selected compounds can be automated using a parallel array synthesizer or prepared using solution-phase or other solid-phase methods and instruments. In addition, the interaction of the highly ranked compounds with the nucleic acid containing the molecular interaction site is assessed as described below.

The interaction of the highly ranked organic compounds with the nucleic acid containing the molecular interaction site can be assessed by numerous methods known to those skilled in the art. For example, the highest ranking compounds can be tested for activity in high-throughput (HTS) functional and cellular screens. HTS assays for each target RNA can be determined by scintillation proximity, precipitation, luminiescence-based formats, filtration based assays, colorometric assays, and the like. Lead compounds can then be scaled up and tested in animal models for activity and toxicity. The assessment preferably comprises mass spectrometry of a mixture of the nucleic acid and at least one of the compounds or a functional bioassay.

Certain preferred evaluation techniques employing mass spectroscopy are disclosed in U.S. patent application Ser. No. 09/076,206 filed May 12, 1998, which is assigned to the assignee of the present application, and which is incorporated herein by reference ill its entirety as exemplary of certain useful and preferred mass spectrometric techniques for use herewith. It is to be specifically understood, however, that it is not essential that these particular mass spectrometric techniques be employed in order to perform the present invention. Rather, any evaluative technique may be undertaken so long as the objectives of the present invention are maintained.

In some embodiments of the invention, the highest ranking 20% of compounds from the hierarchy generated using the DOCK program or QXP are used to generate a further data set of three dimensional representations of organic compounds comprising compounds which are chemically related to the compounds ranking high in the hierarchy. Although the best fitting compounds are likely to be in the highest ranking 1%, additional compounds, up to about 20%, are selected for a second comparison so as to provide diversity (ring size, chain length, functional groups). This process insures that small errors in the molecular interaction sites are not propagated into the compound identification process. The resulting structure/score data from the highest ranking 20%, for example, is studied mathematically (clustered) to find trends or features within the compounds which enhance binding. The compounds are clustered into different groups. Chemical synthesis and screening of the compounds, described above, allows the computed DOCK or QXP scores to be correlated with the actual binding data. After the compounds have been prepared and screened, the predicted binding energy and the observed Kd values are correlated for each compound.

The results are used to develop a predictive scoring scheme, which weighs various factors (steric, electrostatic) appropriately. The above strategy allows rapid evaluation of a number of scaffolds with varying sizes and shapes of different functional groups for the high ranked compounds. In this manner, a further data set of representations of organic compounds comprising compounds which are chemically related to the organic compounds which rank high in the hierarchy can be compared to the numerical representations of the molecular interaction site to determine a further hierarchy ranked in accordance with the ability of the organic compounds to form physical interactions with the molecular interaction site. In this manner, the further data set of representations of the three dimensional structures of compound which are related to the compounds ranked high in the hierarchy are produced and have, in effect, been optimized by correlating actual binding with virtual binding. The entire cycle can be iterated as desired until the desired number of compounds highest in the hierarchy are produced.

Compounds which have been determined to have affinity and specificity for a target biomolecule, especially a target RNA or which otherwise have been shown to be able to bind to the target RNA to effect modulation thereof, can, in accordance with preferred embodiments of this invention, be tagged or labeled in a detectable fashion. Such labeling may include all of the labeling forms known to persons of skill in the art such as fluorophore, radiolabel, enzymatic label and many other forms. Such labeling or tagging facilitates detection of molecular interaction sites and permits facile mapping of chromosomes and other useful processes.

Mass spectrometry (MS) is a powerful analytical tool for the study of molecular structure and interaction between small and large molecules. The current state-of-the-art in MS is such that less than femtomole quantities of material can be readily analyzed using mass spectrometry to afford information about the molecular contents of the sample. An accurate assessment of the molecular weight of the material may be quickly obtained, irrespective of whether the sample's molecular weight is several hundred, or in excess of a hundred thousand, atomic mass units or Daltons (Da). It has now been found that mass spectrometry can elucidate significant aspects of important biological molecules. One reason for the utility of MS as an analytical tool in accordance with the invention is the availability of a variety of different MS methods, instruments, and techniques which can provide different pieces of information about the samples.

One such MS technique is electrospray ionization mass spectrometry (ESI-MS) (Smith et al., *Anal. Chem.,* 1990, 62, 882–899, Snyder, in Biochemical and biotechnological applications of electrospray ionization mass, American Chemical Society, Washington, D.C., 1996; Cole, in Electrospray ionization mass spectrometry: fundamentals, instrumentation, Wiley, New York, 1997). ESI produces highly charged droplets of the sample being studied by gently nebulizing the sample solution in the presence of a very strong electrostatic field. This results in the generation of highly charged droplets that shrink due to evaporation or the neutral solvent and ultimately lead to a "Coulombic explosion" that affords multiply charged ions of the sample material, typically via proton addition or abstraction, under mild conditions. ESI-MS is particularly useful for very high molecular weight biopolymers such as proteins and nucleic acids greater than 10 kDa in mass, for it affords a distribution of multiply-charged molecules of the sample biopolymer without causing any significant amount of fragmentation. The fact that several peaks are observed from one sample, due to the formation of ions with different charges, contributes to the accuracy of ESI-MS when determining the molecular weight of the biopolymer because each observed peak provides an independent means for calculation of the molecular weight of the sample. Averaging the multiple readings of molecular weight so obtained from a single ESI-mass spectrum affords an estimate of molecular weight that is much more precise than would be obtained if a single molecular ion peak were to be provided by the mass spectrometer. Further adding to the flexibility of ESI-MS is the capability to obtain measurements in either the positive or negative ionization modes.

In recent years electrospray ionization mass spectrometry (ESI-MS) has grown extensively as an analytical technique due to its broad applicability for analysis of macromolecules, including proteins, nucleic acids, and carbohydrates. Bowers, et al., *Journal of Physical Chemistry,* 1996, 100, 12897–12910; Burlingame, et al., *J. Anal. Chem.,* 1998, 70, 647R–716R; Biemann, Ann. Rev. Biochem., 1992, 61, 977–1010; and Crain, et al., *Curr. Opin. Biotechnol.,* 1998, 9, 25–34. One of the most significant developments in the field has been the observation, under appropriate solution conditions and analyte concentrations, of specific noncovalently associated macromolecular complexes that have been promoted into the gas-phase intact. Loo, *Mass Spectrometry Reviews,* 997, 16, 1–23; Smith, et al., *Chemical Society Reviews,* 1997, 26, 191–202; Ens, et al., Standing, K. G. and Chernushevich, I. V. Editors, *New Methods for the Study of Biomolecular Complexes* (Proceedings of the NATO Advanced Research Workshop, held 16–20 Jun. 1996, in Alberta, Canada in: NATO ASI Ser., Ser. C. 1998: 510; Kluwer, Dordrechlt, Neth., 1998. Recent examples include multimeric proteins (Fitzgerald, et al., *Proc. Natl. Acad. Sci. USA,* 1996, 93, 6851–6856), enzyme-ligand complexes (Ganguly, et al., *Tetrahedron,* 1993, 49, 7985–7996), protein-DNA complexes (Cheng, et al., *Proc. Nat'l. Acad. Sci. U.S.A.,* 1996, 93, 7022–7027), multimeric DNA complexes (Griffey, et al., *Proc. SPIE-Int. Soc. Opt. Eng.,* 1997, 2985, 82–86), and DNA-drug complexes (Gale, et al., *JACS,* 1994, 116, 6027–6028), the disclosures of which are incorporated herein by reference in their entirety.

Smith and co-workers have demonstrated that under competitive binding conditions in solution, ESI-MS measurements of enzyme-ligand mixtures yield gas-phase ion abundances that correlate with measured solution-phase dissociation constants ($K_D$). Cheng, et al., *JACS,* 1995, 117, 8859–8860, the disclosure of which is incorporated herein by reference in its entirety. They were able to rank the binding affinities of a 256-member library of modified benzenesulfonamide inhibitors to carbonic anhydrase. Levels of free and bound ligands and substrates can be quantified directly from their relative abundances as measured by ESI-MS and that these measurements can be used to quantitatively determine molecular dissociation constants that agree with solution measurements. Jorgensen and co-workers have demonstrated that the relative ion abundance of non-covalent complexes formed between D-and L-tripeptides and vancomycin group antibiotics can be used to measure solution binding constants. Jorgensen, et al., *Anal. Chem.,* 1998, 70, 4427–4432, the disclosure of which is incorporated herein by reference in its entirety. Griffey and co-workers have shown that tandem ESI-MS methods can be used to determine the binding sites for small molecules that bind to RNA targets. Gale, et al., *Journal of the American Society for Mass Spectrometry,* 1995, 6, 1154–1164, the disclosure of which is incorporated herein by reference in its entirety.

Fourier transform ion cyclotron resonance mass spectrometry (FT-ICR MS) can resolve very small mass differences providing determination of molecular mass with unparalleled precision and accuracy. Marshall, et al., *Mass Spectrom. Rev.,* 1998, 17, 1–35. Because each small molecule with a unique elemental composition carries an intrinsic mass label corresponding to its exact molecular mass, identifying closely related library members bound to a macromolecular target requires only a measurement of exact molecular mass. The target and potential ligands do not require radiolabeling, fluorescent tagging, or deconvolution via single compound re-synthesis. Furthermore, adjustment of the concentration of ligand and target allows ESI-MS assays to be run in a parallel formal under competitive or non-competitive binding conditions. Signals can be detected from complexes with dissociation constants ranging from <10 nM to ~100 mM.

Small molecules that bind to structured regions of RNA can exhibit therapeutic effects. For example, aminoglycoside antibiotics inhibit bacterial growth by disrupting essential RNA-protein and RNA-RNA interactions. De Stasio, et al., *EEMBO J,* 1989, 8, 1213–6 and Bryan, L. E. In *New, dimensions in antimicrobial therapy*; Root, R. K., Sande, M. A., Eds., Churchill Livingstone, N.Y., 1984; Vol. 1, pp 17–35. Paromomycin, one of the most widely studied aminoglycosides, binds to the decoding region of the prokaryotic 16S rRNA (the A-site) with a ~200 nM $K^D$, and induces misreading of the genetic code during translation. Wong, et al., *Chem. Biol.,* 1998, 5, 397–406. However, the features of the interaction between RNAs and aminoglycosides that provide binding specificity are poorly characterized. ESI-FTICR is employed to detect specific interactions between two closely related model RNA constructs corresponding to the decoding sites of the prokaryotic and eukaryotic ribosomes and individual members of a collection of aminoglycoside antibiotics.

Matrix-Assisted Laser Desorption/Ionization Mass Spectrometry (MALDI-MS) is another method that can be used for studying biomolecules (Hillenkamp et al., *Anal. Chem.,* 1991, 63, 1193A–1203A). This technique ionizes high molecular weight biopolymers with minimal concomitant fragmentation of the sample material. This is typically accomplished via the incorporation of the sample to be analyzed into a matrix that absorbs radiation from an incident UV or IR laser. This energy is then transferred from the matrix to the sample resulting in desorption of the sample into the gas phase with subsequent ionization and minimal fragmentation. One of the advantages of MALDI-MS over ESI-MS is the simplicity of the spectra obtained as MALDI spectra are generally dominated by singly charged species. Typically, the detection of the gaseous ions generated by MALDI techniques, are detected and analyzed by determining the time-of-flight (TO) of these ions. While MALDI-TOF MS is not a high resolution technique, resolution can be improved by making modifications to such systems, by the use of tandem MS techniques, or by the use of other types of analyzers, such as Fourier transform (FT) and quadrupole ion traps.

Fourier transform mass spectrometry (FTMS) is an especially useful analytical technique because of its ability to make mass measurements with a combination of accuracy and resolution that is superior to other MS detection techniques, in connection with ESI or MALDI ionization (Amster, J. Mass Spectrom., 1996, 31, 1325–1337). Further it may be used to obtain high resolution mass spectra of ions generated by any of the other ionization techniques. The basis for FTMS is ion cyclotron motion, which is the result of the interaction of an ion with a unidirectional magnetic field. The mass-to-charge ratio of an ion (m/q or m/z) is determined by a FTMS instrument by measuring the cyclotron frequency of the ion. The insensitivity of the cyclotron frequency to the kinetic energy of an ion is one of the fundamental reasons for the very high resolution achievable with FTMS. FTMS is an excellent detector in conventional or tandem mass spectrometry, for the analysis of ions generated by a variety of different ionization methods including ESI and MALDI, or product ions resulting from collisionally activated dissociation (CAD).

Collisionally activated dissociation (CAD), also known as collision induced dissociation (CID), is a method by which analyte ions are dissociated by energetic collisions with neutral or charged species, resulting in fragment ions which can be subsequently mass analyzed. Mass analysis of fragment ions from a selected parent ion can provide certain sequence or other structural information relating to the parent ion. Such methods are generally referred to as tandem mass spectrometry (MS or MS/MS) methods and are the basis of the some of MS based biomolecular sequencing schemes being employed today.

FTICR-MS, like ion trap and quadrupole mass analyzers, allows selection of an ion that may actually be a weak non-covalent complex of a large biomolecule with another molecule (Marshall et al., *Anal. Chem.,* 1991, 63, A215–A229; Beu et al., J. Am. Soc. Mass Spectrom., 1993, 4, 566–577; Winger et al., J. Am. Soc. Mass Spectrom., 1993, 4, 566–577); (Huang et al., Anal. Chem., 1991, 63, 732–739), or hyphenated techniques such as LC-MS (Bruins et al., Anal. Chem., 1987, 59, 2642–2646 Huang et al., J. Am. Soc. Mass Spectrom., 1990, 1, 158–165; Huang et al., Anal. Chem., 1991, 63, 732–739) and CE-MS (Cai et al., J. Chromatogr., 1995, 703, 667–692) experiments. FTICR-MS has also been applied to the study of ion-molecule reaction pathways and kinetics.

So-called "Hyphenated" techniques can be used for structure elucidation because they provide the dual features of separation and mass detection. Such techniques have been used for the separation and identification of certain components of mixtures of compounds such as those isolated from natural products, synthetic reactions, or combinatorial chemistry. Hyphenated techniques typically use a separation method as the first step; liquid chromatography methods such as HPLC, microbore LC, microcapillary LC, or capillary electrophoresis are typical separation methods used to separate the components of such mixtures. Many of these separation methods are rapid and offer high resolution of components while also operating at low now rates that are compatible with MS detection. In those cases where flow rates are higher, the use of 'megaflow' ESI sources and sample splitting techniques have facilitated their implementation with on-line mass spectrometry. The second stage of these hyphenated analytical techniques involves the injection of separated components directly into a mass spectrometer, so that the spectrometer serves as a detector that provides information about the mass and composition of the materials separated in the first stage. While these techniques are valuable from the standpoint of gaining an understanding of the masses of the various components of multicomponent samples, they are incapable of providing structural detail. Some structural detail, however, may be ascertained through the use of tandem mass spectrometry, e.g., hydrogen/deuterium exchange or collision induced disassociation.

Typically, tandem mass spectrometry ($MS^n$) involves the coupled use of two or more stages of mass analysis where both the separation and detection steps are based on mass spectrometry. The first stage is used to select an ion or component of a sample from which further structural information is to be obtained. This selected ion is then fragmented by (CID) or photodissociation. The second stage of mass analysis is then used to detect and measure the mass of the resulting fragments or product ions. The advent of FTICR-MS has made a significant impact on the utility of tandem, $MS^n$ procedures because of the ability of FTICR to select and trap specific ions of interest and its high resolution and sensitivity when detecting fragment ions. Such ion selection followed by fragmentation routines can be performed multiple times so as to essentially completely dissect the molecular structure of a sample. A two-stage tandem MS experiment would be called a MS-MS experiment while an n-stage tandem MS experiment would be referred to as a $MS^n$ experiment. Depending on the complexity of the sample and the level of structural detail desired, $MS^n$ experiments at values of n greater than 2 may be performed.

Ion trap-based mass spectrometers are particularly well suited for such tandem experiments because the dissociation and measurement steps are temporarily rather than spatially separated. For example, a common platform on which tandem mass spectrometry is performed is a triple quadrupole mass spectrometer. The first and third quadrupoles serve as mass filters while the second quadrupole serves as a collision cell for CAD. In a trap based mass spectrometer, parent ion selection and dissociation take place in the same part of the vacuum chamber and are effected by control of the radio frequency wavelengths applied to the trapping elements and the collision gas pressure. Hence, while a triple quadrupole mass analyzer is limited to two stages of mass spectrometry (i.e. MS/MS), ion trap-based mass spectrometers can perform $MS^n$ analysis in which the parent ion is isolated, dissociated, mass analyzed and a fragment ion of interest is isolated, further dissociated, and mass analyzed and so on. A number of $MS^4$ procedures and higher have appeared in the literature in recent years and can be used here. (Cheng et al., Techniques in Protein Chemistry, VII, pp. 13–21).

ESI and MALDI techniques have found application for the rapid and straightforward determination of the molecular weight of certain biomolecules (Feng et al., Anal. Chem., 1992, 64, 2090–2095; Nelson et al., Rapid Commun. Mass Spectrom., 1994, 8, 627–631). These techniques have been used to confirm the identity and integrity of certain biomolecules such as peptides, proteins, oligonucleotides, nucleic acids, glycoproteins, oligosaccharides and carbohydrates. Further, these MS techniques have found biochemical applications in the detection and identification of post-translational modifications on proteins. Verification of DNA and RNA sequences that are less than 100 bases in length has also been accomplished using ESI with FTMS to measure the molecular weight of the nucleic acids (Little et al, Proc. Natl. Acad. Sci. USA, 1995, 92, 2318–2322).

ESI tandem MS has been used for the study of high molecular weight proteins, for peptide and protein sequencing, identification of post-translational modifications such as phosphorylation, sulfation or glycosylation, and for the study of enzyme mechanisms (Rossomando et al., Proc. Natl. Acad. Sci. USA, 1992, 89, 5779–578; Knight et al., Biochemistry, 1993, 32, 2031–2035). Covalent enzyme-intermediate or enzyme-inhibitor complexes have been detected using ESI and analyzed by ESI-MS to ascertain the site(s) of modification on the enzyme. The literature has shown examples of protein sequencing where the multiply charged ions of the intact protein are subjected to collisionally activated dissociation to afford sequence informative fragment ions (Light-Wahl et al., Biol. Mass Spectrom., 1993, 22, 112–120). ESI tandem MS has also been applied to the study of oligonucleotides and nucleic acids (Ni el al., Anal. Chem., 1996, 68, 1989–1999; Little et al., Proc. Natl. Acad. Sci., 1995, 92, 2318–2322).

While tandem ESI mass spectra of oligonucleotides are often complex, several groups have successfully applied ESI tandem MS to the sequencing of large oligonucleotides (McLuckey et al., J. Am. Soc. Mass Spectrom., 1992, 3, 60–70; McLuckey et al., J. Am. Chem. Soc., 1993, 115, 12085–12095; Little et al., J. Am. Chem. Soc., 1994, 116, 4893–4897). General rules for the principal dissociation pathways of oligonucleotides, as formulated by McLuckey et al. (J. Am. Soc. Mass Spectrom., 1992, 3, 60–70; McLuckey et al., J. Am. Chem. Soc., 1993, 115, 12085–12095), have assisted interpretation of mass spectra of oligonucleotides, and include observations of fragmentation such as, for example, the stepwise loss of base followed by cleavage of the 3'-C—O bond of the relevant sugar. Besides the use of ESI with tandem MS for oligonucleotide sequencing, two other mass spectrometric methods are also available: mass analysis of products of enzymatic cleavage of oligonucleotides (Pieles et al., Nucleic Acids Res., 1993, 21, 3191–3196; Shaler et al., Rapid Commun. Mass Spectrom., 1995, 9, 942–947; Glover et al., Rapid Commun. Mass Spectrom., 1995, 9, 897–901), and the mass analysis of fragment ions arising from the initial ionization/desorption event, without the use of mass selection techniques (Little et al., Anal. Chem., 1994, 66, 2809–2815; Nordhoff et al., J. Mass Spectrom., 1995, 30, 99–112; Little et al., J. Am. Chem. Soc., 1994, 116, 4893–4897; Little et al., J. Am. Chem. Soc., 1995, 117, 6783–6784). While determining the sequence of deoxyribonucleic acids (DNA) is possible using ESI-MS and CID techniques (McLuckey et al., J. Am. Soc. Mass Spectrom., 1992, 3, 60–70; McLuckey et al., J. Am. Chem. Soc., 1993, 115, 12085–12095), the determination of RNA sequence is much more difficult. Thus while small RNA, such as 6-mers, have been sequenced (McCloskey et al., J. Am. Chem. Soc., 1993, 115, 12085–1095), larger RNA have been difficult to sequence using mass spectrometry.

Electrospray mass spectrometry has been used to study biochemical interactions of biopolymers such as enzymes, proteins and nucleic acids with their ligands, receptors, substrates or inhibitors. While interactions that lead to covalent modification of the biopolymer have been studied for some time, those interactions that are of a non-covalent nature have been particularly difficult to study heretofore by methods other than kinetic techniques. It is now possible to yield information on the stoichiometry and nature of such non-covalent interactions from mass spectrometry. MS can provide information about the interactions between biopolymers and other molecules in the gas phase; however, experiments have demonstrated that the data so generated can be reflective of the solution phase phenomena from which the mass spectra were generated.

ESI is a gentle ionization method that results in no significant molecular fragmentation and preserves even weakly bound complexes between biopolymers and other molecules so that they are detected intact with mass spectrometry. A variety of non-covalent complexes of biomolecules have been studied using ESI-MS and reported in the literature (Loo et al., Bioconjugate Chemistry, 1995, 6, 644–665; Smith et al., J. Biol. Mass Spectrom. 1993, 22, 493–501; Li et al., J. Am. Chem. Soc., 1993, 115, 8409–8413). These include the peptide-protein complexes (Busman et al., Rapid Commun. Mass Spectrom., 1994, 8, 211–216; Loo et al., Biol. Mass Spectrom., 1994, 23, 6–12; Anderegg et al., J. Am. Chem. Soc., 1995, 117, 1374–1377; Baczynskyj et al., Rapid Commun. Mass Spectrom., 1994, 8, 280–286), interactions of polypeptides and metals (Loo er al., J. Am. Soc. Mass Spectrom., 1994, 5, 959–965; Hue et al., J. Mass Spectrom., 1995, 30, 1076–1079; Witkowska et al., J. Am. Chem. Soc., 1995, 117, 3319–3324; Lane et al., J. Cell Biol., 1994, 125, 929–943), protein-small molecule complexes (Ganem et al., ChemTracts-Org. Chem., 1993, 6, 1–22; Henion et al., Ther. Drug Monit., 1993, 15, 563–569; Baca et al., J. Am. Chem. Soc., 1992, 114, 3992–3993), the study of the quaternary structure of multimeric proteins (Baca et al., J. Am. Chem. Soc., 1992, 114, 3992–3993; Light-Wahl et al., J. Am. Chem. Soc., 1994, 116, 5271–5278; Loo, J. Mass Spectrom., 1995, 30, 180–183), and the study of nucleic acid complexes (Light-Wahl et al., J. Am. Chem. Soc., 1993, 115, 803–804; Gale et al., J. Am. Chem. Soc., 1994, 116, 6027–6028; Goodlett et al., Biol. Mass Spectrom., 1993, 22, 181–183; Ganem et al., Tet. Lett., 1993, 34, 1445–1448; Doctycz et al., Anal. Chem., 1994, 66, 3416–3422; Bayer et al., Anal. Chem., 1994, 66, 3858–3863; Greig et al., J. Am. Chem. Soc., 1995, 117, 10765–766).

While data generated and conclusions reached from ESI-MS studies for weak non-covalent interactions generally reflect, to some extent, the nature of the interaction found in the solution-phase, it has been pointed out in the literature that control experiments are necessary to rule out the possibility of ubiquitous non-specific interactions (Smith et al., Biol. Mass Spectrom., 1993, 22, 493–501). Sonic have applied the use of ESI-MS and MALDI-MS to the study of multimeric proteins for the gentleness of the electrospray/desorption process allows weakly bound complexes, held together by hydrogen bonding, hydrophobic and/or ionic interactions, to remain intact upon transfer to the gas phase. The literature shows that not only do ESI-MS data from gas-phase studies reflect the non-covalent interactions found in solution, but that the strength of such interactions may also be determined. The binding constants for the interaction of various peptide inhibitors to src SH2 domain protein, as determined by ESI-MS, were found to be consistent with their measured solution phase binding constants (Loo et al., Proc. $43^{rd}$ ASMS Conf. on Mass Spectrom, and Allied Topics, 1995). ESI-MS has also been used to generate Scatchard plots for measuring the binding constants of vancomycin antibiotics with tripeptide ligands (Lim et al., J. Mass Spectrom., 1995, 30, 708–714).

Similar experiments have been performed to study non-covalent interactions of nucleic acids. Both ESI-MS and MALDI-MS have been applied to study the non-covalent interactions of nucleic acids and proteins. While MALDI does not typically allow for survival of an intact non-covalent complex, the use of crosslinking methods to generate covalent bonds between the components of the complex allows for its use in such studies. Stoichiometry of interaction and the sites of interaction have been ascertained for nucleic acid-protein interactions (Jensen et al., Rapid Commun. Mass Spectrom., 1993, 7, 496–501; Jensen et al., $42^{nd}$ ASMS Conf. on Mass Spectrom, and Allied Topics, 1994, 923). The sites of interaction are typically determined by proteolysis of either the non-covalent or covalently crosslinked complex (Jensen et al., Rapid Commun. Mass Spectrom., 1993, 7, 496–501; Jensen et al., $42^{nd}$ ASMS Conf. on Mass Spectrom, and Allied Topics, 1994, 923; Cohen et al., Protein Sci., 1995, 4, 1088–1099). Comparison of the mass spectra with those generated from proteolysis of the protein alone provides information about cleavage site accessibility or protection in the nucleic acid-protein complex and, therefore, information about the portions of these biopolymers that interact in the complex.

Electrospray mass spectrometry has also been effectively used for the determination of binding constants of noncovalent macromolecular complexes such as those between proteins and ligands, enzymes and inhibitors, and proteins and nucleic acids. Greig et al. (J. Am. Chem. Soc., 1995, 117, 10765–10766) have reported the use of ESI-MS to determine the dissociation constants (KD) for oligonucleotide-bovine serum albumin (BSA) complexes. The $K_D$ values determined by ESI-MS were reported to match solution $K_D$ values obtained using capillary electrophoresis.

Cheng et al. (J. Am. Chem. Soc., 1995, 117, 8859–8860) have reported the use of ESI-FTICR mass spectrometry as a method to determine the structure and relative binding constants for a mixture of competitive inhibitors of the enzyme carbonic anhydrase. Using a single ESI-FTICR-MS experiment these researchers were able to ascertain the relative binding constants for the noncovalent interactions between inhibitors and the enzyme by measuring the relative abundances of the ions of these noncovalent complexes. Further, tile $KD_D$s so determined for these compounds paralleled their known binding constants in solution. The method was also capable of identifying the structures of tight binding ligands from small mixtures of inhibitors based on the high resolution capabilities and multistep dissociation mass spectrometry afforded by the FTICR technique. In a related study, Gao et al. (J. Med. Chem., 1996, 39, 1949–55) have reported the use of ESI-FTICR-MS to screen libraries of soluble peptides in a search for tight binding inhibitors of carbonic anhydrase II. Simultaneous identification of the structure of a tight binding peptide inhibitor and determination of its binding constant was performed. The binding affinities determined from mass spectral ion abundance were found to correlate well with those determined in solution experiments. Further, the applicability of this technique to drug discovery efforts is limited by the lack of information generated with regards to sites and mode of such noncovalent interactions between a protein and ligands.

Also, these methods discuss, and appear to be limited to, the study of ligand interactions with proteins. The suitability of this method of mass spectrometric analysis of binding and dissociation constants for the study of noncovalent interactions of oligonucleotides, nucleic acids, such as RNA and DNA, and other biopolymers has not been described in the literature.

The drug discovery process has recently been revolutionized by the introduction of high throughput synthesis and combinatorial chemistry which afford collections and mixtures of large numbers of synthetic compounds for the purpose of screening for biological activity. Such large mixtures and pools of compounds pose significant challenges for the bioassay and analytical scientist. The analytical challenge is two-fold: separation of the active component of a mixture, and the identification of its structure. A variety of separation methods are available, including LC, HPLC, and CE. However, from the standpoint of separating biologically active components from a mixture of one or more targets with a combinatorial library necessitates the use and development of methods that select for and separate the complex (usually noncovalent) between the ligands and the target. Affinity column methods have been used to selectively isolate and subsequently analyze binding components of mixtures of compounds. For example, Kassel et at. (Techniques in Protein Chemistry VI, J. Crabb, Ed., Academic Press, San Diego, 1995, 39–46) have used an immobilized src SH2 domain protein column to separate and then analyze by HPLC-ESI-MS the structure of high affinity binding phosphopeptides.

A similar technique, ACE-ESI-MS, uses affinity capillary electrophoresis to accomplish the separation of noncovalent complexes formed upon mixing a biomolecular target with a combinatorial library or mixture of compounds. The receptor is typically incorporated into the capillary so that those ligands present in the combinatorial mixture interact with the target and are retained or slowed down within the capillary. Once separated, these noncovalent complexes are analyzed on-line by ESI-MS to ascertain the structures of the complexes and bound components. This method incorporates into one, the two steps that were previously performed separately: the compound/noncovalent complex selection, as has previously been demonstrated for vancomycin (Chu et al., Ace. Chem. Res., 1995, 28, 461–468; Chu et al., J. Org. Chem., 1993, 58, 648–52) and the step of compound identification (Cai et al., J. Chromatogr., 1995, 703, 667–692). For example, ACE-ESI-MS has been applied to mixtures of vancomycin with peptide libraries (Chu et al., J. Am. Chem. Soc., 1996, 118, 7827–35) to allow rapid screening of noncovalent complexes formed, and the identification of peptides that bind to vancomycin.

Another method for the separation and identification of active components from combinatorial libraries is the use of size-exclusion chromatography (SEC) followed by LC/MS or CE/MS analysis. Size exclusion is a simple yet powerful method to separate a biopolymer target and its complexes with small molecules members of a combinatorial library. Once isolated by SEC, these complexes are dissociated, under denaturing solution conditions, and finally the binding ligands are analyzed by mass spectrometry. This method has been applied to the identification of high affinity ligands for human serum albumin (HSA) from combinatorial library of small molecules (Dunaycvskiy et al., Rapid Commun. Mass Spectrom., 1997, 11, 1178–84).

Bio-affinity characterization mass spectrometry (BACMS) is yet another method for the characterization of noncovalent interactions of mixtures of ligands and biomolecular targets (Bruce et al., Rapid Commun. Mass Spectrom., 1995, 9, 644–50). BACMS involves the electrospray ionization of a solution containing both the affinity target and a mixture of ligands (or a combinatorial library), followed by trapping of all the ionic species in the FTICR ion-trap. The complexes of interest are then identified in the mass spectrum and isolated by selected-ion accumulation. This is followed by low energy dissociation or 'heating' to separate the high binding affinity ligands present in the complex. Finally, collisionally activated dissociation (CAD) is used to provide structural information about the high binding affinity ligand. The greatest advantage of BACMS is that the time-consuming techniques usually needed for the study of libraries, such as affinity chromatography, using solid supports for separation and purification of the complexes, followed by analysis to characterize the selected ligands, are all combined into one FTICR-MS experiment. To date, BACMS has only been applied to the study of protein targets.

None of the foregoing methods, however, have demonstrated applicability to a variety of biomolecular targets. Further, such methods do not provide rapid determination of the site of interaction between a combinatorially derived ligand and biopolymer.

Tandem mass spectrometry, as performed using electrospray ionization (ESI) on FTICR, triple quadrupole, or ion-trap mass spectrometers, has been found to be a powerful tool for determining the structure of biomolecules. It is known in the art that both small and large (>3000 kbase) RNA and DNA may be transferred from solution into the gas phase as intact ions using electrospray techniques. Further it is known, to those skilled in the art that these ions retain some degree of their solution structures as ions in the gas phase; this is especially useful when studying noncovalent complexes of nucleic acids and proteins, and nucleic acids and small molecules by mass spectrometric techniques.

Studies have demonstrated that oligonucleotides and nucleic acids obey certain fragmentation patterns during collisionally induced dissociation (CID), and that these fragments and patterns can be used to determine the sequence of the nucleic McLuckey et al., J. Am. Soc. Mass Spectrom., 1992, 3, 60–70; Mcluckey et al., J. Am. Chem.

Soc., 1993, 115, 12085–12095). Electrospray ionization produces several multiply charged ions of the parent nucleic acid, without any significant fragmentation of the nucleic acid. Typically, a single charge state of the nucleic acid is isolated using a triple quadrupole ion trap, or ion cyclotron resonance (ICR) device. This ion is then excited and allowed to collide with a neutral gas such as helium, argon or nitrogen so as to afford cleavage of certain bonds in the nucleic acid ion, or excited and fragmented with a laser pulse. Typically, two series of fragment ions are found to be formed: the a-Base series, and the w-series.

The series of a-Base fragments originates from initial cleavage of the glycosidic bond by simultaneous abstraction of a C-2' proton, followed by the elimination of the 3'-phosphate group and the C-4' proton. This fragmentation scheme results in a residual furan attached to the 3'-phosphate and affords a series of a-Base fragments whose masses increase sequentially from the 5'-terminus of the nucleic acid. Measurement of the masses of these collisionally induced fragments therefore affords the determination of the sequence of the nucleic acid in the 5' to 3' direction. The w series of fragments is generated via cleavage of the nucleic acid in a manner that leaves a 5' phosphate residue on each fragment. Thus monitoring the masses of w-series fragments allows determination of the sequence of the nucleic acid in the 3' to 5' direction. Using the sequence information generated from both series of fragments the sequence of deoxyribonucleic acids (DNA) may be ascertained. Obtaining similar mass spectrometric information for ribonucleic acids (RNA), is a much more difficult task. Collisionally induced dissociation (CID) of RNA is much less energetically favored than is the case for DNA because of the greater strength of the glycosidic bond in RNA. Hence, while small RNA such as 6-mers have been sequenced using CID MS, the sequencing of larger RNA has not been generally successful using tandem MS.

Determination of the structure of biomolecules, such as proteins and nucleic acids, may be attempted using solution biochemical cleavage followed by mass spectrometry. However, these methods are cumbersome and not always successful in that several biochemical cleavage and separation steps need to be performed prior to MS analysis of the cleaved products. Also, the level of information provided with regards to secondary and tertiary structure of biomolecules is limited. Methods available in the scientific literature are therefore greatly limited in terms of the sequence and structural information they provide for biomolecules and biomolecular targets.

One aspect of the present invention provides methods for determining the structure of biomolecular targets such is nucleic acids using mass spectrometry. The structure of nucleic acids, especially RNA, which is often difficult to ascertain, is readily determined using the methods of this invention. The structure of a nucleic acid is determined from the fragmentation pattern observed in $MS^n$ experiments. Directed fragmentation of RNA is facilitated by the selective incorporation of deoxynucleotides or other nucleosidic residues at specific residue locations in the nucleic acid sequence. During CID of such RNA/DNA chimeric nucleic acids, cleavage is facilitated at the sites where deoxynucleotides or the other non-native residues were incorporated. Cleavage is also influenced by the local secondary and tertiary structure of the biomolecule. Therefore, the cleavage patterns observed from a RNA/DNA hybrid reveals the local structure of the nucleic acid, including mismatched base pairs, bulged regions and other features.

Since exposed deoxynucleotide residues are known to be susceptible to CID cleavage in MS experiments, the systematic incorporation of such residues into RNA allows the systematic exploration of the local structure of RNA. Using this embodiment of the invention, it is possible to determine the secondary and tertiary structure of nucleic acids, including features such as mismatched base pairs, loops, bulges, and kink and stem structures.

Determination of the structure of an RNA may be accomplished, using exemplary methods of the invention, as follows. An RNA whose structure is to be determined is synthesized using an automated nucleic acid synthesizer. During RNA synthesis, deoxynucleotides are selectively incorporated into the sequence at specific sites where the structure is to be probed. This RNA/DNA chimeric nucleic acid, which is sensitized to collisional activation, is now used for sequence and structure determination using tandem MS experiments. ESI-MS, followed by trapping of selected ions and subsequent CID of each ion, affords information as to which positions of the nucleic acid hybrid are disordered (or not participating in a higher order structure) and, therefore, available for cleavage. A systematic pattern of deoxynucleotide incorporation into the sequence of the test RNA allows a systematic, mass spectrometric assessment of structure in a certain area of the nucleic acid, or for the entire nucleic acid. Other modified nucleic acid residues may be used instead of DNA. This, chemically modified nucleic acid subunits such as $Z^1$-modified, e.g. 2-O-Alkyl, base-modified, backbone modified or other residues may serve. Such residues will permit assessment of DNA as well as RNA.

The present invention also provides methods for the determination of the site and nature of interactions between a biomolecular target and a binding ligand. This is information of critical value to the process of drug discovery. Current methods of biomolecular screening do hot provide a straightforward means of also determining the nature of the interaction between a binding ligand and the biomolecular target. Information such as the stoichiometry and binding affinity of the interaction often needs to be ascertained from additional biochemical assays, thus slowing down and increasing the cost of drug discovery. It is often the case that binding of a drug or ligand to a biomolecular target, such as a nucleic acid, may lead to a change in conformation of the biomolecule to a different structure. This, too, may contribute to protection of the biomolecule from cleavage.

The present invention provides convenient methods for determining the site or sites on a biomolecular target where a binding ligand interacts. This is accomplished based on the knowledge that collisionally activated dissociation (CID or CAD) of a noncovalent biomolecule-ligand complex may be performed such that cleavage of the complex occurs only at exposed sites of the biomolecules. Thus cleavage sites present on the biomolecule that are involved in binding with the ligand are protected because of the increased structural order from the binding event during CID. ESI-$MS^n$ spectra generated using this method, in the presence and absence of a binding ligand (or drug), will reveal differential fragmentation patterns due to ligand induced protection of cleavage sites. Comparison of the mass spectra generated in the presence and absence of a binding ligand will, therefore, reveal the positions in the biomolecular sequence where the interactions between ligand and biomolecule are occurring.

These methods for determining the sites of interaction between a binding ligand and a biomolecular target are broadly applicable. The biomolecular targets that may be studied using this method include, but are not limited to, peptides, proteins, antibodies, oligonucleotides, RNA, DNA, other nucleic acids, glycopeptides, and oligosaccharides. It is preferred that the biomolecular target be a nucleic acid. It is further preferred that the biomolecular target be a chimeric RNA/DNA nucleic acid, synthesized to selectively incorporate deoxynucleotides, (or other residues) in the sequence at specific locations. The binding ligand may be one of the groups of molecules including, but not limited to, organic or inorganic, small to large molecular weight individual compounds, mixtures and combinatorial libraries of ligands, inhibitors, agonists, antagonists, substrates, and biopolymers, such as peptides or oligonucleotides.

Determination of the sites on an RNA target where interaction occurs with a binding ligand may be accomplished as follows. An RNA target that is to be studied as a biomolecular target is prepared using an automated synthesizer, and selectively incorporating deoxynucleotides into the sequence at specific sites. An aliquot of this RNA/DNA chimeric is used directly for ESI-MS, followed by CID analysis of selectively accumulated ions, to establish the native structure and cleavage patterns of this biomolecular target. A second aliquot of the RNA/DNA chimeric is mixed with a solution of a drug or ligand that is known to bind to the biomolecular target. The target and ligand are anticipated to interact in solution to form a noncovalent complex. Subjecting this solution of the noncovalent biomolecule-ligand complex to the method of this invention leads to ionization of the complex with a retention of the noncovalent interactions and binding stoichiometries. CID of the complex then leads to cleavage of the biomolecule sequence at fragmentation sites that are exposed. Sites where fragmentation would otherwise occur, but which are involved in binding the ligand to the biomolecule, are protected, such that cleavage at or near these sites is prevented during the CID stage. The differences in the fragmentation patterns of the biomolecule when subjected to the methods of this invention in the presence and absence of binding ligand indicate the site(s) on the biomolecule that is protected and, therefore, are involved in binding the ligand.

Likewise, a systematic pattern of deoxynucleotide incorporation into the sequence of the test RNA will allow for a systematic mass spectrometric assessment of binding sites and interactions in a certain area of the nucleic acid, or for the entire nucleic acid, using the method of this invention. This invention, therefore, also provides a new method of 'footprinting' biomolecular targets especially nucleic acids. This footprinting by mass spectrometry is a straightforward method for mapping the structure of biomolecular targets and the sites of interactions of ligands with these targets.

The nature of interactions between the binding ligand and a biomolecular target are also readily studied using the method of this invention. Thus, the stoichiometry and absolute and relative dissociation constant of the biomolecule-ligand noncovalent complex is readily ascertained using the method of this invention. The ratio of the number of ligand molecules and the number of biomolecular receptors involved in (he formation of a noncovalent biomolecule-ligand complex is of significant importance to the biochemist and medicinal chemist. Likewise, the strength of a noncovalent complex, or the binding affinity of the ligand for the biomolecular target, is of significance because it provides an indication of the degree of complementarity between the ligand and the biomolecule. Also, the determination of this binding affinity is important for the rank ordering of different ligands so as to provide structure-activity relationships for a series of ligands, and to facilitate the design of stronger binding ligands for a particular biomolecular target.

The methods of the present invention are also capable of determining both the binding stoichiometry and affinity of a ligand for the biomolecular target being screened in a screening study. Electrospray ionization is known to retain to a significant degree, the solution phase structures of biomolecules and their noncovalent complexes in the gaseous ions it generates. Thus, determination of the stoichiometry of noncovalent complexes simply needs data on the masses of the ligand, biomolecular target and the noncovalent biomolecule-ligand complex. The data needed to accomplish this determination is actually available from the mass spectrometry experiment that may be performed to determine the structure and site of binding of a ligand to the biomolecular target. Based on the knowledge of the structure and sequence of the target biomolecule, MS analysis of the biomolecule-ligand complex reveals the number of ligand and target molecules present in the noncovalent complex. If the noncovalent complex ion observed from the mass spectrum is of an m/z equal to that expected from the addition of the m/z values of one molecule each of the target biomolecule and ligand, then the noncovalent complex is preferably formed from a 1:1 interaction between the biomolecule and ligand. Simple mathematical operations on the molecular weight and charges of the target and ligand can likewise determine higher levels of interactions between ligand and biomolecule. The high resolution of a FTICR mass spectrometer allows direct identification of the bound ligand based on exact measurement of the molecular mass of the complex relative to unbound nucleic acid.

The use of mass spectrometry, in accordance with this invention can provide information on not only the mass to charge ratio of ions generated from a sample, but also the relative abundance of such ions. Under standardized experimental conditions, it is therefore possible to compare the abundance of a noncovalent biomolecule-ligand complex ion with the ion abundance of the noncovalent complex formed between a biomolecule and a standard molecule, such as a known substrate or inhibitor. Through this comparison, binding affinity of the ligand for the biomolecule, relative to the known binding of a standard molecule, may be ascertained. In addition, the absolute binding affinity can also be determined.

Determination of the nature of the interaction of a ligand with a biomolecular target may be carried out as exemplified for the binding of a small molecule ligand with a nucleic acid target. A chimeric RNA/DNA biomolecular target whose binding to a test ligand is to be studied is first prepared via automated synthesis protocols. An aliquot of a known concentration of chimeric nucleic acid is treated with a known concentration and quantity of a standard compound that is known to bind that nucleic acid, such as the aminoglycoside paromomycin which is known to bind to the 16S A-site of RNA. ESI-MS, followed by CID of the paromomycin-nucleic acid complex, affords a control spectrum for the interactions and complex. A second aliquot of the chimeric nucleic acid is next treated with a test ligand using quantities and concentrations similar to those used for the control experiment. Application of the method of the invention to this nucleic acid-ligand noncovalent complex affords a test spectrum that reveals the nature of the biomolecule-ligand interaction. Analysis of the noncovalent nucleic acid-ligand complex based on the known molecular weights of the two components of the complex allows the determination of the number of nucleic acid molecules and ligands present in the complex. Further, comparison of the abundance of the nucleic acid-ligand complex ion with the abundance of the ion generated from the e.g. paromomycin-nucleic acid complex (or complex with any other known interacting species) provides a convenient and direct estimate of the binding affinity of the test ligand compared to the standard, paromomycin. Since the standard is well characterized, its solution binding affinity should be known from other experiments or literature sources. For example, paromomycin binds to a test 27-mer RNA with a ~1μFM affinity. Knowing the binding affinity of the test ligand relative to paromomycin from the MS experiment, it is now possible to determine the micromolar binding affinity of the test ligand for the nucleic acid target being studied. Relative binding affinity may also be measured by testing a standard compound and test ligand simultaneously as in a mixture with the target biomolecule, in a single test assay.

Another object of the present invention is to provide general methods for the screening of compounds for drug discovery. The invention provides methods for the screening of a wide variety of biomolecular targets that include, but are not limited to, peptides, proteins, receptors, antibodies, oligonucleotides, RNA, DNA, RNA/DNA hybrids, nucleic acids, oligosaccharides, carbohydrates, and glycopeptides. The molecules that may be screened by using the methods of this invention include, but are not limited to, organic or inorganic, small to large molecular weight individual compounds, mixtures and combinatorial libraries of ligands, inhibitors, agonists, antagonists, substrates, and biopolymers, such as peptides or oligonucleotides.

The primary challenge when screening large collections and mixtures of compounds is not in finding biologically relevant activities, for this has been demonstrated in many different cases, but in identifying the active components from such screens, and often from mixtures and pools of compounds that are found to be active. One solution that has been practiced by the art-skilled in high throughput drug discovery is the iterative deconvolution of mixtures. Deconvolution essentially entails the resynthesis of that combinatorial pool or mixture that was found to be active in screening against a target of interest. Resynthesis may result in the generation of a set of smaller pools or mixtures, or a set of individual compounds. Rescreening and iterative deconvolution are performed until the individual compounds that are responsible for the activity observed in the screens of the parent mixtures are isolated.

However, analytical techniques are limited in their ability to adequately handle the types of mixtures generated in combinatorial efforts. The similarity of members of combinatorial mixtures or pools, and the complexity of such mixtures, prohibit effective analytical assessment until the mixtures have been deconvoluted into individual compounds, or at the very least into pools of only a handful of components. While this process of deconvolution, involving resynthesis, rescreening and analysis, is very cumbersome and time-consuming, it is also very costly. A general method that alleviates these problems by rapidly revealing active mixtures and identifying the active components of such mixtures is clearly needed to save time and money in the drug discovery process.

The present invention solves the need for a method to rapidly assess the activity of combinatorial mixtures against a biomolecular target and also identify the structure of the active components of Such mixtures. This is exemplified by the screening of combinatorial mixtures for binding to a nucleic acid target as follows. A chimeric RNA/DNA target of known sequence is selected as the screening target based on biological relevance. This chimeric nucleic acid target is prepared via automated synthesis. An aliquot of the nucleic acid is used at a concentration of 10 μM and treated with e. q. paromomycin acetate at a concentration of 150 nM. A sample of the mixture is analyzed by the method of the invention to demonstrate binding of the paromomycin by observation of the paromomycin-nucleic acid complex ion. Next, an aliquot of this mixture is treated with a DMSO solution of a combinatorial mixture of compounds such that the final concentration of each component of the mixture is ~150 nM. This sample is then subjected to ESI-MS, and the mass spectrum monitored for the appearance of new signals that correspond to new nucleic acid-ligand noncovalent complexes formed with components of the combinatorial library.

The relative dissociation constants of these new complexes are determined by comparing the abundance of these new ions with the abundance of the paromomycin-nucleic acid complex ion whose binding affinity for the target is known is priori. Algorithmic deconvolution of the new complex ions observed, while taking into account the masses of the target and the components of the combinatorial library, provides the molecular weights of the binding ligands present in the observed noncovalent complexes. Alternatively, the identity of the binding ligand may also be determined by first isolating the newly observed complex ion using a triple quadrupole ion-trap or an ion cyclotron resonance device (ICR) followed by conventional identification by mass spectrometry fragment analysis. For example, upon isolation, a noncovalent complex ion is 'heated' or dissociated into the constituent ligand and biomolecule ions. This MS/MS experiment then can be tuned to study fragmentation of the ligand. This information provides direct evidence of the structure of the bound ligand. This method of the present invention, therefore, provides both the identity and relative binding affinity of members of combinatorial or other mixtures of compounds that bind to the nucleic acid target.

Not only does the present invention provide methods for the determination of the molecular weight and absolute and relative binding affinity of the binding components of a combinatorial or other mixture of compounds, but it also provides valuable information about the site of binding on the biomolecular target. Such information permits the identification of compounds having particular biological activity and gives rise to useful drugs, veterinary drugs, agricultural chemicals, industrial chemicals, diagnostics and other useful compounds. This can also be accomplished as part of the same mass spectrometric procedure by isolating the newly observed complex ions using a triple quadrupole ion-trap or an ion cyclotron resonance device (ICR). For example, upon isolation, a noncovalent complex ion is collisionally activated to cleave the chimeric nucleic acid target at exposed deoxynucleotide sites. This MS/MS procedure, then, can be tuned to study fragmentation of the biomolecular target.

Comparison of the cleavage and fragment patterns so obtained for the nucleic acid component of the noncovalent complex with patterns obtained for the native chimeric nucleic acid alone reveals the locations on the nucleic acid that are protected by the binding of the ligand. This indicates the binding sites for the ligand on the nucleic acid. Comparison of the cleavage patterns to those observed from the CID of the standard-nucleic acid complex ion provide correlations between the sites of binding of the new ligand and standard. In this fashion, ligands that bind to nucleic acid targets may be identified such that they compete for the same binding site on the nucleic acid where the standard binds, or bind at completely different and new sites on the nucleic acid. Both these types of observations are of value from a drug discovery standpoint.

The methods of the present invention can be used to identify metal ion binding sites on any of the biomolecules described herein. Preferably, the metal ion binding site binds alkali metals or alkaline earth metals. More preferably, the metal ions are $Na^+$, $Mg^{++}$ and $Mn^{++}$.

Drug discovery, using any one of a number of different types of biomolecular targets attends use of the methods of this invention which can rapidly screen large combinatorial libraries and mixtures of compounds for binding activity against a specific target.

It is possible that combinatorial libraries and mixtures of compounds being used for screening may contain components that are similar in mass because their elemental compositions are similar while their structures are different, or at the very least, isomeric or enantiomeric. In such instances, a simple algorithmic calculation of the molecular weight of a bound ligand will be insufficient to provide the identity of the ligand for there may be multiple components of the same molecular mass. The methods of the invention are also capable of addressing and resolving such problems of ligand identification. The use of MS/MS experiments to further fragment the bound ligand, following selective ion accumulation of the ligand ion from the noncovalent complex, is a simple technique that provides structural detail of the bound ligand. This mass and structural information provided by the methods of this invention is expected to resolve the vast majority of mass redundancy problems associated with the screening of large combinatorial libraries and mixtures of compounds.

In a preferred embodiment, the present invention also provides method for simultaneously screening multiple biomolecular targets against combinatorial libraries and mixtures or collections of compounds. This is a significant advantage of the present invention over current state-of-the-art techniques in the screening of compounds for such binding. There is believed to be no prior technique that allows the simultaneous and rapid screening of multiple targets, while providing structural detail on the target and binding ligand at the same time. In addition to providing methods for the rapid and simultaneous screening of multiple biomolecular targets, the present invention also provides methods for determining the structure and nature of binding of both the target and binding ligand.

As discussed above, mass spectrometry methods of the present invention provide a direct means for screening and identifying those components of combinatorial mixtures that bind to a target biomolecule in solution. In order to enhance efficiency, it is preferable to multiplex the screening process by simultaneously screening multiple targets for binding activity against a combinatorial library or mixture of compounds. This strategy is normally limited by the distribution of charge states and the undesirable mass/charge overlap that will be generated from all possible noncovalent biomolecule-ligand complexes that could be formed during such a screening assay. This problem of overlapping peaks in the mass spectra is further exacerbated if the biomolecular targets being screened are of similar sequence, composition, or molecular weight. In such instances it would not be possible to ascertain in a rapid and simple operation the composition of biomolecule-ligand complexes because of the extensive mass redundancy present in the pool of biomolecules being studied and possible in the combinatorial library being screened.

The method of the present invention alleviates the problem of biomolecular target mass redundancy through the use of special mass modifying molecular weight tags. These mass modifying tags are typically uncharged or positively charged groups such as, but not limited to, alkyl and tetraalkylammonium groups, and polymers such as, but not limited to, polyethylene glycols (PEG), polypropylene, polystyrene, cellulose, sephadex, dextrans, cyclodextrins, peptides, and polyacrylamides. These mass modifying tags may be selected based on their molecular weight contribution and their ionic nature. These mass modifying tags may be attached to the biopolymeric targets at one or more sites including, but not limited to, the 2'—O—, 3'-terminus, 5'-terminus or along the sugar-phosphate backbone of nucleic acid targets. Addition of mass modifying tags to the 5'terminus of synthetic oligonucleotides can be realized either using conventional phosphoramidite chemistry, other conventional chemistry or by biochemical or enzymatic means. Such mass modification of a nucleic acid may be carried out using conventional, manual or automated techniques. Alternatively, addition of mass modifying tags may be performed at the 3'-terminus by the use of appropriately modified polymer or CPG supports for solid-phase synthesis of nucleic acids. Mass modification at the 3'terminus may also be done by biochemical or enzymatic means. It is also possible to attach mass modifying tags to the internucleotide linkages of a nucleic acid. This may be performed via the use of appropriately modified phosphoramidites, or other nucleoside building blocks during nucleic acid synthesis or via post-synthetic modification of the internucleotide linkage. Further, attachment of mass modifying tags to nucleic acid targets may also be accomplished via the use of bifunctional linkers at any functional site on the nucleic acid. Similarly, when working with other classes of biomolecular targets these mass modifying tags may likewise be incorporated at one or more positions on the biomolecule. As will be apparent, inclusion in either target or ligand of isotopic mass labels may also be useful.

Thus, similar nucleic acid and other biological targets may be differentially tagged for rapid mass spectrometric screening by the methods of this invention. When noncovalent complexes are observed from this multiplexed screening of multiple nucleic acid targets with mixtures of small molecular weight combinatorial libraries, the constituent ligand and biomolecule are readily identified using conventional mass analyzers such as quadrupole, ion trap, ICR, magnetic sector, or TOF and followed by MS/MS. This is because the mass modifying tags make the m/z (mass to charge ratio) of the signal arising from each target biomolecule-ligand complex ion of similar charge, distinct in the mass spectrum, and which results in cleanly separated ion peaks. Mass redundancy and peak overlap are both avoided by the use of mass modifying tags.

Thc present invention is also highly useful in combination with other techniques for the identification of ligands which interact with molecular interaction sites on RNA and other nucleic acids. Molecular interaction sites attend RNA and are believe to be highly important in the functioning of such RNA. The nucleotide sequences of molecular interaction sites are highly conserved, even among taxonomically diverse species. Moreover, such molecular interaction sites have specific structures which provide opportunities for ligand binding. Ascertaining which ligands bind to such sites as well as determining the relative affinities and specificities for the binding of each ligand provides lead compounds for drug discovery, therapeutics, agricultural chemistry, industrial chemistry and otherwise.

The present mass spectrometric techniques, especially the MASS techniques and those which possess similar analytical robustness and power, are ideally suited for cooperating with drug and other discovery and identification programs such as those which determine ligand binding to molecular interaction sites. The identification of molecular interaction sites in RNA and other nucleic acids and the determination of hierarchies of molecular ligands which likely bind to such molecular interaction sites can be evaluated through the present techniques. Thus, in accordance with preferred embodiments of the present invention, a hierarchy of ligands ranked in accordance with their anticipated or calculated likelihood of binding to a molecular interaction site of an RNA are actually synthesized. Such synthesis is preferably accomplished in an automated or robotized fashion, preferably from instruction sets provided in attendance to the ranked hierarchy of ligands. The compounds may be prepared in a library or mixture since the present mass spectrometric methods can evaluate pluralities of compounds and their complexes with RNA simultaneously.

After the ligands are synthesized, preferably in library form, they are contacted with the RNA having the molecular interaction site of interest. Complexation or binding (conventionally, non-covalent binding) is permitted to occur. The complexed RNA —ligand library is then analyzed by mass spectrometry. A principal object of the analysis is preferably the determination of which ligands bind to the RNA molecular interaction site and, among those, which ones rank more highly in terms of specificity and affinity. Accordingly, it is possible to identify from a mixture or library of compounds, which ones are the most interactive with a particular molecular interaction site so as to be able to modulate it. Such compounds can either he used themselves, or, more likely, be used,is lead compounds for modification into drugs, agricultural chemicals, environmental chemicals, industrial and food chemicals and otherwise.

As described above, it is highly desirable to challenge RNAs having molecular interaction sites with libraries of compounds which have already been predicted or calculated to be likely to interact with the interaction sites. It is preferred that such molecules belong to ranked hierarchies so as to give rise to the greatest likelihood of finding highly potent modulators of the target RNA.

While there are a number of ways to identify compounds likely to interact with molecular interaction sites of RNA and other biological molecules, preferred methodologies are described in U.S. Ser. Nos. 09/076,440, 09/076,405, 091076, 447, 09/076,206, 09/076,214, and 09/076,404, each of which was filed on May 12, 1998 and each assigned to the assignee of this invention. All of the foregoing applications are incorporated by reference herein in their entirety.

One mass spectrometric method which is particularly useful when combined with the techniques of the foregoing commonly owned inventions provides the determination of specificity and affinity of ligands to RNA targets. MASS (multi target affinity/specificity screening) techniques can provide high throughput screening methods to analyze the specificity and affinity of ligands to molecular interaction sites of nucleic acids, especially RNA. MASS employs high performance electrospray ionization Fourier transform ion cyclotron resonance mass spectrometry (ESI-FTICR-MS) to a) determine exact chemical composition of affinity selected ligands originating from a combinatorial library, b) determine relative dissociation constants (Kd) of ligands complexed to the target(s), and c) determine the location of ligand binding. This information can be gathered from each target(s) or library set in a single assay in less than 15 minutes. This scheme benefits from two unique aspects of the ESI-FTICR combination. The "soft" nature of the electrospray ionization process allows specific noncovalent complexes to be ionized and transferred into the gas phase intact where they are amenable to subsequent characterization by mass spectrometry. The high resolving power afforded by the FTICR platform facilitates the characterization of complex mixtures which, when combined with the high mass accuracy inherent to FTICR, provides unambiguous identification of ligands complexed with the molecular interaction site or sites of a target or targets.

Binding site information can be obtained by comparing the gas phase fragmentation patterns of the free and complexed target and absolute binding affinities while relative binding constants are derived from the relative abundance of complexes using a complex with a known Kd as an internal standard. With knowledge of the specificity and affinity of ligands to the molecular interaction site of a target RNA, the desired lead or ultimate compound for modulation of the RNA can be determined. Therapeutic, agricultural chemical, industrial chemical and other products which benefit from modulation of such RNA attend this result.

The simultaneous screening of a combinatorial library of molecules of mass 700–750, against two nucleic acid targets of the same molecular weight but different sequence, is demonstrated by the use of mass modifying tags. If both nucleic acids targets being studied are 27-mer RNAs of mass 8927, then screening a library of molecules of mass 700–750 could afford a bewildering jumble of noncovalent complex ions in the mass spectrum of the mixture of the two nucleic acids and the library. However if one of the two targets is mass modified, for example by the use of a PEG chain of mass 3575 attached at the 5' terminus of the target, then the mass spectrum will be significantly simplified. It is known that a 27-mer will generate multiply-charged ion signals, following electrospray ionization, of mass/charge values 1486.8, 1784.4, and 2230.8 for the $(M-6H)^{6-}$, $(M-5H)^{5-}$, and the $(M-4H)^{4-}$charge states. Upon binding to small molecules of mass 700–750, the unmodified RNA-ligand complexes are anticipated to occur in the 1603.2–1611.6, 1924.4–1934.4, and 2405.8–2418.3 m/z range. If the second nucleic acid target were not modified in any way, the signals from its complexes would have occurred in the same regions. However, using the mass modified RNA, bearing the PEG chain of mass 3575, results in the observation of the corresponding mass modified RNA-ligand complexes to occur in the 2199–2207.4, 2639–2649 and 3299–3311 m/z range. Thus all signals from the second mass modified nucleic acid would be cleanly resolved from those of the first RNA. These noncovalent complex ions may be selected e.g. by triple, quadrupole, ion trap or ICR techniques, and studied further by MS/MS to afford detailed understanding of the sites of ligand-RNA interaction, and the nature of these interactions, as has been discussed above.

In a further embodiment, the methods of this invention are applicable for the determination of the specificity of binding interactions between a ligand and a biomolecular target. By simultaneously screening multiple biomolecular targets with one or more compounds, using the methods of this invention, it is possible to ascertain whether a ligand binds specifically to only one target biomolecule, or whether the binding observed with the target is reproduced with control biomolecules as well, and is therefore non-specific. This is an important distinction to be made when screening large libraries and collections of compounds for binding to biomolecular targets. It is desirable to quickly distinguish those ligands that are selective or specific for the biomolecular target of interest from those that are non-specific and bind to any and all targets. From the standpoint of drug discovery, it is most often the case that undesirable biological activities arise from the indiscriminate, non-specific binding of molecules to unrelated biomolecules. The present invention provides a valuable and straightforward method for assessing the specificity of interactions between a ligand and a panel of targets.

The use of mass modifying tags for the simultaneous screening of multiple biomolecular targets is applicable to the determination of binding specificity of a ligand as well. Mass modifying tags may be used to differentiate several biomolecular targets that serve as a control panel for screening a combinatorial library of individual compounds against a specific biomolecular target. When simultaneously screening multiple biomolecular targets using the mass spectrometric methods of this invention, it is necessary to ensure good separation of the ions that result from each target and its complex with the binding ligand. This peak overlap is easily eliminated by the facile introduction of different mass modifying tags onto the different biomolecular targets being studied. A mixture of the biomolecular target and the control panel is mixed with the ligand being evaluated. This solution is then ionized by ESI-MS, and the noncovalent complex ions observed may be directly identified as having resulted from the binding of the ligand to a specific target from the several biomolecular targets present in the mixture. In this way, a qualitative indication of specificity or selectivity of binding for the desired target versus the control biomolecules may be obtained. This selectivity may also be quantitated through the use of appropriate standards of known binding affinity and comparison of the ligand-biomolecule complex ion abundance to the abundance of the standard-biomolecule abundance. Further, details on the nature of the specific or non-specific interaction of the ligand with the different biomolecules may also be obtained following ion-selection and subsequent MS/MS experiments, as discussed above.

Likewise, it is also possible to determine the proportional binding of a ligand to two or more biomolecular targets using the methods of this invention. Thus by the use of appropriate mass modifying tags on the different biomolecular targets, the different noncovalent complexes formed via differential binding of the ligand can be readily distinguished in the mass spectrometer. Quantitation of the binding is possible by measuring the abundance of these ions. Comparing the relative abundances of these ions provides a means to determine the proportional binding of the ligand to the different biomolecular targets.

Yet another application of the methods of the present invention is to determine the differential binding of ligands to biomolecular targets of different origin. When studying the binding of small molecule ligands to RNA targets, it is straightforward to distinguish between the noncovalent ligand-RNA complexes generated from binding to the two different RNA targets, even though both may be screened simultaneously as a mixture in the same assay. Further, it is also possible to determine specificity and selectivity of the ligand for one versus the other RNA, and to determine the relative affinities of binding to each RNA target.

The methods of the present invention are applicable to the study of a wide variety of biomolecular targets that include, but are not limited to, peptides, proteins, receptors, antibodies, oligonucleotides, RNA, DNA, RNA/DNA hybrids, nucleic acids, modified oligonucleotides, peptide-nucleic acids (PNAs), oligosaccharides, carbohydrates, and glycopeptides. Further these biomolecular targets may be synthetic or isolated from natural sources. Biomolecular targets of natural origin include, but are not limited to, those obtained from microbial, plant, animal, viral or human materials, such as, but not limited to, cells, cell extracts, fluids, tissues and organs.

The molecules that may be screened by using the methods of this invention include, but are not limited to, organic or inorganic, small to large molecular weight individual compounds, and combinatorial mixture or libraries of ligands, inhibitors, agonists, antagonists, substrates, and biopolymers, such as peptides or oligonucleotides.

Combinatorial mixtures include, but are not limited to, collections of compounds, and libraries of compounds. These mixtures may be generated via combinatorial synthesis of mixtures or via admixture of individual compounds. Collections of compounds include, but are not limited to, sets of individual compounds or sets of mixtures or pools of compounds. These combinatorial libraries may be obtained from synthetic or from natural sources such as, for example to, microbial, plant, marine, viral and animal materials. Combinatorial libraries include at least about twenty compounds and as many as a thousands of individual compounds and potentially even more. When combinatorial libraries are mixtures of compounds these mixtures typically contain from 20 to 5000 compounds preferably from 50–1000, more preferably from 50–100. Combinations of from 100–500 are useful as are mixtures having from 500–1000 individual species. Typically, members of combinatorial libraries have molecular weight less than about 5000 Da.

The mass spectrometry techniques that may be used in the methods of this invention include all of the techniques and systems described herein or are subsequently developed. Tandem techniques are also useful, including combinations of all of the foregoing and LC/MS. The mass spectrometers used in the methods of this invention may be a single quadrupole, triple quadrupole, magnetic sector, quadrupole ion trap, time-of-flight instrument, and FTICR. Future modifications to mass spectrometry are expected to give rise to improved techniques which may also be useful herein.

In another embodiment of the present invention, binding of mixtures of aminoglycosides can be measured simultaneously against multiple RNA targets of identical length and similar (or identical) molecular weight. Addition of a neutral mass tag to one of the RNA targets shifts those to a higher mass/charge ratio, where complexes with small molecules can be identified unambiguously. An appropriately placed neutral mass tag does not alter RNA-ligand binding. Preferably, this method is demonstrated with model RNAs corresponding to the decoding region of the prokaryotic and eukaryotic small subunit rRNAs and a mixture of compounds, such as, for example, five aminoglycosides. In the examples set forth below, complexes are observed between the aminoglycoside library and the prokaryotic rRNA model, while no aminoglycoside was observed to bind to the mass tagged eukaryotic rRNA model. The differential binding data is consistent with the eukaryotic A-site rRNA having a different confirmation compared to the prokaryotic A-site that prevents entry and binding of neomycin-class aminoglycosides. Mass spectrometric analysis of neutral mass-tagged macromolecular targets represents a new high throughput screening paradigm in which the interaction of multiple targets against a collection of small molecules can be evaluated in parallel.

Figure 68:
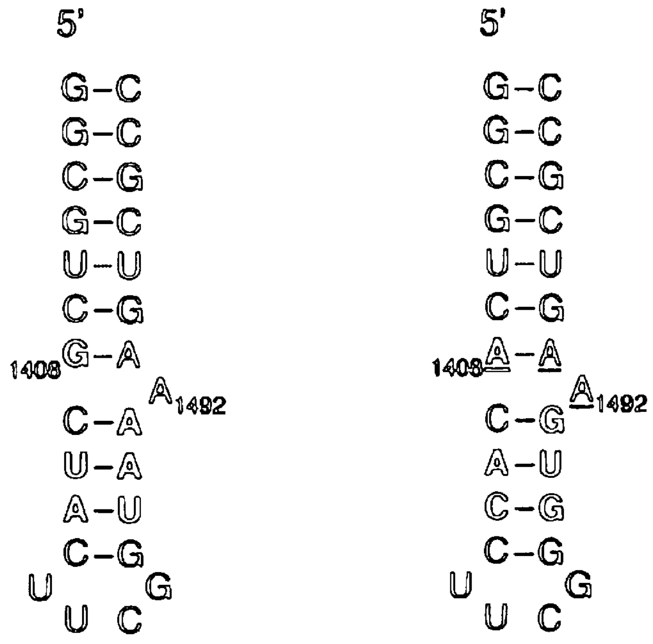
FIG. 68 depicts secondary structures of the 27 base RNA models used in this work corresponding to the 18S (eukaryotic) SEQ ID NO:382 and 16S (prokaryotic) SEQ ID NO:35 A-sites.

The preferred model system employed herein comprises a library comprised of five 2-deoxystreptamine aminoglycoside antibiotics which have a range of binding affinities for the decoding sites of the prokaryotic and eukaryotic ribosomal RNA ranging from ~28 nM to ~1.5 mM. FIG. 68 illustrates the secondary structures for the 27-nucleotide models of the 16S and 18S rRNA decoding sites. These constructs consist of a 7 base pair stem structure containing a non-canonical U—U and a purine-adenosine mismatch base pair adjacent to a bulged adenosine residue closed by a UUCG tetraloop. NMR studies of a complex between 16S and paromomycin show that the RNA makes primary hydrogen bond, electrostatic, and stacking contacts with the aminoglycoside (Fourmy, et al., *Science,* 1996, 274, 1367–1371) and that paromomycin binds in the major groove of the model A-site RNA within the pocket created by the A-A base pair and the single bulged adenine. The masses for the two RNA models differ by only 15.011 Da and the $(M-5H^{+})^{5-}$ species of these constructs differ by only 3 m/z units. While the high resolution capabilities of the FTICR mass spectrometer can easily resolve these species, mass spectra from a solution containing both RNAs are complicated by overlap among the signals from free RNA ions and their sodium and potassium-adducted species.

Methods to increase the separation between the associated signals in the mass spectra due to overlap among signals from RNAs 16S and 18S are described herein. RNA targets modified with additional uncharged functional groups conjugated to their 5'-termini have been synthesized. Such a synthetic modification is referred to herein as a neutral mass tag. The shift in mass, and concomitant m/z, of a mass-tagged macromolecule moves the family of signals produced by the tagged RNA into a resolved region of the mass spectrum.

When simultaneously screening of untagged 165 and untagged 185 against a combinatorial library of small molecules, if a complex were observed at 515.011 Da higher than 16S, it would not be possible to directly determine (without tandem MS methods) whether the complex corresponded to a ligand weighing 515.011 Da complexed to the 16S target or a ligand weighing 500.000 Daltons complexed to 185. Furthermore, because positively charged ligands can have non-specific interactions with RNA oligomers, it is often desirable to assay libraries for specific and non-specific binding by screening against two or more RNA targets simultaneously (e.g. a structured target sequence and an unstructured control sequence) in a single ESI-MS experiment. This multiplex advantage can be further exploited in the RNA-drug discovery arena in which libraries are to be assayed against multiple RNA targets of similar, or identical, mass. A single analysis in which 5 RNA targets are screened against a combinatorial library of 200 components facilitates the direct evaluation of 1000 RNA-ligand interactions from the acquisition of a single mass spectrum.

While the ability to shift the m/z range of closely related macromolecules is highly desirable as described above, it is preferably desired that the mass tag does not alter key physical properties of the target or the ligand binding properties. Preferably, an 18-atom mass tag ($C_{12}H_{25}O_{72}$) attached to the 5'-terminus of the RNA oligomer through a phosphodiester linkage can be employed. The mass tag has no appreciable affect on oligonucleotide solubility, ionization efficiency, or UV absorbance, and does not alter RNA-ligand binding. This latter attribute is evidenced by the data in FIG. 69 that illustrates the conserved ratio of free:bound RNA for the untagged and tagged RNA models of the bacterial decoding site under competitive binding conditions with paromomycin.

Aminoglycoside antibiotics inhibit bacterial growth by disrupting essential prokaryotic RNA-protein and RNA-RNA interactions. In vivo, a therapeutic effect is realized because paromomycin alters essential RNA interactions in prokaryotes (by binding to the 16S A-site with high affinity) but does appreciably disrupt the function of the eukaryotic RNA complexes (owing to the low affinity of paromomycin for the 18S A-site). A compound that binds both the 16-S and 18S A-sites with similar affinity would likely inhibit bacterial growth but might also have deleterious cytotoxic effects in eukaryotic cells and would not make a suitable therapeutic agent. Thus, the 16S/18S model RNA system can serve not only as an interesting target for new generation antibiotics, but as a well characterized control for our mass spectrometry based RNA-ligand affinity assay.

Figure 70:
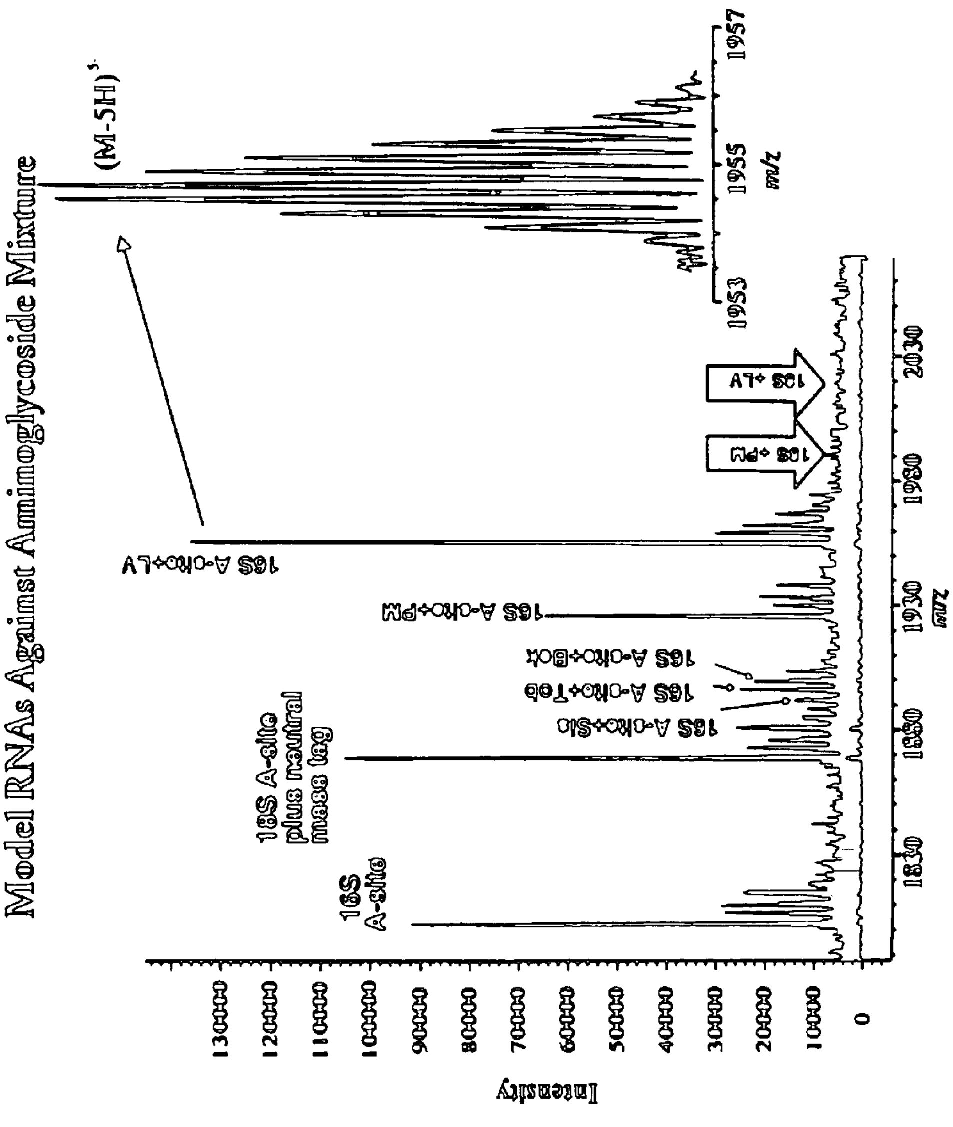
FIG. 70 depicts mass spectra from simultaneous screening of 16S A-site and 18S A-site Model RNAs against a mixture of aminoglycosides.

The ESI-FTICR mass spectrum depicted in FIG. 70 was acquired from a 10 mM mixture of untagged 16S and tagged 18S in the presence of an equimolar mixture of five aminoglycosides. It is to be understood that other biomolecules may be used in place of the aminoglycosides. The aminoglycosides have been selected from two classes of 2-deoxystreptamines: 4,5-disubstituted (paromomycin, and lividomycin), and 4,6-disubstituted (tobramycin, sisomicin, and bekanamycin), present at 500 nM each. Complexes corresponding to 1:1 binding of individual aminoglycosides were observed between 16S and all members of the aminoglycoside mixture, with the apparent affinities estimated from the abundances of the respective complexes differing substantially. Signal intensities from the complexes with paromomycin (m/z 1925.572) and lividomycin (m/z 1954.790) are consistent with MS-measured dissociation constants of 110 nM and 28 nM, respectively. The intensities of 16S complexes with tobramycin (m/z 1895.960), bekanamycin (m/z 1899.171), and sisomicin (m/z 1891.972) were reduced, consistent with solution dissociation constants of ~1.5 mM. Wang, et al., *Biochemistry,* 1997, 36, 768–779. Hence, under these assay conditions, the MS-observed ion abundances reflect the solution dissociation constants. The inset in FIG. 70 demonstrates the ability to resolve the isotopic envelope for each complex and allows mass differences to be calculated from homo-isotopic species, thus, measuring the difference in m/z between the RNA target and the RNA-ligand complex allows precise mass determination of the ligand. The spectrum is calibrated using multiple isotope peaks of the $(M-5H^{+})^{5-}$ and $(M-4H^{+})^{4-}$ charge states of the free RNA as internal mass standards which brackets the m/z range in which complexes are observed. The average mass measurement error obtained for the complexes in FIG. 70 is 2.1 ppm when m/z differences are measured between the most abundant (4 $^{13}C$) isotope peak of 16S and each complex. This post calibration scheme is easily automated which enables rapid, high precision mass measurements of affinity selected ligands against multiple targets in a high throughput mode.

The enhanced affinity of lividomycin for 16S relative to affinity of paromomycin for 16S is interesting. While lividomycin is believed to bind to the 16S ribosomal subunit, the exact site of interaction has not been established. Lividomycin has two significant structural differences from paromomycin. First, the additional mannopyranosyl ring could generate new macromolecular contacts with the RNA. However, the orientation of paromomycin ring IV is disordered in the NMR-derived structure for the complex with 16S. In addition, a hydroxyl group on ring I that makes a contact with A1492 is missing. The relatively high abundance of the 16S-lividomycin complex suggests that lividomycin binds at or near the 16S A-site, and generates additional contacts that enhance the binding affinity nearly 4-fold. Perhaps the most striking feature of the spectrum in FIG. 70 is the complete absence of complexes between 18S and paromomycin or lividomycin. This result suggests there must be poor shape and electrostatic complementarity between the 4,5-disubstituted 2-DOS class of aminoglycoside and the conserved architecture of the eukaryotic ribosomal decoding site.

Thus, according to the invention, RNA targets with similar (or identical) molecular masses can be labeled with small neutral molecules to measure binding between the targets and ligands using mass spectrometry. By screening multiple targets against ligand mixtures simultaneously, the information content of the assay is enhanced, resulting in a dramatic reduction in the number of analyses required. Although the increased complexity of the multi-substrate/ligand mixtures places high demands on the mass analyzer, the methods described herein facilitate the simultaneous analysis of numerous targets under identical solution conditions and ligand concentrations, further enhancing the high-throughput nature of the screening strategy and allowing direct comparisons of binding affinities for closely related targets. This concept of "rational" target design should also be applicable in studies of proteins that differ in amino acid sequence.

The present invention is also directed to nucleic acids comprising a joined sequence of at least twenty-four nucleotides but not more than seventy nucleotides and having secondary structure defined by three nucleotides forming a first side of a first double stranded region, two nucleotides forming a first side of an internal loop region, four nucleotides forming a first side of a second double stranded region, four or five nucleotides forming an end loop region, four nucleotides forming a second side of the second double stranded region, four nucleotides forming a second side of the internal loop region, and three nucleotides forming a second side of the first double stranded region. The nucleic acid can be preferably up to 70 nucleotides, 65 nucleotides, 60 nucleotides, 50 nucleotides, 40 nucleotides or 30 nucleotides.

In preferred embodiments, the two nucleotides forming the first side of the internal loop region are of the sequence NC. In other preferred embodiments, the four nucleotides forming the first side of the second double stranded region are of the sequence NNNN and the four nucleotides forming the second side of the second double stranded region are of the sequence NANN. In other preferred embodiments, the four or five nucleotides forming the end loop region are of the sequence NNNUN or NNUN. Preferably, the nucleic acid comprises a portion of vimentin RNA. More preferably, the nucleic acid comprises a portion of the 3' UTR of vimentin mRNA.

In other preferred embodiments, the nucleic acid fragment comprise the consensus sequence NNNNCNNNNNNNUN-NANNNNNNNN (SEQ ID NO:1) or NNNNCNNNNNNUNNANNNNNNNN (SEQ ID NO:65) and wherein the sequence has a first double stranded region, an internal loop region, a second double stranded region and an end loop region. In other preferred embodiments, an in silico representation of a nucleic acid fragment that is conserved across at least two species comprises the consensus sequence NNNNCNNNNNNNUNNANNNNNNNN (SEQ ID NO:1) or NNNNCNNNNNNUN-NANNNNNNNN (SEQ ID NO:65). In other preferred embodiments, a purified and isolated nucleic acid fragment that is conserved across at least two species comprises the sequence NNNNCNNNNNNNUNNANNNNNNNN (SEQ ID NO:1) or NNNNCNNNNNNUNNANNNNNNNN (SEQ ID NO:65). In other preferred embodiments, a purified and isolated nucleic acid fragment comprises the human sequence (SEQ ID NO:2) UUUACAACAUAAUCUAGU-UUACAGAAAAAUC. In other preferred embodiments, an in silico representation of a nucleic acid fragment comprises the human sequence UUUACAACAUAAUCUAGUUUA-CAGAAAAAUC (SEQ ID NO:2).

The present invention is also directed to the purified and isolated nucleic acids described above. In addition, the present invention is also directed to the nucleic acids described above in silico.

The present invention is also directed to nucleic acids comprising a joined sequence of at least forty-one nucleotides but not more than seventy nucleotides and having secondary structure defined by three nucleotides forming a first side of a first double stranded region, three nucleotides forming a first side of a first internal loop region, five or six nucleotides forming a first side of a second double stranded region, one to three nucleotides forming a first side of a second internal loop region, four nucleotides forming a first side of a third double stranded region, four to six nucleotides forming an end loop region, four nucleotides forming a second side of the third double stranded region, one nucleotide forming a second side of the second internal loop region, six nucleotides forming a second side of the second double stranded region and optionally having a single nucleotide bulge, seven or nine nucleotides forming a second side of the first internal loop region, and three nucleotides forming a second side of the first doubled stranded region. The nucleic acid can be preferably up to 70 nucleotides, 65 nucleotides, 60 nucleotides, or 50 nucleotides.

In preferred embodiments, the nucleotides forming the first side of the first double stranded region are of the sequence NNN and the nucleotides forming the second side of the first double stranded region are of the sequence UUN. In other preferred embodiments, tile nucleotides forming the first side or tie first internal loop region are of the sequence NAN. In other preferred embodiments, the nucleotides forming the second side of the first internal loop region are of the sequence GGAAACUNN or GGAAACU. In other preferred embodiments, the nucleotides forming the first side of the second double stranded region are of the sequence AUGGGN or AUGGG and the nucleotides forming the second side of the second doubled stranded region that optionally has the bulge are of the sequence UCCUAU. In other preferred embodiments, the nucleotides forming the first side of the second internal loop region are of the sequence NNU or U. In other preferred embodiments, the nucleotide forming the second side of the second internal loop region is U. In other preferred embodiments, the nucleotides forming the first side of the third double stranded region are of the sequence CACA and the nucleotides forming the second side of the third double stranded region are UGUG. In other preferred embodiments, the nucleotides forming the end loop region are of the sequence NNUANC or NNUAC. Preferably, the nucleic acid comprises a portion of ornithine decarboxylase RNA. More preferably, the nucleic acid comprises a portion of the 3' UTR of omithine decarboxylase mRNA.

In other preferred embodiments, the nucleic acid comprises the consensus sequence NNNNANAUGGGNNNU-CACANNUANCUGUGUUCCUAUGGAAACUNNUUN (SEQ ID NO:3), NNNNANAUGGGNNNUCACANNU-ACUGUGUUCCUAUGGAAACUNNUUN (SEQ ID NO:66), NNNNANAUGGGNNNUCACANNUACUGUG-UUCCU AUGGAAACUNUUN(SEQ ID NO:67), NNNNANAUGGGNNNUCACANNUACUGUG-UUCCUAUGGAAACUUUN (SEQ BD NO:68), NNNNANAUGGGNNNUCACANNUANCUGU-GUUCCUAUGGAAACUNUUN (SEQ ID NO:69), NNNNANAUGGGNNNUCACANNUANCUGU-GUUCCUAUGGAAACUUUN (SEQ ID NO:70), NNNNANAUGGGNNUCACANNUANCUGUG-UUCCUAUGGAAACUNNUUN (SEQ ID NO:71), NNNNANAUGGGNNUCACANNUACUGUG-UUCCUAUGGAAACUNNUUN (SEQ D NO:72), NNNNANAUGGGNNUCACANNUACUGUG-UUCCUAUGGAAACUNUUN (SEQ ID NO:73), NNNNANAUGGGNNUCACANNUACUGUG-UUCCUAUGGAAACUUUN (SEQ ID NO:74), NNNNANAUGGGNNUCACANNUANCUGUG-UUCCUAUGGAAACUNUUN (SEQ ID NO:75), NNNNANAUGGGNNUCACANNUANCUGUG-UUCCUAUGGAAACUUUN (SEQ ID NO:76), NNNNANAUGGGNUCACANNUANCUGUG-UUCCUAUGGAAACUNNUUN (SEQ ID NO:77), NNNNANAUGGGNUCACANNUACUGUG-UUCCUAUGGAAACUNNUUN (SEQ ID NO:78), NNNNANAUGGGNUCACANNUACUGUG-UUCCUAUGGAAACUNUWUN (SEQ ID NO:79), NNNNANAUGGGNUCACANNUACUGUG-UUCCUAUGGAAACUUUN (SEQ ID NO: 80), NNNNANAUGGGNUCACANNUANCUGUG-UUCCUAUGGAAACUNUUN (SEQ ID NO: 81), NNNNANAUGGGNUCACANNUANCUGUG-UUCCUAUGGAAACUUUN (SEQ ID NO:82), NNNNANAUGGGUCACANNUANCUGUG-UUCCUAUGGAAACUNNUUN (SEQ ID NO:83), NNNNANAUGGGUCACANNUACUGUGUUC-CUAUGGAAACUNNUUN (SEQ ID NO:84), NNNNAN-AUGGGUCACANNUACUGUGUUCCUAUG-GAAACUNUUN (SEQ ID NO:85), NNNNANAUGGGUCACANNUACUGUGUUC-CUAUGGAAACUUUN (SEQ ID NO:86), NNNNAN-AUGGGUCACANNUANCUGUGUUCCUAUG-GAAACUNUUN (SEQ ID NO:87), or NNNNANAUGGGUCACANNUANCUGUG-UUCCUAUGGAAACUUUN (SEQ ID NO:88) and having a first double stranded region, a first internal loop region, a second double stranded region, a second internal loop region, a third double stranded region and an end loop region. In other preferred embodiments, a purified and isolated nucleic acid fragment comprises the human sequence (SEQ ID NO:4) UAGGAUAUGGGUCACACU-UAUCUGUGUUCCUAUGGAAACUAUUUG. In other preferred embodiments, a purified and isolated nucleic acid fragment comprises the mouse sequence (SEQ ID NO:5) UAGGAGAUGGGGGUCACACUUACUGUG-UUCCUAUGGAAACUUUG. In other preferred embodiments, a purified and isolated nucleic acid fragment comprises the rat sequence (SEQ ID NO:6) UAG-GAGAUGGGGGGUCACACUUACUGUGUUC-CUAUGAAACUUUUG.

The present invention is also directed to the purified and isolated nucleic acids described above. In addition, the present invention is also directed to the nucleic acids described above in silico.

The present invention is also directed to nucleic acids comprising a joined sequence of at least twenty-six nucleotides but not more than seventy nucleotides and having secondary structure defined by five or six nucleotides forming a first side of a first double stranded region, one to three nucleotides forming a first side of an internal loop region, four nucleotides forming a first side of a second double stranded region, four to six nucleotides forming an end loop region, four nucleotides forming a second side of the second double stranded region, one nucleotide forming a second side of the internal loop region, and six nucleotides forming a second side of the first double stranded region and optionally having a single nucleotide bulge. The nucleic acid can be preferably up to 70 nucleotides, 65 nucleotides, 60 nucleotides, 50 nucleotides, 40 nucleotides, or 30 nucleotides.

In preferred embodiments, the nucleotides forming the first side of the first double stranded region are of the sequence AUGGGN or AUGGG and the nucleotides forming the second side of the first doubled stranded region that optionally has the bulge are of the sequence UCCUAU. In other preferred embodiments, the nucleotides forming the first side of the internal loop region are of the sequence NNU or U. In other preferred embodiments, the nucleotide forming the second side of the internal loop region is U. In other preferred embodiments, the nucleotides forming the first side of the second double stranded region are of the sequence CACA and the nucleotides forming the second side of the second double stranded region are UGUG. In other preferred embodiments, the nucleotides forming the end loop region are of the sequence NNUANC or NNUAC. Preferably, the nucleic acid comprises a portion of omithine decarboxylasc RNA. More preferably, the nucleic acid comprises a portion of the 3' UTR of ornithine decarboxylase mRNA.

In other preferred embodiments, a nucleic acid comprises the consensus sequence AUGGGNNNUCACANNUAN-CUGUGUUCCUAU (SEQ ID NO:7), AUGGGNNNUCA-CANNUACUGUGUUCCUAU (SEQ ID NO:89), AUGGGNNUCACANNUANCUGUGUUCCUAU (SEQ ID NO:90), AUGGGNNUCACANNUACUGUGUUC-CUAU (SEQ ID NO:91), AUGGGNUCACANNUANCU-GUGUUCCUAU (SEQ ID NO:92), AUGGGNUCACAN-NUACUGUGUUCCUAU (SEQ ID NO:93), AUGGGUCACANNUANCUGUGUUCCUAU (SEQ ID NO:94), or AUGGGUCACANNUACUGUGUUCCUAU (SEQ ID NO:95) and having a first double stranded region, an internal loop region, a second double stranded region and an end loop region. A purified and isolated nucleic acid fragment comprising the human sequence (SEQ ID NO:8) AUGGGUCACACUUAUCUGUGUUCCUAU. In other preferred embodiments, a purified and isolated nucleic acid fragment comprising the mouse sequence (SEQ ID NO:9) AUGGGGGUCACACUUACUGUGUUCCUAU. In other preferred embodiments, a purified and isolated nucleic acid fragment comprising the rat sequence (SEQ ID NO:10) AUGGGGGGUCACACUUACUGUGUUCCUAU.

The present invention is also directed to the purified and isolated nucleic acids described above. In addition, the present invention is also directed to the nucleic acids described above iii silico.

The present invention is also directed to nucleic acids comprising a joined sequence of at least seventeen nucleotides but not more than seventy nucleotides and having secondary structure defined by five nucleotides forming a first side of a double stranded region, seven nucleotides forming an end loop region, and five nucleotides forming a second side of the double stranded region. The nucleic acid can be preferably up to 70 nucleotides, 65 nucleotides, 60 nucleotides, 50 nucleotides, 40 nucleotides, 30 nucleotides, or 20 nucleotides.

In preferred embodiments, the nucleotides forming the first side of the double stranded region are of the sequence CAAGN, CAAGC, or CAAGU and the nucleotides forming the second side of the doubled stranded region are of the sequence GCUUG. In other preferred embodiments, the nucleotides forming the end loop region are of the sequence NUUUNUA, GUUUGUA, AUUUGUA, or AUUUAUA. In other preferred embodiments, the nucleotides forming the second side of the double stranded region are of the sequence GCUUG.

Preferably, the nucleic acid comprises a portion of omithine decarboxylase RNA. More preferably, the nucleic acid comprises a portion of the 3' UTR of ornithine decarboxylase mRNA.

In other preferred embodiments, a nucleic acid comprises the consensus sequence (SEQ ID NO:11) CAAGNNU-UUNUAGCUUG and having a first double stranded region and an end loop region. In other preferred embodiments, a purified and isolated nucleic acid fragment comprising the human sequence (SEQ ID NO:12) CAAGCAUUU-GUAGCUUGU. In other preferred embodiments, a purified and isolated nucleic acid fragment comprising the mouse sequence CAAGCGUWUGUAGCUUGU or CAAGCAU-UUAUAGCULJGU (SEQ ID NO:14). In other preferred embodiments, a purified and isolated nucleic acid fragment comprising the rat sequences (SEQ ID NO:15) CAAGCAU-UUGUAGCUUGU.

The present invention is also directed to the purified and isolated nucleic acids described above. In addition, the present invention is also directed to the nucleic acids described above in silico.

The present invention is also directed to nucleic acids comprising a joined sequence of at least seventeen nucleotides but not more than seventy nucleotides and having secondary structure defined by five nucleotides forming a first side of a first double stranded region, four nucleotides forming a first end loop region, five nucleotides forming a second side of the first double stranded region, three nucleotides forming a first side of a first internal loop region, five nucleotides forming a first side of a second double stranded region, one nucleotide forming a first side of a second internal loop region, six nucleotides forming a first side of a third double stranded region, eight nucleotides forming a second end loop region, six nucleotides forming a second side of the third double stranded region, one nucleotide forming a second side of the second internal loop region, five nucleotides forming a second side of the second double stranded region, two nucleotides forming a second side of the first internal loop region, three nucleotides forming a first side of a fourth double stranded region, five nucleotides forming a third end loop region, and three nucleotides forming a second side of the fourth double stranded region. The nucleic acid can be preferably up to 70 nucleotides, 65 nucleotides, 60 nucleotides, 50 nucleotides, 40 nucleotides, 30 nucleotides, or 20 nucleotides.

In preferred embodiments, the nucleotides forming the first side of the second double stranded region are of the sequence AAANU, AAAAU, or AAAUU and the nucleotides forming the second side of the second doubled stranded region are of the sequence G GUUUU, GGUU, GGUGU, or GGUUC. In other preferred embodiments, the nucleotide forming the first side of the second internal loop region is U and the nucleotide forming the second side of the second internal loop region is N, U or C. In other preferred embodiments, the nucleotides forming the first side of the third double stranded region are of the sequence UAUAUU and the nucleotides forming the second side of the third doubled stranded region are of the sequence NAUNNA, GAUAUA, AAUGUA, GAUGCA, or GAUGUA. In other preferred embodiments, the nucleotides forming the second end loop region are of the sequence UAUUNUUN, UAUUUUUU, UAUUGUUG, or UAUUUUUG. In other preferred embodiments, the nucleotides forming the first side of the first internal loop region are of the sequence UUU and the nucleotides forming the second side of the first internal loop region are of the sequence NC, CC, GC, UC, or AC. In other preferred embodiments, the nucleotides forming the first side of the fourth double stranded region are of the sequence UAN, UAC, or UAA and the nucleotides forming the second side of the fourth doubled stranded region are of the sequence NUA, GUA, or CUA. In other preferred embodiments, the nucleotides forming the third end loop region are of the sequence CUNUU, CUUUU, or CUAUU. Preferably, the nucleic acid comprises a portion of interleukin-2 RNA. More preferably, the nucleic acid comprises a portion of the 3' UTR of interleukin-2 mRNA.

In other preferred embodiments, a nucleic acid comprising the consensus sequences UAUUUAUUUAAAUAU-UUAAANUUUAUAUUUAUUNUUNNAUN-NANGNUNNNCUANCUNUUNUA and having a first double stranded region, a first end loop region, a first internal loop region, a second double stranded region, a second internal loop region, a third double stranded region, a second end loop region, a fourth doble stranded region, and a third end loop region. In other preferred embodiments, a purified and isolated nucleic acid fragment comprising the human sequence (SEQ ID NO:17) UAUUUAUUUAAAUAU-UUAAAUUUUAUAUUUAUUGUUGAAU-GUAUGGUUUGCUACCUAUUGUA.

The present invention is also directed to the purified and isolated nucleic acids described above. In addition, the present invention is also directed to the nucleic acids described above in silico. The present invention is also directed to nucleic acids comprising a joined sequence of at least thirty-two but not more than seventy nucleotides and having secondary structure defined by five nucleotides forming a first side of a first double stranded region, one nucleotide forming a first side of a first internal loop region, six nucleotides forming a first side of a second double stranded region, eight nucleotides forming a first end loop region, six nucleotides forming a second side of the second double stranded region, one nucleotide forming a second side of the first internal loop region, and five nucleotides forming a second side of the first double stranded region. The nucleic acid can be preferably up to 70 nucleotides, 65 nucleotides, 60 nucleotides, 50 nucleotides, or 40 nucleotides.

In preferred embodiments, the nucleotides forming the first side of the first double stranded region are of the sequence AAANU, AAAAU, or AAAUU and the nucleotides forming the second side of the first doubled stranded region are of the sequence GNUNN, GUUUU, GGUUU, GGUGU, or GGUUC. In other preferred embodiments, the nucleotide forming the first side of the first internal loop region is U and the nucleotide forming the second side of the first internal loop region is N, U or C. In other preferred embodiments, the nucleotides forming the first side of the second double stranded region are of the sequence UAUAUU and the nucleotides forming the second side of the second doubled stranded region are of the sequence NAUNNA, GAUAUA, AAUGUA, GAUGCA, or GAUGUA. In other preferred embodiments, the nucleotides forming the first end loop region are of the sequence UAUUNUUN, UAUUUUUU, UAUUGUUG, or UAUUG-UUG. Preferably, the nucleic acid comprises a portion of interleukin-2 RNA. More preferably, the nucleic acid comprises a portion of the 3' UTR of interleukin-2 mRNA.

In other preferred embodiments, a nucleic acid comprises the consensus sequence (SEQ ID NO:18) AAANU-UUAUAUUUAUUNUUNNAUNNANGNUNN and has a first double stranded region, a first internal loop region, a second double stranded region, and an end loop region. In other preferred embodiments, a purified and isolated nucleic acid fragment comprises the human sequence (SEQ ID NO:19) AAAUUUUAUAUUUAUUGUUGAAUGUAUG-GUUU.

The present invention is also directed to the purified and isolated nucleic acids described above. In addition, the present invention is also directed to the nucleic acids described above in silico.

The present invention is also directed to nucleic acids comprising a joined sequence of at least forty-three but not more than seventy nucleotides and having secondary structure defined by six nucleotides forming a first side of a first double stranded region, three nucleotides forming a first side of a first internal loop region, six nucleotides forming a first side of a second double stranded region, four nucleotides forming a first end loop region, six nucleotides forming a second side of the second double stranded region, two nucleotides forming a second side of the first internal loop region, six nucleotides forming a second side of the first double stranded region, one nucleotide forming a bulge between the first double stranded region and a third double stranded region, two or four nucleotides forming a first side of a third double stranded region, three nucleotides forming a second end loop region, and two or four nucleotides forming a second side of the third double stranded region. The nucleic acid can be preferably up to 70 nucleotides, 65 nucleotides, 60 nucleotides, or 50 nucleotides.

In preferred embodiments, the nucleotides forming the first side of the first double stranded region are of the sequence NNUNNN, GAUAAA, UAUAAA, or UCUGUU and the nucleotides forming the second side of the first doubled stranded region are of the sequence UNUNNN, UUUGUA, UCUGUA, or UUUUGU. In other preferred embodiments, tile nucleotide forming tile first side of the first internal loop region is NNN, UAU, CUA, or CAU and the nucleotide forming the second side of the first internal loop region is UU. In other preferred embodiments, the nucleotides forming the first side of the second double stranded region are of the sequence NGAUCN, GGAUCU, or AGAUCA and the nucleotides forming the second side of the second doubled stranded region are of the sequence NGAUNC, AGAUUC, UGAUCC, or UGAUUC. In other preferred embodiments, the nucleotides forming the first side of the third stem region are of the sequence N(or absent)N(or absent)CC, GCCC, or CC and the nucleotides forming the second side of the third stem region are of the sequence NNNN, GGGC, or GCGU. Preferably, the nucleic acid comprises a portion of interleukin-2 RNA. More preferably, the nucleic acid comprises a portion of the 3' UTR of interleukin-2 mRNA.

In other preferred embodiments, a nucleic acid comprising the consensus sequence NNUNNNNNNNGAUC-NUNNNNGAUNCUUUNUNNNANNCCNNNNNNN (SEQ ID NO:20), NNUNNNNNNNGAUC-NUNNNNGAUNCUUUNUNNNACCNNNNNNN (SEQ ID NO: 96), or NNUNNNNNNNNNGAUNCWU-NUNNNACCNNNNBN (SEQ ID NO:97) and having a first double stranded region, a first internal loop region, a second double stranded region, ark and a first end loop region, a third double stranded region, and a second end loop region. In other preferred embodiments, a purified and isolated nucleic acid fragment comprising the human sequence (SEQ ID NO:21) UAUAAAUAUGGAUCUUUUAUGAUUCU-UUUUGUAAGCCCUAGGGGC. In other preferred embodiments, a purified and isolated nucleic acid fragment comprising the mouse or rat sequence (SEQ ID NO:22) GAUAAAUAUGGAUCUUUAAAGAUUCU-UUUUGUAAGCCCCAAGGGC.

The present invention is also directed to the purified and isolated nucleic acids described above. In addition, the present invention is also directed to the nucleic acids described above in silico.

The present invention is also directed to nucleic acids comprising a joined sequence of at least twenty-nine but not more than seventy nucleotides and having secondary structure defined by five nucleotides forming a first side of a first double stranded region, four nucleotides forming a first side of a first end loop region, five nucleotides forming a second side of the first double stranded region, two nucleotides forming a bulge between the first double stranded region and a second double stranded region, five nucleotides forming a first side of a second double stranded region, three nucleotides forming a second end loop region, and five nucleotides forming a second side of the second double stranded region. The nucleic acid can be preferably up to 70 nucleotides, 65 nucleotides, 60 nucleotides, 50 nucleotides, nucleotides, or 30 nucleotides.

In preferred embodiments, the nucleotides forming the first side of the first double stranded region are of the sequence NNNGA, UAAGA, AAAGA, UAUGA, or UUUGA and the nucleotides forming the second side of the first doubled stranded region are of the sequence UUNNG, UUUUG, or UUCUG. In other preferred embodiments, the nucleotides forming the first end loop region are of the sequence UNCU, UUCU, or UCCU. In other preferred embodiments, the nucleotides forming the first side of the second double stranded region are of the sequence AGCCC and the nucleotides forming the second side of the second doubled stranded region are of the sequence GNGNN, GGGCU, or GCGUG. In other preferred embodiments, the nucleotides forming the second end loop region are of the sequence NAN, UAC, UAG, CAA, or UAA. Preferably, the nucleic acid comprises a portion of interleukin-2 RNA. More preferably, the nucleic acid comprises a portion of the 3'UTR of interleukin-2 mRNA.

In other preferred embodiments, a nucleic acid comprising the consensus sequence (SEQ ID NO:23) NNNGAUN-CUUUNNGUAAGCCCNANGNGNN and having a first double stranded region, a first end loop region, a second double stranded region, and a second end loop region. In other preferred embodiments, a purified and isolated nucleic acid fragment comprising the human sequence (SEQ ID NO:24) UAUGAUUCUUUUUGUAAGC-CCUAGGGGCU. In other preferred embodiments, a purified and isolated nucleic acid fragment comprising the mouse sequence (SEQ ID NO:25) AAAGAUUCUUUUU-GUAAGCCCCAAGGGCU. In other preferred embodiments, a purified and isolated nucleic acid fragment comprising the rat sequence AAAGAUUCUUUUU-GUAAGCCCCAAGGGCU.

The present invention is also directed to the purified and isolated nucleic acids described above. In addition, the present invention is also directed to the nucleic acids described above in silico.

The present invention is also directed to nucleic acids comprising a joined sequence of at least twenty-six but not more than seventy nucleotides and having secondary structure defined by six or seven nucleotides forming a first side of a first double stranded region, four nucleotides forming a first end loop region, seven or eight nucleotides forming a second side of the first double stranded region and having a single nucleotide bulge, one nucleotide linking the first double stranded region and a second double stranded region, three nucleotides forming a first side of the second double stranded region, three nucleotides forming a second end loop region, and two or three nucleotides forming a second side of the second double stranded region. The nucleic acid can be preferably up to 70 nucleotides, 65 nucleotides, 60 nucleotides, 50 nucleotides, 40 nucleotides, or 30 nucleotides.

In preferred embodiments, the nucleotides forming the first side of the first double stranded region are of the sequence NNNNNN(or absent)N, AUAACCU, UGGUAAA, UGAUAAU, UGAUAAA, GAUAACC, GAUAAAC, UGAUAU, GAGACCC, or GACAAAC and the nucleotides forming the second side of the first doubled stranded region are of the sequence N(or absent) UGNCUNN, UGUCUCC, UUGUCUCA, UUGCCUCA, UUGUCUCC, UUGUCUCU, CUGUCUUU, or CUGUCUCA. In other preferred embodiments, the nucleotides forming the first end loop region are of the sequence NNNN, UAAU, CUAA, UUAA, UACU, or AAAU. In other preferred embodiments, the nucleotides forming the first side of the second double stranded region are of the sequence NNN, AUC, AUU, ACU, GUC, CCC, or AAU and the nucleotides forming the second side of the second doubled stranded region are of the sequence NNN(pr absent), GA, AGU, ACU, GCG, or AC. In other preferred embodiments, the nucleotides forming the second end loop region are of the sequence NNN, ACU, GUC, AGG, GAA, or CCU. Preferably, the nucleic acid comprises a portion of interleukin-4 RNA. More preferably, the nucleic acid comprises a portion of the 5' UTR of interleukin-4 mRNA.

In other preferred embodiments, a nucleic acid comprising the consensus sequences NNNNNNNNNNUGNCUNNNNNNNNNNNNN and having a first double stranded region, a first end loop region, a second double stranded region, and a second end loop region. In other preferred embodiments a purled and isolated nucleic acid fragment comprising the human sequence (SEQ ID NO: 27) UGAUAAACUAAUUGCCUCACAUUGUCACU. In other preferred embodiments, a purified and isolated nucleic acid fragment comprising the mouse sequences GAUAAACUUAAUUGUCUCUCGUCACUGA, UGAUAUUACUCUGUCUUUCCCCAG GGCG, (SEQ ID NO:29) or GAGACCCAAAUCUGUCUCACAAUGAAAC (SEQ ID NO:30).

The present invention is also directed to the purified and isolated nucleic acids described above. In addition, the present invention is also directed to the nucleic acids described above in silico.

The present invention is also directed to nucleic acids comprising a joined sequence of at least nineteen but not more than seventy nucleotides and having secondary structure defined by three nucleotides forming a first side of a first double stranded region, one nucleotide forming a first side of an internal loop region, three nucleotides forming a first side of a second double stranded region, five nucleotides forming an end loop region, three nucleotides forming a second side of the second double stranded region, one nucleotide forming a second side of the internal loop region, and three nucleotides forming a second side of the first double stranded region. The nucleic acid can be preferably up to 70 nucleotides, 65 nucleotides, 60 nucleotides, 50 nucleotides, 40 nucleotides, 30 nucleotides, or 20 ; nucleotides.

In preferred embodiments, the nucleotides forming the first side of the first double stranded region are of the sequence NNN, AUU, AAG, GAG, AUG, GAA, GAC, AAU, AAA, or CCA and the nucleotides forming the second side of the first doubled stranded region are of the sequence NNN, UAU, UUU, AAA, CCU, ACU, or GCU. In other preferred embodiments, the nucleotides forming the first end loop region are of the sequence NNNNN, UAAAA, AUAUC, AAAAA, AUAUU, UUAAU, CUAUU, AUGAG, UAAGG, CUUCC, or AGGAG. In other preferred embodiments, the nucleotides forming the first side of the second double stranded region are of the sequence NNN, UUA, UGA, UUU, UAA, CCA, or AAA and the nucleotides forming the second side of the second doubled stranded region arc of the sequence NNN, UAA, UUA, AGC, AAA, AAU, UUC, or CAA. Preferably, the nucleic acid comprises a portion of interleukin-4 RNA. More preferably, the nucleic acid comprises a portion of the 3' UTR of interleukin-4 mRNA.

In other preferred embodiments, a nucleic acid comprising the consensus sequence (SEQ ID NO:31) NNNNNNNNNINNNNNNNNNN and having a first double stranded region, an internal loop region, a second double stranded region, and an end loop region. In other preferred embodiments, a purified and isolated nucleic acid fragment comprising the mouse sequence (SEQ ID NO:32) AAUCUGAAUGAGAAUGCCU, AUUGCCAUAAGGUUCUACCU (SEQ ID NO:33). CCACUGAAGGAGCAAGGCU (SEQ ID NO:34).

The present invention is also directed to the purified and isolated nucleic acids described above. In addition, the present invention is also directed to the nucleic acids described above iii silico.

The following examples are meant to be exemplary of preferred embodiments of the invention and are not meant to be limiting.

EXAMPLES

Example 1

The Iron Responsive Element (Method A)

1. Selecting RNA Target

To illustrate the strategy for identifying small molecule interaction sites, the iron responsive element (IRE) in the mRNA encoded by the human ferritin gene is identified. The IRE is a typical example of an RNA structural element that is used to control the level of translation of mRNAs associated with iron metabolism. The structure of the IRE was recently determined using NMR spectroscopy. In addition, NMR analysis of IRE structure is described in Gdaniec, et al., Biochem., 1998, 37, 1505–1512 and Addess, et al., *J. Mol. Biol.,* 1997, 274, 72–83. The IRE is an RNA element of approximately 30nucleotides that folds into a hairpin structure and binds a specific protein. Because this structure has been so well studied and it known to appear in the mRNA of many species, it serves an excellent example of how Applicants' methodology works.

2. Determining Nucleotide Sequence of the RNA Target

The human mRNA sequence for ferritin is used as the initial mRNA of interest or master sequence. The ferritin protein sequence is also used in the analysis, particularly in the initial steps used to find related sequences. In the case of human ferritin gene, the best input is the full length annotated mRNA and protein sequence obtained from UNIGENE. However, for many genes of interest the same level of detailed information is not available. In these cases, alternative sources of master sequence information is obtained from sources such as, for example, GenBank, TIGR, dbEST division of GenBank or from sequence information obtained from private laboratories. Applicants' methods work using any level of input sequence in formation, but requires fewer steps with a high quality annotated input sequence.

3. Identifying Similar Sequences

Figure 10:
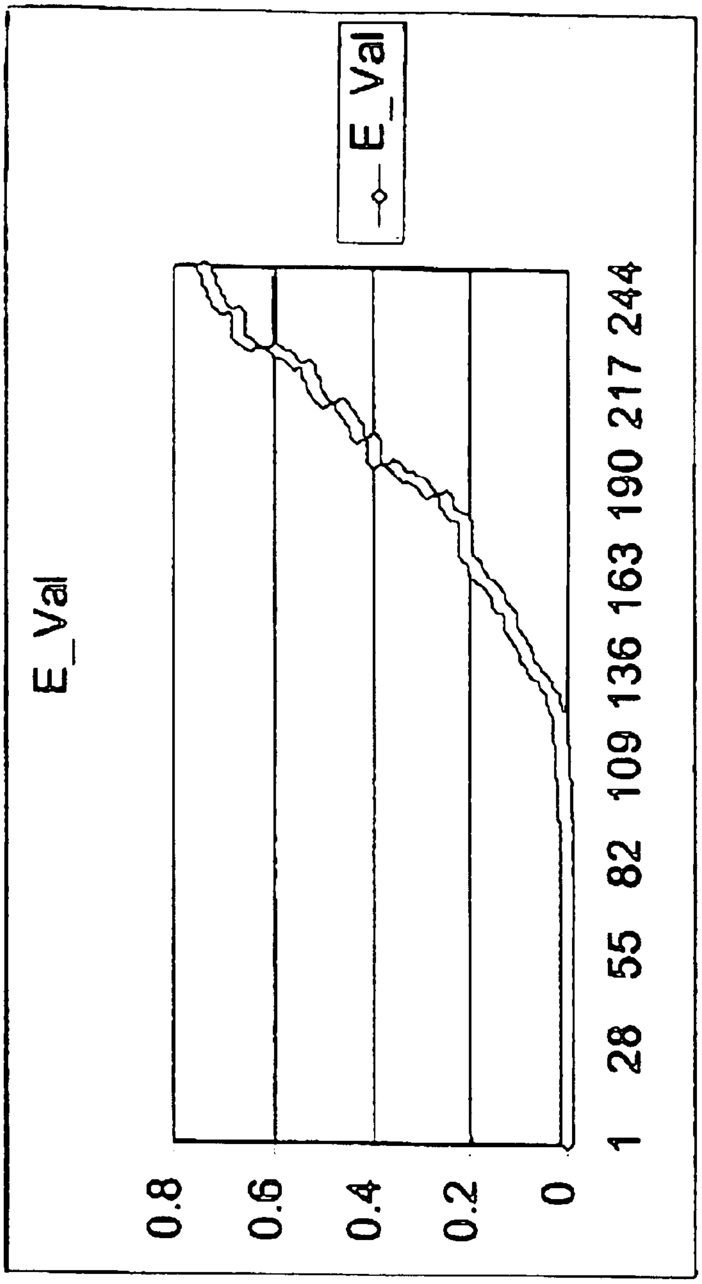
FIG. 10 shows a set of e-value scores for ferritin.
Figure 11:
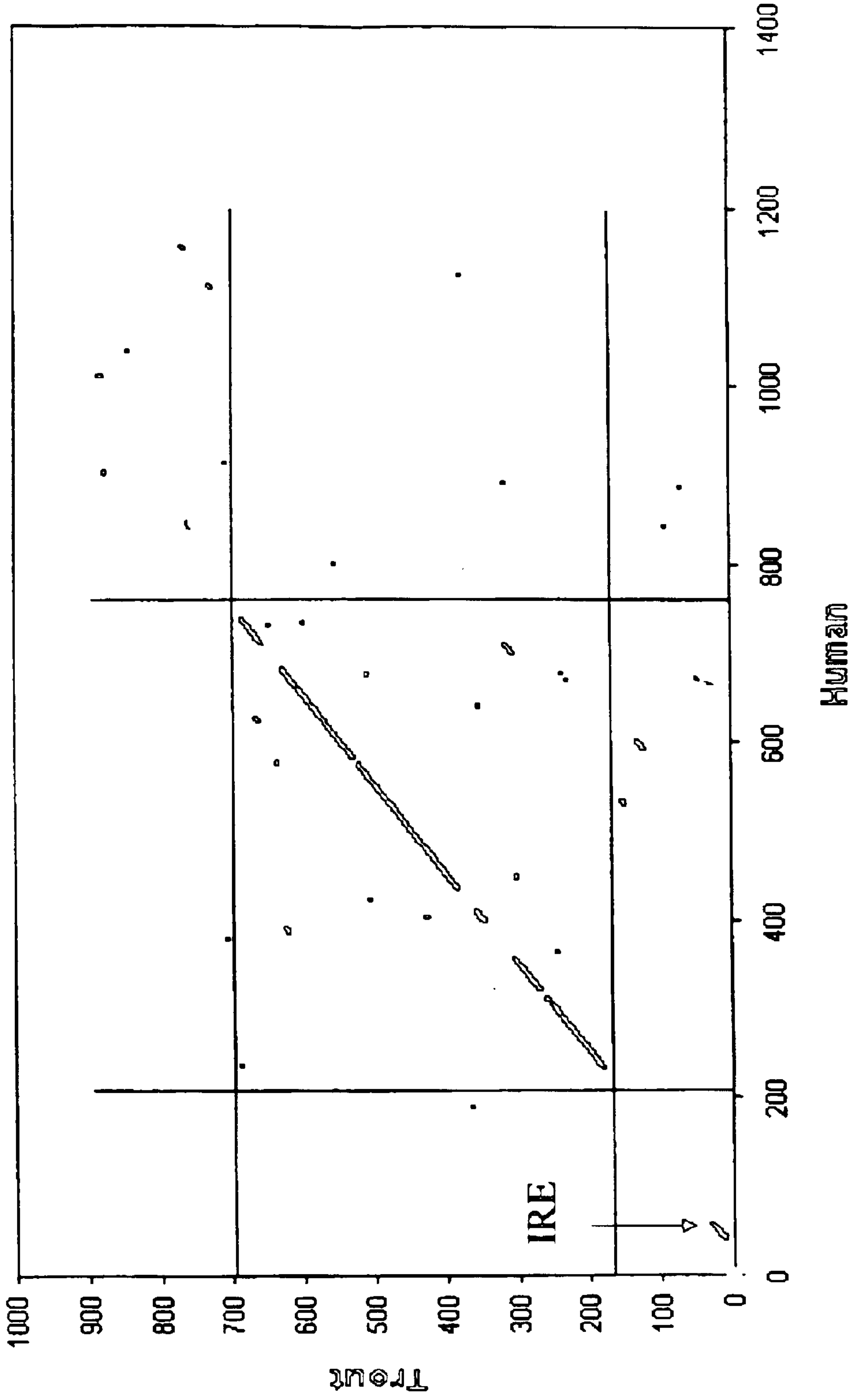
FIG. 11 is a representative scatter plot of an interspecies sequence comparison between human and trout for a ferritin RNA.

An early step in the process is to use the master sequence (nucleotide or protein) to find and rank related sequences in the database (orthologs and paralogs). Sequence similarity search algorithms are used for this purpose. All sequence similarity algorithms calculate a quantitative measure of similarity for each result compared with the master sequence. An example of a quantitative result is an E-value obtained from the Blast algorithm. The E-values for a blast search of the non-redundant GenBank database using ferritin mRNA as the query sequence illustrates the use of quantitative analysis of sequence similarity searches. The E-value is the probability that a match between a query sequence and a database sequence occurs due to random chance. Therefore, the lower an E-value the more likely that two sequences are truly related. A plot of the lowest E-value scores for ferritin is shown in FIG. 10. Sequences that meet the cutoff criteria are selected for more detailed comparisons according to a set of rules described below. Since an objective of the sequence similarity search to find distantly related orthologs and paralogs it is preferable that the cutoff criteria not be too stringent, or the target of the search may be excluded.

4. Identification of Conserved Regions

Identification of conserved regions is performed by pairwise sequence comparisons using Q-Compare in conjunction with CompareOverWins. Conservation of structure between genes with related function from different species is a major indication that can be used to find good drug binding sites. Conserved structure can be identified by using distantly related sequences and piecing together the remnants of conserved sequence combining it with an analysis of potential structure. Sequence comparisons are made between pairs of mRNAs from different species using Q-compare that can identify traces of sequence conservation from even very divergent organisms. Q-compare, in conjunction with CompareOverWins, compares every region of each sequence by sliding one sequence over the other from end to end and measuring the number of matches in a window of a specific size.

Figure 12:
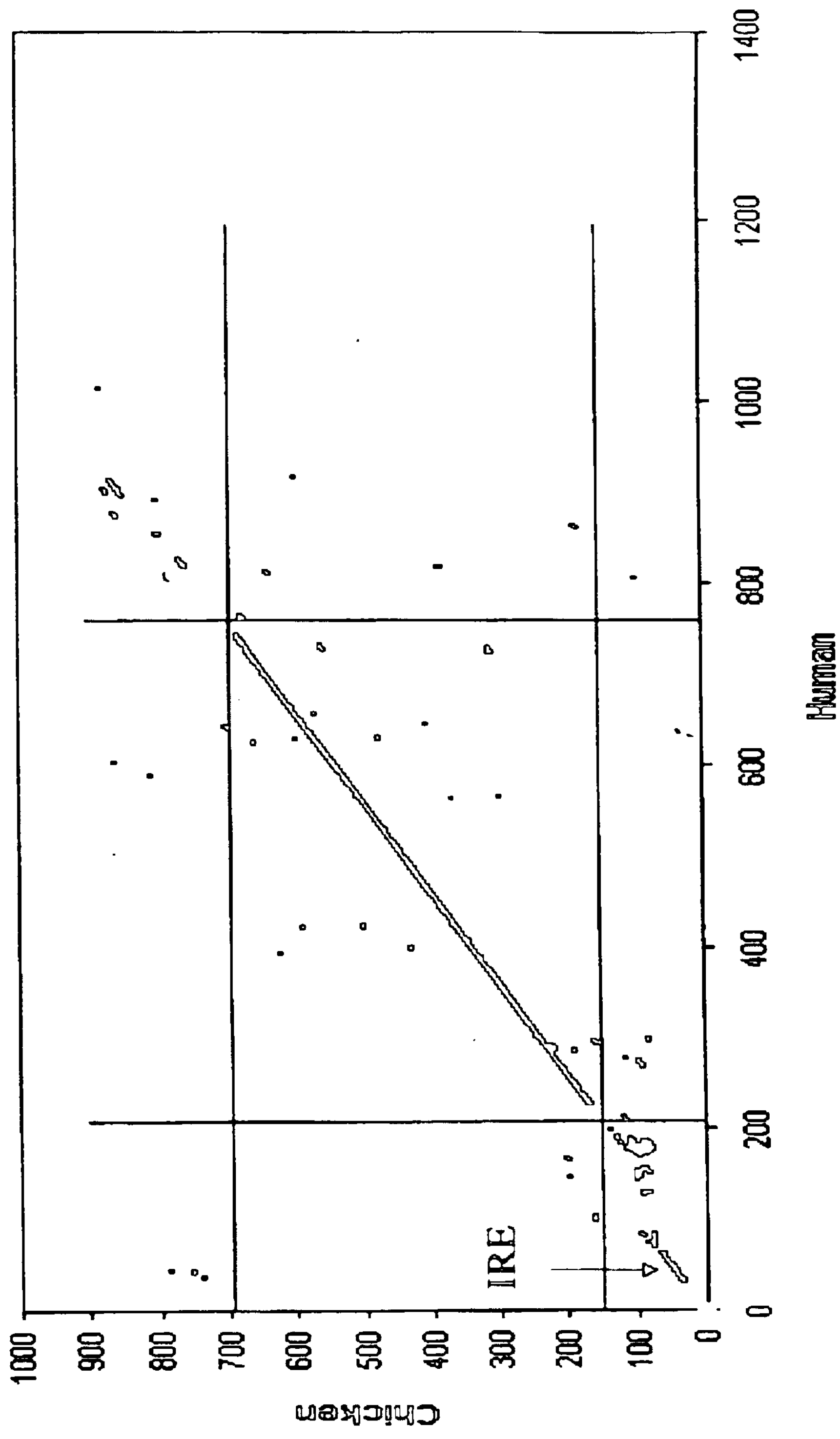
FIG. 12 is representative scatter plot of an interspecies sequence comparison between human and chicken for a ferritin RNA.

When the human mRNA and mouse mRNA sequences for ferritin, which each contain an IRE in the 5'-UTR, are analyzed in this manner, a plot showing the regions of sequence similarity is produced, as shown in FIG. 19. Pairwise analysis of the human and mouse ferritin mRNA sequences illustrate several important aspects of this type of analysis. Regions of each mRNA that encode the amino acid sequence have the highest degree of similarity, while the untranslated regions are less similar. In FIG. 19, the location of the IRE is indicated. In both the human and mouse ferritin mRNAs the IREs are located in the extreme 5' end of each in RNA. This demonstrates an important point—the sequence conservation in the region of the IRE structure does not stand out against the background of sequence similarity between the human and mouse ferritin sequences. In contrast, in the comparison of human and trout (FIG. 1) or human and chicken (FIG. 12) ferritin mRNAs, the IREs can be immediately identified. This is because the sequence of the UTRs between human and trout or human and chicken are separated by greater evolutionarily distance than human and mouse, which is logical in view of the evolutionary distance that separates humans from birds and fish compared with other mammals. Comparing the human sequence to that of birds and fish is informative because the natural drift due to evolution has allowed many sequence changes in the UTRs. However, the IRE sequences are more constrained because they form an important structure. Thus, they stand out better and can be more readily identified.

The same principle applies when comparing the trout and chicken ferritin sequences to each other. While both are separated from humans by hundreds of millions of years of evolution, they are also well separated from each other. This illustrates another important tactic used in the present invention—comparison of two non-human RNA sequences can be used to find a regulatory RNA structure without having the actual human sequence. The non-human comparison work can actually direct one skilled in the art where to look to find a human counterpart as a potential drug target.

Evolutionary distances can be used to decide which sequences not to compare as well as which to compare. As with the human and mouse, comparison of trout and salmon are less informative because the species are too close and the IRE does not stand out above the UTR background. Comparison of human and Drosophia ferritin mRNA sequences fail to find the IREs in either species, even though they are present. This is because the sequence of the IREs between humans and Drosophila have diverged even though the structure is conserved. However, if the Drosophila and mosquito ferritin mRNAs are compared, the IREs are identified, again illustrating that the human sequence need not be in hand to identify a regulatory element relevant to drug discovery in humans.

Figure 13:
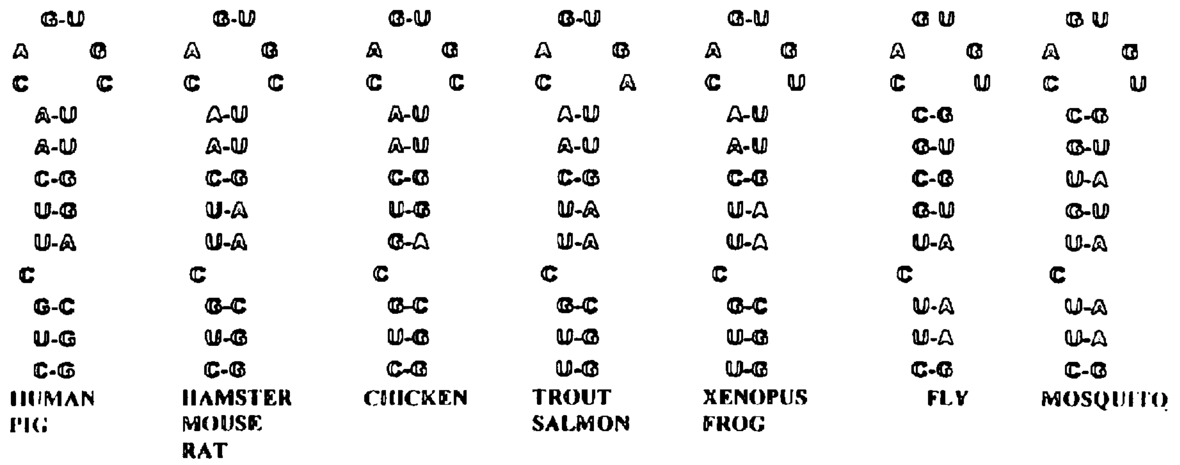
FIG. 13 shows a representative lookup table used in Q-compare or CompareOverWins.

The software used in the present invention makes the decision whether or not to compare sequences pairwise using a lookup table based upon the evolutionary distances between species. An example of a small lookup table using the examples described above is shown in FIG. 13. The lookup table in the present invention includes all species that have sequences deposited in GenBank. Q-Compare in conjunction with CompareOverWins decides which sequences to compare pairwise.

5. Identification Of Secondary Structure

Sets of sequences that show evidence of conservation in orthologs and paralogs or other related genes are analyzed for the ability to form internal structure. This is accomplished by analyzing each sequence in a matrix where the sequence is plotted 5' to 3' on the X axis and its reverse complement is plotted 5' to 3' on the Y axis, such as in, for example, self-complementary analysis. Matches that correspond to potential intramolecular base pairs are scored according to a table of values. When the human ferritin IRE sequence is analyzed in this fashion, the diagonals indicate potential self- complementary regions. Each of the 13 IRE sequences described in this example were analyzed in the same fashion. While each of the sequences can form a variety of different structures, the structure most likely to occur is one common to all the sequences. By superimposing the plots of all 13 individual sequences (see, FIG. 8), the potential structure common to all the sequences is deduced.

Example 2

The Iron Responsive Element (Method B)

2. Determining Nucleotide Sequence of the RNA Target

The human mRNA sequence for ferritin was used as the initial mRNA of interest or master sequence. The ferritin protein sequence was also used in the analysis, particularly in the initial steps used to find related sequences. In the case of human ferritin gene, the best input is the full length annotated mRNA (gi507251) and protein sequence obtained from UNIGENE. However, for many genes of interest the same level of detailed information is not available. In these cases, alternative sources of master sequence information is obtained from sources such as, for example, Hovergen and GenBank. The present methods work using any level of input sequence information, but requires fewer steps with a high quality annotated input sequence.

3. Identifying Similar Sequences

Figure 55:
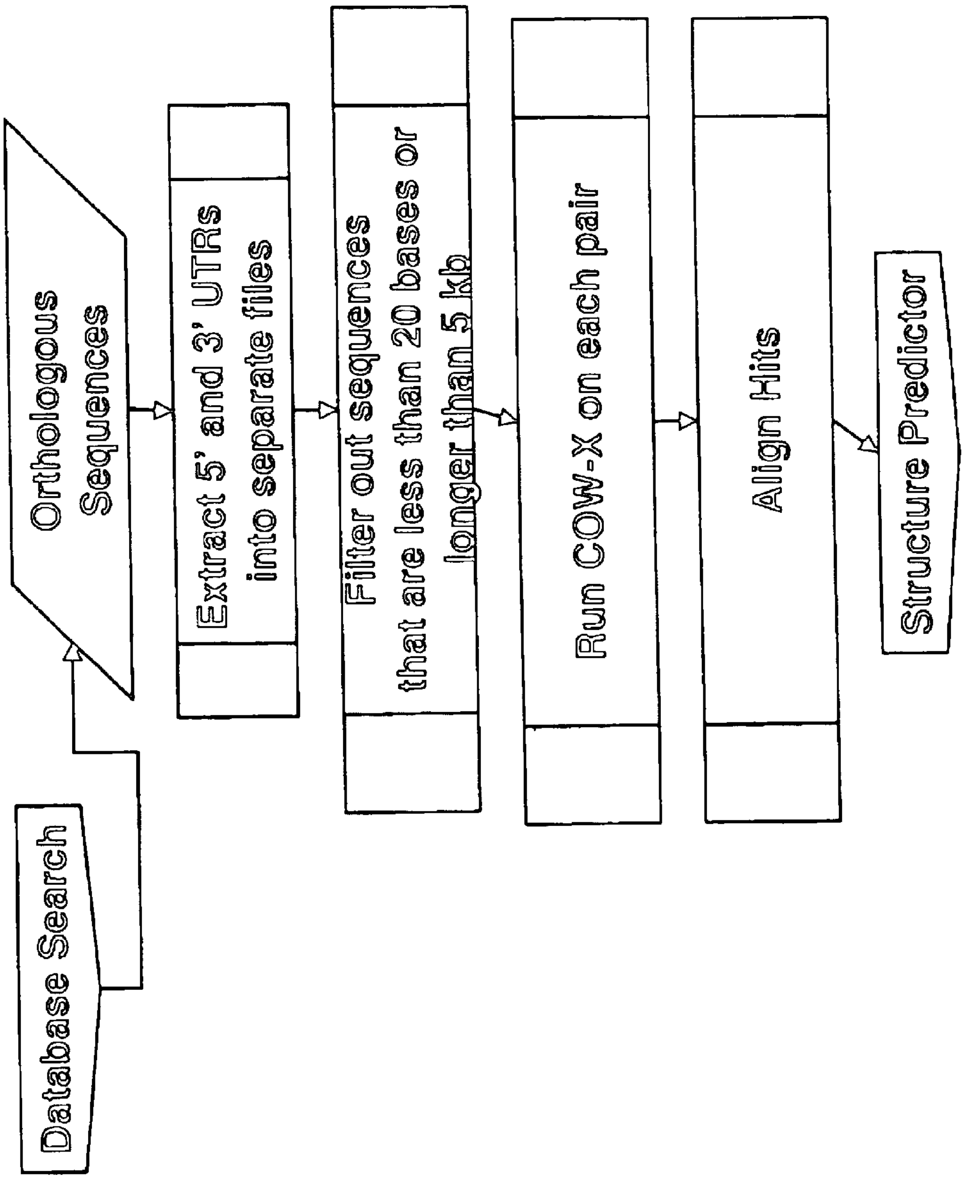
FIG. 55 shows a representative flow scheme showing preferred steps for a preferred SEALS strategy.

An alternate, and preferred, approach to finding orthologs is the use of Rovergen database and query tools that have been described in Duret, et al., *Nuc. Acids Res.,* 1994, 22, 2360–2365, which is incorporated herein by reference in its entirety. Hovergen was used to identify related sequences (tree classification at the species level and classification at the order level). Sequences corresponding to each of these orthologs was saved in GenBank format and grouped together in a single data file. Untranslated regions in both the 5' and 3' flanks of the coding region was extracted using SEALS and COWX, as shown in FIG. 55.

4. Identification of Conserved Regions

The IRE sequences are more constrained because they form an important structure. Thus, they stand out better and can be more readily identified even in closely related sequences. However, for this to work for any gene, the compare algorithm has been rewritten (see, FIGS. 5A–C). This new tool, CompareOverWins, allows a dynamic selection of both the range of window sizes, as well the hit threshold. This algorithm needs as its input parsed and separated 5' and 3' UTR sequences. Tools available within the Seals genome analysis package described earlier can be used to achieve this. FIG. 55 describes the steps involved.

Figure 5D:
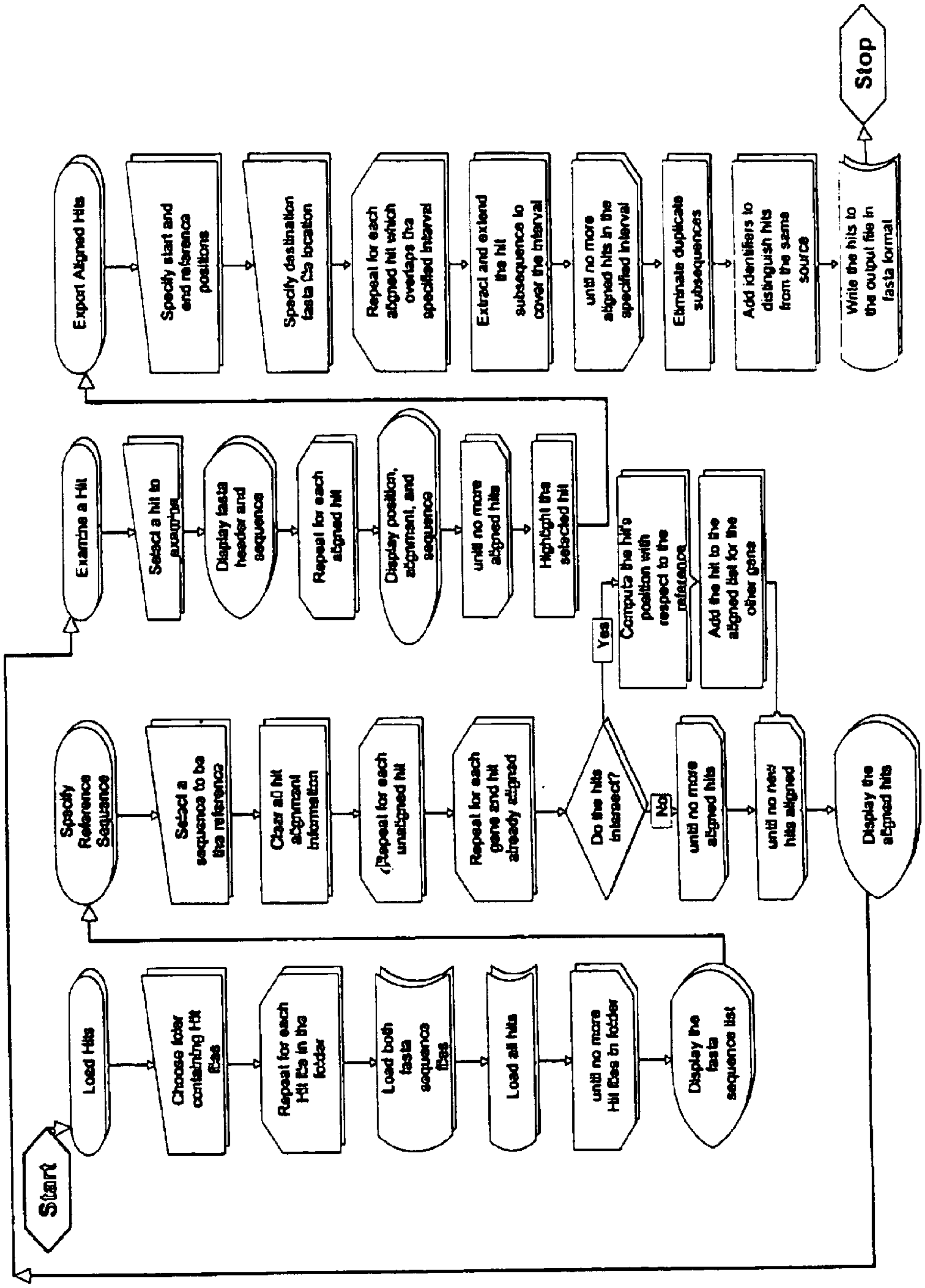
Figure 56:
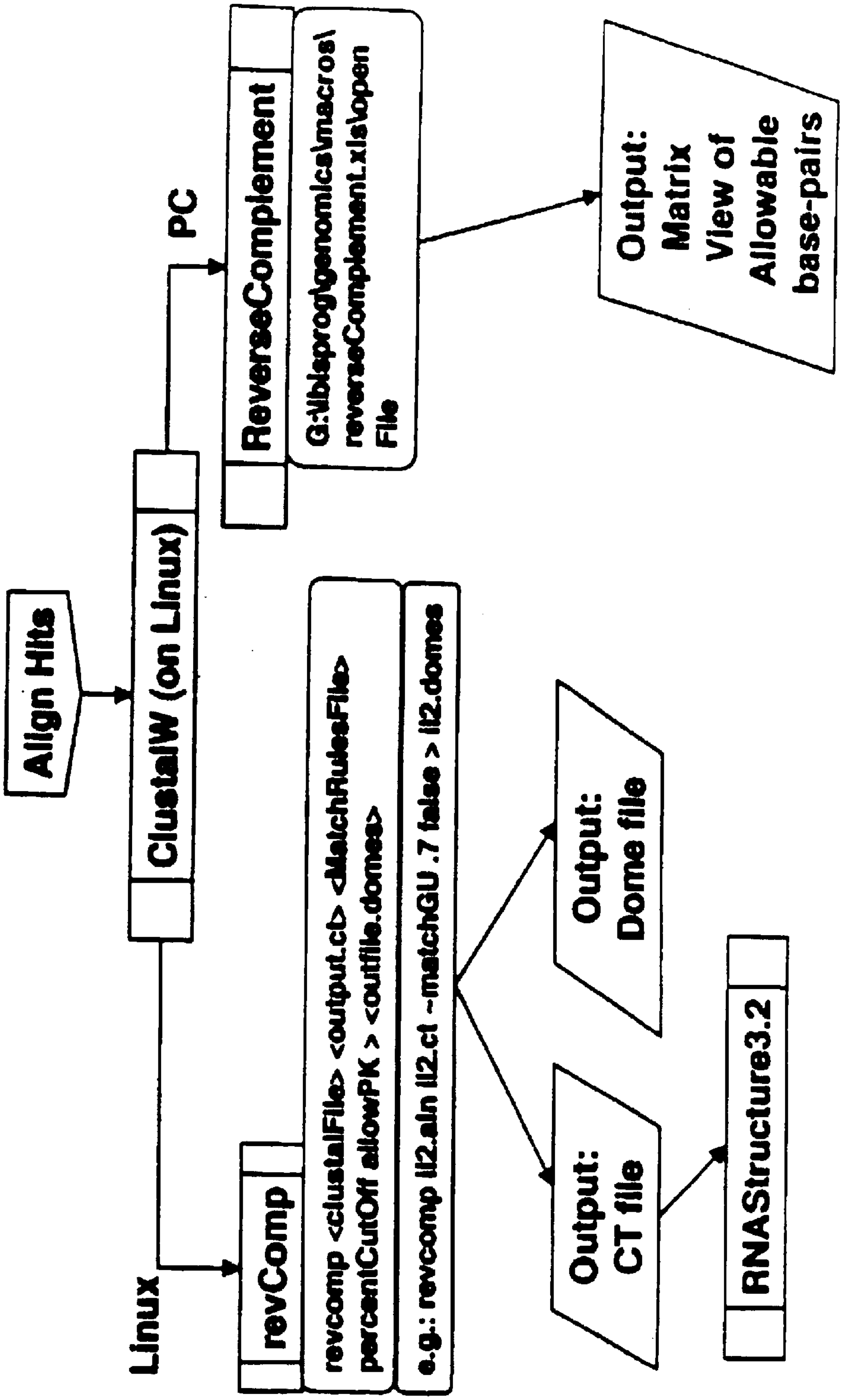
FIG. 56 shows a representative flow scheme showing preferred steps for a preferred Structure Predictor strategy.

To identify the IRE using the methods described herein, the compare over windows algorithm was used and the results visualized using AlignHits (FIG. 5D for the algorithm). In addition to optimizing the thresholding, CompareOverWins also extracts the sequence corresponding to the hits. ClustalW (version 1.74) was used on the extracted sequences to create a locally gapped alignment. A representative flow scheme for this approach is shown in FIG. 56.

5. Identification Of Secondary Structure

Sets of sequences that show evidence of conservation in orthologs and paralogs or other related genes are analyzed for the ability to form internal structure. This is accomplished by analyzing each sequence in a matrix where the sequence is plotted 5' to 3' on the X axis and its complement is plotted 5' to 3' on the Y axis, such as in, for example, self-complementary analysis. Matches that correspond to potential intramolecular base pairs are scored according to a table of values. When the human ferritin IRE sequence is analyzed in this fashion, the diagonals indicate potential self-complementary regions. Each of the 13 IRE sequences described in this example were analyzed in the same fashion. While each of the sequences can form a variety of different structures, the structure most likely to occur is one common to all the sequences. By superimposing the plots of all 13 individual sequences, the potential structure common to all the sequences is deduced.

The above scheme has been implemented algorithmically into a program called RevComp (see, FIG. 53). RevComp creates a sorted list of all the structures. Representative results can be viewed either as a "dome" ouptut or as a "connect" or "ct" file which can be used in one of many RNA structure viewing programs (RNA Structure, RNA Viz, etc.).

Example 3

Histone

Histone 3'UTR represents another classic stem-loop structure that has been studied extensively (EMBO, 1997, 16, 769). At the post-transcriptional level, the stem-loop structure in the 3' untranslated region of the histone mRNA has been shown to be very important. Son, Saenghwahak Nyusu, 1993, 13, 64–70. The analysis shown below describes the use of this known structure to validate the strategy and methods described herein.

Phylogenetic tree outputs for all Histone orthologs in Hovergen database was obtained. Each of these orthologs was saved in GenBank format and grouped together in a single data file. Untranslated regions in both the 5' and 3' flanks of the coding regions were extracted and compared using SEALS and COWX as described earlier (see, FIGS. 55 and 56).

Following extraction and comparison by SEALS and COWX, Align Hits was used to determine potentially interesting regions. The sequences corresponding to the region of interest was extracted from all species for alignment with CLUSTAL W (1.74). Following extraction of sequence information from Align Hits, CLUSTALW (1.74) was used to provide multiple sequence alignment shown. Each of the putative hit sequences was analyzed for the ability to form internal structure. This was accomplished by analyzing each sequence in a matrix where the sequence was plotted 5' to 3' on the X axis and its complement is plotted 5' to 3' on the Y axis. Base-pairs along the diagonals indicate potential self-complementary regions that can form secondary structures. A representative sequence alignment in a dome format can show potential stem formation between the base pairs. Following conversion of the dome format file to a ct file, RNA Structure 3.21 is used to visualize the structure.

Example 4

Vimentin

Vimentin is an intermediate filament protein whose 3'UTR is highly conserved between species. Previous studies by Zehner et al., (*Nuc. Acids Res.,* 1997, 25, 3362–3370) has shown that a proposed a complex stem-loop structure contained within this region may be important for vimentin mRNA functions such as mRNA localization. The same region was identified using the present analysis, thus validating the present approach. In addition, based on the analyses described herein, a second stem-loop structure that occurs downstream of the previously proposed structure that may have a role in regulating vimentin function as well has been identified.

A representative phylogenetic tree output for all Vimentin orthologs in Hovergen database was obtained. Each of these orthologs was saved in GenBank format and grouped together in a single data file. Untranslated regions in both the 5' and 3' flanks of the coding regions were extracted and compared using SEALS and COWX as described earlier (see, FIGS. 55 and 56).

Following extraction and comparison by SEALS and COWX, Align Hits was used to determine potentially interesting regions. Two such regions appeared, and were used for subsequent analyses. Following extraction of sequence information from Align Hits for the first region, CLUSTAL W was used to provide multiple sequence alignment. Potential stem formation between base pairs was given above the sequence alignment in a dome format. Following conversion of the dome format file to a ct file, RNA Structure 3.21 was used to visualize the structure. This structure is very similar to the one proposed by Zehner et al. Zehner et al. presented a detailed chemical analysis of their proposed structure for the minimal binding domain in the 3' UTR of Vimentin. This analysis included cleavage with single-strand-specific (ChS or T1) or double-strand-specific (V1) nucleases as well as after exposure to lead acetate.

Following extraction of sequence information from Align Hits for the second region, CLUSTAL W was used to provide multiple sequence alignment. The potential stem formation between base pairs in the second region was given above the sequence alignment in a dome format. Following conversion of the dome format file to a ct file, RNA Structure 3.21 was used to visualize the structure for the second region.

Example 5

Transferrin Receptor

Similar to regulation of ferritin (Examples 1 and 2), another known function of the IRE is in the regulation of transferrin receptor. Five IREs have been identified in the 3 UTRs of known transferring receptor mRNAs. Kuhn et al., EMBO J, 1987, 6, 1287–93 and Casey et al., Science, 1988, 240, 924–928, each of which is incorporated herein by reference in its entirety. All 5 IREs have been shown to interact with iron regulatory proteins (IRP) independently. The present techniques were applied to identify these conserved elements in transferrin receptors.

A representative phylogenetic tree output for all Transferrin receptor orthologs in Hovergen database was obtained. Each of these orthologs was saved in GenBank format and grouped together in a single data file. Untranslated regions in both the 5' and 3' flanks of the coding region were extracted and compared using SEALS and COWX as described earlier (see, FIGS. 55 and 56).

Following extraction and comparison by SEALS and COWX, Align Hits was used to determine potentially interesting regions. The first region, between base pairs 920 to 990, in the 3 prime UTR of transferrin receptor was extracted from all species for alignment with CLUSTAL W (174).

Following extraction of sequence information from Align Hits for the first region, CLUSTAL W (1.74) was used to provide multiple sequence alignment. A representative potential stem formation between base pairs was given above the sequence alignment in a dome format. Following conversion of the dome format file to a ct file, RNA Structure 3.21 was used to visualize the structure. The second region, between base pairs 990 to 1050, in the 3 prime UTR of transferrin receptor was extracted from all species for alignment with CUSTAL W (1.74).

Following extraction of sequence information from Align Hits for the second region, CLUSTAL W (1.74) was used to provide multiple sequence alignment. Potential stem formation between base pairs was given above the sequence alignment in a dome format. Following conversion of the dome format file to a ct file, RNA Structure 3.21 was used to visualize the structure. Following extraction and comparison by SEALS and COWX, Align Hits was used to determine potentially interesting regions. The third region, between base pairs 1372 to 1423, in the 3 prime UTR of transferrin receptor was extracted from all species for alignment with CLUSTAL W Following extraction of sequence information from Align Hits for the third region, CLUSTAL W (1.Ex.34) was used to provide multiple sequence alignment. Potential stem formation between base pairs was given above the sequence alignment in a dome format. Following conversion of the dome format file to a ct file, RNA Structure 3.21 was used to visualize the structure. Following extraction and comparison by SEALS and COWX, Align Hits was used to determine potentially interesting regions. The fourth region, between base pairs 1439 to 1479, in the 3 prime UTR of transferrin receptor was extracted from all species for alignment with CLUSTAL W (1.74).

Following extraction of sequence information from Align Hits for the fourth region, CLUSTALW (1.Ex.34) was used to provide multiple sequence alignment. Potential stem formation between base pairs was given above the sequence alignment in a dome format. Following conversion of the dome format file to a ct file, RNA Structure 3.21 was used to visualize the structure. Following extraction and comparison by SEALS and COWX, Align Hits was used to determine potentially interesting regions. The fifth region, between base pairs 1479 to 1542, in the 3 prime UTR of transferrin receptor was extracted from all species for alignment with CLUSTAL W (1.74).

Following extraction of sequence information from Align Hits for the fifth region, CLUSTAL W (1.Ex.34) was used to provide multiple sequence alignment. Potential stem formation between base pairs was given above the sequence alignment in a dome format. Following conversion of the dome format file to a ct file, RNA Structure 3.21 was used to visualize the structure.

Example 6

Ornithine Decarboxylase

Orinithine decarboxylase (ODC) is the first enzyme in the polyamine biosynthetic pathway. Studies have shown existence of translational regulatory elements both in the 5' and 3' untranslated regions (Grens et al., *J. Biol. Chem.,* 1990, 265, 11810). Secondary structures have been proposed to exist in both these regions, though there is no conclusive evidence for it. The methods described herein identified two structures in the 3'UTR, as shown below. The presence of one of these structures was verified using mass spectrometry probing (Griffey, et al., *Proc. SPIE-Int. Soc. Opt. Eng.,* 2985 (Ultrasensitive Biochemical Diagnostics II): 82–86, which is incorporated herein by reference in its entirety). Two representative sequences that showed slight variation in their lengths were made into RNA and subjected to MS structure probing. Results confirm the presence of a stem-loop structure. Accordingly, identification of a novel secondary structure can be identified from the methods described herein, and such existence has been independently verified by structure probing.

Phylogenetic tree outputs for all Ornithine Decarboxylase orthologs in Hovergen database were obtained. Each of these orthologs was saved in GenBank format and grouped together in a single data file. Untranslated regions in both the 5' and 3' flanks of the coding region were extracted and compared using SEALS and COWX as described earlier (see, FIGS. 55 and 56).

Following extraction and comparison by SEALS and COWX, Align Hits was used to determine potentially interesting regions. Two such regions appeared, and were used for subsequent analyses. Following extraction of sequence information from the first region, CLUSTAL W (1.74) was used to provide multiple sequence alignment shown. Each of the putative hit sequences was analyzed for the ability to form internal structure in a reverse complement matrix. This was accomplished by analyzing each sequence in a matrix where the sequence is plotted 5' to 3' on the X axis and its complement is plotted 5' to 3' on the Y axis. Base-pairs along the diagonals indicate potential self-complementary regions that can form secondary structures. Domes view of the potential stem formation between base pairs in region 1 is given above the sequence alignment was determined using RevComp. RNA Structure 3.2 was used to visualize the structure.

Mass spectrometry analyses techniques were used to probe for structure. The cluster alignment of the first region of ornithine decarboxylase 3' UTR showed presence of gaps/inserts in the multiple alignment. Two representative RNAs (gi404561 and gi35135) from the alignments were used for this experiment. Analysis of the pattern of induced fragmentation showed a very strong likelihood for base-paring along the top half of the stem-loop structure. This corresponds to bases 11–14 and 20–23 in 404561 or bases 8–11 and 18–21 in 35135. Bulged bases (G9 in 404561 or U22 in 35135) also showed characteristic fragmentation pattern. The bottom-half of the structure appeared to be less stable, and showed some fragmentation where our analyses had predicted base-paring. This was particularly true in the sequence 35135. This region, however, has several contiguous A-U or G-U base-pairs which tend to be less stable, and therefore have a higher probability of fragmentation.

Following extraction of sequence information from Align Hits for the second region, CLUSTAL W was used to provide multiple sequence alignment. Potential stem formation between base pairs in the second region was given above the sequence alignment in a dome format. Following conversion of the dome format file to a ct file, RNA Structure 3.21 was used to visualize the structure for the second region.

Example 7

Interleukin-2 (11,-2)

A representative phylogenetic tree output for all IL-2 orthologs in Hovergen database was obtained. Each of these orthologs was saved in GenBank format and grouped together in a single data file. Untranslated regions in both the 5' and 3' flanks of the coding region were extracted and compared using SEALS and COWX as described earlier (see, FIGS. 55 and 56).

Following extraction and comparison by SEALS and COWX, Align Hits was used to determine potentially interesting regions in the 3'UTR region. Two such regions appear, and were used for subsequent analyses. Following extraction of sequence information from Align Hits for the first region, CLUSTAL W (1.74) was used to provide multiple sequence alignment. Domes view of the potential stem formation between base pairs in the first region was given above the sequence alignment using RevComp. RNA Structure 3.2 was used to visualize the structure. Following extraction of sequence information from Align Hits for the second region, CLUSTAL W (1.74) was used to provide multiple sequence alignment. Potential stem formation between base pairs in the second region was given above the sequence alignment in a dome format. Following conversion of the dome format file to a ct file, RNA Structure 3.21 was used to visualize the structure for the second region.

Figure 58:
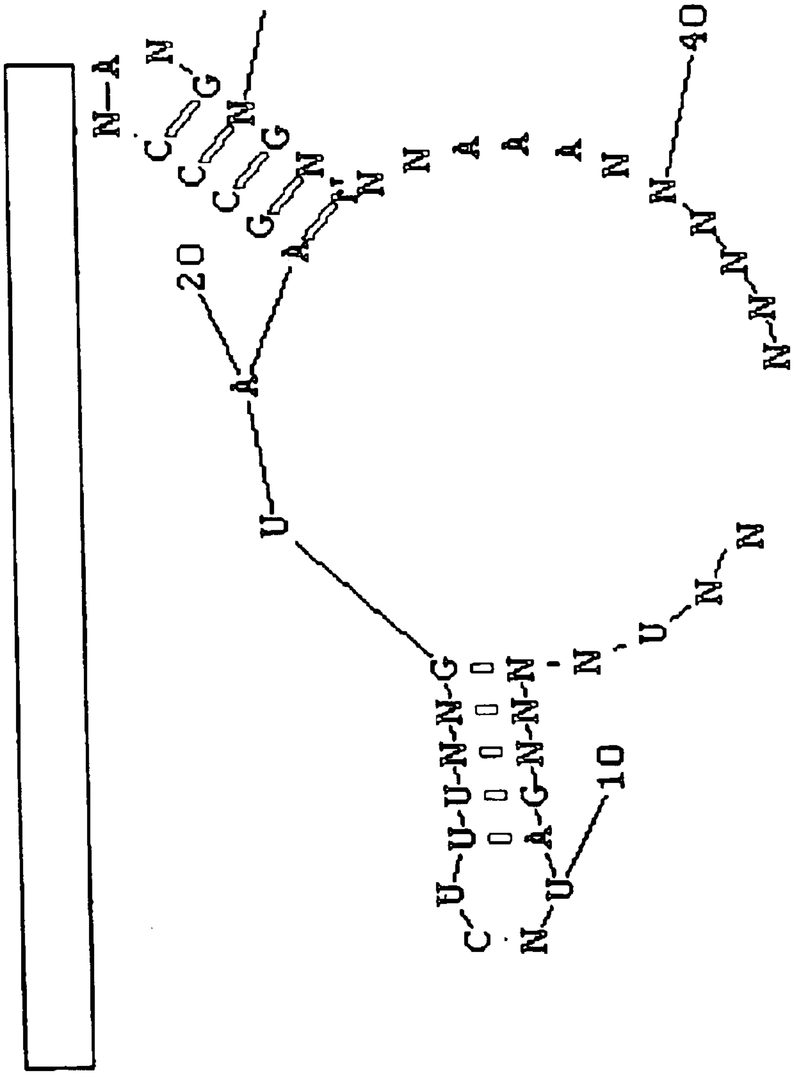
FIG. 58 shows a representative structure drawing of region 3 of IL-2 3' UTR.

In addition to the two regions described above, a third region, downstream of, and partially overlapping the second region, was identified using an alternate reference sequence (3087784.fa). Following extraction of sequence information from Align Hits for this region, CLUSTAL W (1.74) was used to provide multiple sequence alignment. Potential stem formation between base pairs in the third region is shown in FIG. 57 above the sequence alignment in a dome format. Following conversion of the dome format file to a ct file, RNA Structure 3.21 was used to visualize the structure for the third region (see, FIG. 58).

Example 8

Interleukin-4 (IL4)

Representative phylogenetic tree output for all IL-4 orthologs in Hovergen database was obtained. Each of these orthologs was saved in GenBank format and grouped together in a single data file. Untranslated regions in both the 5' and 3' flanks of the coding region were extracted and compared using SEALS and COWX as described earlier (see, FIGS. 55 and 56).

Following extraction and comparison by SEALS and COWX, Align Hits was used to determine potentially interesting regions in the 5'UTR region. Following extraction of sequence information from Align Hits for the above region, CLUSTAL W (1.74) was used to provide multiple sequence alignment. Domes view of the potential stem formation between base pairs in the region was given above the sequence alignment using RevComp. RNA Structure 3.2 was used to visualize the structure.

Align Hits was used to view hits in the 3'UTR region of IL4. Following extraction of sequence information from Align Hits for the 3' UTR region, CLUSTAL W (1.74) was used to provide multiple sequence alignment. Potential stem formation between base pairs in the second region was given above the sequence alignment in a dome format. Following conversion of the dome format file to a ct file, RNA Structure 3.21 was used to visualize the structure for the second region.

Example 9

General Procedure for Automated Synthesis of Library Plates

ArgoGel-OH™ (360 mg, loading 0.43 mmole/g) was suspended in 16 mL solution of 3:1 $CH_2Cl_21$/DMF. The suspension was distributed equally among 12 wells of a 96 well polypropylene synthesis plate (30 mg per well). The solvent was drained and the resin dried overnight in vacuo over $P_2O_5$. All solid reagents were dried in vacuo overnight over $P_2O_5$ prior to use. For method 1, the Mitsunobu reagent 1 was dried, then dissolved in anhydrous $CH_2Cl_2$ to a concentration of 0.15M. FMOC-Amino Acids (Novabiochem, Bachem Calif.) were dissolved to a concentration of 0.30 M in a solution of 2:1 anhydrous $CH_2Cl_2$/DMF for method 1, and to a concentration of 0.22 M in DMF containing 0.44 M collidine for synthesis for method 2. Sulfonyl chlorides were dissolved to a concentration of 0.2M in Pyridine. Pyridine proved to be an acceptable solvent for most sulfonyl chlorides, but when solubility was limited, cosolvents such as MeCN, DMSO, $CH_2Cl_2$, DMF, and NMP (up to 50%) have been employed. FMOC protection were removed with a solution of 10% piperidine in anhydrous DMF prepared and used the day ol synthesis. Low water wash solvents were employed to ensure maximum coupling efficiency of the initial amino-acid to the resin. Prior to loading reagents, moisture sensitive reagent lines were purged with argon for 20 minutes. Reagents were dissolved to appropriate concentrations and installed on the synthesizer. Large bottles (containing 8 delivery lines) were used for wash solvents and the delivery of activator. Small septa bottles containing the amino acids and sulfonyl chlorides allow anhydrous preparation and efficient installation of multiple reagents by using needles to pressurize the bottle, and as a delivery path. After all reagents were installed, the lines were primed with reagent, flow rates measured, then entered into the reagent table (.tab file) and the dry resin loaded plate removed from vacuum and installed in the machine for subsequent synthesis. After cleavage from support and centrifugal evaporation of solvent, the products were dissolved in $MeOH/CH_2Cl_2$ mixtures, then assayed for purity by TLC (typically 10% $MeOH/CH_2Cl_2$) on silica gel using both UV and 12 visualization, and for product identity by electrospray mass spectroscopy (negative mode). Selected samples were dissolved in DMSO-$_6$ and examined by $^1H$ NMR.

Example 10

General Hydroxamic Acid Synthesis Method 1 (FIG. 34)

The commercial ArgoGel-OH™ resin (10 $\mu$mole) was washed with $CH_2Cl_2$ (6×), then treated with the appropriate FMOC-amino acid (3 eq.) and 1 (3 eq.). After 30 min, the wells were drained, and the process repeated to give a total of 4 treatments (12 eq.). The resin was washed with $CH_2Cl_2$ (6×), DMF (4×), and the FMOC removed with 10% piperidine in DMF (4×). The washes were collected, diluted appropriately, and the amount of FMOC chromophore released quantitated by UV (c 7800 L*mol$^{-1*}$cm$^{-1}$, γ=301 nm). This value was used to calculate the yield of the final products. The resin was then washed with DMF (4×), then $CH_2Cl_2$ (6×), and treated with the appropriate sulfonyl chloride (4×6 eq. for 15 min.) in pyridine, and washed with $CH_2Cl_2$ (6×), DMF (6×), and $CH_2Cl_2$ (10×). At this point the resin could be treated with 90:5:5 TFA/$H_2O$/$Et_3SiH$ for 4 h, then subjected to the above washing procedure to remove any side chain protection on the molecules if necessary. The plates were then removed from the instrument, and individual wells treated with 4 M hydroxylamine (50% aqueous) in 1,4-dioxane for 24 h. The filtrate was collected into a deep well 96 well plate, the samples frozen, then lyophilized to provide the desired hydroxamic acids. Addition of fresh 1,4-dioxane and repetition of the lyophilization process twice gave compounds free of any residual hydroxylamine (by $^1$H NMR of selected products).

Example 11

General Hydroxamic Acid Synthesis Method 2 (FIG. 35)

Resin 6 was prepared from ArgoGel-Wang-OH™ resin according to published procedures and this resin (10 μmole) was washed with DMF (6×), $CH_2Cl_2$ (6×), then treated with the appropriate FMOC-amino acid (3 eq.) in DMF+collidine (6 eq.) and HATU (3 eq.). After 30 min, the wells were drained, and the process repeated to give a total of 4 treatments (12 eq.) The resin was washed with $CH_2Cl_2$ (6×), DMF (4×), and the FMOC removed with 10% piperidine in DMF (4×). The washes were collected, diluted appropriately, and the amount of FMOC chromophore released quantitated by UV (C 7800 L*mol$^{-1}$, γ=301 nm). This value was used to calculate the yield of the final products. The resin was washed with DMF (4×), then $CH_2Cl_2$ (6×), and treated with the appropriate sulfonyl chloride (4×6 eq. for 15 min.) in pyridine, and washed with $CH_2Cl_2$ (6×), DMF (8×), DMSO (8×), and $CH_2Cl_2$ (10×). The plates were then removed from the instrument, and individual wells treated with 90:5:5 TFA/$Et_3SiH$/$H_2O$ for 4 i. The filtrate was collected into a deep well 96 well plate, the resin washed (3×) with TFA, and the samples concentrated in a centrifugal vacuum concentrator. Addition of fresh 1,4-dioxane or isopropanol and repetition of the concentration process twice, followed by drying in vacuo overnight gave the desired hydroxamic acids.

The methods of both Examples 2 and 3 were utilized to produce a library of compounds resulting from the combination of FMOC-amino acids and sulfonyl chlorides shown in Table 2.

TABLE 2

Reagents Used to Prepare Hydroxamic Acids 5 by Automated Synthesis[a]

| | FMOC-Amino Acid Used[b] | | Sulfonyl Chloride Used[c] |
|---|---|---|---|
| a | D-Val[d] | i | 1-napthalene |
| b | D-Ile | ii | 2-napthalene |
| c | D-Leu | iii | 2-thiophene |
| d | D-Ala | iv | 2-mesitylene |
| e | D-cyclo-hexyl-Ala | | 3-nitrobenzene |
| f | D-norvaline | vi | 4-bromobenzene |
| g | D-norleucine | vii | 4-chlorobenzene |
| h | D-alloiso-leucine | viii | 4-iodobenzene |
| i | D-α-t-Butylglycine[c] | ix | 4-nitrobenzene |
| j | D-Met | x | 4-methoxybenzene[d] |
| k | D-Phenyl-glycine | xi | 4-t-Butylbenzene |
| l | D-Phe | xii | trifluoromethane[d] |
| m | D-4-Chloro-Phe | xiii | -toluene |
| n | 3-(2-napthyl)-D-Ala | xiv | 3-(trifluoromethyl)benzene |
| o | 3-(3-pyridyl)-D-Ala | xv | 4-(trifluromethoxy)benzene |
| p | -(2-thienyl)-D-Ala | xvi | 4-(methylsulfonyl)benzene |
| q | D-Tyr(tBu)[d] | xvii | 4-(benzenesulfonyl)thiophene-2- |
| r | D-Trp | xviii | 4-ethylbenzene |
| s | D-Cys(tBu) | xix | 4-cyanobenzene |
| t | S-Bn-D-penicillamine | xx | 4-methoxy-2,3,6-trimethylbenzene |
| u | glycine | xxi | benzo-2,1,3-thiadiazole-4- |
| v | aminoisobutyric acid | xxii | 1-Melhyliniidazole-4- |
| w | D-Thr(tBu)[e] | xxiii | 5-chloro-3-methylbenzo[B]thiophene-2-[d] |
| x | D-Ser(tBu) | xxiv | benzofurazan-4- |
| y | D-His(Trt)[d] | xxv | 3,5-dichlorobenzene |
| z | D-Pro | xxvi | 3,4-dimethoxybenzene |
| aa | D-Tic | xxvii | 4-(n-butoxy)benzene |
| bb | D-Lys(BOC) | xxviii | 2,4-dichlorobenzene |
| cc | D-Asp(OtBu) | xxix | 4-trifluoromethylbenzene |
| dd | D-Glu(OtBu) | xxx | 2,5-dimethoxybenzene |
| ee | L-Val | xxxi | 3,4-dichlorobenzene[d] |
| ff | L-Ala | xxxii | 4-n-propylbenzene[d] |
| gg | L-Phe[d] | xxxiii | 4-isopropylbenzene[d] |
| hh | D-Asn(Trt)[e] | xxxiiv | 2,5-dichlorothiophene-3- |
| ii | D-Gln(Trt)[c] | xxxv | 2-[1-methyl-5-(trifluoromethyl)pyrazol-3-yl]thiophene-5- |
| jj | D-Arg(Pmc)[d] | xxxvi | 2-[3-(trifluoromethyl)pyrid-2-yl sulfonyl]thiophene-5- |

[a]All possible combinations of reagents shown were utilized to attempt the preparation of 1296 hydroxamic acids according to method 2 (FIG. 35).
[b]Standard abbreviations used for FMOC-amino acids. All amino acids used were obtained from Novabiochem, Bachem, or Synthetech.
[c]Truncated chemical names are given in the table. Appending 'sulfonyl chloride' to the prefix listed gives the appropriate name. All sulfonyl chlorides used were obtained from Aldrich, Lancaster, or Maybridge.
[d]Also prepared via method 1 (FIG. 34).
[e]Failed in method 1.

Example 12

Representative Parallel Array Synthesizer Input Files

The software inputs accept tab delimited text files from any text editor. Examples for the synthesis of hydroxamic acids via the procedure of FIG. 34 are shown in Table 3 (.cmd file), Table 4 (.seq file), and Table 5 (.tab file). Only several wells worth of synthesis are shown for brevity. For an entire plate to be prepared, only additional sulfonyl chlorides and additional amino acids need to be added to the tab file, and additional combinations of the two need to be added to the seq file such that it contains 96 lines, with each line corresponding to a unique compound prepared.

The identity and purity of the compounds was determined by electrospray mass spectroscopy (negative mode) and thin layer chromatography on silica employing $MeOH/CH_2Cl_2$ solvent mixtures (TLC). The synthesis products in approximately every third well were assayed by TLC and electrospray mass spectroscopy, and the desired compounds were generally present with purities of 60 to 90% when using either of the synthesis methods described above.

TABLE 3

Example .cmd file (general synthesis procedure) which executes the synthesis shown in FIG. 34. The cleavage from support with hydroxylamine is performed separately.

```
INITIAL_WASH
    BEGIN
        Repeat 6
            Add CH2Cl2 300
            Drain 20
        End_Repeat
    END
COUPLE_AMINO_ACID
    BEGIN
        Repeat 4
            Add <SEQ> 100 + <ACT1> 200
            Wait 1800
            Drain 20
        End_Repeat
        Repeat 6
            Add CH2Cl2 300
            Drain 20
        End_Repeat
        Repeat 4
            Add DMF 300
            Drain 20
        End_Repeat
    END
REMOVE_FMOC
    BEGIN
        Load_Tray
        Repeat 4
            Add PIPERIDINE_DMF 300
            Wait 250
            Drain 20
        End_Repeat
        Remove_Tray
        Repeat 4
```

TABLE 3-continued

Example .cmd file (general synthesis procedure) which executes the synthesis shown in FIG. 34. The cleavage from support with hydroxylamine is performed separately.

```
            Add DMF 300
            Drain 20
        End_Repeat
        Repeat 6
            Add CH2Cl2 300
            Drain 20
        End_Repeat
    END
SULFONYLATE_AMINO_ACID
    BEGIN
        Next_Sequence
        Repeat 4
            Add <SEQ> 300
            Wait 900
            Drain 20
        End_Repeat
        Repeat 6
            Add CH2Cl2 300
            Drain 20
        End_Repeat
    END
FINAL_WASH
    BEGIN
        Repeat 6
            Add DMF 300
            Drain 20
        End_Repeat
        Repeat 8
            Add CH2Cl2 300
            Drain 20
        End_Repeat
        Repeat 2
            Add CH2Cl2 300
            Drain 60
        End_Repeat
    END
```

TABLE 4

Example .seq File (list of compounds to make)

| | | | | |
|---|---|---|---|---|
| 1 | A1 | 10 | FMOC_D_ALA | 4_MEO_BENZENE_SO2CL |
| 2 | A2 | 10 | FMOC_D_VAL | 2_NAPTHYLENE_SO2CL |
| 3 | A3 | 10 | FMOC_D_PHE | 3_CF3_BENZENE_SO2CL |
| 4 | A4 | 10 | FMOC_D_NAL | 4_CL_BENZENE_SO2CL |
| 5 | A5 | 10 | FMOC_D_SER(OTBU) | 4_MEO_BENZENE_SO2CL |
| 6 | A6 | 10 | FMOC_D_ARG_PMC | 2_NAPTHYLENE_SO2CL |
| 7 | A7 | 10 | PMOC_D_ALA | 3_CF3_BENZENE_SO2CL |
| 8 | A8 | 10 | FMOC_D_VAL | 4_CL_BENZENE_SO2CL |
| 9 | A9 | 10 | FMOC_D_PHE | 4_MEO_BENZENE_SO2CL |
| 10 | A10 | 10 | FMOC_D_NAL | 2_NAPTHYLENE_SO2CL |
| 11 | A11 | 10 | FMOC_D_SER(OTBU) | 3_CF3_BENZENE_SO2CL |
| 12 | A12 | 10 | FMOC_D_ARG_PMC | 4_CL_BENZENE_SO2CL |

TABLE 5

| Example .tab (list of reagents to use) | | | |
|---|---|---|---|
| AMINO_ACIDS | | | |
| BEGIN | | | |
| 1 | FMOC_D_ALA | 265 | 0.30 |
| 2 | FMOC_D_VAL | 265 | 0.30 |
| 3 | FMOC_D_PHE | 265 | 0.30 |
| 4 | FMOC_D_NAL | 265 | 0.30 |
| 5 | FMOC_D_SER(OTBU) | 265 | 0.30 |
| 6 | FMOC_D_ARG_PMC | 265 | 0.30 |
| END | | | |
| SOLVENTS | | | |
| BEGIN | | | |
| 67 | CH2CL2 | 330 | 1 |
| 66 | DMF | 240 | 1 |
| END | | | |
| SULFONYLCHLORIDES | | | |
| BEGIN | | | |
| 9 | 4_MEO_BENZENE_SO2CL | 220 | 0.20 |
| 10 | 2_NAPTHYLENE_SO2CL | 220 | 0.20 |
| 11 | 3_CF3_BENZENE_SO2CL | 220 | 0.20 |
| 12 | 4_CL_BENZENE_SO2CL | 220 | 0.20 |
| END | | | |
| DEBLOCK | | | |
| BEGIN | | | |
| 68 | PIPERIDINE_DMF | 230 | 1 |
| END | | | |
| ACTIVATORS | | | |
| BEGIN | | | |
| 69 | BETAINE 300 0.15 Activates AMINO_ACIDS | | |
| END | | | |

Example 13

Manual Solution Synthesis of Active Compounds

Methyl (2R)-2-amino-3-(2-naphthyl)propanoate.

To a suspension of D-napthylalanine hydrochloride (2.15 g, 10 mmole, Bachem Calif.) in MeOH (17 mL) was added TMS-C1 (2.8 mL, 22 mmole) dropwise with stirring. The mixture was allowed to stir overnight, and the resulting solution concentrated in vacuo, then dried over KOH to afford 2.65 g (100%) of methyl (2R)-2-amino-3-(2-naphthyl)propanoate, which was >95% pure by $^1$H NMR, and used without further purification: $R_f$ 0.63 (4:1:1 n-BuOH/AcOH/$H_2O$); $^1$H NMR (DMSO-$d_6$) δ 8.76 (bs, 3H), 8.00-7.30 (m, 7H), 4.39 (t, 1H), 3.69 (s, 3H), 3.66 (m, 2H); MS (APCI$^+$) m/e 230 (M+H).

(2R)-2-(((4-bromophenyl)sulfonyl)amino)-3-(2-naphthyl)propanehydroxamic acid(5n-vi).

A suspension of D-Napthylalanine hydrochloride methyl ester (1.33 g, 5 mmole), (i-$Pr_2$)NEt (2.61 mL, 15 mmole) and 4-bromobenzesulfonyl chloride (1.53 g, 6 mmol) in $CH_2Cl_2$ (50 mL) was stirred at rt overnight. The solution was washed with 5% $NaHCO_3$, dried ($Na_2SO_4$), concentrated, then chromatographed ($CH_2Cl_2$ to 1% MeOH/$CH_2Cl_2$) and concentrated to provide 2.05 g of the sulfonamide ester. This material was dissolved in 1,4-dioxane (50 mL) and 25 mL of aqueous hydroxylamine (50% w/w) was added. The mixture was allowed to stand at rt for 48 h, then concentrated onto silica, chromatographed (2% to 10% MeOH/$CH_2Cl_2$), the solid residue triturated with water, and dried to provide 1.45 g (64%) of 5n-vi: $R_f$ 0.35 (2% MeOH/$CH_2Cl_2$); $^1$H NMR (DMSO-$d_6$) δ 9.26 (bs, 1H), 7.90-7.20 (m, 11H), 3.88 (dd, 1H), 2.90 (m, 2H); MS (electrospray) m/e 447, 449 (M−H). Anal. Calcd for $C_{19}H_{11}N_2O_4SBr \circ 0.5H_2O$: C, 49.79; H, 3.96; N, 6.11. Found: C, 49.71; H, 3.90; N, 5.97.

(2R)-3-(2-naphthyl)-2-((2-naphthylsulfonyl)amino) propanehydroxamic acid (5-n-ii).

A suspension of D-Napthylalanine hydrochloride methyl ester (1.33 g, 5 mmole), (i-$Pr_2$)NEt (2.61 mL, 15 mmole) and 4-napthalenesulfonyl chloride (1.36 g, 6 mmol) in $CH_2Cl_2$ (50 mL) was stirred at rt overnight. The solution was washed with 5% NaH $CO_3$, dried ($Na_2SO_4$), concentrated, then chromatographed ($CH_2Cl_2$ to 1% MeOH/$CH_2Cl_2$) and concentrated to provide 2.02 g of the sulfonamide ester. This material was dissolved in 1,4-dioxane (50 mL) and 25 mL of aqueous hydroxylamine (50% w/w) was added. The mixture was allowed to stand at rt for 48 h, then concentrated onto silica, chromatographed (2% to 10% MeOH/$CH_2Cl_2$), and dried to provide 1.15 g (55%) of 5-n-ii: $R_f$ 0.33 (2% MeOH/$CH_2Cl_2$); $^1$H NMR (DMSO-$d_6$) δ 9.19 (bs, 2H), 8.17 (s, 1H), 7.95-7.35 (m, 12H), 7.17 (d, 1H), 3.97 (t, 1H), 2.83 (m, 2H); MS (electrospray) m/e 419 (M+H). Anal. Calcd for $C_{23}H_{20}N_2O_4S \circ_{0.75} H_2O$: C, 63.85; H, 4.99; N, 6.45. Found: C, 63.57; H, 4.74; N, 6.74.

Example 14

Antibacterial Testing

The crude compounds were screened in a representative high throughput screening assay for antibacterial activity, and compounds 5-n-ii and in-vi were found to have activities minimum inhibitory concentrations (MIC's) of 0.7–1.5 μM and 3–6 μM against *E. coli*, respectively. This activity was verified by manual solution synthesis of analytically pure material as described in Example 6 above, which had identical activity.

Example 15

Functional Screening

The compounds are screened for binding affinity using MASS or conventional high-throughput functional screens. The best scoring compounds from docking a 256-member library against the 16S A-site ribosomal RNA structure are shown in the table below. The DOCK scores ranged from −308.8 to −144.2 as listed in Table 6. The MASS assay was performed with the 27-mer model RNA sequence of the 16S A-site whose NMR structure has been determined. The transcription/translation assay was based on expression of a luciferase plasmid.

TABLE 6

DOCK scores correlated with mass spectrometry and biological assay

| Compound | DOCK score | MASS $K_D$ | Activity[1] |
|---|---|---|---|
| Paromomycin | −308.8 | 0.5 μM | 0.3 μM |
| 170046 | −303.4 | >50 | >100 |
| 169999 | −299.0 | >50 | >100 |
| 169963 | −293.9 | >50 | >100 |
| 170070 | −290.2 | >50 | >100 |
| 169970 | −288.9 | 1.5 | 2.5 |
| 169961 | −288.5 | 5.0 | 10 |
| 170003 | −287.8 | >50 | >100 |
| 169995 | −286.4 | >50 | >100 |
| 169993 | −286.0 | >50 | >100 |
| 170072 | −282.6 | >50 | >100 |
| 170078 | −281.6 | 5.0 | 10 |
| 169985 | −280.1 | 4.0 | 10 |
| 169998 | −278.0 | >50 | >100 |

Paromomycin is an aminoglycoside antibiotic known to bind to the A-site RNA structure. The NMR structure was determined with paromomycin bound at the A-site. Paromomycin had the best DOCK contact score, along with high chemical and energy scores. The docking results for these compounds have been correlated with their binding affinity for a 16S RNA fragment using MASS mass spectrometry, and their ability to inhibit protein synthesis in a transcription/translation assay. Four of the 12 compounds with the best DOCK scores had good affinity (<10 μM) for the RNA in the MASS assay and inhibited translation of a luciferase plasmid at <10 μM. In addition, all 9 of the "good" binders in the MASS assay scored in the top 30% in the DOCK calculation.

Ibis compound 169970 had the best energy score of any compound, but had a poor contact score. This result suggests that the biological activity may be increased further by modifying the structure to increase the number of close contacts with the 16S A-site RNA.

Example 16

Target Site of TAR

The NMR solution structure of TAR RNA (Varani, et al., J. Mol. Biol., 1995, 253, 313) has been used in the study of virtual screening for HIV-I TAR RNA ligands. The (77 compounds present in the Available Chemicals Database (ACD) have been partitioned into a number of subsets according to their formal charges (neutral, +1, +2, etc) and DOCKed to the TAR structure. Five aminoglycoside antibiotics were among the 20 compounds with the best binding energies.

Figure 36:
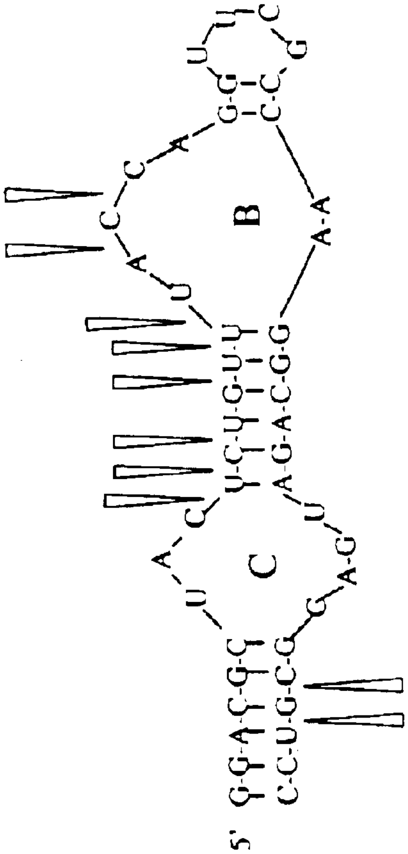
FIG. 36 shows exemplary compounds which were docked to TAR with subsequent evaluation of the solvation/desolvation energy.

In addition, a number of compounds were docked to TAR with subsequent evaluation of the solvation/desolvation energy. An exemplary result is illustrated in FIG. 36 which shows that ACD 00001199 and ACD 00192509 show relatively low energies of solvation/desolvationi as well as low $IC_5$, values.

Example 17

L11/Thiostrepton —An Example Of A High Throughput RNA/Protein Assay

RNA molecules play a numerous roles in cellular functions that range from structural to enzymatic in nature. These RNA molecules may work as single large molecules, in complexes with one or more proteins, or in partnership with one or more RNA molecules. Some of these complexes, such as those found in the ribosome, have been virtually intractable as high throughput screening targets due to their immense size and complexity. The ribosome presents a particularly rich source of RNA structures and functions that would appear, at first glance, to be highly effective drug targets. A large number of natural antibiotics exist that are directed against ribosomal targets indicating the general success of this strategy. These include the aminoglycosides, kirromycin, neomycin, paromomycin, thiostrepton, and many others. Thiostrepton, a cyclic peptide based antibiotic, inhibits several reactions at the ribosomal GTPase center of the 50S ribosomal subunit. Evidence exists that thiostrepton acts by binding to the 23S rRNA component of the 50S subunit at the same site as the large ribosomal protein L11. The binding of L11 to the 23S rRNA causes a large conformation shift in the proteins tertiary structure. The binding of thiostrepton to the rRNA appears to cause an increase in the strength of the L11/23S rRNA interactions and prevents a conformational transition event in the L11 protein thereby stalling translation. Unfortunately, thiostrepton has very poor solubility, relatively high toxicity, and is not generally useful as an antibiotic. The discovery of new, novel, antibiotics directed against these types of targets would be of great value.

The design of high throughput assays to discover new antibiotics directed against ribosomal targets has been difficult, in part, due to the large structures involved and the low binding affinity of the RNA/protein interactions. Recently, a tremendous amount of data has been generated concerning RNA structures in the ribosome. This data has elucidated a number of structures and enabled the prediction of many others. Further, the use of the SPA assay format allows for assays to be run without washing or other steps that lower the concentrations of binding components. This allows one to examine binding interactions with very low (>1 μM) Kd's.

The mode of action of thiostrepton appears to be to stabilize a region of the 23S rRNA and by doing so prevent a structural transition in the L11 protein. Among the many assays that look at RNA/protein interactions, an SPA assay has been designed to look for small molecules that could be effective as thiostrepton 'like' agents. This assay uses a radiolabeled small fragment of the 23S rRNA, a biotinylated 75 amino acid fragment of the L11 protein that contains the 23S rRNA binding domain and thiostrepton. The folding conditions of the secondary and tertiary structures of the 23S rRNA fragment have been examined as have the binding conditions of the L11 fragment to the 23S rRNA. The L11-thiostrepton assay has been optimized so that the 23S rRNA fragment is in an unfolded state prior to the addition of compounds. Addition of the L11 fragment to this unfolded RNA results in no detectable binding interaction. The high throughput assay is run by mixing the 23S rRNA fragment, under destabilizing conditions, with compounds of interest, incubating this mixture, and then adding the L11 fragment. Streptavidin-coated SPA beads are added for binding detection. Thiostrepton is used as a positive control. Addition of thiostrepton to the RNA promotes the correct secondary and/or tertiary folding of the structure and allows the L11 fragment to bind leading to the generation of a signal in the assay.

A tested paradigm has been developed for designing, developing and performing high and low throughput assays to look at RNA/protein function, structure, and binding in bacteria. The L11 thiostrepton assay described above is but one of a number of RNA/protein interaction and functional assays that have been designed and developed for high and low throughput screening. Others include functional assays to measure RnaseP, RnaseE, and EF-Tu activity. An assays to examine the function of the bacterial signal recognition particle and S30 assembly is also contemplated.

Example 18

P48-4.5S Interaction

The P48 protein-blinding region of the 4.5S RNA present in the signal recognition particle of bacteria has been selected as a target. The binding of P48 to 4.5S RNA is essential for bacteria to survive, and development of an inhibitor of this binding should generate a novel; class of antimicrobial agent. Using compounds (2×105) from the Available Chemicals Directory (ACD), as well as from additional libraries, initial screening using DOCK (Meng, et al., *J. Comp. Chem.,* 1992, 13, 505–524, incorporated herein by reference in its entirety) (version 4.0) can be carried out. This should leave about 15–20% of the database which have reasonably good shape complementarity in docking to the NMR structure of the 46mer, which is from the assymetric bulged regions of *E. coli* 4.5S RNA. A pseudobrownian Monte Carlo search in torsion angle space is performed using the program ICM (version 2.6), coupled with local minimization of each conformation, for automated flexible docking of that truncated set of potential ligands to the NMR structure and score for predicted affinity using an empirical free energy function.

Approximately 2000 of the best scoring compounds will be examined for experimental testing of their capability to inhibit the binding of P48 to 4.5S RNA. Inhibition of P48-4.5S RNA binding produced by the selected compounds will be measured using $(his)_6$-tagged P48 and $^{33}P$—RNA in a high-throughput scintillation proximity assay system. The structure-activity relationship among these 2000 compounds will serve as the basis for an expanded synthetic effort.

Docking of small molecules to the region of the asymmetric RNA bulges is expected to identify compounds with a high probability of selectively destabilizing the 4.5S—P48 interaction in vitro. The structure for the target RNA, shown in FIG. 37, will be determined using NMR in the first phase of this proposal. Compounds (approaching 2×105) from the Available Chemicals Directory (ACD) will be docked to the structure and scored for predicted affinity. The best molecules will be screened for their ability to disrupt the RNA-protein interaction. Quantitative structure-activity relationship (QSAR) studies will be performed on the most active compounds to identify critical features and interactions with the RNA. New compounds (20,000) will be prepared through combinatorial addition and/or repositioning of hydrogen bonding, aromatic, and charged functional groups to enhance the activity and specificity of the compounds for the bacterial SRP relative to the human counterpart. In addition, a pseudobrownian Monte Carlo search in torsion angle space using the program ICM2.6 (Abagyan, et al., *J. Comp. Chem.,* 1994, 15, 488–506, incorporated herein by reference in its entirety) will be performed, coupled with local minimization of each conformation, for automated flexible docking of the truncated database to the NMR structural models.

In order to rank the ligands after flexible docking is completed, a function to estimate their binding free energies is used. There are a number of empirical methods for estimation or the free energy of binding, but empirical free energy function derived from the thermodynamic binding cycle is intended to be used (Filikov, er al., *J. Comp.-Aided Molec. Design* 1998, 12, 1–12, which is incorporated herein by reference in its entirety).

Example 19

Inhibition of Translation of an mRNA Containing a Molecular Interaction Site by a "Small" Molecule Identified by Molecular Docking Translation of mRNAs in eukaryotic cells follows formation of an initiation complex at the 5'-cap ($m^7$ Gppp). A variety of initiation factors bind to the 5'-cap to form a pre-initiation complex before the 40S ribosomal subunit binds to the 5'-untranslated region upstream of the AUG start codon. Pain, Eur. J. Biochem.; 1996, 236, 747–771. It has been demonstrated that RNA secondary structures near the 5'-cap can affect the rates of translation of mRNAs. Kozak, *J. Biol. Chemistry,* 1991, 266, 19867–19870. These RNA structures can bind proteins and inhibit the level of translation. Standart, et al., *Biochimie,* 1994, 76, 867–879. The translational machinery has an ATP-dependant RNA helicase activity associated with the eIF-4a/eIF-4b complex, and under normal conditions, the RNA structures are opened by the helicase and do not slow the rate of translation of the mRNA. The eIF-4a has a low (- μM) affinity for the pre-initiation complex.

Figure 38A:
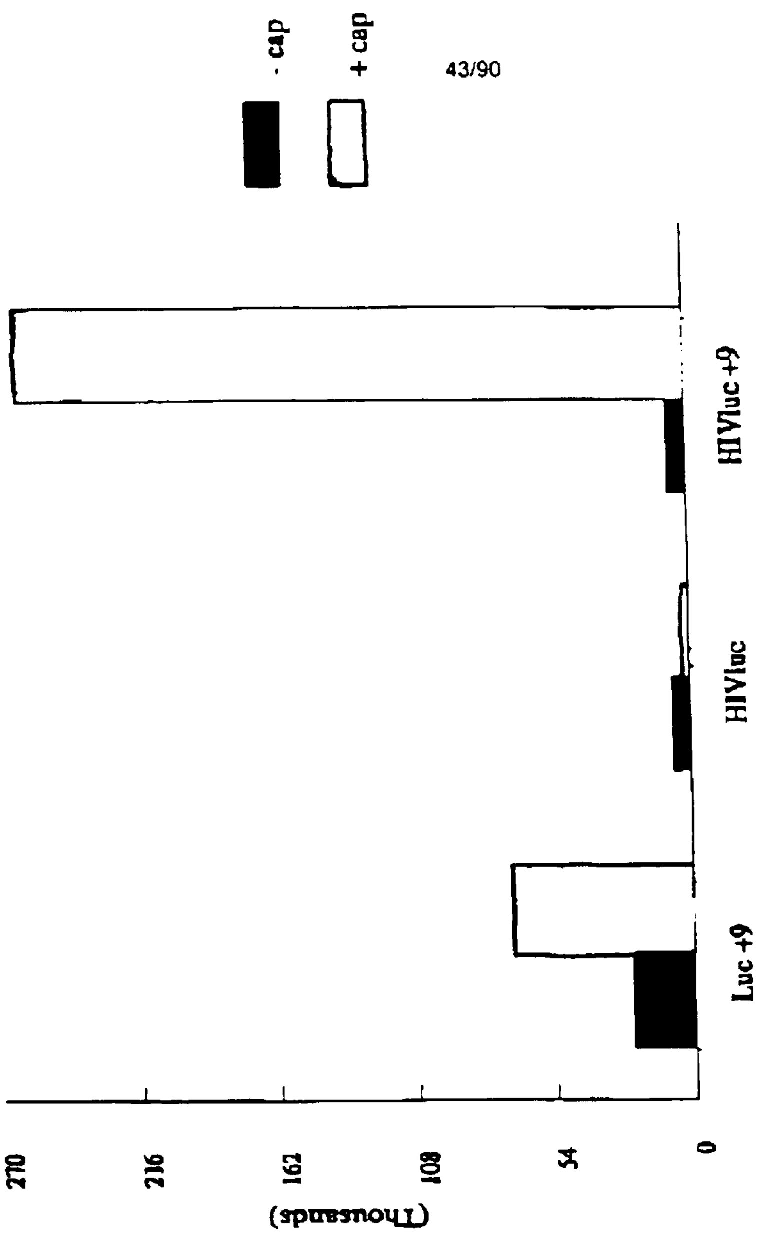
FIG. 38A shows a representative demonstration of cap-dependent translation of three DNA plasmids with a wheat germ lysate system: a) a luciferase gene with a 9 base leader sequence before the AUG start codon; b) translation of a construct with the TAR RNA structure adjacent to the cap; c) translation of a construct with the TAR RNA structure separated from the cap by a 9 base leader sequence. Solid bars: no added $m^7G$. Hatched bars: added $m^7G$.
Figure 38B:
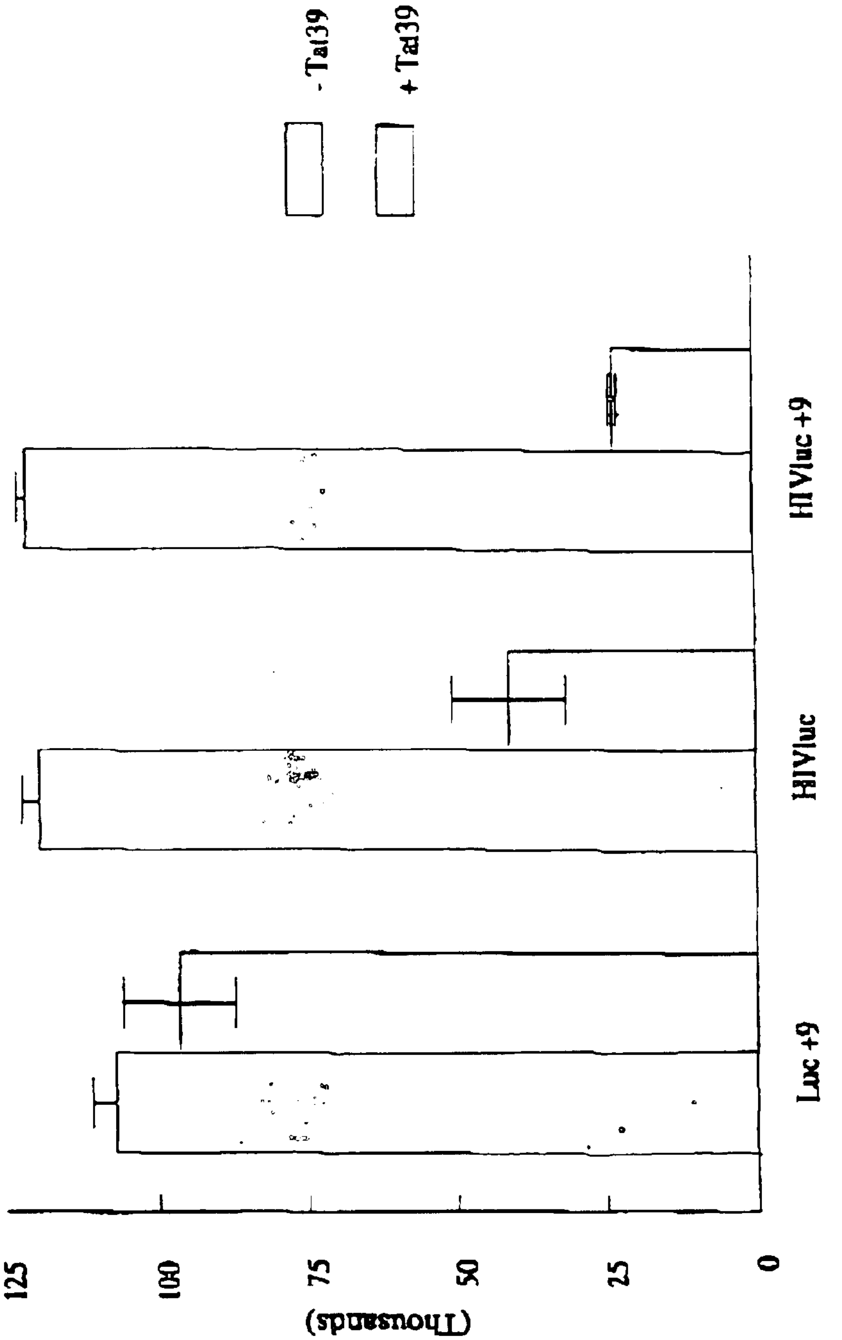
FIG. 38B shows an exemplary inhibition of translation of an mRNA construct containing the TAR RAN structure by a 39 amino acid tat peptide: a) translation of a luciferase mRNA with a 9 base leader sequence with and without 10 $\mu$M added tat peptide; b) translation of luciferase mRNA containing the TAR RNA structure adjacent to the cap; c) translation of the luciferase/TAR RNA construct with a 9 base leader in the presence/absence of 10 $\mu$M tat peptide.

It is believed that stabilization of mRNA structures near the 5'-cap also could be effected by specific "small" molecules, and that such binding would reduce the translational efficiency of the mRNA. To test this hypothesis, a plasmid was constructed containing the luciferase message behind a 5'-UTR containing a 27-mer RNA construct of the HIV TAR stem-loop bulge whose structure had been determined by NMR. The resulting mRNA could be expressed and capped in a wheat germ lysate translation system supplemented with T7 polymerase following addition of $m^7G$ to the lysate (see, FIG. 38A). Insertion of a 9-base leader before the TAR structure (HIVluc+9) enhanced the translational efficiency, presumably by allowing the pre-initiation complex to form. The helicase activity associated with the pre-initiation complex can transiently melt out the TAR RNA structure, and the message is translated (see, FIG. 38A). Addition of a 39 amino acid tat peptide to the lysate stabilized the TAR RNA structure and inhibited the expression of the luciferase protein, as expected from a specific interaction between the TAR RNA and tat (see, FIG. 38B).

"Small" organic molecules were then found that could inhibit the translation of the TAR-luciferase mRNA by stabilizing the TAR RNA structure. Compounds for the Available Chemicals Directory were docked to the TAR RNA structure and scored for binding energies. Among the best 25 compounds was ACD 00001199, whose structure is shown below. This compound has been shown to bind to TAR RNA with sufficient affinity to disrupt the interaction with tat peptide at a 1 μM concentration.

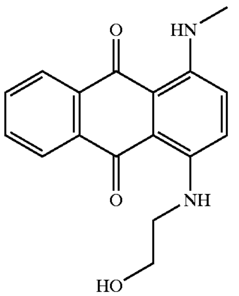

ACD 00001199 Structure

Figure 39:
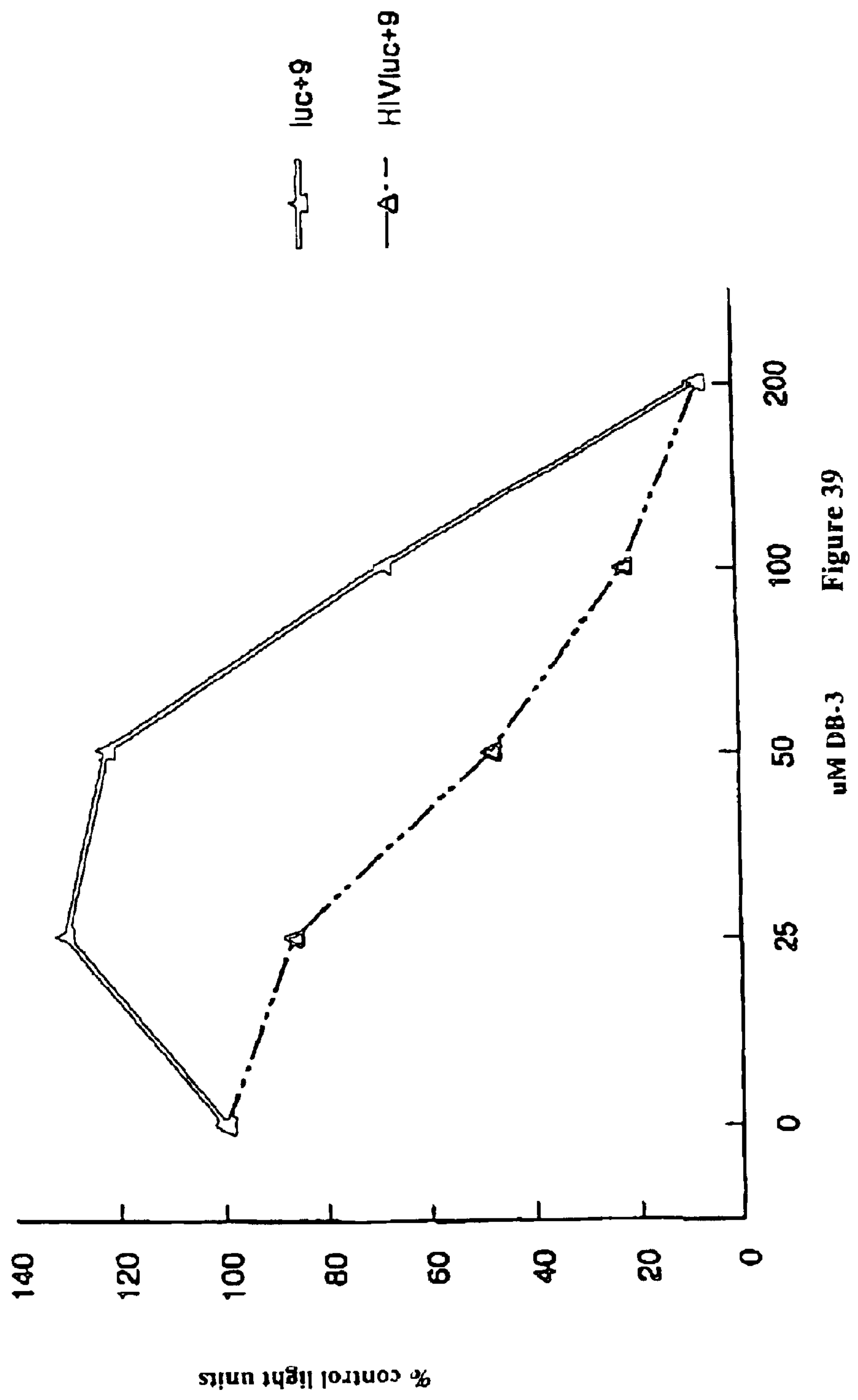
FIG. 39 shows an exemplary dose-dependent inhibition of translation of a luciferase mRNA construct containing a TAR RNA structure in the 5'-UTR by ACD 00001199 (DecpBlue-3). Solid line: inhibition of translation of the control luc+9 plasmid. Dashed line: inhibition of expression of the luc+9 mRNA containing the TAR RNA structure of the 5'-UTR.

Addition of 00001199 to the wheat germ lysate translation system with the luciferase mRNA produced some inhibition of translation at very high concentrations (see, FIG. 39). However, the compound was much more efficient in inhibiting translation of the luciferase mRNA containing the TAR RNA structure in the 5'-UTR, reducing translation by 50% at a 50 μM concentrations of small molecules which do not bind specifically to the TAR RNA structure did not affect translation of either mRNA construct (data not shown). CL Example 20

Determining The Structure of a 27-mer RNA Corresponding to the 16S rRNA A Site

In order to study the structure of the 27-mer RNA corresponding to the 16S rRNA A site, of sequence 5'-GGC-GUC-ACA-CCU-UCG-GGU-GAA-GUC-GCC-3' (SEQ ID NO:35) a chimeric RNA/DNA molecule that incorporates three deoxyadenosine (dA) residues at positions 7, 20 and 21 was prepared using standard nucleic acid synthesis protocols on an automated synthesizer. This chimeric nucleic acid of sequence 5'-GGC-GUC-dACA-CCU-UCG-GGU-GdAdA-GUC-GCC-3' (SEQ ID NO:36) was injected as a solution in water into an electrospray mass spectrometer. Electrospray ionization of the chimeric afforded a set of multiply charged ions from which the ion corresponding to the $(M-5H)^{5}$-form of the nucleic acid was further studied by subjecting it to collisionally induced dissociation (CID). The ion was found to be cleaved by the CID to afford three fragments of m/z 1006.1, 1162.8 and 1066.2. These fragments correspond to the $w_7^{(2-)}$, $W_8^{(2-)}$ and the $a_7$-$B^{(2-)}$ fragments respectively, that are formed by cleavage of the chimeric nucleic acid adjacent to each of the incorporated dA residues.

The observation that cleavage and fragmentation of the chimeric RNA/DNA has occurred adjacent to all three dA sites indicates that the test RNA is not ordered around the locations where the dA residues were incorporated. Therefore, the test RNA is not structured at the 7, 20 and 21 positions.

A systematic series of chimeric RNA/DNA molecules is synthesized such that a variety of molecules, each incorporating deoxy residues at different site(s) in the RNA. All such RNA/DNA members are comixed into one solution. MS analysis, as described above, are conducted on the comixture to provide a complete map or 'footprint' that indicates the residues that are involved in secondary or tertiary structure and those residues that are not involved in any structure. See FIG. 40.

Example 21

Determining the Binding Site for Paromomycin on a 27-mer RNA Corresponding to the 16S rRNA A Site In order to study the binding of paromomycin to the RNA of Example 20, the chimeric RNA/DNA molecule of Example 20 was synthesized using standard automated nucleic acid synthesis protocols on an automated synthesizer. A sample of this nucleic acid was then subjected to ESI followed by CID in a mass spectrometer to afford the fragmentation pattern indicating a lack of structure at the sites of dA incorporation, as described in Example 20. This indicated the accessibility of these dA sites in the structure of the chimeric nucleic acid.

Next, another sample of the chimeric nucleic acid was treated with a solution of paromomycin and the resulting mixture analyzed by ESI followed by CID using a mass spectrometer. The electrospray ionization was found to produce a set of multiply charged ions that was different from that observed the nucleic acid alone. This was also indicative of binding of the paromomycin to the chimeric nucleic acid, because of the increased mass of the observed ion complex. Further, there was also observed, a shift in the distribution of the multiply charged ion complexes which reflected a change in the conformation of the nucleic acid in the paromomycin-nucleic acid complex into a more compact structure.

Figure 41A:
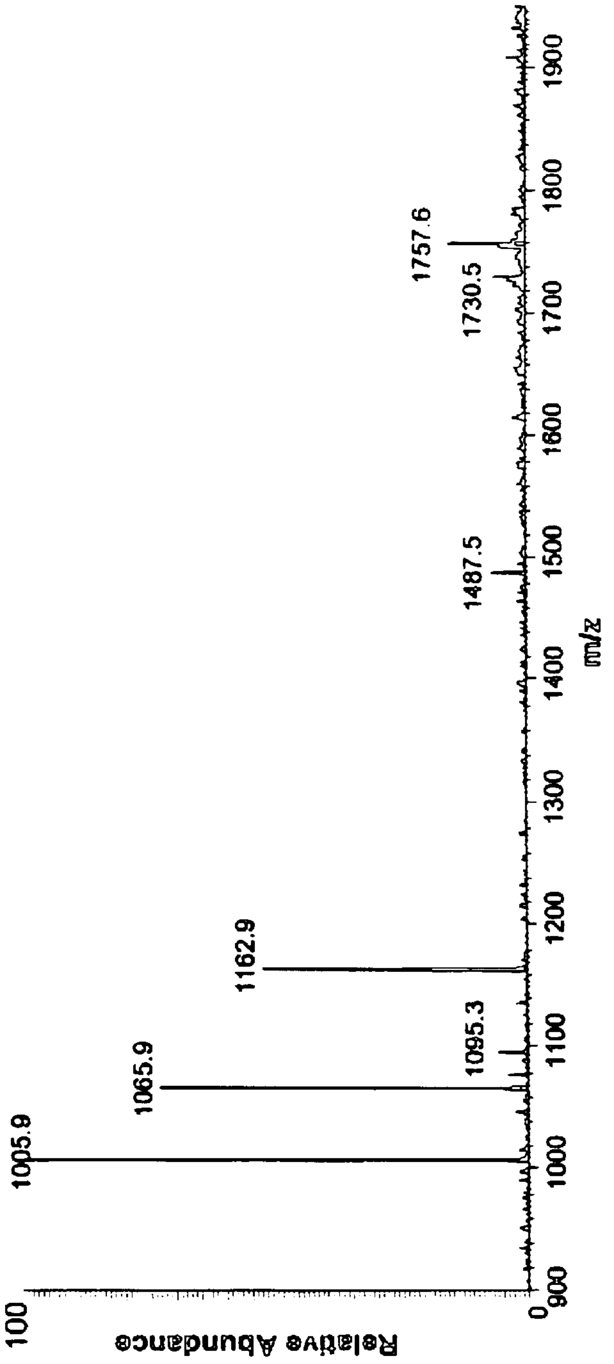
FIGS. 41A and 41B show the ESI-CID-MS of a 27-mer RNA/DNA hybrid in the presence and absence of paromomycin, respectively.
Figure 41B:
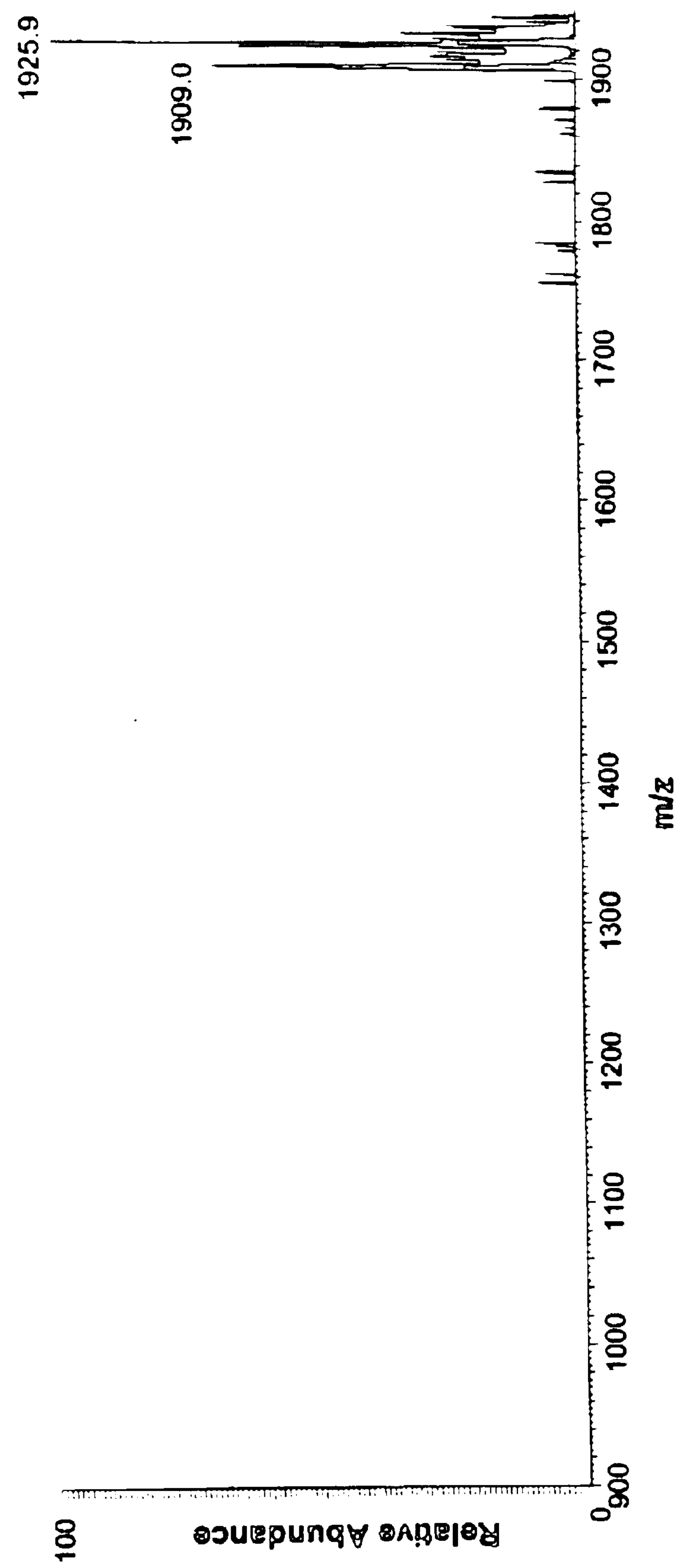

Cleavage and fragmentation of the complex by CID afforded information regarding the location of binding of the paromomycin to the chimeric nucleic acid. CID was found to produce no fragmentation at the dA sites in the nucleic acid. Thus paromomycin must bind at or near all three dA residues. Paromomycin therefore is believed to bind to the dA bulge in this RNA/DNA chimeric target, and induces a conformational change that protects all three dA residues from being cleaved during mass spectrometry. See FIGS. 41A and 41B.

Example 22

Determining the Identity of Members of a Combinatorial Library that Bind to a Biomolecular Target 1 mL (0.6 O.D.) of a solution of a 27-mer RNA containing 3 dA residues (from Example 20) was diluted into 500 $\mu$L of 1:1 isopropanol:water and adjusted to provide a solution that was 150 mM in ammonium acetate, pH 7.4 and wherein the RNA concentration was 10 mM. To this solution was added an aliquot of a solution of paromomycin acetate to a concentration of 150 nM. This mixture was then subjected to ESI-MS and the ionization of the nucleic acid and its complex monitored in the mass spectrum. A peak corresponding to the $(M-5H)^{5}$- ion of the paromomycin-27mer complex is observed at an m/z value of 1907.6. As expected, excess 27-mer is also observed in the mass spectrum as its $(M-5H)^{5}$- peak at about 1784. The mass spectrum confirms the formation of only a 1:1 complex at 1907.6 (as would be expected from the addition of the masses of the 27-mer and paromomycin) and the absence of any bis complex that would be expected to appear at an m/z of 2036.5.

To the mixture of the 27-mer RNA/DNA chimeric and paromomycin was next added 0.7 mL of a 10 $\mu$M stock solution of a combinatorial library such that the final concentration of each member of the combinatorial library in this mixture with 27-mer target was –150 nM. This mixture of the 27-mer, paromomycin and combinatorial compounds was next infused into an ESI-MS at a rate of 5 mL/min. and a total of 5O scans were summed (4 nicroscanis each), with 2 minutes of signal averaging, to afford the mass spectrum of the mixture.

Figure 42A:
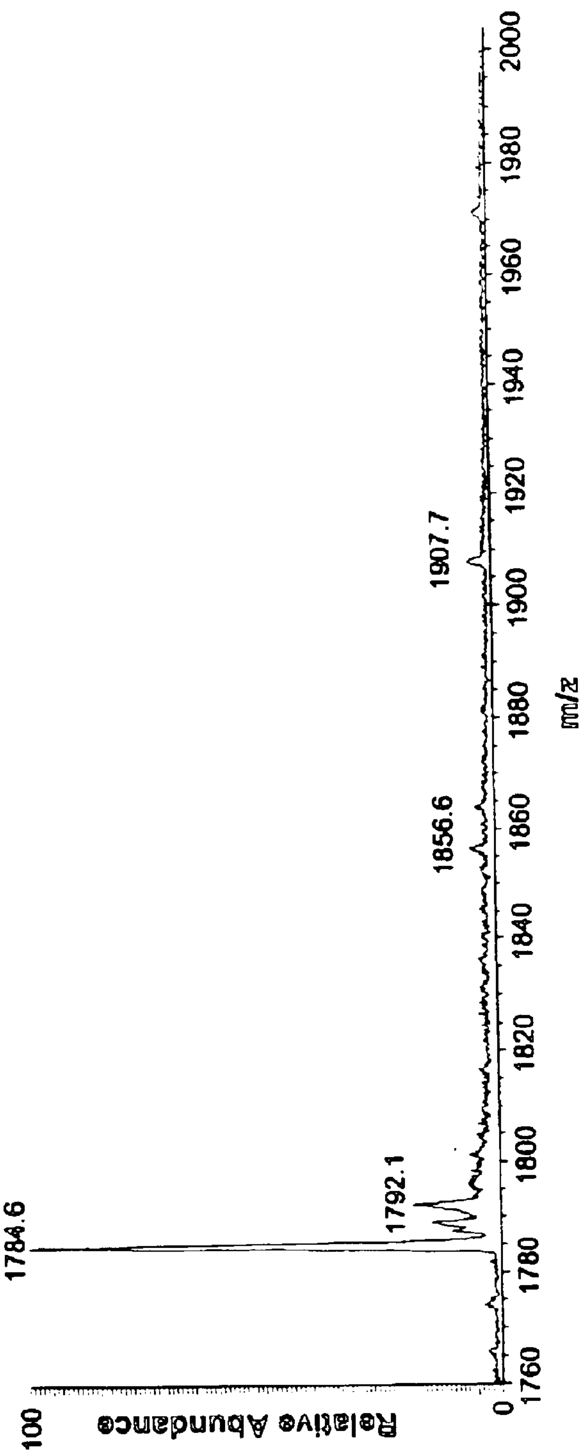
FIGS. 42A and 42B show the ESI-MS of a 27-mer RNA/DNA hybrid target in the presence of paromomycin alone (panel a), and in the presence of both paromomycin and a combinatorial library (panel b), respectively.
Figure 42B:
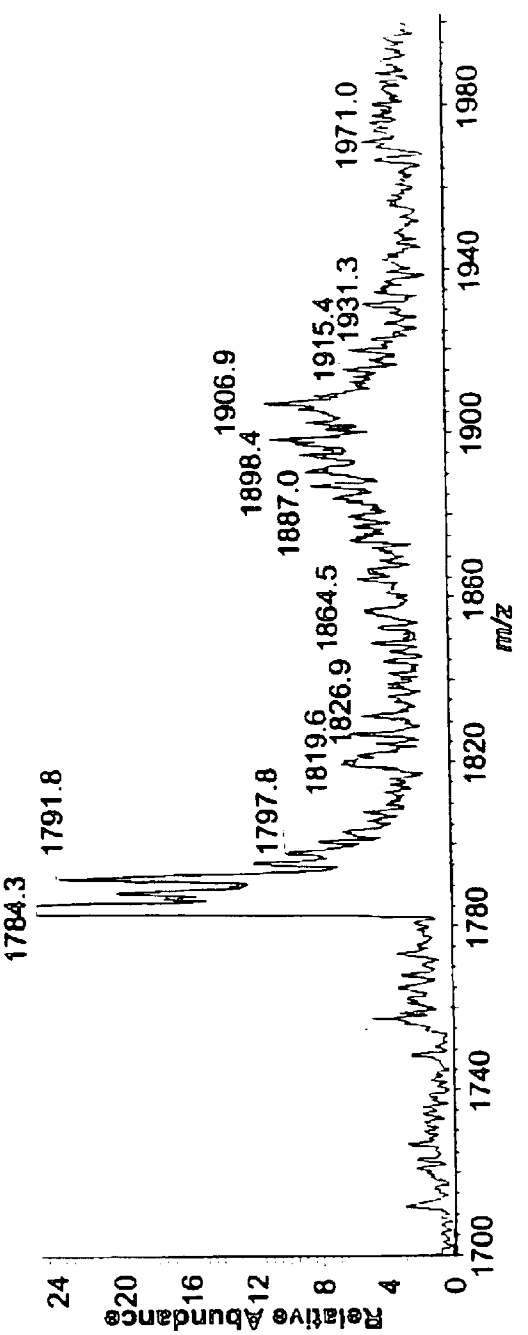

The ESI mass spectrum so obtained, shown in FIGS. 42A and 42B, demonstrated the presence of new signals for the (M–5H)5- ions at m/z values of 1897.8, 1891.3 and 1884.4. Comparing these new signals to the ion peak for the 27-mer alone the observed values of m/z of those members of the combinatorial library that are binding to the target can be calculated. The masses of the binding members of the library were determined to be 566.5, 534.5 and 482.5, respectively. Knowing the structure of the scaffold, and substituents used in the generation of this library, it was possible to determine what substitution pattern (combination of substituents) was present in the binding molecules.

It was determined that the species of 111/z 482.5, 534.5 and 566.5 would be the library members that bore the acetic acid +MPAC groups, the aromatic +piperidyl guanidine groups and the MPAC+guanidylethylamide groups, respectively. In this manner, if the composition of the combinatorial library is known a priori, then the identity of the binding components is straightforward to elucidate.

The use of FTMS instrumentation in such a procedure enhances both the sensitivity and the accuracy of the method. With FTMS, this method is able to significantly decrease the chemical noise observed during the electrospray mass spectrometry of these samples, thereby facilitating the detection of more binders that may be much weaker in their binding affinity. Further, using FTMS, the high resolution of the instrument provides accurate assessment of the mass of binding components of the combinatorial library and therefore direct determination of the identity of these components if the structural make up of the library is known.

Example 23

Determining the Site of Binding for Members of a Combinatorial Library that Bind to a Biomolecular Target The mixture of 27-mer RNA/DNA chimeric nucleic acid, as target, with paromomycin and the combinatorial library of compounds from Example 22 was subjected to the same ESI-MS method as described in Example 22. The ESI spectrum from Example 21 showed new signals arising from the complexes formed from binding of library members to the target, at ritiz values of 1897.8, 1891.3 and 1884.4. The paromomycin-27mer complex ion was observed at an in/z of 1907.3.

Two complex ions were selected from this spectrum for further resolution to determine the site of binding of their component ligands on the 27-mer RNA/DNA chimeric. First, the ions at 1907.3, that correspond to the paromomycin-27mer complex, were isolated via an ion-isolation procedure and then subjected to CID. No cleavage was found to occur and no fragmentation was observed in the mass spectrum. This indicates that the paromomycin binds at or near in the bulged region of this nucleic acid where the three dA residues are present. Paromomycin therefore protects the dA residues in the complex from fragmentation by CID.

Figure 43:
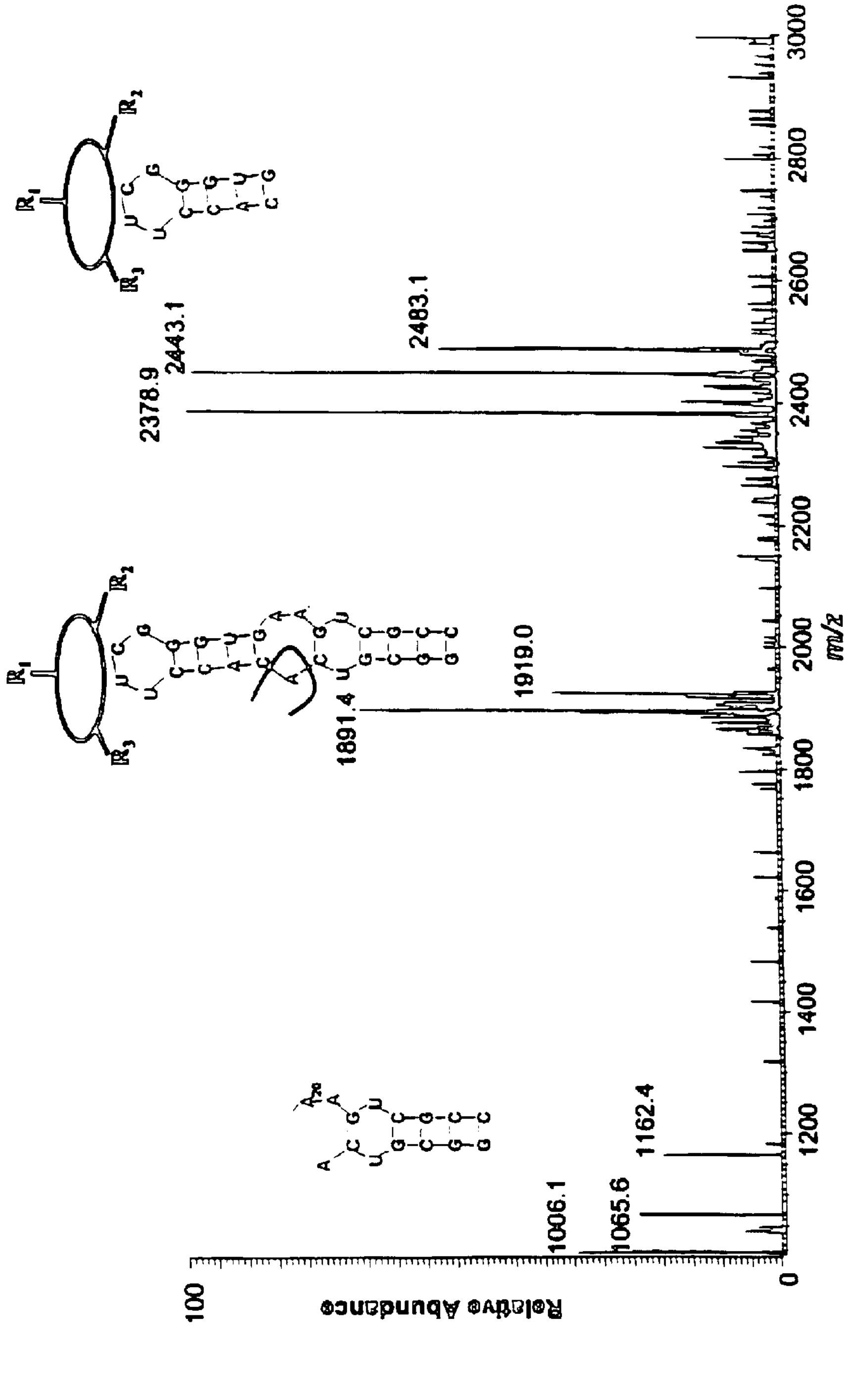
FIG. 43 shows the ESI-CID-MS spectrum of a combinatorial library member-27mer RNA/DNA hybrid noncovalent complex ion of m/z 1919.0.
Figure 44:
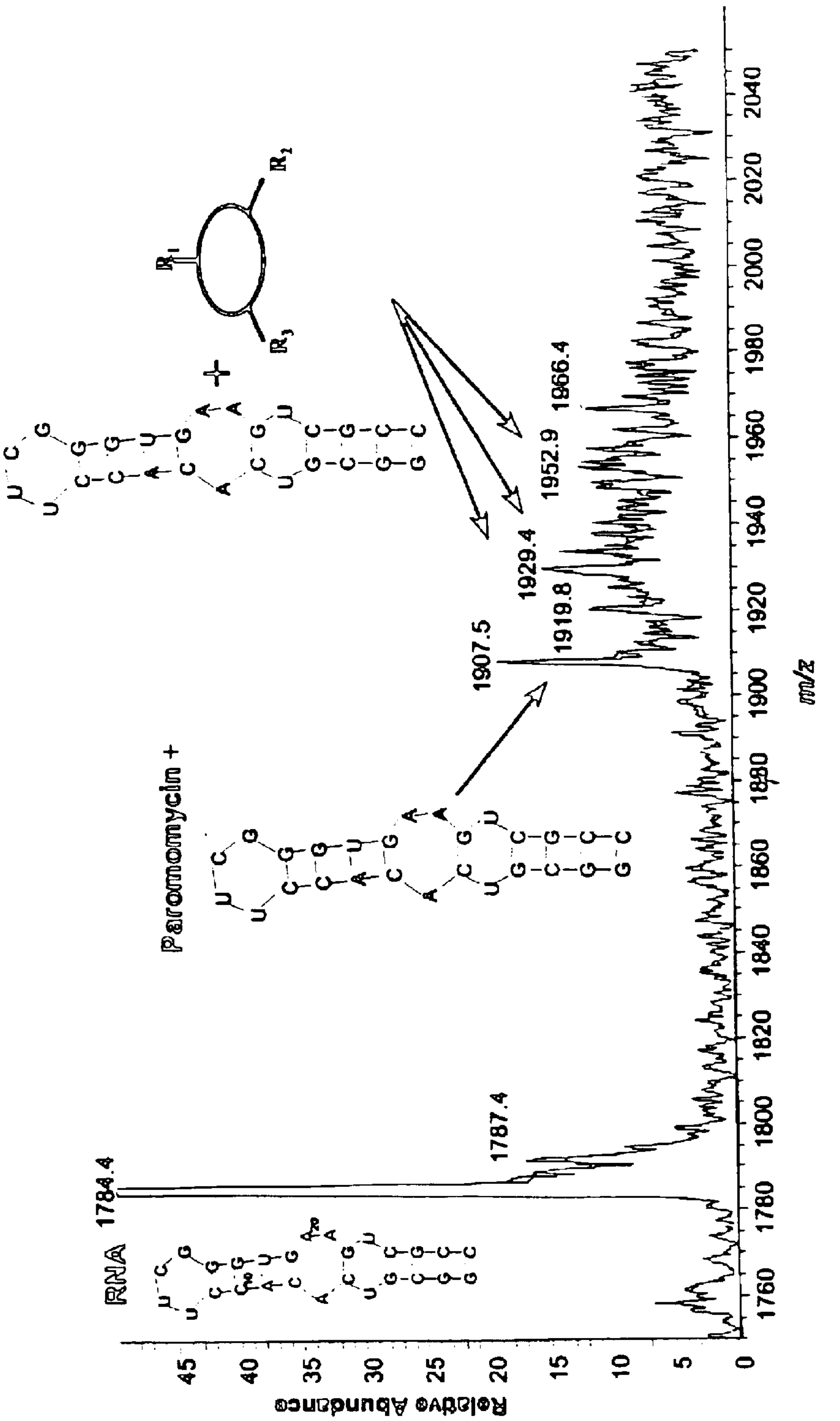
FIG. 44 shows the ESI-MS of a combinatorial library screened against a 27mer RNA/DNA hybrid.

Similarly, the ions at m/z 1897.8, that correspond to the complex of a library member with the 27mer target, were isolated via an ion-isolation procedure and then subjected to CID using the same conditions used for the previous complex, and the data was averaged for 3 minutes. The resulting mass spectrum (FIG. 43) revealed six major fragment ions at m/z values of 1005.8, 1065.6, 1162.8, 2341.1, 2406.3 and 2446.0. The three fragments at m/z 1005.8, 1065.6 and 1162.8 correspond to the $w_6^{(2-)}$, $a_7$-$B^{(2)}$ and $w_7$-$B^{(2-)}$ ions from the nucleic acid target. The three ions at higher masses of 2341.1, 2406.3 and 2446.0 correspond to the $a_{20}$-$B^{(3-)}$ ion +566 Da, $w_{21}$-$^{(3-)}$ ion +566 Da and the $a_{21}$,-$B^{(3-)}$- ion +566 Da. The data demonstrates at least two findings: first, since only the nucleic acid can be activated to give fragment ions in this ESI-CID experiment, the observation of new fragment ions indicates that the 1897.8 ion peak results from a library member bound to the nucleic acid target. Second, the library member has a molecular weight of 566. This library member binds to the GCUU tetraloop or the four base pairs in the stem structure of the nucleic acid target (the RNA/DNA chimeric corresponding to the 16S rRNA A site) and it does not bind to the bulged A site or the 6-base pair stem that contains the U*U mismatch pair of the nucleic acid target.

Further detail on the binding site of the library member can be gained by studying its interaction with and influence on fragmentation of target nucleic acid molecules where the positions of deoxynucleotide incorporation are different.

Example 24

Determining the Identity of a Member of a Combinatorial Library that Binds to a Biomolecular Target and the Location of Binding to the Target A 10 mM solution of the 27-mer RNA target, corresponding to the 16S rRNA A-site that contains 3 dA residues (from Example 20), in 100 mM ammonium acetate at pH 7.4 was treated with a solution of paromomycin acetate and an aliquot of a DMSO solution of a second combinatorial library to be screened. The amount of paromomycin added was adjusted to afford a final concentration of 150 nM. Likewise, the amount of DMSO solution of the library that was added was adjusted so that the final concentration of each of the 216 member components of the library was ~150 nM. The solution was infused into a Finnigan LCQ ion trap mass spectrometer and ionized by electrospray. A range of 1000–3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M\text{-}5H)^{5-}$ ion and 2230.8 for the $(M-4H)^4$ ion. The paromomycin-nucleic acid complex was also observed as signals of the $(M-5HT)^{5-}$ ion at m/z 1907.1 and the $(M-4H)^{4-}$ ion at m/z 2384.4 u.

Analysis of the spectrum for complexes of members of the combinatorial library and the nucleic acid target revealed several new signals that arise from the noncovalent binding of members of the library with the nucleic acid target. At least six signals for such noncovalent complexes were observed in the mass spectrum. Of these the signal at the lowest m/z value was found to be a very strong binder to the nucleic acid target. Comparison of the abundance of this ligand-nucleic acid complex ion with the abundance of the ion derived from the paromomycin-nucleic acid complex revealed a relative binding affinity (apparent $K_D$) that was similar to that for paromomycin.

MS/MS experiments, with ~6 minutes of signal averaging, were also performed on this complex to further establish the molecular weight of the bound ligand. A mass of 730.0+2 Da was determined, since the instrument performance was accurate only to ±1.5 Da. Based on this observed mass of the bound ligand and the known structures of the scaffold and substituents used in generating the combinatorial library, the structure of the ligand was determined to bear either of three possible combinations of substituents on the PAP5 scaffold The MS/MS analysis of this complex also revealed weak protection of the dA residues of the hybrid RNA/DNA from CID cleavage. Observation of fragments with mass increases of 730 Da showed that the molecule binds to the upper stem-loop region of the rRNA target.

Example 25

Determining the Identity of Members of a Combinatorial Library that Bind to a Biomolecular Target and the Location of Binding to the Target A 10 mM solution of the 27-mer RNA target, corresponding to the 16S rRNA A-site that contains 3 dA residues (from Example 20), in 100 mM amnionium acetate at pH 7.4 was treated with a solution of paromomycin acetate and an aliquot of a DMSO solution of a third combinatorial library to be screened. The amount of paromomycin added was adjusted to afford a final concentration of 150 nM. Likewise, the amount of DMSO solution of the library that was added was adjusted so that the final concentration of each of the 216 member components of the library was 150 nM. The solution was infused into a Finnigan LCQ ion trap mass spectrometer and ionized by electrospray. A range of 1000-3000 m/z was scanned for ions of the nucleic acid target and its complexes generated from binding with paromomycin and members of the combinatorial library. Typically 200 scans were averaged for 5 minutes. The ions from the nucleic acid target were observed at m/z 1784.4 for the $(M\text{-}5H)^{5-}$ ion and 2230.8 for the $(M-4H)^{4-}$ ion. The paromomycin-nucleic acid complex was also observed as signals of the $(M-5H)^{5-}$ ion at m/z 1907.1 and the $(M-4H)^{5-}$ ion a(m/z 2384.4 u.

Analysis of the spectrum for complexes of members of the combinatorial library and the nucleic acid target revealed several new signals that arise from the noncovalent binding of members of the library with the nucleic acid target. At least two major signals for such noncovalent complexes were observed in the mass spectrum. MS/MS experiments, with 6 minutes of signal averaging, were also performed on these two complexes to further establish the molecular weights of the bound ligands.

The first complex was found to arise from the binding of a molecule of mass 720.2+2 Da to the target. Two possible structures were deduced for this member of the combinatorial library based on the structure of the scaffold and substituents used to build the library. These include a structure of mass 720.4 and a structure of mass 721.1. MS/MS experiments on this ligand-target complex ion using CID demonstrated strong protection of the A residues in the bulge structure of the target. Therefore this ligand must bind strongly to the bulged dA residues of the RNA/DNA target.

Figure 45:
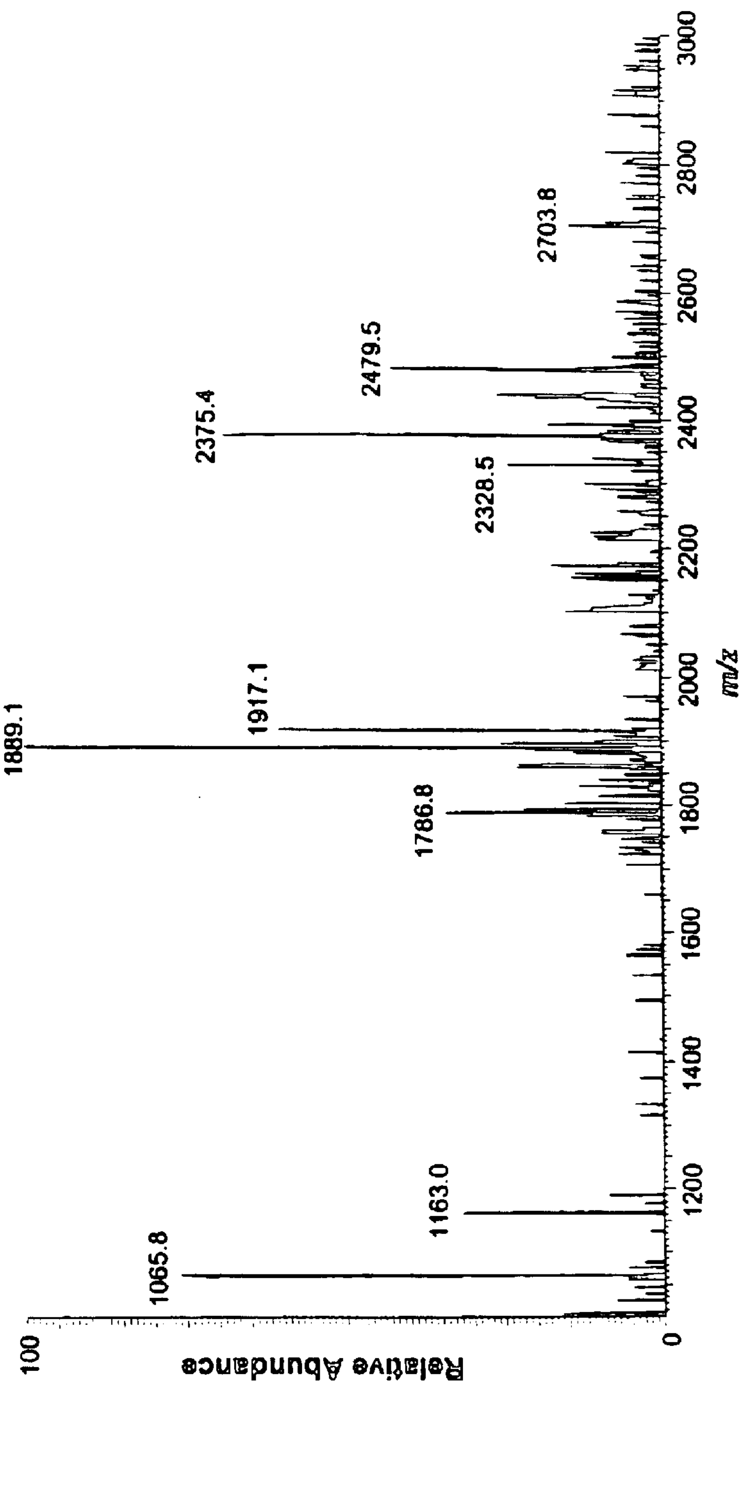
FIG. 45 shows the ESI-MS-MS analysis of the signal of m/z 1917.8 u arising from the binding of a member of mass 665 from another combinatorial library.
Figure 46:
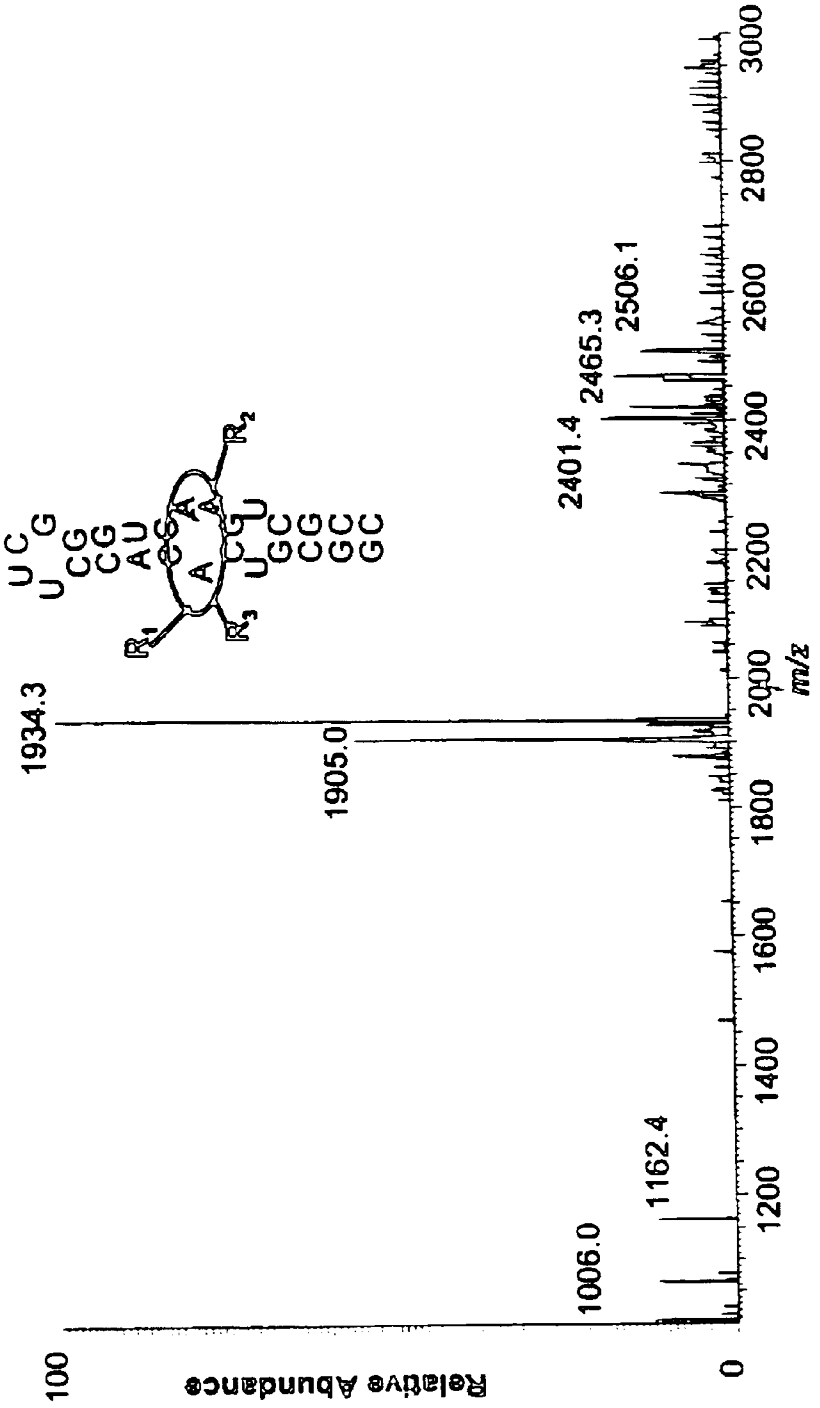
FIG. 46 shows the ESI-MS-MS analysis of the signal of m/z 1934.3 u arising from the binding of a member of mass 720 from a library.

The second major complex observed from the screening of this library was found to arise from the binding of a molecule of mass 665.2+2 Da to the target. Two possible structures were deduced for this member of the library based on the structure of the scaffold and substituents used to build the library. MS/MS experiments on this ligand-target complex ion using CID demonstrated strong fragmentation of the target. Therefore this ligand must not hind strongly to the bulged dA residues of the RNA/DNA target. Instead the fragmentation pattern, together with the observation of added mass bound to fragments from the loop portion of the target, suggest that this ligand must bind to residues in the loop region of the RNA/DNA target. See FIG. 45.

Example 26

Simultaneous Screening of a Combinatorial Library of Compounds against Two Nucleic Acid Targets The two RNA targets to be screened are synthesized using automated nucleic acid synthesizers. The first target (A) is the 27-mer RNA corresponding to the 16S rRNA A site and contains 3 dA residues, as in Example 20. The second target (B) is the 27-mer RNA bearing 3 dA residues, and is of identical base composition but completely scrambled sequence compared to target (A). Target (B) is modified in the last step of automated synthesis by the addition of a mass modifying tag, a polyethylene glycol (PEG) phosphoramidite to its 5'-terminus. This results in a mass increment of 3575 in target (B), which bears a mass modifying tag, compared to target (A).

A solution containing 10 mM target (A) and 10 mM mass modified target (B) is prepared by dissolving appropriate amounts of both targets into 100 mM ammonium acetate at pH 7.4. This solution is treated with a solution of paromomycin acetate and an aliquot of a DMSO solution of the combinatorial library to be screened. The amount of paromomycin added is adjusted to afford a final concentration of 150 nM. Likewise, the amount of DMSO solution of the library that is added is adjusted so that the final concentration of each of the 216 member components of the library is −150 nM. The library members are molecules with masses in the 700-750 Da range. The solution is infused into a Finnigan LCQ ion trap mass spectrometer and ionized by electrospray. A range of 1000-3000 m/z is scanned for ions of the nucleic acid target and its complexes generated from binding with paromomycin and members of the combinatorial library. Typically 200 scans are averaged for 5 minutes.

The ions from the nucleic acid target (A) are observed at m/z 1486.8 for the $(M-6H)^{6-}$ ion, 1784.4 for the $(M-5H)^{5-}$ ion and 2230.8 for the $(M-4H)^{4-}$ ion. Signals from complexes of target (A) with members of the library are expected to occur with m/z values in the 1603.2–1611.6, 1924.4–1934.4 and 2405.8–2418.3 ranges.

Signals from complexes of the nucleic acid target (B), that bears a mass modifying PEG tag, with members of the combinatorial library are observed with m/z values in the 2199–2207.4, 2639–2649 and 3299–3311 ranges. Therefore, the signals of noncovalent complexes with target (B) are cleanly resolved from the signals of complexes arising from the first target (A). New signals observed in the mass spectrum are therefore readily assigned as arising from binding of a library member to either target (A) or target (B).

Extension of this mass modifying technique to larger numbers of targets via the use of unique, high molecular weight neutral and cationic polymers allows for the simultaneous screening of more than two targets against individual compounds or combinatorial libraries.

Example 27

Simultaneous Screening of a Combinatorial Library of Compounds against Two Peptide Targets The two peptide targets to be screened are synthesized using automated peptide synthesizers. The first target (A) is a 27-mer polypeptide of known sequence. The second target (B) is also a 27-mer polypeptide that is of identical amino acid composition but completely scrambled sequence compared to target (A). Target (B) is modified in the last step of automated synthesis by the addition of a mass modifying tag, a polyethylene glycol (PEG) chloroformate to its amino terminus. This results in a mass increment of 3600 in target (B), which bears a mass modifying tag, compared to target (A).

A solution containing 10 mM target (A) and 10 mM mass modified target (B) is prepared by dissolving appropriate amounts of both targets into 100 mM ammonium acetate at pH 7.4. This solution is treated an aliquot of a DMSO solution of the combinatorial library to be screened. The amount of DMSO solution of the library that is added is adjusted so that the final concentration of each of the 216 member components of the library is ~150 nM. The library members are molecules with masses in the 700–750 Da range. The solution is infused into a Finnigan LCQ ion trap mass spectrometer and ionized by electrospray. A range of 1000–3000 m/z is scanned for ions of the polypeptide target and its complexes generated from binding with members of the combinatorial library. Typically 200 scans are averaged for 5 minutes.

The ions from the polypeptide target (A) and complexes of target (A) with members of the library are expected to occur at much lower m/z values that the signals from the polypeptide target (B), that bears a mass modifying PEG tag, and its complexes with members of the combinatorial library. Therefore, the signals of noncovalent complexes with target (B) are cleanly resolved from the signals of complexes arising from the first target (A). New signals observed in the mass spectrum are therefore readily assigned as arising from binding of a library member to either target (A) or target (B). In this fashion, two or more peptide targets may be readily screened for binding against an individual compound or combinatorial library.

Example 28

Gas-phase Dissociation of Nucleic Acids for Determination of Structure

Nucleic acid duplexes can be transferred from solution to the gas phase as intact duplexes using electrospray ionization and detected using a Fourier transform, ion trap, quadrupole, time-of-flight, or magnetic sector mass spectrometer. The ions corresponding to a single charge state of the duplex can be isolated via resonance ejection, off-resonance excitation or similar methods known to those familiar in the art of mass spectrometry. Once isolated, these ions can be activated energetically via blackbody irradiation, infrared multiphoton dissociation, or collisional activation. This activation leads to dissociation of glycosidic bonds and the phosphate backbone, producing two series of fragment ions, called the w-series (having an intact 3'-terminus and a 5'-phosphate following internal cleavage) and the a-Base series (having an intact 5'-terminus and a 3'-furan). These product ions can be identified by measurement of their mass/charge ratio in an MS/MS experiment.

Figure 47:
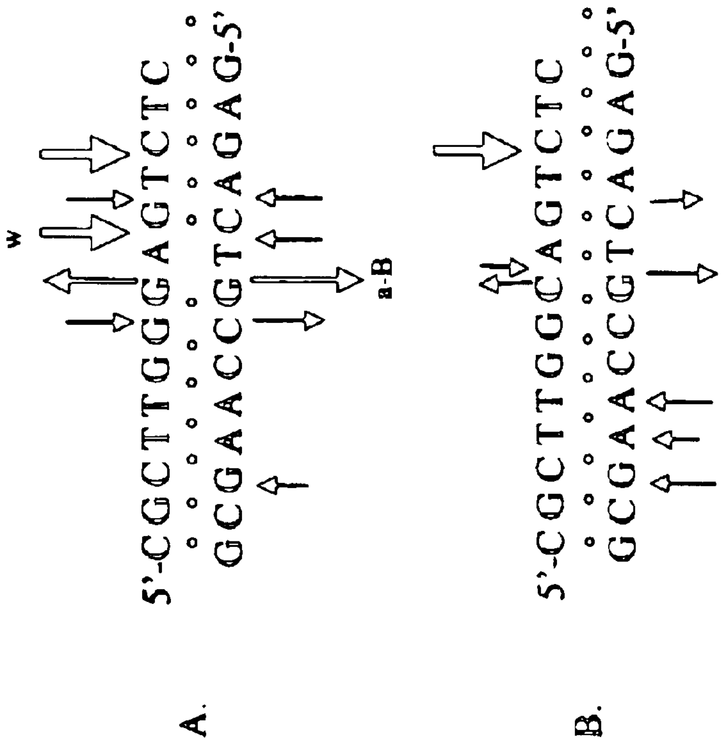
FIGS. 47 and 48 show graphical representations of the abundances of w and a-Base ions resulting from (CID) of ions from a DNA:DNA duplex. SEQ ID NO:39 (top) and SEQ ID NO:40 (bottom) are shown in FIG. 47. SEQ ID NO:41 (top), SEQ ID NO:42 (middle), and SEQ ID NO:43 (bottom) are shown in FIG. 48.
Figure 48:
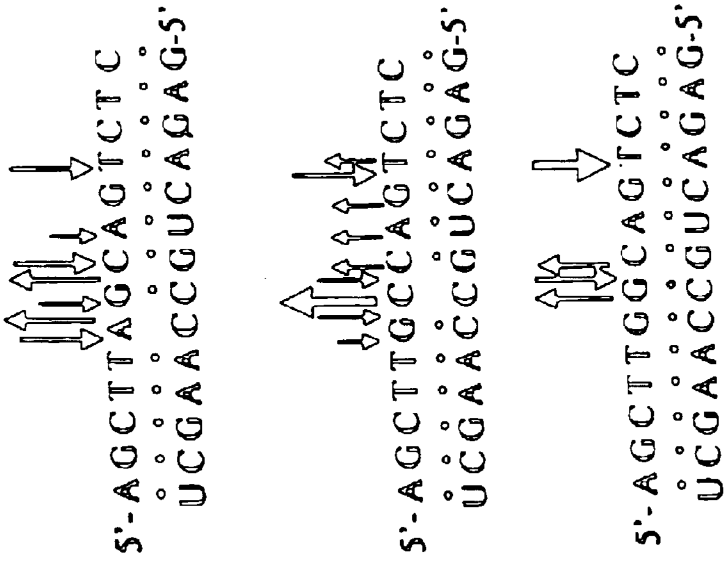

An example of the power of this method is presented in FIGS. 47 and 48. Shown in FIG. 47 part A is a graphical representation of the abundances of the w and a-Base ions resulting from collisional activation of the $(M-5H)^{5-}$ ions from a DNA:DNA duplex containing a G—G mismatch base pair. The w series ions are highlighted in black and point toward the duplex, while the a-Base series ions are highlighted in gray and point away from the duplex. The more abundant the fragment ion, the longer and thicker the respective arrow. Substantial fragmentation is observed in both strands adjacent to the mismatched base pair. The results obtained following collisional activation of the control DNA:DNA duplex ion is shown in FIG. 47 part B. Some product ions are common, but the pattern of fragmentation differs significantly from the duplex containing the mismatched base pair. Analysis of the fragment ions and the pattern of fragmentation allows the location of the mismatched base pair to be identified unambiguously. In addition, tile results suggest that the gas phase structure of the duplex DNA ion is altered by the presence of the mismatched pair in a way which facilitates fragmentation following activation.

A second series of experiments with three DNA:RNA duplexes are presented in FIG. 48. In the upper figure, an A-C mismatched pair has been incorporated into the duplex. Extensive fragmentation producing w and a-Base ions is observed adjacent to the mismatched pair. However, the increased strength of the glycosidic bond in RNA limits the fragmentation of the RNA strand. Hence, the fragmentation is focussed onto the DNA strand. In the central figure, a C—C mismatched base pair has been incorporated into the duplex, and enhanced fragmentation is observed at the site of the mismatched pair. As above, fragmentation of the RNA strand is reduced relative to the DNA strand. The lower figure contains the fragmentation observed for the control RNA:DNA duplex containing all complementary base pairs. A common fragmentation pattern is observed between the G5-T4 bases in all three cases. However, the extent of fragmentation is reduced in the complementary duplexes relative to the duplexes containing base pair mismatches.

Example 29

Figure 49:
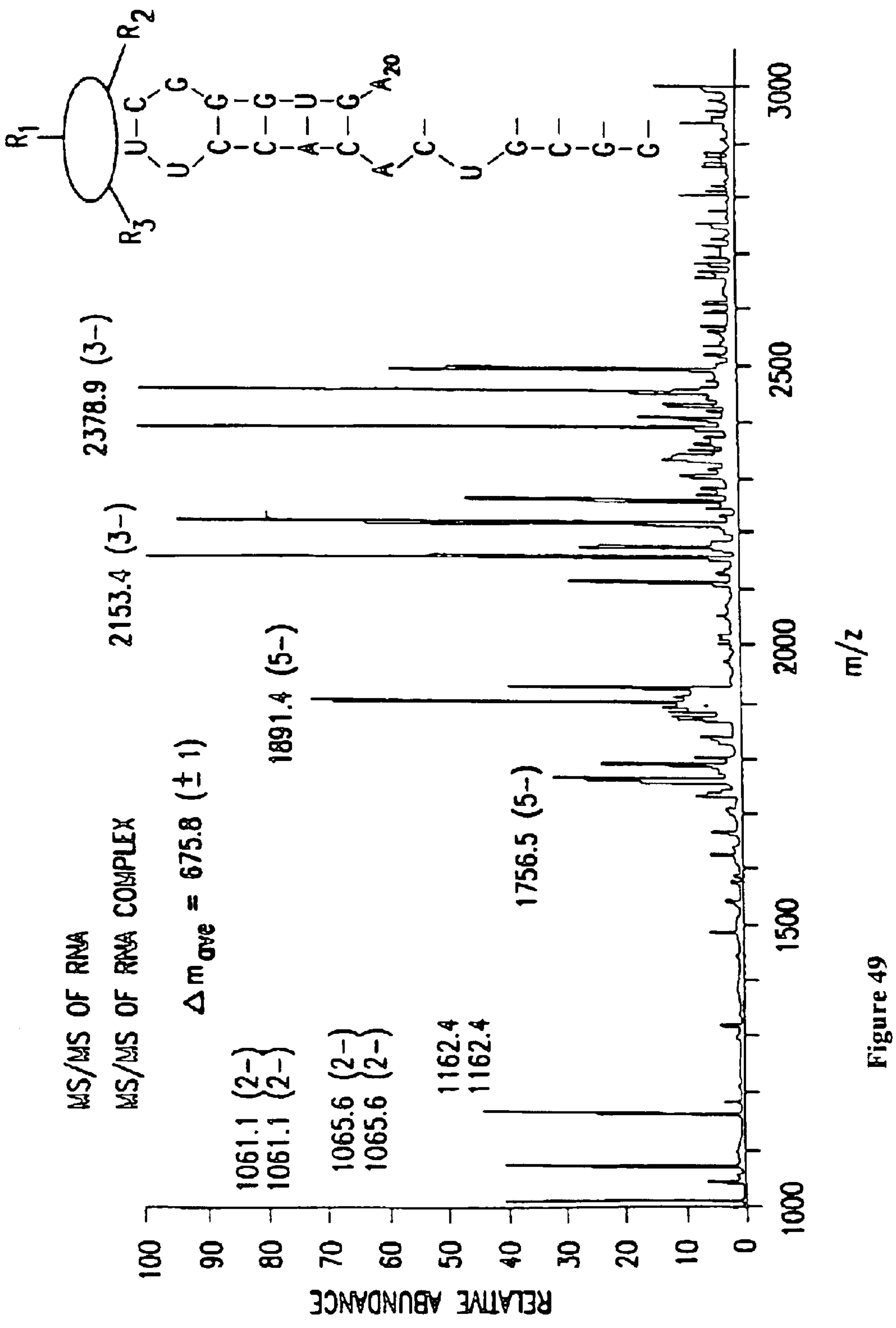
FIGS. 49, 50 and 51 depict MASS analyses to determine the binding of ligands to a molecular interaction site.
Figure 50:
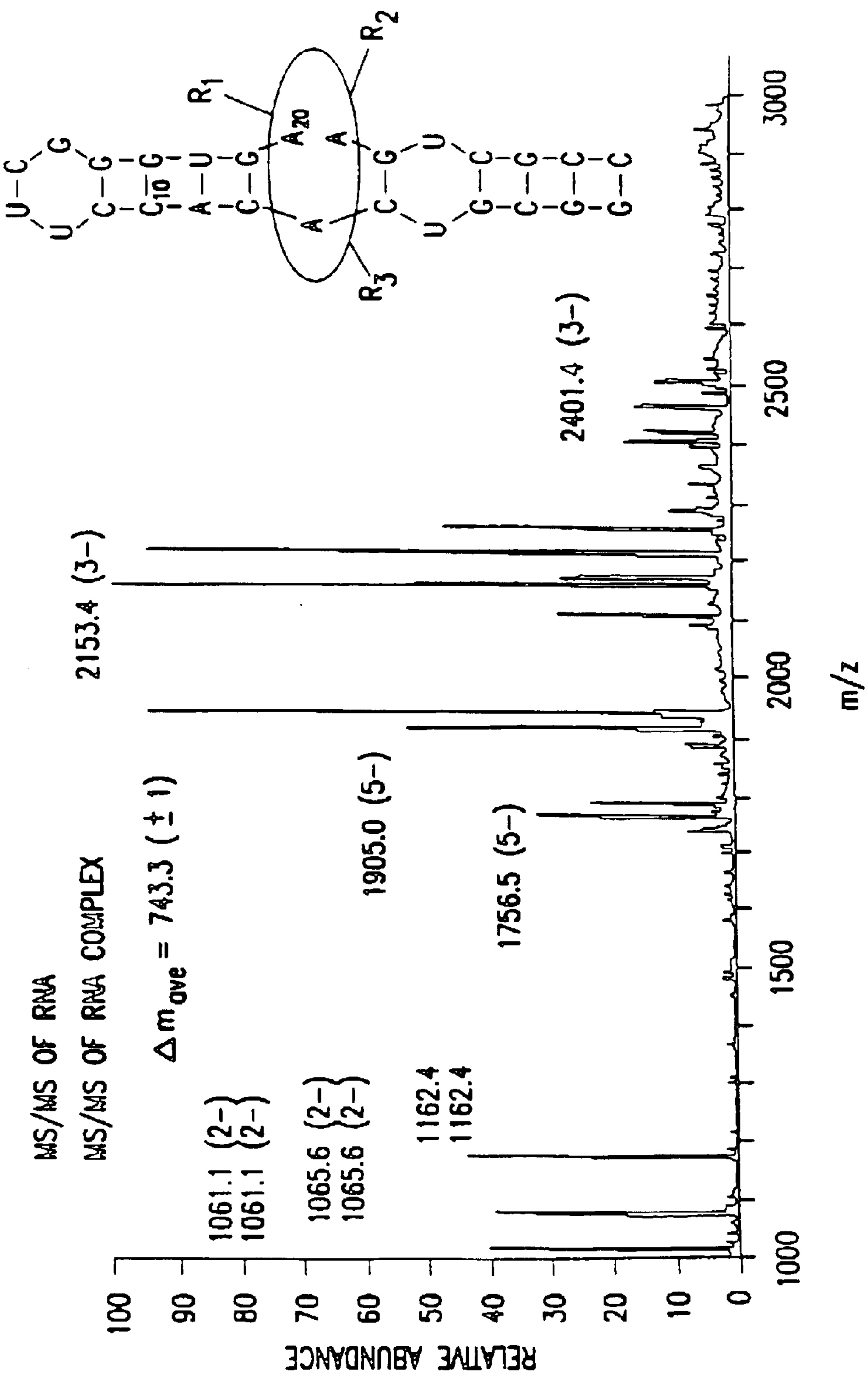

MASS Analysis of RNA —Ligand complex to determine binding of ligand to Molecular Interaction Site The ability to discern through mass spectroscopy whether or not a proposed ligand binds to a molecular interaction site of an RNA can be shown. FIGS. 49 and 50 depict the mass spectroscopy of an RNA segment having a stem-loop structure with a ligand, schematically illustrated by an unknown, functionalized molecule. The ligand is combined with the RNA fragment under conditions selected to facilitate binding and the result in complex is analyzed by a multi target affinity/specificity screening (MASS) protocol. This preferably employs electrospray ionization Fourier transform ion cyclotron resonance mass spectrometry as described hereinbefore and in the references cited herein. “Mass chromatography” as described above permits one to focus upon one bimolecular complex and to study the fragmentation of that one complex into characteristic ions. The situs of binding of ligand to RNA can, thus, be determined through the assessment of such fragments; the presence of fragments corresponding to molecular interaction site and ligand indicating the binding of that ligand to that molecular interaction site.

FIG. 49 depicts a MASS Analysis of a Binding Location for a non-A Site Binding molecule. The isolation through “mass chromatography” and subsequent dissociation of the (M-5H) 5- complex is observed at m/z 1919.8. The mass shift observed in select fragments relative to the fragmentation observed for the free RNA provides information about where the ligand is bound. The (2-) fragments observed below m/z 1200 correspond to the stem structure of the RNA; these fragments are not mass shifted upon Complexation. This is consistent with the ligand not binding to the stem structure.

FIG. 50 shows a MASS Analysis of Binding Location for the non-A Site Binding molecule. Isolation (i.e. “mass chromatography”) and subsequent dissociation of the (M−5H)5- complex observed at m/z 1929.4 provides significant protection from fragmentation in the vicinity of the A-site. This is evidenced by the reduced abundance of the w and a-base fragment ions in the 2300–2500 m/z range. The mass shift observed in select fragments relative to the fragmentation observed for the free RNA provides information about where the ligand is bound. The exact molecular mass of the RNA can act as an internal or intrinsic mass label for identification of molecules bound to the RNA. The (2-) fragments observed below m/z 1200 correspond to the stem structure of the RNA. These fragments are not mass shifted upon Complexation —consistent with ligand not being bound to the stem structure. Accordingly, the location of binding of ligands to the RNA can be determined.

Example 30

Determination of Specificity and Affinity of Ligand libraries to RNA Targets A preferred first step of MASS screening involves mixing the RNA target (or targets) with a combinatorial library of ligands designed to bind to a specific site on the target molecule(s). Specific noncovalent complexes formed in solution between the target(s) and any library members are transferred into the gas phase and ionized by ESI. As described herein, from the measured mass difference between the complex and the free target, the identity of the binding ligand can be determined. The dissociation constant of the complex can be determined in two ways: if a ligand with a known binding affinity for the target is available, a relative Kd can be measured by using the known ligand as an internal control and measuring the abundance of the unknown complex to the abundance of the control, alternatively, if no internal control is available, Kd’s can be determined by making a series of measurements at different ligand concentrations and deriving a Kd value from the “titration” curve.

Because screening preferably employs large numbers of similar, preferably combinatorially derived, compounds, it is preferred that in addition to determining whether something from the library binds the target, it is also determined which compound(s) are the ones which bind to the target. With highly precise mass measurements, the mass identity of an unknown ligand can be constrained to a unique elemental composition. This unique mass is referred to as the compound's "intrinsic mass label." For example, while there are a large number of elemental compositions which result in a molecular weight of approximately 615 Da, there is only one elemental composition ($C_{2\text{-}3}H,5NiO,_{4}$) consistent with a monoisotopic molecular weight of 615.2963012 Da. For example, the mass of a ligand (paromomycin in this example) which is noncovalently bound to the 16S A-site was determined to be 615.2969 +0.0006 (mass measurement error of 1 ppm) using the free RNA as an internal mass standard. A mass measurement error of 100 ppm does not allow unambiguous compound assignment and is consistent with nearly 400 elemental compositions containing only atoms of C, H, N, and O. The isotopic distributions shown in the expanded views are primarily a result of the natural incorporation of 13C atoms; because high performance FTICR can easily resolve the 12C–13C mass difference, each component of the isotopic cluster can be used as an internal mass standard. Additionally, as the theoretical isotope distribution of the free RNA can be accurately simulated, mass differences can be measured between "homoisotopic" species (in this example the mass difference is measured between species containing four 13C atoms). Once the identity of a binding ligand is determined, the complex is isolated in the gas phase (i.e. "mass chromatography") and dissociated. By comparing the fragmentation patterns of the free target to that of the target complexed with a ligand, the ligand binding site can be determined. Dissociation of the complex is performed either by collisional activated dissociation (CAD) in which fragmentation is effected by high energy collisions with neutrals, or infrared multiphoton dissociation (IRMPD) in which photons from a high power IR laser cause fragmentation of the complex.

Figure 51:
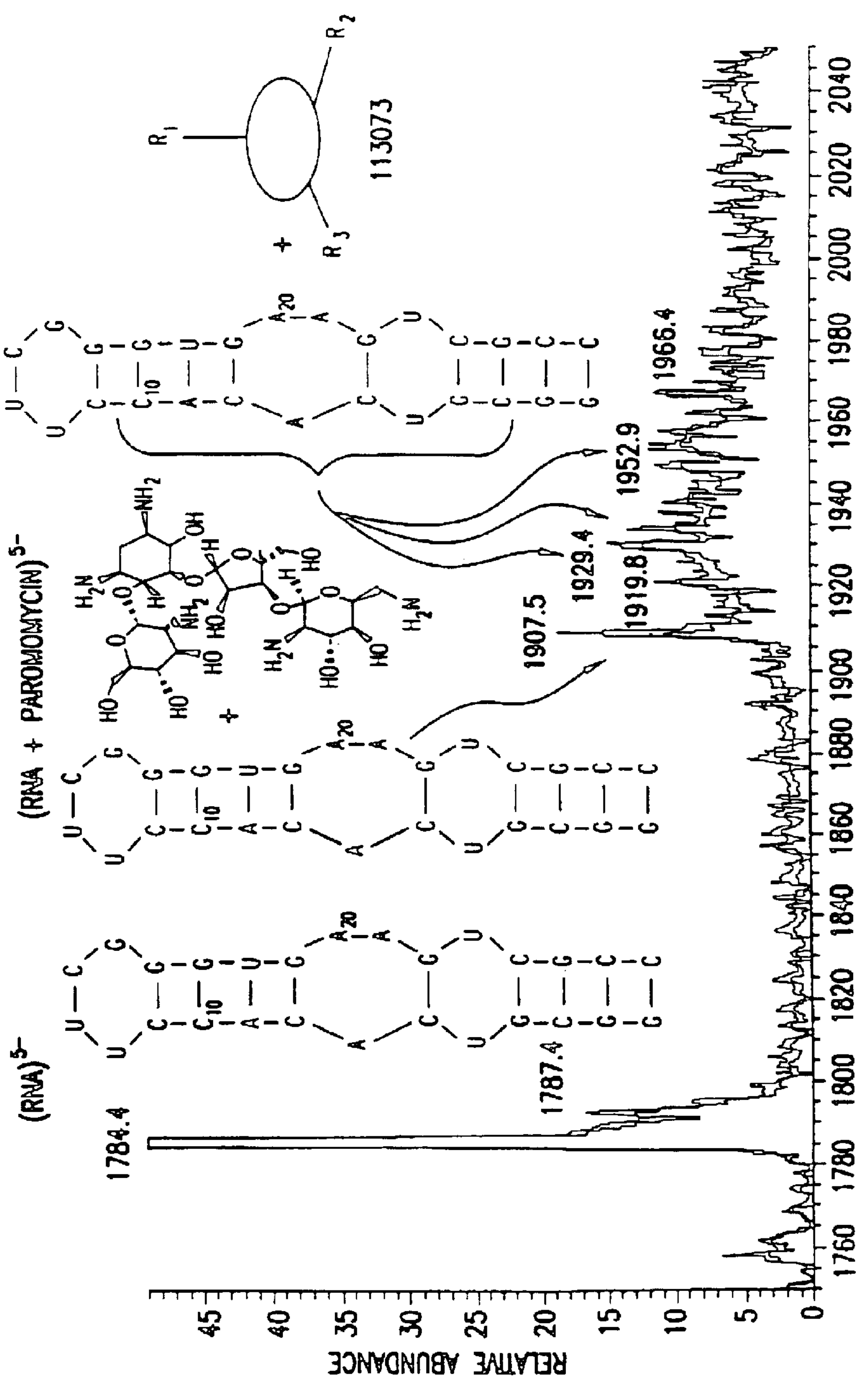

A 27-mer RNA containing the A-site of the 16S rRNA was chosen as a target for validation experiments. See FIG. 51. The aminoglycoside paromomycin is known to bind to the unpaired adenosine residues with a Kd of 200 nM and was used as an internal standard. The target was at an initial concentration of 100 mM while the paromomycin and each of the 216 library members were at an initial concentration of 150 nM. While this example was performed on a quadrupole ion trap which does not afford the high resolution or mass accuracy of the FTICR, it serves to illustrate the MASS concept. Molecular ions corresponding to the free RNA are observed at m/z 1784.4 (M−5H+)5- and 2230.84 (M−4H+) 4-. The signals from the RNA-paromomycin internal control are observed at m/z 1907.14 (M−5H+)5- and 2384.4 4 (M−4H+)4-. In addition to the expected paromomycin complex, a number of complexes are observed corresponding to binding of library members to the target. See FIG. 52.

One member of this library (MW =675.8+1.5) forms a strong complex with the target but MS/MS studies reveal that the ligand does not offer protection of A-site fragmentation and therefore binds to the loop region. Another member of Isis 13069 having an approximate mass of 743.8+1.5 demonstrates strong binding to the target and, as evidenced by MS/MS experiments provides protection of the unpaired A residues, consistent with binding at the A-site.

The rapid and parallel nature of the MASS approach allows large numbers of compounds to be screened against multiple targets simultaneously, resulting in greatly enhanced sample throughput and information content. In a single assay requiring less than 15 minutes, MASS can screen 10 targets against a library containing over 500 components and report back which compounds bind to which targets, where they bind, and with what binding affinity.

Example 31

Comparison of QXP Predicted Ligand-DNA Structures to X-ray Crystallography

The utility of QXP in the context of ligands that bind to nucleic acid targets was evaluated. The X-ray data for netropsin (a minor groove binding drug) bound to two different duplex DNA sequences (PDB ID: 261d and 195d respectively (PDB IDs are identification codes for structures deposited in the Protein Data Bank, maintained at the Research Collaboratory for Structural Bioinformatics)) and an intercalator bound to an octamer duplex (PDB ID: 2d55) were used in validation studies. Root mean square (rms) deviations between the lowest energy docked structure (with randomly disordered ligands as initial structures) and the energy minimized X-ray structure fall with in 0.6 A in all the cases. Given that QXP method employs Monte Carlo type algorithm to search the conformational space and to make sure that the method is reliable in yielding global minimum, at least 10 QXP docking simulations were run with very different initial ligand structures. The performance of the QXP docking method can be quantified by its ability to identify the bound conformation of the ligand within 1.0 Å rms deviation from the crystallographically observed conformation. In the test cases described above, the success rate of the QXP runs is in the 80% range. The nearly linear correlation between the rms deviation from the crystal structure and the score of the docked structure indicates that the QXP method is sufficiently accurate in predicting structures of ligand-receptor complexes.

Example 32

Prediction of Paromomycin-RNA Complex Structure Using the QXP method

The QXP method was used to derive an accurate structure of a bound ligand to the RNA target. The NMR structure of the bacterial 16S ribosomal A site bound to paromomycin (Fourmy et at., *Science,* 1996, 274, 1367; PDB ID: 1pbr) was used as the reference state. The aminoglycoside antibiotic was removed from the ligand-RNA complex. The conformation space of paromomycin was exhaustively searched using the QXP method for the lowest energy conformers. The target RNA was held rigid whereas the paromomycin was treated as fully flexible. Multiple docking searches with the randomly disrupted paromomycin as initial structures were performed. The representative lowest energy structure identified from the search (dark grey) is superimposed on the NMR structure (light grey) of the bound complex.

Example 33

Figure 52:
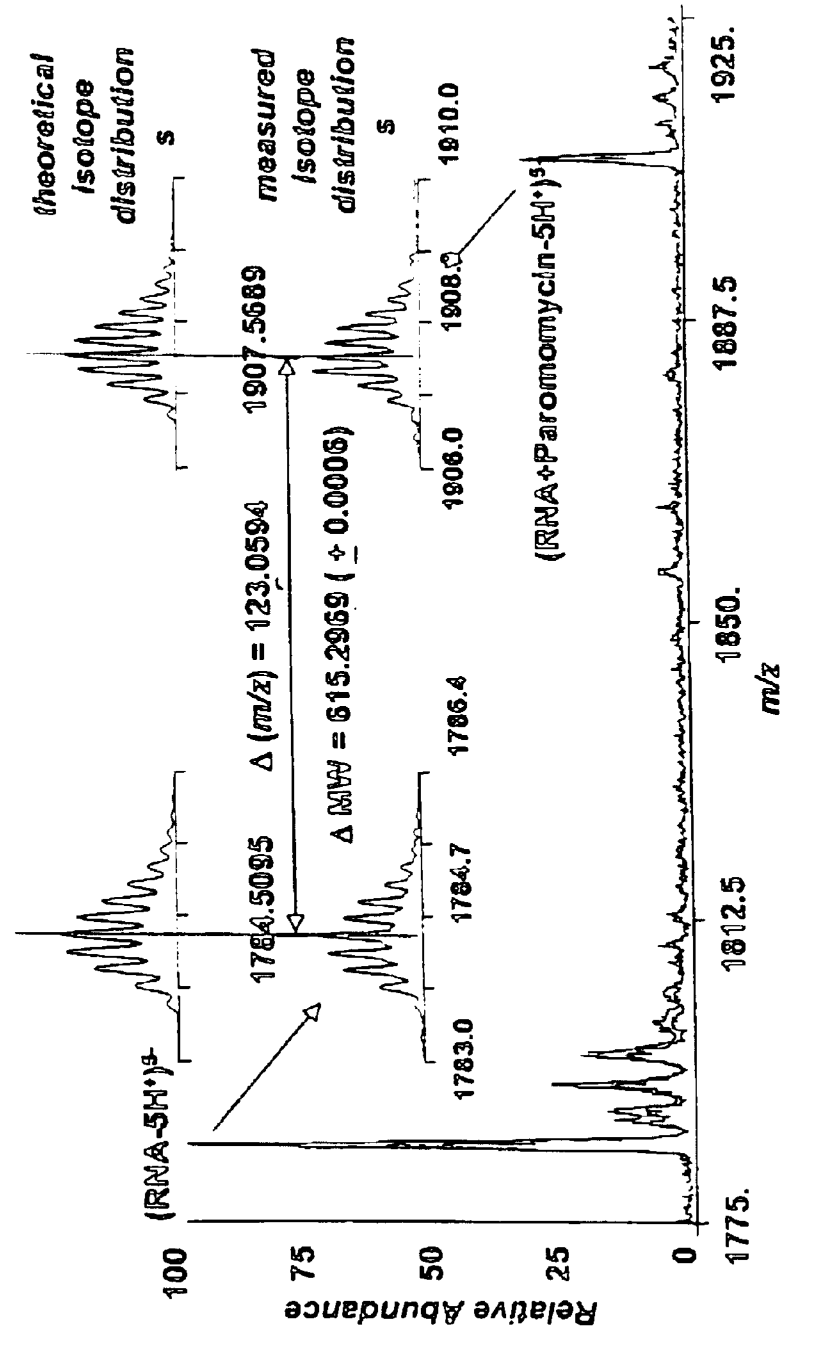
FIG. 52 depicts high precision ESI-FTICR mass measurement of the interaction of the 16S A site of an RNA complexed with paromomycin.

High Precision ESI-FTICR Mass Measurement Of 16S A Site RNA/Paromomycin Complex Electrospray ionization Fourier transform ion cyclotron resonance mass spectrometry was performed on a solution containing 5 mM 16S RNA (the 27-mer construct shown in FIG. 149) and 500 nM paromomycin is depicted in FIG. 52.

A 1: I complex was observed between the paromomycin and the RNA consistent with specific aminoglycoside binding at the A-site. Thc insets show the measured and calculated isotope envelopes of the (M−5H+)5-species of the free RNA and the RNA-paromomycin complex. High precision mass measurements were acquired using isotope peaks of the $(M-5H)^{5-}$ and $(M-4H)^{4-}$ charge states of the free RNA as internal mass standards and measuring the m/z difference between the free and bound RNA.

Example 34

Figure 59:
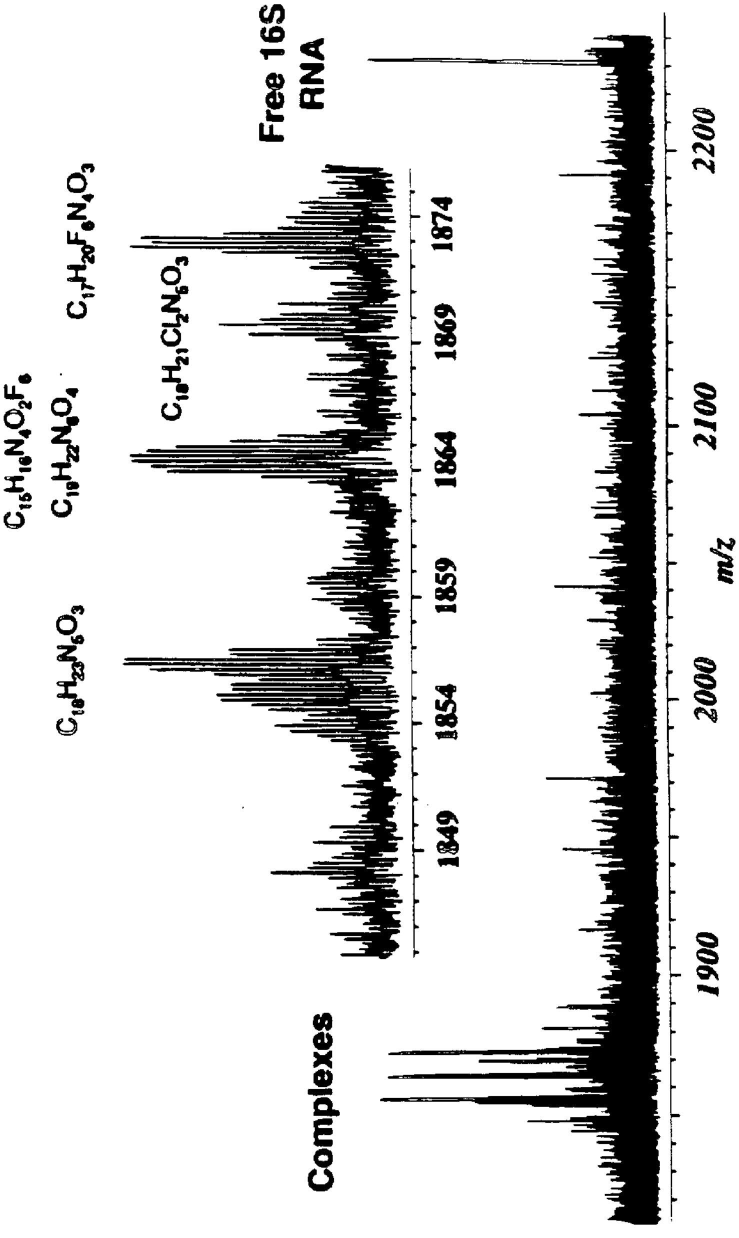
FIG. 59 depicts FTMS spectrum obtained from a mixture of a 16S RNA model (10 $\mu$M) and a 60-member combinatorial library.

FTMS spectrum was obtained from a mixture of a 16S RNA model (10 mM) and a 60-member combinatorial library. Signals from complexes are highlighted in the insert. Binding of a combinatorial library containing 60 members to the 16S RNA model have been examined under conditions where each library member was present at 5-fold excess over the RNA. As shown in FIG. 59, complexes between the 16S RNA and ~5 ligands in the library were observed.

Figure 60:
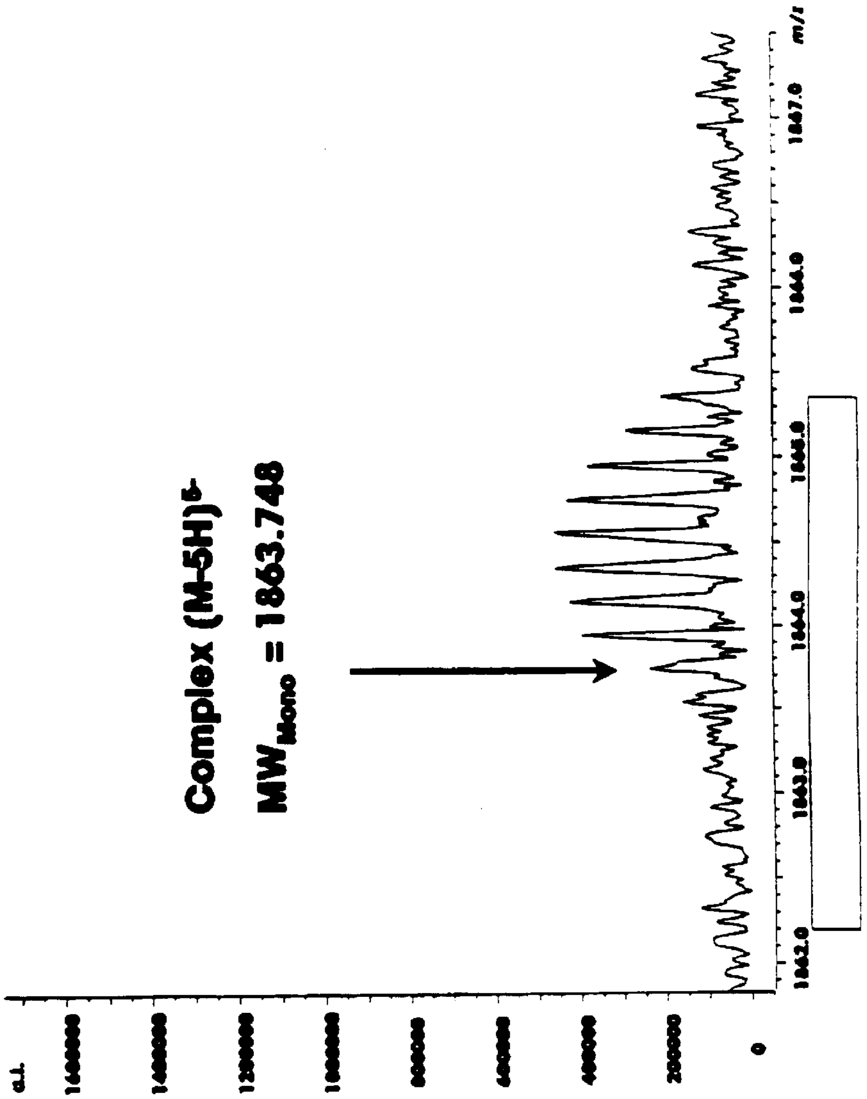
FIG. 60 depicts an expanded view of the 1863 complex from FIG. 59.

An expanded view of the 1863 complex from FIG. 59 is shown in FIG. 60. Two of the compounds in the library had a nominal mass of 398.1 Da. Their calculated molecular weights based on molecular formulas indicate that they differ in mass by 46 mDa. Accurate measurement of the molecular mass for the respective monoisotopic (all $^{12}C$, $^{14}N$, and $^{16}O$) $[M-5H]^{5}$- species of the complex (m/z 1863.748) and the free RNA (m/z 1784.126) allowed the mass of the ligand to be calculated as 398.110±009 Da.

Figure 61:
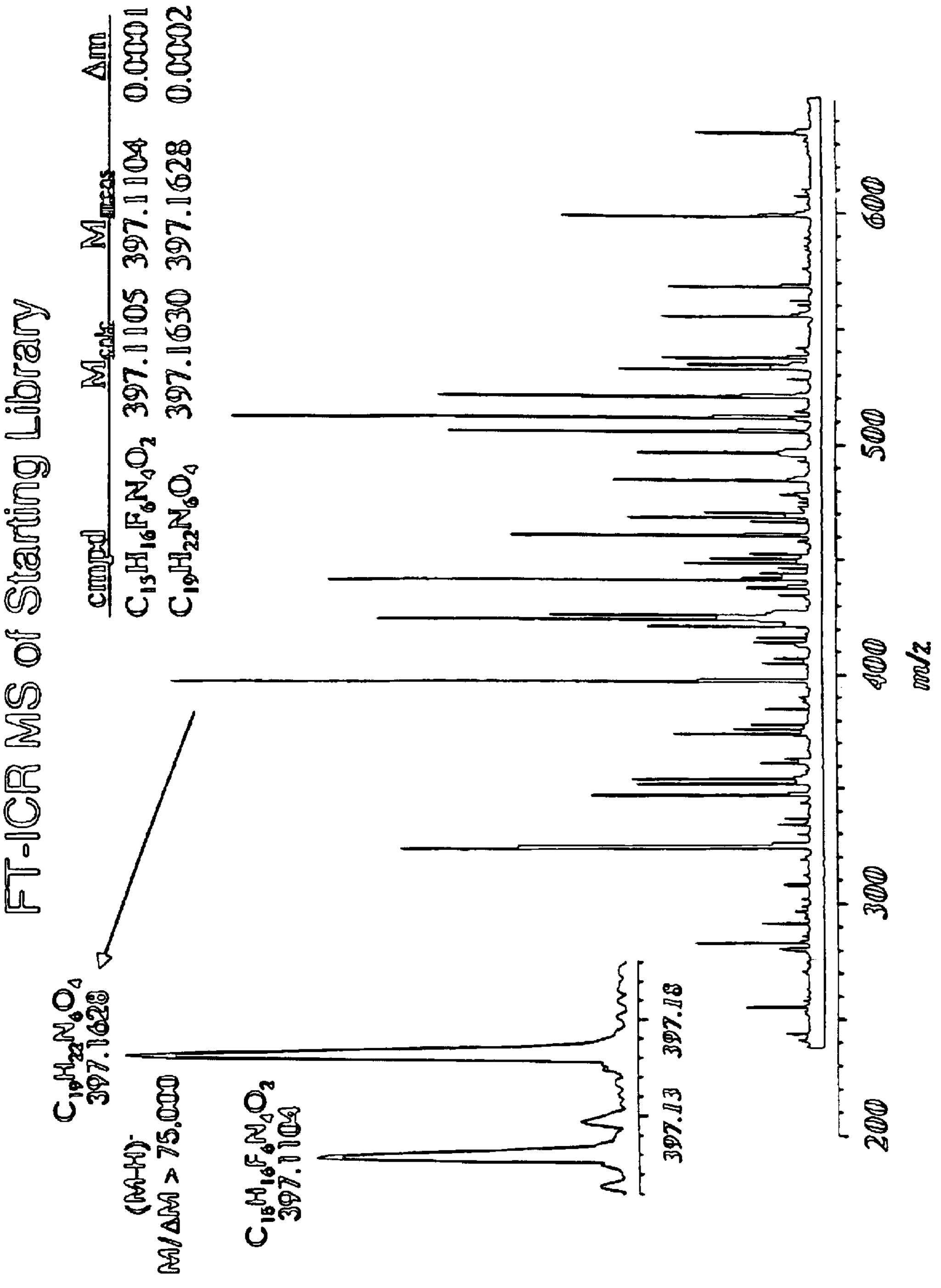
FIG. 61 depicts mass of a binding ligand determined from a starting library of compounds.

FIG. 61 shows high resolution ESI-FTICR spectrum of the library used in FIGS. 59 and 60, demonstrating that both library members with a nominal molecular weight of 398.1 were present in the synthesized library.

Example 35

Compound Identification From A 60-Member Combinatorial Library With MASS

Based on the high precision mass measurement of the complex, the mass of the binding ligand was determined to be consistent with the library member having a chemical formula of $C_{15}H_{16}N_4O_2F_6$ and a molecular weight of 398.117 Da (FIG. 62). Thus, the identity of the binding ligand was unambiguously established.

Example 36

Elemental Composition Constraints

Use of exact mass measurements and elemental constraints can be used to determine the elemental composition of an "unknown" binding ligand. General constraints on the type and number of atoms in an unknown molecule, along with a high precision mass measurement, allow determination of a limited list of molecular formulas which are consistent with the measured mass. Referring to FIG. 63, the elemental composition is limited to atoms of C, H, N, and O and further constrained by the elemental composition of a "known" moiety of the molecule. Based on these constraints, the enormous number of atomic combinations which result in a molecular weight of 615.2969±0.0006 are reduced to two possibilities. In addition to unambiguously identifying intended library members, this technique allows one skilled in the art to identify unintended synthetic by-products which bind to the molecular target Example 37

Determination Of The MASS $K_d$ For 16S-Paromomycin

Figure 64:
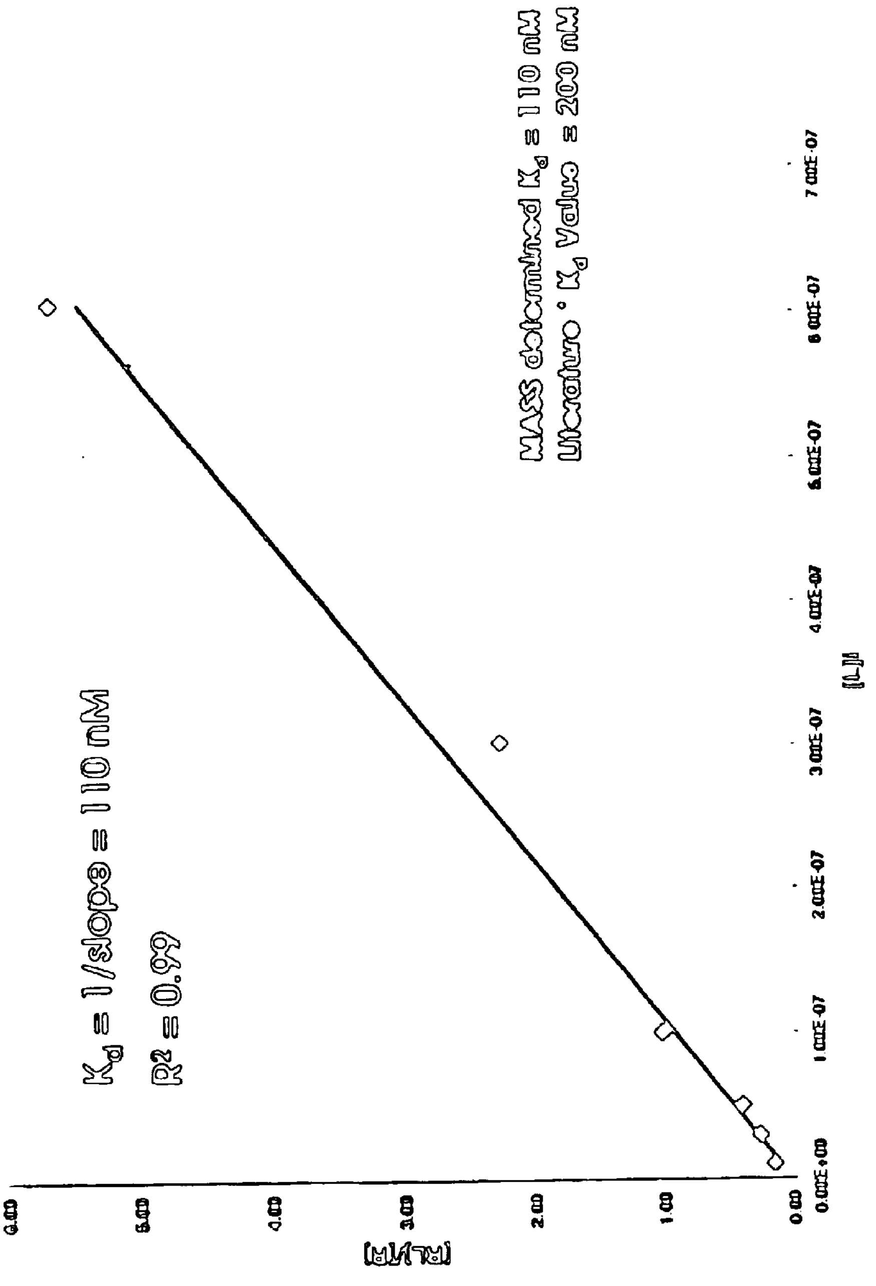
FIG. 64 depicts ESI-MS measurements of a solution containing a fixed concentration of RNA at different concentrations of ligand.

The results of direct determination of solution phase dissociation constants (Kd's) by mass spectrometry is shown in FIG. 64. ESI-MS measurements of a solution containing a fixed concentration of RNA at different concentrations of ligand were obtained. By measuring the ratio of bound:unbound RNA at varying ligand concentrations, the Kd was determined by 1/slope of the "titration curve". The MS derived value of 110 nM is in good agreement with previously reported literature value of 200 nM.

Example 38

Multi-Target Affinity/Specificity Screening

For the determination of ligand binding site by tandem mass spectrometry, a solution containing the molecular target or targets is mixed with a library of ligands and given the opportunity to form noncovalent complexes in solution. These noncovalent complexes are mass analyzed. The noncovalent complexes are subsequently dissociated in the gas phase via IRMPD or CAD. A comparison of the fragment ions formed from dissociation of the complex with the fragment ions formed from dissociation of the free RNA reveals the ligand binding site.

Example 39

MASS Analysis of 27-Member Library With 16S A-Site RNA

Figure 65:
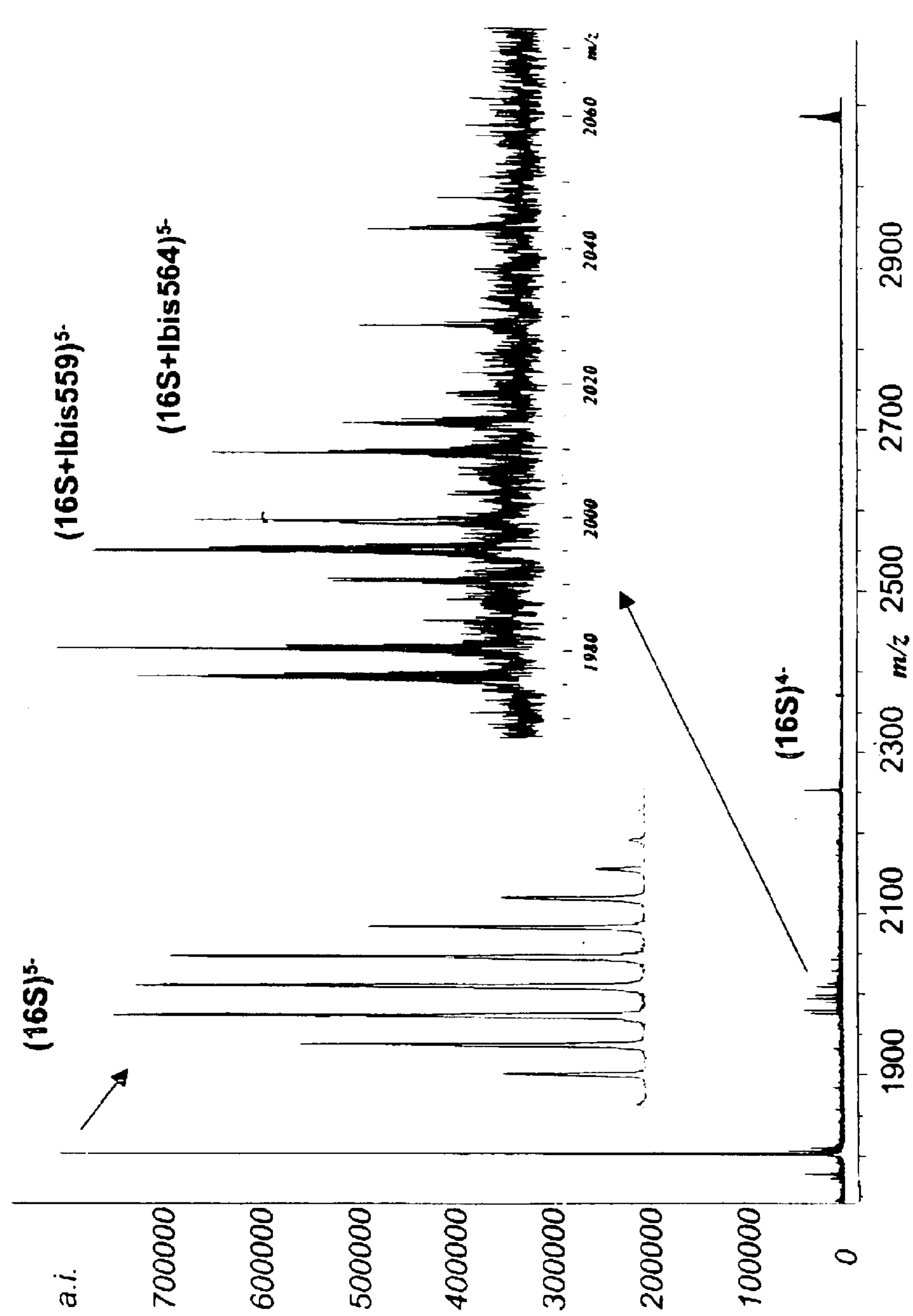
FIG. 65 depicts MASS screening of a 27 member library against a 27-mer RNA construct representing the prokaryotic 16S A-site.

FIG. 65 shows MASS screening of a 27 member library against a 27-mer RNA construct representing the prokaryotic 16S A-site. The inset reveals that a number of compounds formed complexes with the 16S A-site.

Example 40

MASS Protection Assay

Figure 66:
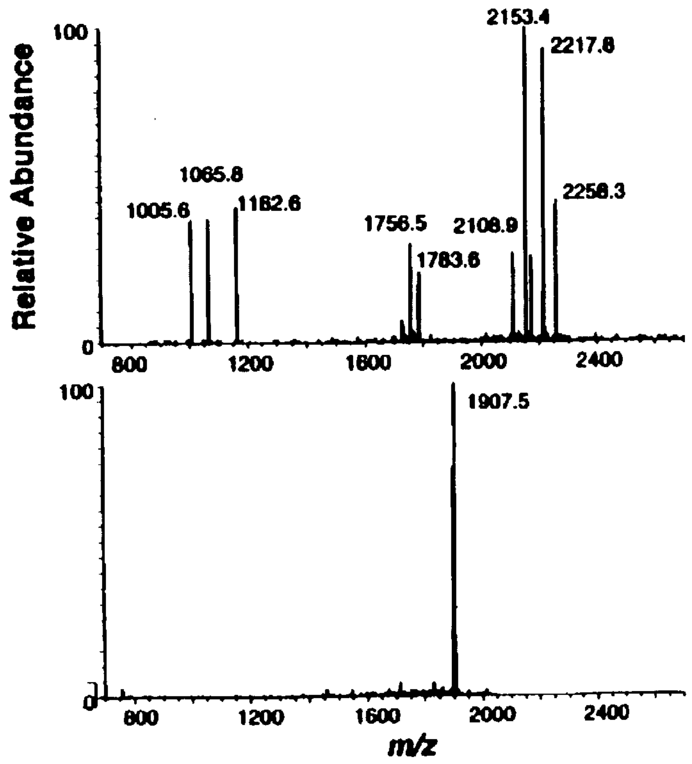
FIG. 66 depicts MS/MS of a 27-mer RNA construct representing the prokaryotic 16S A-site containing deoxyadenosine residues at the paromomycin binding site.

MS/MS of a 27-mer RNA construct representing the prokaryotic 16S A-site containing deoxyadenosine residues at the paromomycin binding site is shown in FIG. 66. The top spectrum was acquired by CAD of the [M−5H]5- ion (m/z 1783.6) from uncomplexed RNA and exhibits significant fragmentation at the deoxyadenosine residues. The bottom spectrum was acquired from by CAD of the [M−5H] 5- ion of the 16S-paromomycin complex (m/z 1907.5) under identical activation energy as employed in the top spectrum. No significant fragment ions are observed in the bottom spectrum consistent with protection of the binding site by the ligand.

Figure 67:
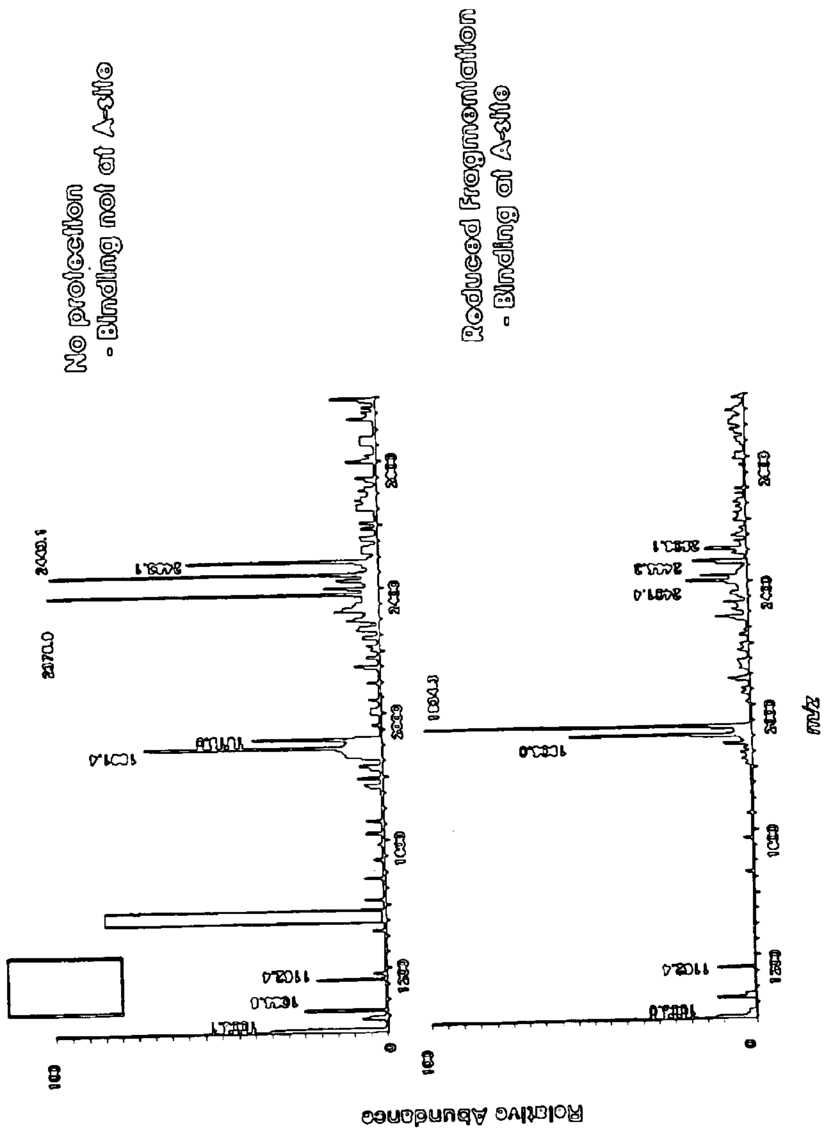
FIG. 67 depicts MS-MS spectra obtained from a mixture of a 27-mer RNA construct representing the prokaryotic 16S A-site containing deoxyadenosine residues at the paromomycin binding and the 216 member combinatorial library respectively.

Two combinatorial libraries containing 216 tetraazacyclophanes dissolved in DMSO were mixed with a buffered solution containing 10 mM 16S RNA (see FIG. 68) such that each library member was present at 100 nM. The resulting mass spectra, shown in FIG. 67 reveal >10 complexes between 16S RNA and library members with the same nominal mass. MS-MS spectra obtained from a mixture of a 27-mer RNA construct representing the prokaryotic 16S A-site containing deoxyadenosine residues at the paromomycin binding and the 216 member combinatorial library. In the top spectrum, ions from the most abundant complex from the first library [M−5H];5-m/z 1919.0) were isolated and dissociated. Dissociation of this complex generates three fragment ions at m/z 1006.1, 1065.6, and 1162.4 that result from cleavage at each dA residue. More intense signals are observed at m/z 2378.9, 2443.1, and 2483.1. These ions correspond to the w21 (3-), a20- B(3-), and a21-B(3-) fragments bound to a library member with a mass of 676.0+0.6 Da. The relative abundances of the fragment ions are similar to the pattern observed for uncomplexed RNA, but the masses of the ions from the lower stem and tetraloop are shifted by complexation with the ligand. This ligand offers little protection of the deoxyadenosine residues, and must bind to the lower stem-loop. The library did not inhibit growth of bacteria. In the bottom spectrum, dissociation of the most abundant complex from a mixture of 16S RNA and the second library having m/z 1934.3 with the same collisional energy yields few fragment ions, the predominant signals arising from intact complex and loss of neutral adenine. The reduced level of cleavage and loss of adenine for this complex is consistent with binding of the ligand at the model A site region as does paromomycin. The second library inhibits transcription/translation at 5 mM, and has an MIC of 2–20 mM against *E. coli*(imp-) and S. pyogenes.

Example 41

Neutral Mass Tag Of Eukaryotic And Prokaryotic A-Sites

FIG. 68 shows secondary structures of the 27 base RNA models used in this work corresponding to the 18S (eukaryotic) and 16S (prokaryotic) A-sites. The base sequences differ in seven positions (bold), the net mass difference between the two constructs is only 15.011 Da. Mass tags were covalently added to the 5' terminus of the RNA constructs using tradition phosphoramadite coupling chemistry.

Figure 69:
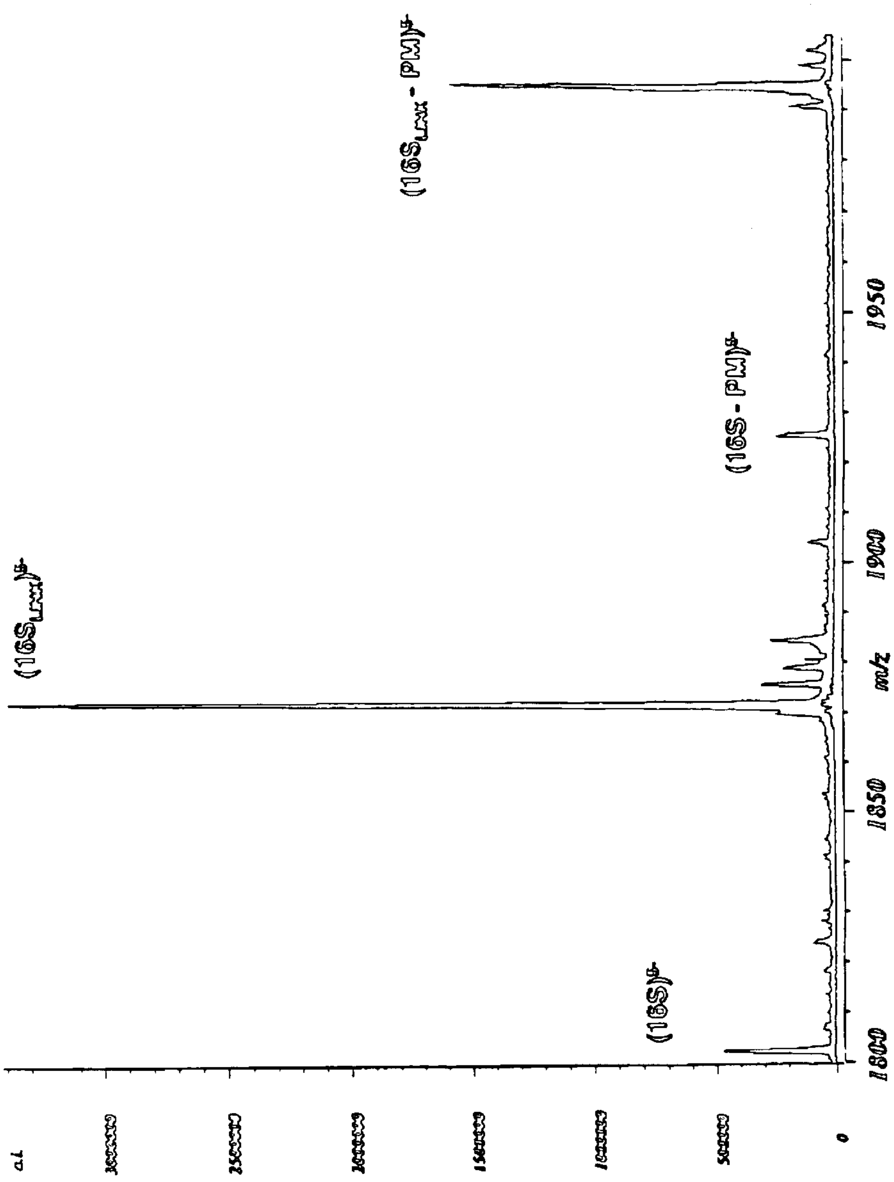
FIG. 69 depicts ESI-FTICR spectrum of a mixture of 27-base representations of the 16S A-site with (7 $\mu$M) and without (1 $\mu$M) an 18 atom neutral mass tag attached to the 5-terminus in the presence of 500 nM paromomycin.

Methodology to increase the separation between the associated signals in the mass spectra was developed in view of the overlap among signals from RNAs 16S and 18S. RNA targets modified with additional uncharged functional groups conjugated to their 5'-termini were synthesized. Such a synthetic modification is referred to herein as a neutral mass tag. The shift in mass, and concomitant m/z, of a mass-tagged macromolecule moves the family of signals produced by the tagged RNA into a resolved region of the mass spectrum. ESI-FTICR spectrum of a mixture of 27-base representations of the 16S A-site with (7 mM) and without (1 mM) an 18 atom neutral mass tag attached to the 5- terminus in the presence of 500 nM paromomycin is shown in FIG. 69. The ratio between unbound RNA and the RNA-paromomycin complex was equivalent for the 16S and 16S+tag RNA targets demonstrating that the neutral mass tag does not have an appreciable effect on RNA-ligand binding.

Example 42

Simultaneous Screening Of 16S A-Site And 18S A-Site Model RNAs Against Aminoglycoside Mixture Paromomycin, lividomycin (MW=761.354 Da), sisomicin (MW=447.269 Da), tobramycin (MW=467.2591 Da), and bekanamycin (MW=483.254 Da) were obtained from Sigma (St. Louis, Mo.) and ICN (Costa Mesa, Calif.) and were dissolved to generate 10 mM stock solutions. 2' methoxy analogs of RNA constructs representing the prokaryotic (16S).rRNA and eukaryotic (18S) rRNA A-site (FIG. 68) were synthesized in house and precipitated twice from 1 M ammonium acetate following deprotection with ammonia (pH 8.5). The mass-tagged constructs contained an 18-atom mass tag ($C_{12}H_{25}O_9$) attached to the 5'-terminus of the RNA oligomer through a phosphodiester linkage.

All mass spectrometry experiments were performed using an Apex 11 70e electrospray ionization Fourier transform ion cyclotron resonance mass spectrometer (Bruker Daltonics, Billerica) employing an actively shielded 7 tesla superconducting magnet. RNA solutions were prepared in 50 mM $NH_4OAc$ (pH 7), mixed 1: v:v with isopropanol to aid desolvation, and infused at a rate of 1.5 mL/min using a syringe pump. Ions were formed in a modified electrospray source (Analytica, Branford) employing an off axis, grounded electrospray probe positioned ca. 1.5 cm from the metalized terminus of the glass desolvation capillary biased at 5000 V. A counter-current flow of dry oxygen gas heated to 225° C. was employed to assist in the desolvation process. Ions were accumulated in an external ion reservoir comprised of an RF-only hexapole, a skimmer cone, and an auxiliary electrode for 1000 ms prior to transfer into the trapped ion cell for mass analysis. Each spectrum was the result of the coaddition of 16 transients comprised of 256 datapoints acquired over a 90,909 kHz bandwidth resulting in a 700 ms detection interval. All aspects of pulse sequence control, data acquisition, and post acquisition processing were performed using a Bruker Daltonics datastation running XMASS version 4.0 on a Silicon Graphics (San Jose, Calif.) R5000 computer.

Mass spectrometry experiments were performed in order to detect complex formation between a library containing five aminoglycosides (Sisomicin (S is), Tobramycin (Tob), Bekanomycin (Bek), Paromomycin (PM), and Livodomycin (LV)) and two RNA targets simultaneously. Signals from the $(M-5H+)^{5-}$ charge states of free 16S and 18S RNAs are detected at m/z 1801.515 and 1868.338, respectively. As shown in FIG. 69, the mass spectrometric assay reproduces the known solution binding properties of aminoglycosides to the 16S A site model and an 18S A site model with a neutral mass linker. Consistent with the higher binding affinity of theses aminoglycosides for the 16S A-site relative to the 18S A-site, aminoglycoside complexes are observed only with the 16S rRNA target. Note the absence of 18S-paromomycin and 18S-lividomycin complexes, which would be observed at the m/z's indicated by the arrows. The inset demonstrates the isotopic resolution of the complexes. Using multiple isotope peaks of the $(M-5H+)^{5-}$ and $(M-4H+)^{4-}$ charge states of the free RNA as internal mass standards, the average mass measurement error of the complexes is 2.1 ppm. High affinity complexes were detected between the 16S A site 27mer RNA and paromomycin and lividomycin, respectively. Weaker complexes were observed with sisomycin, tobramycin and bekamycin. No complexes were observed between any of the aminoglycosides and the 18S A site model. Thus, this result validates the mass spectrometric assay for identifying compounds that will bind specifically to the target RNAs. No other type of high throughput assay can provide information on the specificity of binding for a compound to two RNA targets simultaneously. The binding of lividomycin to the 16S A site had been inferred from previous biochemical experiments. The mass spectrometer has been used herein to measure a $K_D$ of 28 nM for lividomycin and 110 nM for paromomycin to the 16S A site 27mer. The solution KD for paromomycin has been estimated to be between 180 nM and 300 nM.

Example 43

Targeted Site-Specific Gas-Phase Cleavage of Oligoribonucleotides-Application in Mass Spectrometry-Based Identification of Ligand Binding Sites Fragmentation of oligonucleotides is a complex process, but appears related to the relative strengths of the glycosidic bonds. This observation is exploited by incorporating deoxy-nucleotides selectively into a chimeric 2'-O-methylribonucleotide model of the bacterial rRNA A site region. Miyaguchi, et al., *Nucl. Acids Res.,* 1996, 24, 3700–3706; Fourmy, et al., *Science,* 1996, 274, 1367–1371; and Fourmy, et al., *J. Mol. Biol.,* 1998, 277, 333–345. During CAD, fragmentation is directed to the more labile deoxynucleotide sites. The resulting CAD mass spectrum contains a small subset of readily assigned complementary fragment ions. Binding of ligands near the deoxyadenosine residues inhibits the CAD process, while complexation at remote sites does not affect dissociation and merely shifts the masses of specific fragment ions. These methods are used to identify compounds from a combinatorial library that preferentially bind to the RNA model of the A site region.

Figure 71:
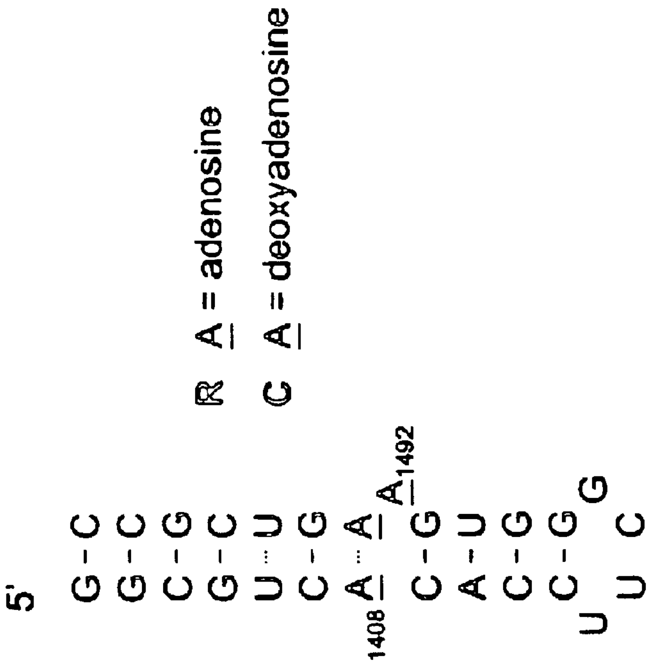
FIG. 71 depicts sequences and structures for oligonucleotides R and C.

The 27-mer model of a segment of the bacterial A site region has been prepared as a full ribonucleotide (see FIG. 71, compound R), and as a chimeric 2'-O-methylribonucleotide containing three deoxyadenosine residues (see FIG. 71, compound C). RNAs R and C have been prepared using conventional phosphoramidite chemistry on solid support. Phosphoramidites were purchased from Glen Research and used as 0.1 M solutions in acetonitrile. RNA R was prepared following the procedure given in Wincott, et al., *Nucl. Acids Res.,* 1995, 23, 2677–2684, the disclosure of which is incorporated herein by reference in its entirety. RNA C was prepared using standard coupling cycles, deprotected, and precipitated from 10 M $NH_4OAc$. The aminoglycoside paromomycin binds to both R and C with kD values of 0.25 and 0.45 micromolar, respectively. The reported kD values are around 0.2 μM. Recht, et al., J. Mol. Biol., 1996, 262, 421–436, Wong, et al., *Chem. Biol.,* 1998, 5, 397–406, and Wang, et al., *Biochemistry,* 1997, 36, 768–779. Paromomycin has been shown previously to bind in the major groove of the 27mer model RNA and induce a conformational change, with contacts to A1408, G1494, and G1491. Miyaguchi, et al., *Nucl. Acids Res.,* 1996, 24, 3700–3706; Fourmy, et al., *Science,* 1996, 274, 1367–1371; and Fourmy, et al., *J. Mol. Biol.,* 1998, 277, 333–345.

Figure 72A:
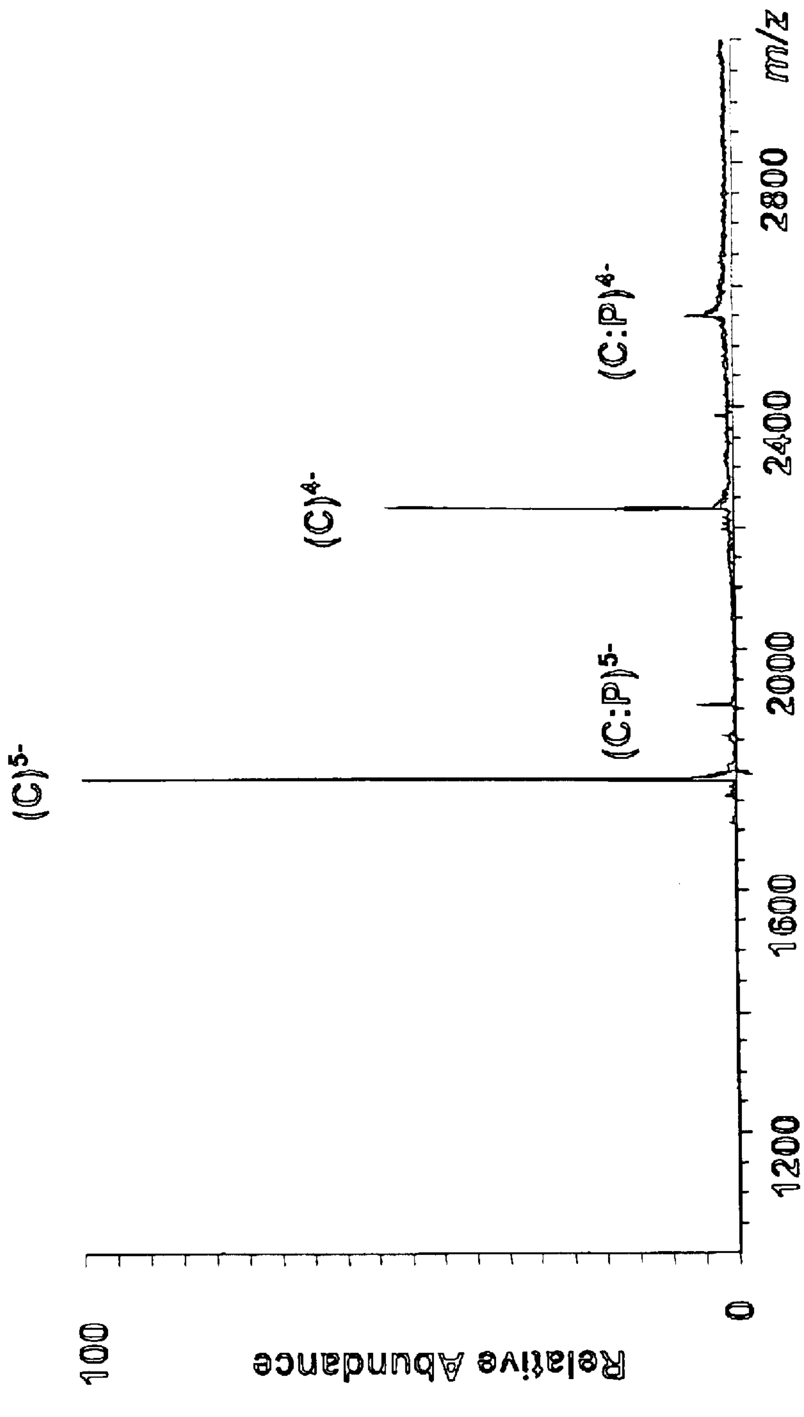
FIG. 72A depicts mass spectrum obtained from a mixture of 5 $\mu$M C and 125 nM paromomycin.
Figure 72B:
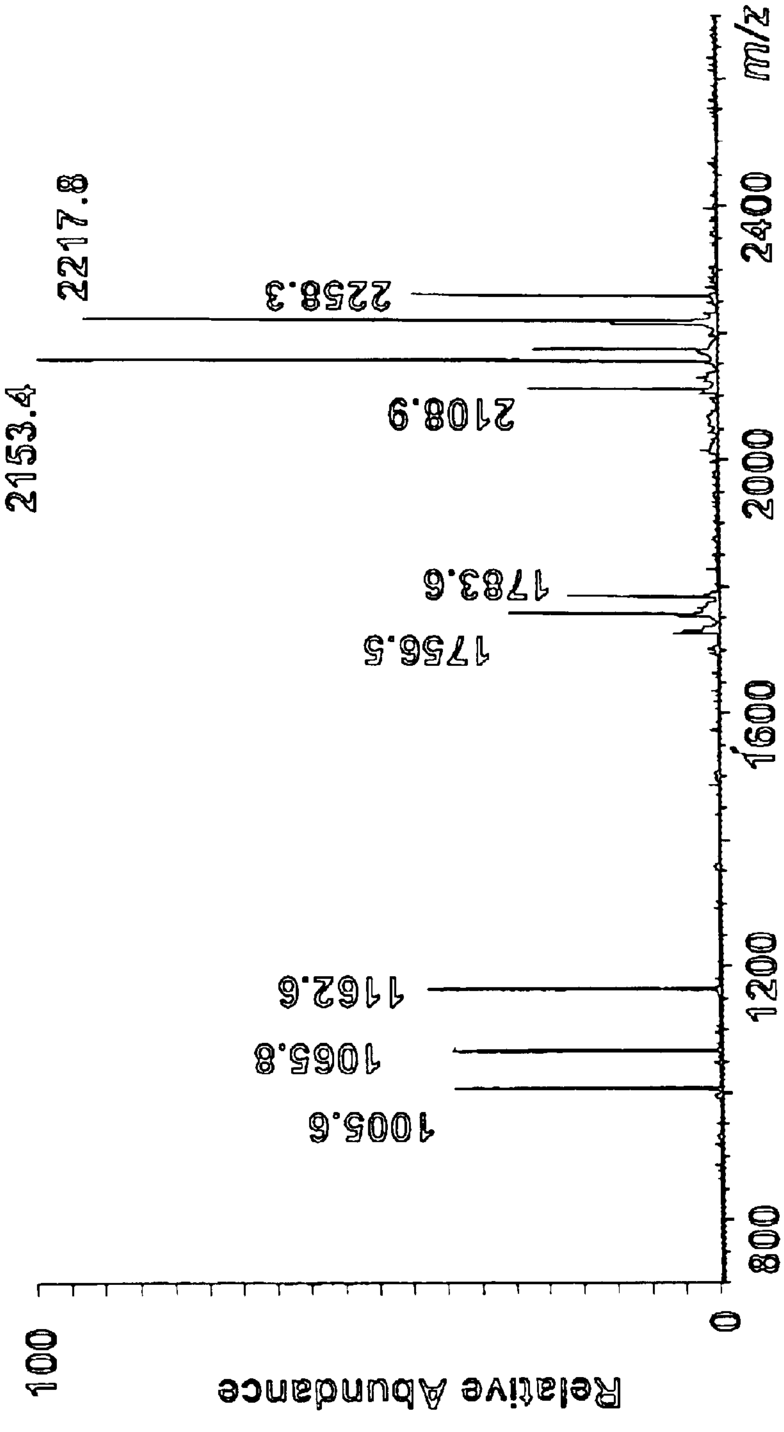
FIG. 72B depicts MS-MS spectrum obtained following isolation of $[M-5H]^{5-}$ ions (m/z 1783.6) from uncomplexed C.
Figure 72C:
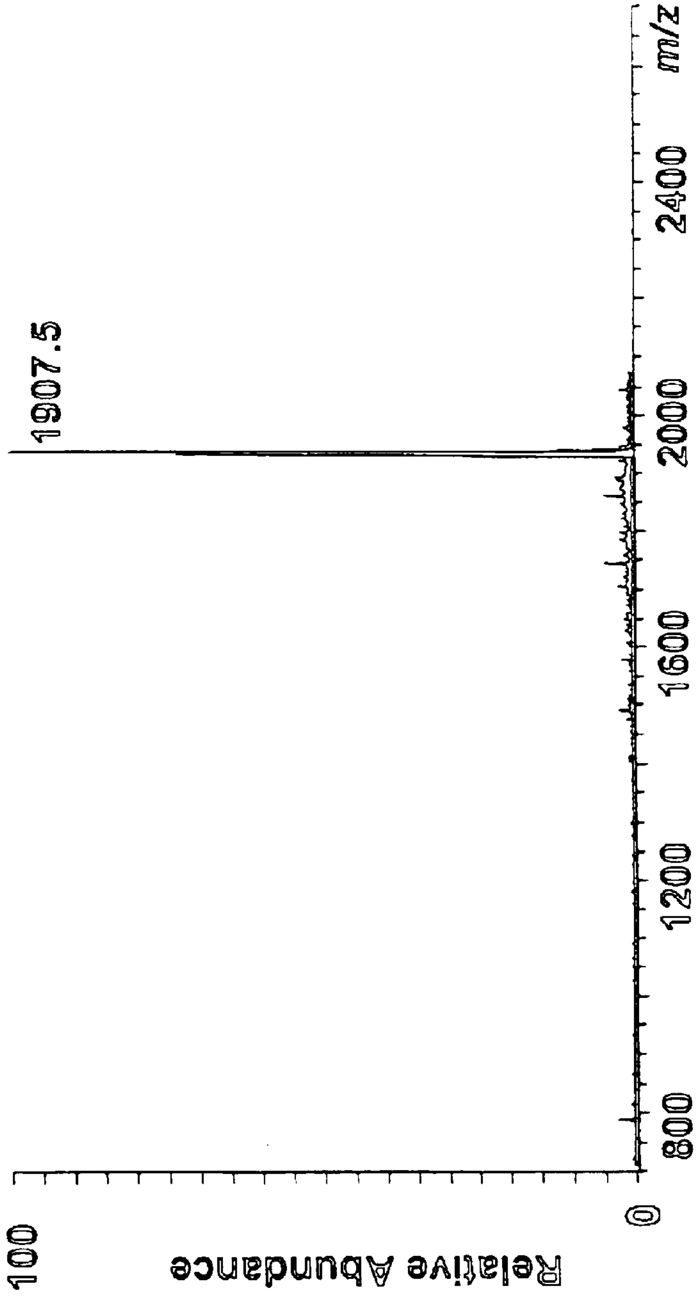
FIG. 72C depicts MS-MS spectrum obtained following isolation of $[M-5H]^{5-}$ ions (m/z 1907.5) from C complexed with paromomycin.

The mass spectrum obtained from a 5 μM solution of C mixed with 125 nM paromomycin (FIG. 72A) contains [M−5H]5- ions from free C at m/z 1783.6 and the [M−5H]5- ions of the paromomycin-C complex at m/z 1907.3. Mass spectrometry experiments have been performed on an LCQ quadrupole ion trap mass spectrometer (Finnigan; San Jose, Calif.) operating in the negative ionization mode. RNA and ligand were dissolved in a 150 mM ammonium acetate buffer at pH 7.0 with isopropyl alcohol added (1:1 v:v) to assist the desolvation process. Parent ions have been isolated with a 1.5 m/z window, and the AC voltage applied to the end caps was increased until about 70% of the parent ion dissociates. The electrospray needle voltage was adjusted to −3.5 kV, and spray was stabilized with a gas pressure of 50 psi (60:40 $N_2$:$O_2$). The capillary interface was heated to a temperature of 180° C. The He gas pressure in the ion trap was 1 mTorr. In MS-MS experiments, ions within a 1.5 Da window having the desired m/z were selected via resonance ejection and stored with q) 0.2. The excitation RF voltage was applied to the end caps for 30 ms and increased manually to 1.1 Vpp to minimize the intensity of the parent ion and to generate the highest abundance of fragment ions. A total of 128 scans were summed over m/z 700–2700 following trapping for 100 ms. Signals from the [M−4H]4- ions of C and the complex are detected at m/z 2229.8 and 2384.4, respectively. No signals are observed from more highly charged ions as observed for samples denatured with tripropylamine. In analogy with studies of native and denatured proteins, this is consistent with a more compact structure for C and the paromomycin complex. The CAD mass spectrum obtained from the [M−5H]5- ion of C is presented in FIG. 72B. Fragment ions are detected at m/z 1005.6 (w6)2-, 1065.8 (a7-B)2-, 1162.6 (w7)2-, 1756.5 (M-Ad)5-, 2108.9 (w21-Ad)3-, 2153.4 (a20-B)3-, 2217.8 (w21)3-, and 2258.3 (a21-B)3-;. McLuckey, et al., *J. Am. Soc. Mass Spectrum.,* 1992, 3, 60–70 and McLuckey, et al., *J. Am. Chem. Soc.,* 1993, 115, 12085–12095. These fragment ions all result from loss of adenine from the three deoxyadenosine nucleotides, followed by cleavage of the 3'-C—O sugar bonds. The CAD mass spectrum for the [M−5H]5- ion of the complex between C and paromomycin obtained with the same activation energy is shown in FIG. 72C. No fragment ions are detected from strand cleavage at the deoxyadenosine sites using identical dissociation conditions of FIG. 72B. The change in fragmentation pattern observed upon binding of paromomycin is consistent with a change in the local charge distribution, conformation, or mobility of A1492, A1493, and A1408 that precludes collisional activation and dissociation of the nucleotide.

Figure 73A:
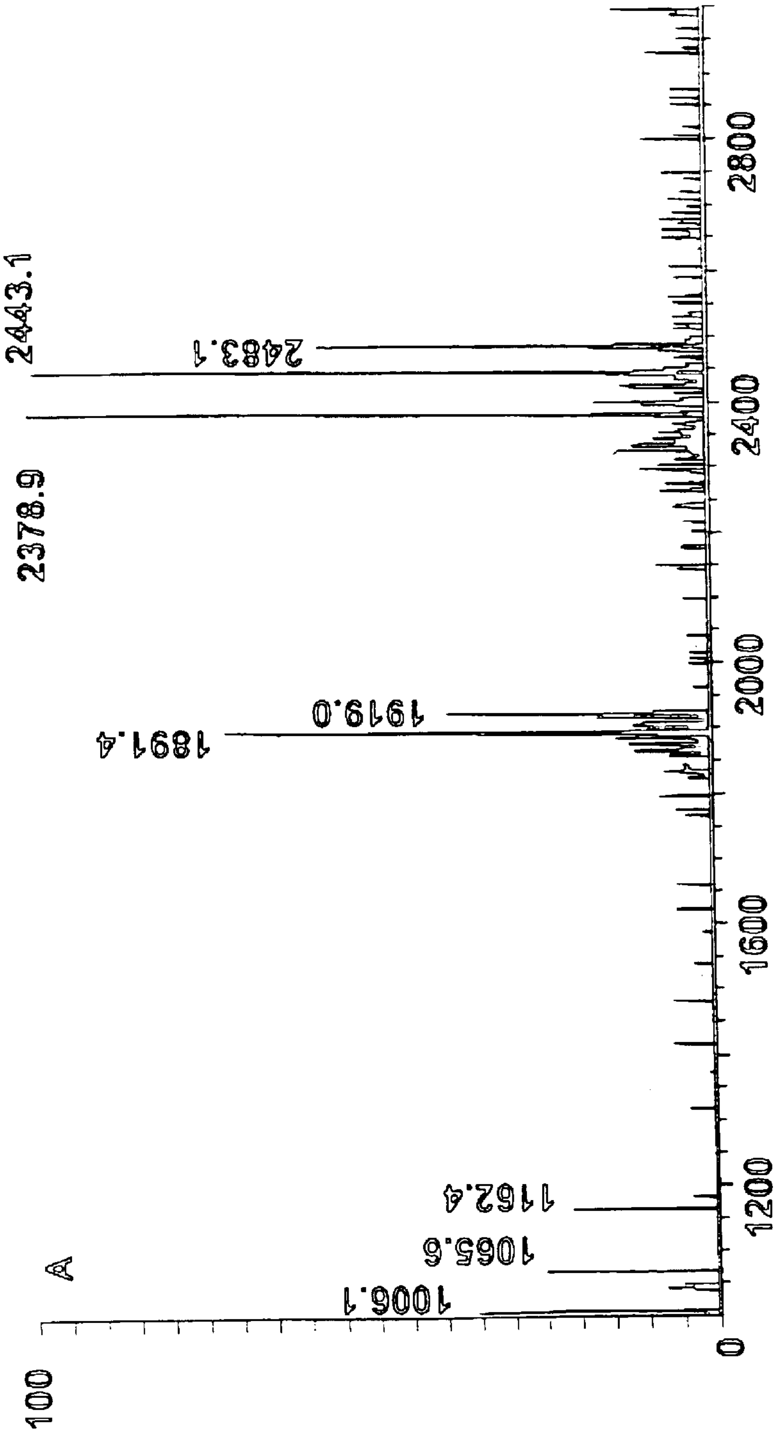
FIG. 73A depicts MS-MS spectrum obtained from a mixture of 10 $\mu$M C and a 216 member combinatorial library following isolation of $[M-5H]^{5-}$ ions (m/z 1919.0) from C complexed with ligands of mass 676.0±0.6.
Figure 73B:
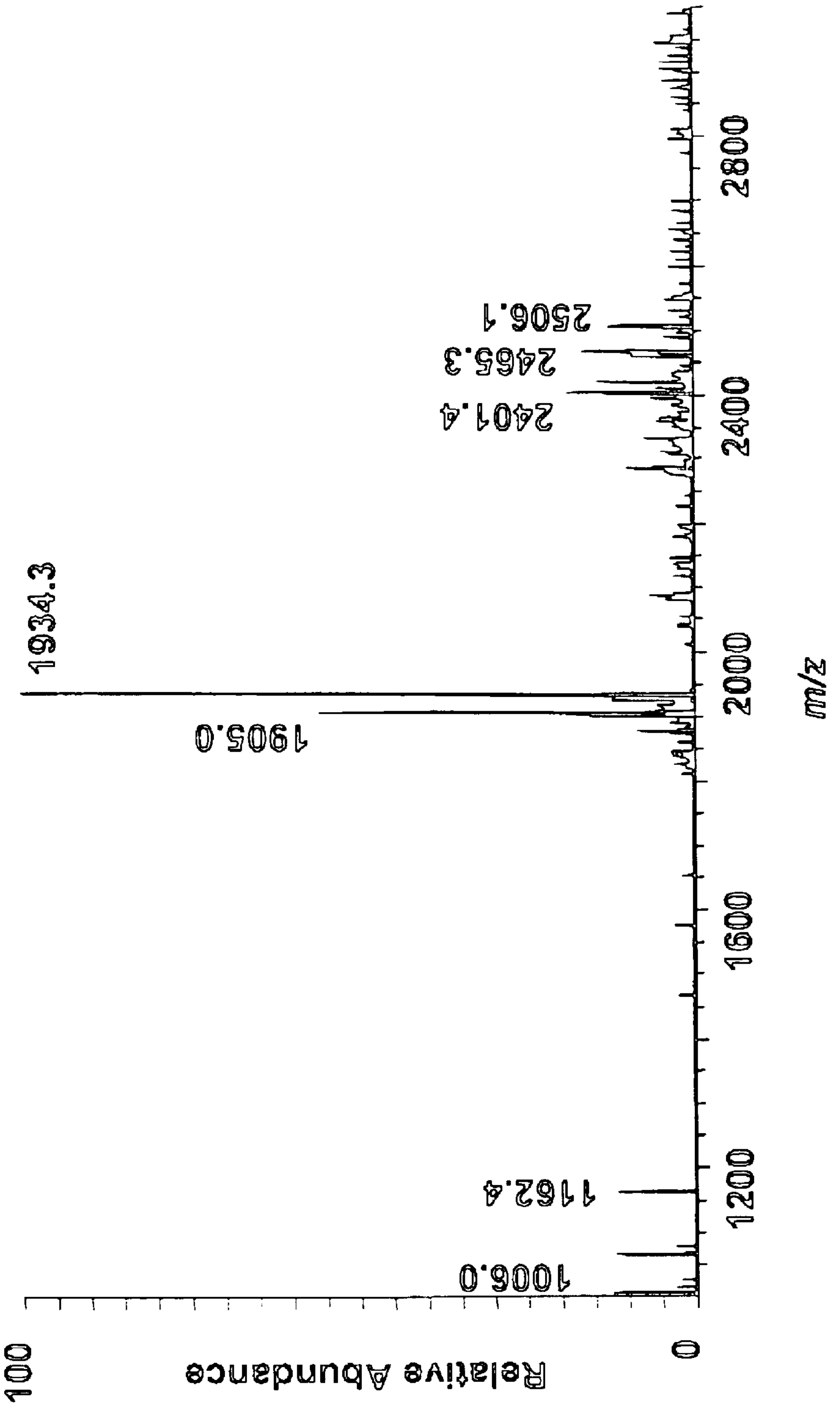
FIG. 73B depicts MS-MS spectrum obtained from a mixture of 10 $\mu$M C and a 216 member combinatorial library following isolation of $[M-5H]^{5-}$ ions (m/z 1934.3) from C complexed with ligands of mass 753.5±0.6.

Two combinatorial libraries containing 216 tetraazacyclophanes dissolved in DMSO were mixed with a buffered solution containing 10 μM C such that each library member is present at 100 nM. The resulting mass spectra reveal >10 complexes between C and library members with the same nominal mass. Ions from the most abundant complex from the first library ($[M-5H];^{5-}$ m/z 1919.0) were isolated and dissociated. As shown in FIG. 73A, dissociation of this complex generates three fragment ions at m/z 1006.1, 1065.6, and 1162.4 that result from cleavage at each dA residue. More intense signals are observed at m/z 2378.9, 2443,1, and 2483.1. These ions correspond to the $w_{21}$ $^{(3-)}$, $a_{20}$-$B^{(3-)}$, and $a_{21}$-$B^{(3-)}$ fragments bound to a library member with a mass of 676.0=0.6Da. The relative abundances of the fragment ions are similar to the pattern observed for uncomplexed C, but the masses of the ions from the lower stem and tetraloop are shifted by complexation with the ligand. This ligand offers little protection of the deoxyadenosine residues, and must bind to the lower stem-loop. The libraries have been synthesized from a mixture of charged and aromatic functional groups, and are described as libraries 25 and 23 in: An, et al., *Bioorg. Med. Chem. Lett.,* 1998, in press. Dissociation of the most abundant complex from a mixture of C and the second library having m/z 1934.3 with the same collisional energy (FIG. 73B) yields few fragment ions, the predominant signals arising from intact complex and loss of neutral adenine. The mass of the ligand (753.5 Da) is consistent with six possible compounds in the library having two combinations of functional groups. The reduced level of cleavage and loss of adenine from this complex is consistent with binding of the ligand at the model A site region as does paromomycin. The second library inhibits transcription/translation at 5 μm, and has an MIC of 2–20 μM against *E. coli* (imp-) and S. pyogenes.

Mass spectrometry-based assays provide many advantages for identification of complexes between RNA and small molecules. All constituents in the assay mixture carry an intrinsic mass label, and no additional modifications with radioactive or fluorescent tags are required to detect the formation of complexes. The chemical composition of the ligand can be ascertained from the measured molecular mass of the complex, allowing rapid deconvolution of libraries to identify leads against an RNA target. Incorporation of deoxynucleotides into a chimeric oligoribonucleotide generates a series of labile sites where collisionally-activated dissociation is favored. Binding of ligands at the labile sites affords protection from CAD observed in MS-MS experiments. This mass spectrometry-based protection methods of the invention can be used to establish the binding sites for small molecule ligands without the need for additional chemical reagents or radiobabeling of the RNA. The methodology can also be used in DNA sequencing and identification of genomic defects.

In accordance with preferred embodiments of the present invention, enhanced accuracy of determination of binding between target biomolecules and putative ligands is desired. It has been found that certain mass spectrometric techniques can give rise to such enhancement. As will be appreciated, the target biomolecule will always be present in excess in samples to be spectroscopically analyzed. The exact composition of such target will, similarly, be known. Accordingly, the isotopic abundances of the parent (and other) ions deriving from the target will be known to precision.

In accordance with preferred embodiments, mass spectrometric data is collected from a sample comprising target biomolecule (or biomolecules) which has been contacted with one or more, preferably a mixture of putative or trial ligands. Such a mixture of compounds may be quite complex as discussed elsewhere herein. The resulting mass spectrum will be complex as well, however, the signals representative of the target biomolecule(s) will be easily identified. It is preferred that the isotopic peaks for the target molecule be identified and used to internally calibrate tile mass spectrometric data thus collected since the M/e for such peaks is known with precision. As a result, it becomes possible to determine the exact mass shift (with respect to the target signal) of peaks which represent complexes between the target and ligands bound to it. Given the exact mass shifts, the exact molecular weights of said ligands may be determined. It is preferred that the exact molecular weights (usually to several decimal points of accuracy) be used to determine the identity of the ligands which have actually bound to the target.

In accordance with other preferred embodiments, the information collected can be placed into a relational or other database, from which further information concerning ligand binding to the target biomolecule can be extracted. This is especially true when the binding affinities of the compounds found to bind to the target are determined and included in the database. Compounds having relatively high binding affinities can be selected based upon such information contained in the database.

It is preferred that such data collection and database manipulation be achieved through a general purpose digital computer. An exemplary software program has been created and used to identify the small molecules bound to an RNA target, calculate the binding constant, and write the results to a relational database. The program uses as input a file that lists the elemental formulas of the RNA and the small molecules which are present in the mixture under study, and their concentrations in the solution. The program first calculates the expected isotopic peak distribution for the most abundant charge state of each possible complex, then opens the raw FTMS results file. The program performs a fast Fourier transform of the raw data, calibrates the mass axis, and integrates the signals in the resulting spectrum such as the exemplary spectrum shown in FIG. 74. The peaks in the spectrum are preferably identified via centroiding as shown in FIG. 75, are integrated, and preferably stored in a database. An exemplary data file is shown in FIG. 76. The expected and observed peaks are correlated, and the integrals converted into binding constants based on the intensity of an internal standard. The compound identity and binding constant data are written to a relational database. This approach allows large amounts of data that are generated by the mass spectrometer to be analyzed without human intervention, which results in a significant savings in time.

Figure 74:
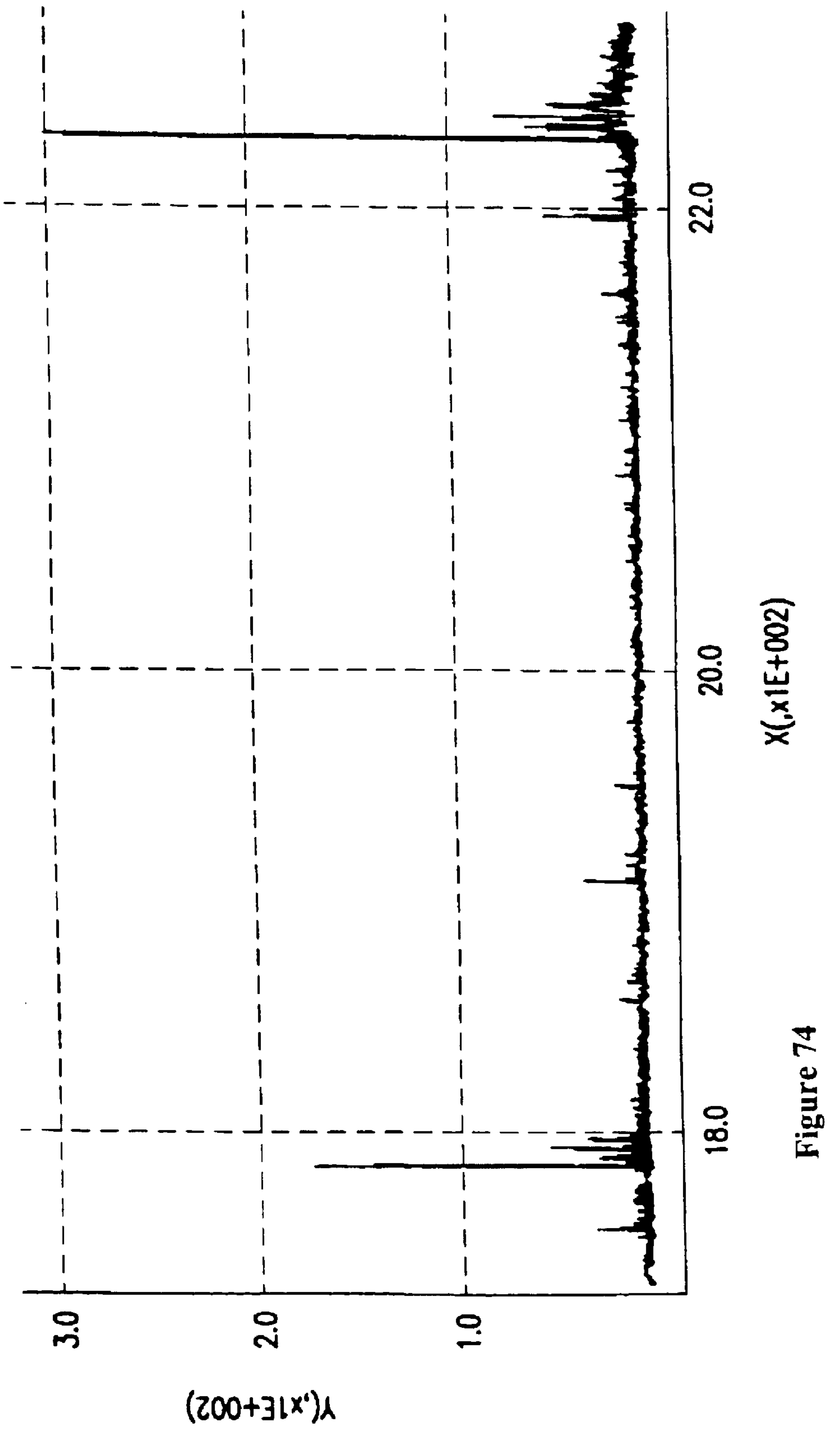
FIG. 74 depicts electrospray ionization Fourier transform ion cyclotron resonance mass spectrometry of a target/putative ligand mixture.
Figure 75:
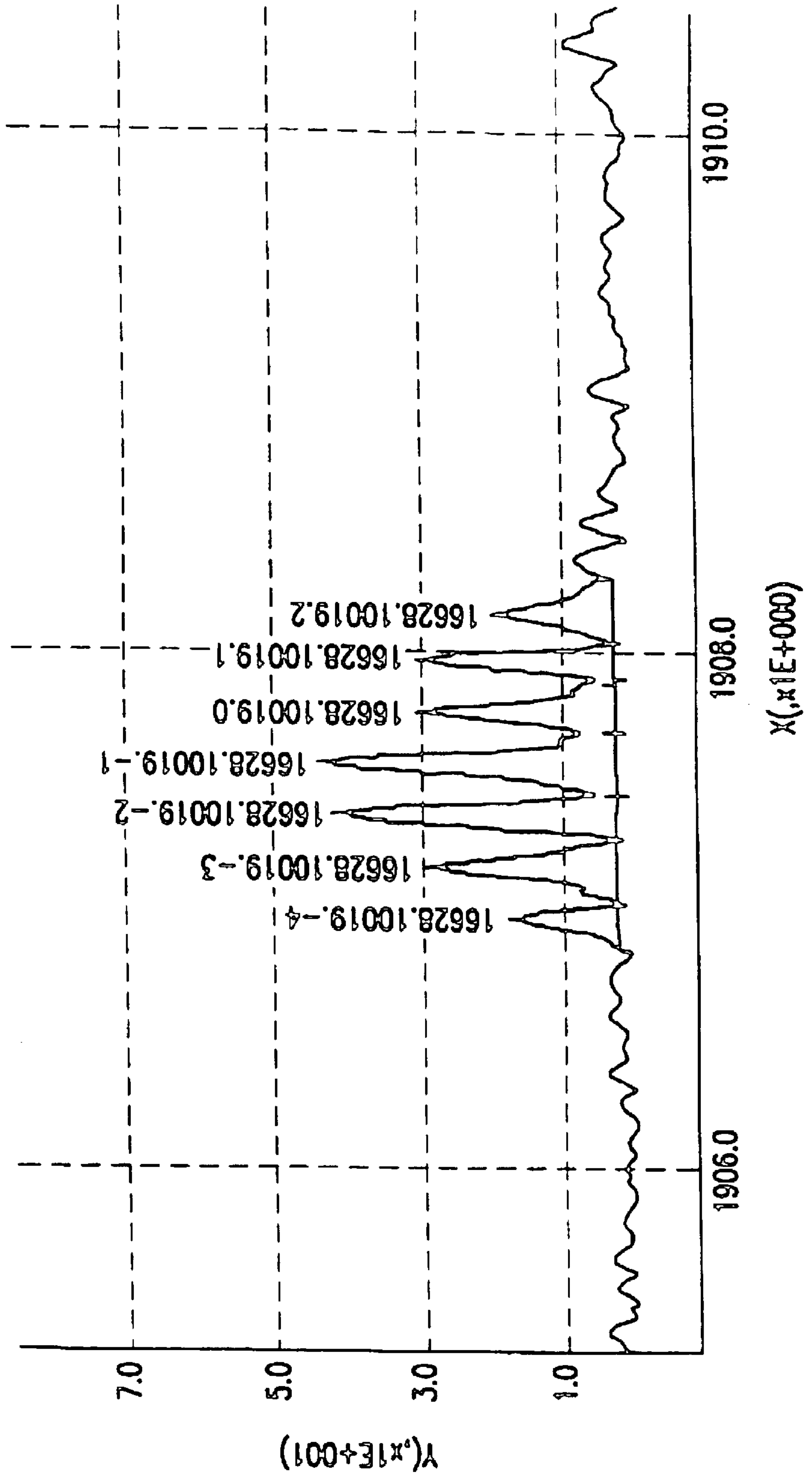
FIG. 75 shows isotope clusters from the spectrum of FIG. 74.

FIG. 74 depicts electrospray ionization Fourier transform ion cyclotron resonance mass spectrometry of a solution which is 5 mM in 16S RNA (Ibis 16628) and 500 nM in the ligand bis 10019. The raw time-domain dataset is automatically apodized and zerofilled twice prior to Fourier transformation. The spectrum is automatically post-calibrated using multiple isotope peaks of the $(M-5H+)^{5-}$ and $(M-4H+)^{4-}$ charge states of the free RNA as internal mass standards and measuring the m/z difference between the free and bound RNA. The isotope distribution of the free RNA is calculated a priori and the measured distribution is fit to the calculated distribution to ensure that m/z differences are measured between homoisotopic species (e.g. monoisotopic peaks or isotope peaks containing 4 $^{13}$C atoms).

Figure 77:
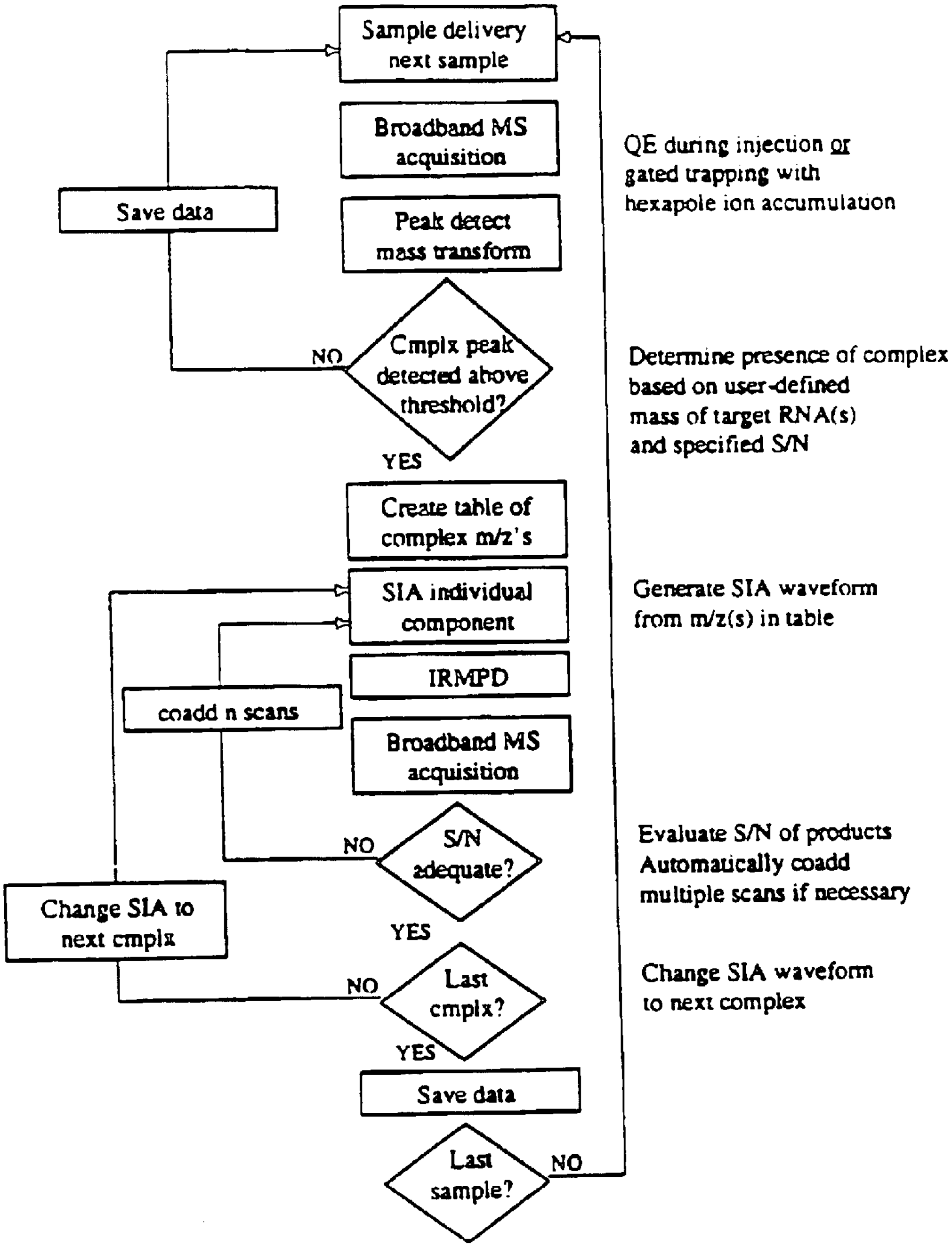
FIG. 77 shows an exemplary flow chart for a computer program for effecting certain methods in accordance with the invention.

FIG. 75 shows isotope clusters observed in the m/z range where RNA-ligand complexes are expected are further analyzed by peak centroiding and integration. FIG. 76 depicts data tabulated and stored in a relational database. Peaks which correspond to complexes between the RNA target and ligands are assigned and recorded in the database. If an internal affinity standard is employed, a relative Kd is automatically calculated from the relative abundance of the standard complex and the unknown complex and recorded in the database. FIG. 77 depicts a flow chart for one computer program for effectuating certain aspects of the present invention.

When computer controlled collection of the foregoing information is provided and computer control of relational databases is employed, the present invention is capable of very high throughput analysis of mass spectrometric binding information. Such control facilitates the identification of ligands having high binding affinities for the target biomolecules. Thus, automation permits the automatic calculation of the mass of the binding ligand or ligands, especially when the mass of the target is used for internal calibration purposes. From the precise mass of the binding ligands, their identity may be determined in an automated way. The dissociation constant for the ligand —target interaction may also be ascertained using either known Kd and abundance of a reference complex or by titration with multiple measurements at different target/ligand ratios. Further, tandem mass spectrometric analyses may be performed in an automated fashion such that the site of the small molecule, ligand, interaction with the target can be ascertained through fragmentation analysis. Computer input and output from the relational database is, of course, preferred.

What is claimed is:

1. A purified and isolated RNA fragment up to 70 nucleotides that is conserved across at least two species comprising the sequence NNNGAUNCUUUNNGUAAGCCCNANGNGNN (SEQ ID NO:23).

2. A purified and isolated RNA fragment up to 70 nucleotides comprising the human sequence UAUGAUUCUUUUUGUAAGCCCUAGGGGCU(SEQ ID NO:24).

3. A purified and isolated RNA fragment up to 70 nucleotides comprising the mouse sequence AAAGAUUCUUUUUGUAACCCCCAAGGGCU (SEQ ID NO:25).

4. A purified and isolated RNA fragment up to 70 nucleotides comprising the rat sequence AAAGAUUCUUUUUGUAAGCCCCAAGGGCU (SEQ ID NO:25).

* * * * *